(12) United States Patent
Jaeger et al.

(10) Patent No.: US 12,351,618 B2
(45) Date of Patent: Jul. 8, 2025

(54) ENGINEERED TRIMERIC CD70 PROTEINS AND USES THEREOF

(71) Applicant: Fred Hutchinson Cancer Center, Seattle, WA (US)

(72) Inventors: Carla A. Jaeger, Seattle, WA (US); Colin E. Correnti, Seattle, WA (US); Stanley R. Riddell, Sammamish, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 210 days.

(21) Appl. No.: 17/767,843

(22) PCT Filed: Oct. 8, 2020

(86) PCT No.: PCT/US2020/054855
§ 371 (c)(1),
(2) Date: Apr. 8, 2022

(87) PCT Pub. No.: WO2021/072127
PCT Pub. Date: Apr. 15, 2021

(65) Prior Publication Data
US 2023/0174618 A1 Jun. 8, 2023

Related U.S. Application Data

(60) Provisional application No. 62/984,695, filed on Mar. 3, 2020, provisional application No. 62/971,712, filed on Feb. 7, 2020, provisional application No. 62/912,510, filed on Oct. 8, 2019.

(51) Int. Cl.
| | | |
|---|---|---|
| *C07K 14/705* | (2006.01) | |
| *A61K 40/11* | (2025.01) | |
| *A61K 40/31* | (2025.01) | |
| *A61K 40/42* | (2025.01) | |
| *A61P 35/00* | (2006.01) | |
| *C07K 14/00* | (2006.01) | |
| *C07K 14/21* | (2006.01) | |
| *C07K 14/435* | (2006.01) | |
| *C07K 14/725* | (2006.01) | |
| *C07K 14/78* | (2006.01) | |
| *C12N 5/0783* | (2010.01) | |
| *A61K 38/00* | (2006.01) | |
| *A61K 39/00* | (2006.01) | |

(52) U.S. Cl.
CPC ........ *C07K 14/70575* (2013.01); *A61K 40/11* (2025.01); *A61K 40/31* (2025.01); *A61K 40/4204* (2025.01); *A61K 40/4211* (2025.01); *A61K 40/4252* (2025.01); *A61P 35/00* (2018.01); *C07K 14/00* (2013.01); *C07K 14/21* (2013.01); *C07K 14/43504* (2013.01); *C07K 14/43563* (2013.01); *C07K 14/7051* (2013.01); *C07K 14/70517* (2013.01); *C07K 14/7056* (2013.01); *C07K 14/70578* (2013.01); *C07K 14/78* (2013.01); *C12N 5/0636* (2013.01); *A61K 38/00* (2013.01); *A61K 2039/5156* (2013.01); *A61K 2239/22* (2023.05); *A61K 2239/38* (2023.05); *A61K 2239/48* (2023.05); *C07K 2319/20* (2013.01); *C07K 2319/21* (2013.01); *C07K 2319/22* (2013.01); *C07K 2319/30* (2013.01); *C07K 2319/41* (2013.01); *C07K 2319/42* (2013.01); *C07K 2319/43* (2013.01); *C12N 2501/2302* (2013.01); *C12N 2501/515* (2013.01); *C12N 2501/599* (2013.01); *C12N 2510/00* (2013.01)

(58) Field of Classification Search
CPC .................. C07K 14/70575; C12N 5/0636
See application file for complete search history.

(56) References Cited

U.S. PATENT DOCUMENTS

| | | |
|---|---|---|
| 5,821,333 A | 10/1998 | Carter |
| 6,040,177 A | 3/2000 | Riddell |
| 7,300,774 B1 | 11/2007 | Kornbluth |
| 10,640,543 B2 | 5/2020 | Hill et al. |
| 2018/0371042 A1 | 12/2018 | Sahin et al. |
| 2020/0102362 A1 | 4/2020 | Fischer et al. |

FOREIGN PATENT DOCUMENTS

| | | |
|---|---|---|
| WO | WO0119958 A2 | 3/2001 |
| WO | WO2005103077 A1 | 11/2005 |
| WO | WO2008025992 A2 | 3/2008 |
| WO | 2016112983 A1 | 7/2016 |

(Continued)

OTHER PUBLICATIONS

Correnti, "Engineering and functionalization of large circular tandem repeat protein nanoparticles", Nature Structural & Molecular Biology, Nature Publishing Group, vol. 27, No. 4, Mar. 23, 2020, pp. 342-350.

(Continued)

*Primary Examiner* — Thane Underdahl
(74) *Attorney, Agent, or Firm* — C. Rachal Winger; Chrystal Quisenberry; Lee & Hayes PC

(57) ABSTRACT

Engineered trimeric CD70 proteins for use in ex vivo T cell manufacturing are described. Use of the proteins during manufacturing creates expanded T cell populations with enhanced properties such as earlier proliferation in culture; selective expansion of nave and memory T cell subsets; longer persistence in vivo following administration to a subject; and improved therapeutic effect. Use of the proteins as therapeutics provide anti-cancer and anti-viral effects. The proteins can also be used as agonistic cell culture reagents in in vitro uses.

18 Claims, 72 Drawing Sheets

Specification includes a Sequence Listing.

(56) References Cited

FOREIGN PATENT DOCUMENTS

| WO | WO2017068192 A1 | 4/2017 |
| WO | 2017096236 A1 | 6/2017 |
| WO | 2018144514 A2 | 8/2018 |
| WO | WO2021072127 A2 | 4/2021 |

OTHER PUBLICATIONS

Extended European Search Report Dated Nov. 8, 2023 for European Application No. 20874924.2, 9 pages.

Hodneland, et al., "Selective immobilization of proteins to self-assembled monolayers presenting active site-directed capture ligands," PNAS, vol. 99, No. 8, 2002, pp. 5048-5052.

Klebanoff, et al., "Sorting through subsets: which T-cell populations mediate highly effective adoptive immunotherapy?" J. Immunother., vol. 35, No. 9, 2012, pp. 651-660.

Song, et al., "CD27 costimulation augments the survival and antitumor activity of redirected human T cells in vivo," Blood., vol. 119, No. 3, 2012, pp. 696-706.

Terakura, et al., "Generation of CD19-chimeric antigen receptor modified CD8+ T cells derived from virus-specific central memory T cells," Blood, vol. 119, No. 1, 2012, pp. 72-82.

Wang, et al., "Phenotypic and functional attributes of lentivirus-modified CD19-specific human CD8+ central memory T cells manufactured at clinical scale," J. Immunother, vol. 35, No. 9, 2012, pp. 689-701.

Beck, et al., "The C-terminal domain of cartilage matrix protein assembles into a triple-stranded alpha-helical coiled-coil structure," J. Mol. Biol., vol. 256, No. 5, pp. 909-923.

Boudko, et al., "The crucial role of trimerization domains in collagen folding," Int. J. Biochem. Cell. Biol., vol. 44, No. 1, 2012, pp. 21-32.

Chen, et al., "Fusion protein linkers: property, design and functionality," Adv. Drug. Deliv. Rev., vol. 65, No. 10, 2013, pp. 1357-1369.

Doyle, et al., "Rational Design of a Helical Tandem Repeat Proteins with Closed Architectures," Nature, vol. 000, 2015, 14 pages.

Fairhead and Howarth, "Site-specific biotinylation of purified proteins using BirA," Methods Mol. Biol., vol. 1266, 2015, pp. 171-184.

Harbury, et al., "A switch between two-, three-, and four-stranded coiled coils in GCN4 leucine zipper mutants," Science, vol. 262, No. 5138, 1993, pp. 1401-1407.

Invitation to Pay Additional Fees Dated Jan. 11, 2021 for International Application No. PCT/US2020/054855, 3 Pages.

Kanagavelu, et al., "Soluble multi-trimeric TNF superfamily ligand adjuvants enhance immune responses to a HIV-1 Gag DNA vaccine," Vaccine, vol. 30, No. 4, 2012, 32 pages.

International Preliminary Report on Patentability Dated Dec. 1, 2021 for International Application No. PCT/US2020/054855, 18 pages.

Search Report and Written Opinion Dated Mar. 26, 2021 for International Application No. PCT/US2020/054855, 22 pages.

Thiemann, et al., "A Single-Chain-Based Hexavalent CD27 Agonist Enhances T Cell Activation and Induces Anti-Tumor Immunity," Frontiers in Oncology, vol. 8, No. 387, 2018, 17 pages.

FIG. 1C

CD70:
MPEEGSGCSVRRRPYGCVLRAALVPLVAGLVICLVVCIQRFAQAQQQLPLESLGWDVAELQLN
HTGPQQDPRLYWQGGPALGRSFLHGPELDKGQLRIHRDGIYMVHIQVTLAICSSTTASRHHPT
TLAVGICSPASRSISLLRLSFHQGCTIASQRLTPLARGDTLCTNLTGTLLPSRNTDETFFGVQWV
RP (SEQ ID NO: 1)

Cytoplasmic Domain: MPEEGSGCSVRRRPYGC (SEQ ID NO: 2)

Transmembrane Domain: VLRAALVPLVAGLVICLVVCI (SEQ ID NO: 3)

Extracellular Domain:
QRFAQAQQQLPLESLGWDVAELQLNHTGPQQDPRLYWQGGPALGRSFLHGPELDKGQLRIH
RDGIYMVHIQVTLAICSSTTASRHHPTTLAVGICSPASRSISLLRLSFHQGCTIASQRLTPLARGD
TLCTNLTGTLLPSRNTDETFFGVQWVRP (SEQ ID NO: 4)

FIG. 2

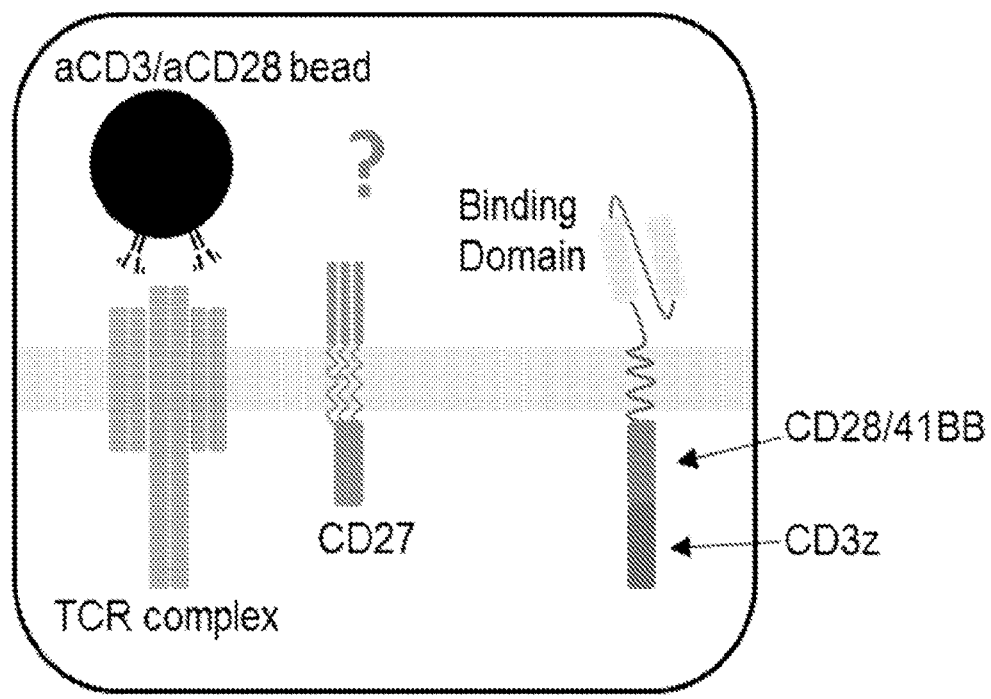

FIG. 4E

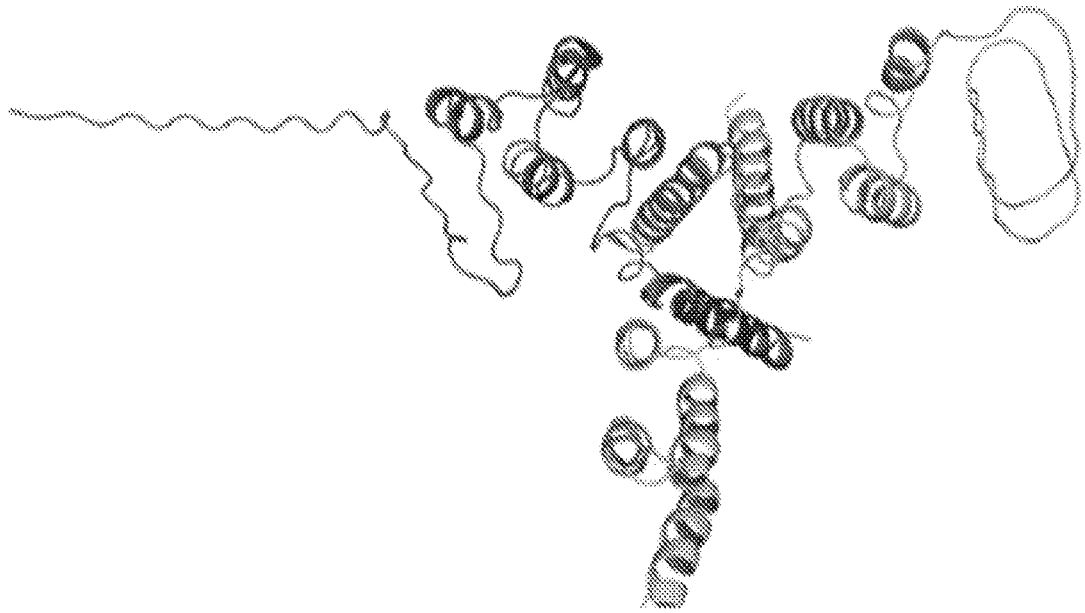

FIG. 5A

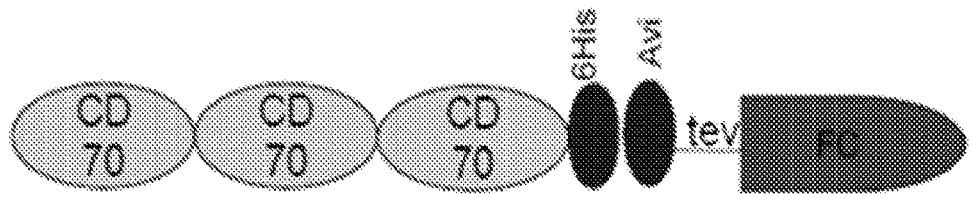

FIG. 5B

MDT-000762-2: hsCD70_SC-His-Avi-Tev-Fc_hsIgG1:
METDTLLLWVLLLWVPGSTGQRFAQAQQQLPLESLGWDVAELQLNHTGPQQDPRLYWQGGP
ALGRSFLHGPELDKGQLRIHRDGIYMVHIQVTLAICSSTTASRHHPTTLAVGICSPASRSISLLRL
SFHQGCTIASQRLTPLARGDTLCTNLTGTLLPSRNTDETFFGVQWVRPGSQRFAQAQQQLPLE
SLGWDVAELQLNHTGPQQDPRLYWQGGPALGRSFLHGPELDKGQLRIHRDGIYMVHIQVTLAI
CSSTTASRHHPTTLAVGICSPASRSISLLRLSFHQGCTIASQRLTPLARGDTLCTNLTGTLLPSR
NTDETFFGVQWVRPGSQRFAQAQQQLPLESLGWDVAELQLNHTGPQQDPRLYWQGGPALG
RSFLHGPELDKGQLRIHRDGIYMVHIQVTLAICSSTTASRHHPTTLAVGICSPASRSISLLRLSFH
QGCTIASQRLTPLARGDTLCTNLTGTLLPSRNTDETFFGVQWVRPGGGGSHHHHHHGGSGLN
DIFEAQKIEWHEGSENLYFQGGGSEPKSSDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSL
SPGK (SEQ ID NO: 5)

FIG. 5B cont'd

Sequence Subcomponents:

Signal Peptide: METDTLLLWVLLLWVPGSTG (SEQ ID NO: 6)

hsCD70 Extracellular Domain:
QRFAQAQQQLPLESLGWDVAELQLNHTGPQQDPRLYWQGGPALGRSFLHGPELDKGQLRIH
RDGIYMVHIQVTLAICSSTTASRHHPTTLAVGICSPASRSISLLRLSFHQGCTIASQRLTPLARGD
TLCTNLTGTLLPSRNTDETFFGVQWVRP (SEQ ID NO: 4)

Linker: GS

Linker: GGGS (SEQ ID NO: 8)

His: HHHHHH (SEQ ID NO: 9)

Avi: GLNDIFEAQKIEWHE (SEQ ID NO: 10)

Tev: ENLYFQG (SEQ ID NO: 11)

hsIgG1:
EPKSSDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK (SEQ ID NO: 12)

FIG. 5C

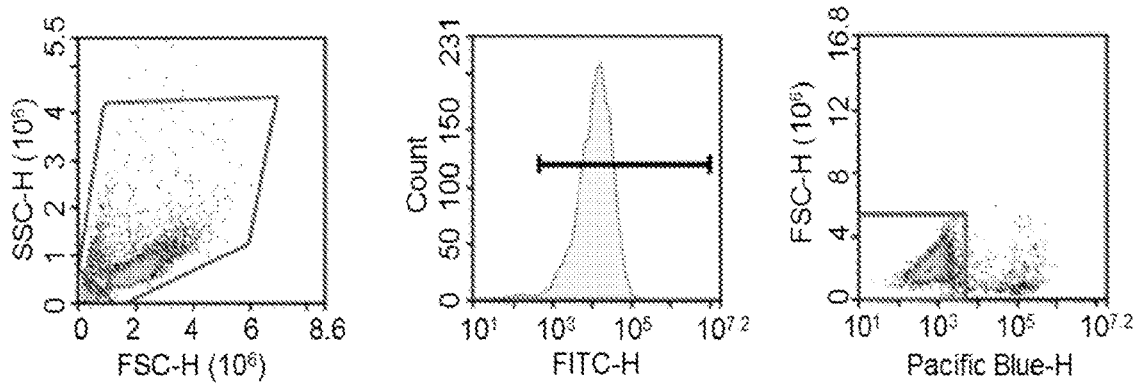

FIG. 6A

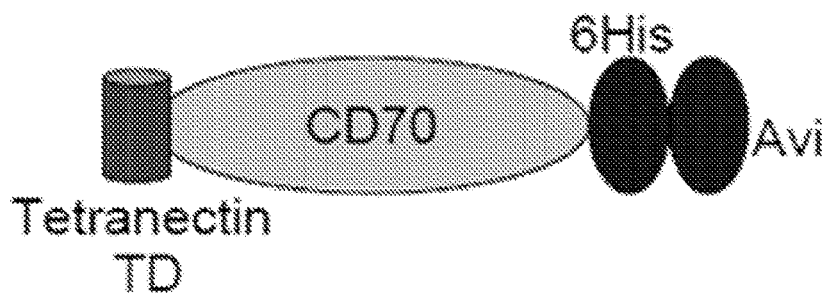

FIG. 6B

MDT-000763: hsTetranectin_TD-hsCD70-His-Avi:
METDTLLLWVLLLWVPGSTGEPPTQKPKKIVNAKKDVVNTKMFEELKSRLDTLAQEVALLKEQ
QALQTVGGGGSQRFAQAQQQLPLESLGWDVAELQLNHTGPQQDPRLYWQGGPALGRSFLH
GPELDKGQLRIHRDGIYMVHIQVTLAICSSTTASRHHPTTLAVGICSPASRSISLLRLSFHQGCTI
ASQRLTPLARGDTLCTNLTGTLLPSRNTDETFFGVQWVRPGGGSHHHHHHGLNDIFEAQKIEW
HE (SEQ ID NO: 13)

Sequence Subcomponents:

Signal Peptide: METDTLLLWVLLLWVPGSTG (SEQ ID NO: 6)

hsTetranectin_TD:
EPPTQKPKKIVNAKKDVVNTKMFEELKSRLDTLAQEVALLKEQQALQTVGGGGS (SEQ ID NO: 14)

hsCD70_ECD:
QRFAQAQQQLPLESLGWDVAELQLNHTGPQQDPRLYWQGGPALGRSFLHGPELDKGQLRIH
RDGIYMVHIQVTLAICSSTTASRHHPTTLAVGICSPASRSISLLRLSFHQGCTIASQRLTPLARGD
TLCTNLTGTLLPSRNTDETFFGVQWVRP (SEQ ID NO: 4)

Linker: GGGS (SEQ ID NO: 8)

His tag: HHHHHH (SEQ ID NO: 9)

Avi: GLNDIFEAQKIEWHE (SEQ ID NO: 10)

FIG. 7A

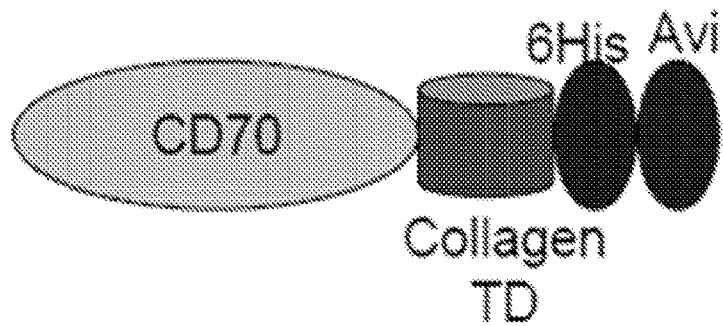

FIG. 7B

MDT-000764-2: hsCD70-Collagen_TD-His-Avi:
METDTLLLWVLLLWVPGSTGQRFAQAQQQLPLESLGWDVAELQLNHTGPQQDPRLYWQGGP
ALGRSFLHGPELDKGQLRIHRDGIYMVHIQVTLAICSSTTASRHHPTTLAVGICSPASRSISLLRL
SFHQGCTIASQRLTPLARGDTLCTNLTGTLLPSRNTDETFFGVQWVRPGSNLVTAFSNMDDML
QKAHLVIEGTFIYLRDSTEFFIRVRDGWKKLQLGELIPIPAGSHHHHHHGGSGLNDIFEAQKIEW
HE (SEQ ID NO: 15)

Trimer_Collagen-hsCD70:
MELWGAYLLLCLFSLLTQVTTEPPTQKPKKIVNAKKDVVNTKMFEELKSRLDTLAQEVALLKEQ
QALQTVCLKGGGGSQRFAQAQQQLPLESLGWDVAELQLNHTGPQQDPRLYWQGGPALGRS
FLHGPELDKGQLRIHRDGIYMVHIQVTLAICSSTTASRHHPTTLAVGICSPASRSISLLRLSFHQG
CTIASQRLTPLARGDTLCTNLTGTLLPSRNTDETFFGVQWVRPGGGSHHHHHHGLNDIFEAQKI
EWHE (SEQ ID NO: 16)

hsCD70-hsCollagen_TD-Avi:
METDTLLLWVLLLWVPGSTGDYKDEHHHHHHGGSQDSTSDLIPAPPLSKVPLQQNFQDNQFQ
GKWYVVGLAGNAILREDKDPQKMYATIYELKEDKSYNVTSVLFRKKKCDYWIRTFVPGCQPGE
FTLGNIKSYPGLTSYLVRVVSTNYNQHAMVFFKKVSQNREYFKITLYGRTKELTSELKENFIRFS
KSLGLPENHIVFPVPIDQCIDGGGSENLYFQGGSQRFAQAQQQLPLESLGWDVAELQLNHTGP
QQDPRLYWQGGPALGRSFLHGPELDKGQLRIHRDGIYMVHIQVTLAICSSTTASRHHPTTLAV
GICSPASRSISLLRLSFHQGCTIASQRLTPLARGDTLCTNLTGTLLPSRNTDETFFGVQWVRPG
SNLVTAFSNMDDMLQKAHLVIEGTFIYLRDSTEFFIRVRDGWKKLQLGELIPIPAGSHHHHHHG
GSGLNDIFEAQKIEWHE (SEQ ID NO: 17)

FIG. 7B cont'd

Sequence Subcomponents:

IgK/Signal Peptide: METDTLLLWVLLLWVPGSTG (SEQ ID NO: 6)

Signal Peptide: MELWGAYLLLCLFSLLTQVTT (SEQ ID NO: 18)

hsCD70:
QRFAQAQQQLPLESLGWDVAELQLNHTGPQQDPRLYWQGGPALGRSFLHGPELDKGQLRIH
RDGIYMVHIQVTLAICSSTTASRHHPTTLAVGICSPASRSISLLRLSFHQGCTIASQRLTPLARGD
TLCTNLTGTLLPSRNTDETFFGVQWVRP (SEQ ID NO: 4)

hsTetranectin trimer:
EPPTQKPKKIVNAKKDVVNTKMFEELKSRLDTLAQEVALLKEQQALQTVCLK (SEQ ID NO: 19)

Collagen_TD: NLVTAFSNMDDMLQKAHLVIEGTFIYLRDSTEFFIRVRDGWKKLQLGELIPIPA
(SEQ ID NO: 20)

His tag: HHHHHH (SEQ ID NO: 9)

Linker: GS

Linker: GGS

Linker: GGGGS (SEQ ID NO: 21)

Avi: GLNDIFEAQKIEWHE (SEQ ID NO: 10)

sFLAG: DYKDE (SEQ ID NO: 22)

Tev: ENLYFQGGS (SEQ ID NO: 23)

FIG. 8A

FIG. 8B

MDT-001100: hsCD70_SC-Toroidx6_SS_tetramer-His:
METDTLLLWVLLLWVPGSTGQRFAQAQQQLPLESLGWDVAELQLNHTGPQQDPRLYWQGGP
ALGRSFLHGPELDKGQLRIHRDGIYMVHIQVTLAICSSTTASRHHPTTLAVGICSPASRSISLLRL
SFHQGCTIASQRLTPLARGDTLCTNLTGTLLPSRNTDETFFGVQWVRPGGSQRFAQAQQQLP
LESLGWDVAELQLNHTGPQQDPRLYWQGGPALGRSFLHGPELDKGQLRIHRDGIYMVHIQVT
LAICSSTTASRHHPTTLAVGICSPASRSISLLRLSFHQGCTIASQRLTPLARGDTLCTNLTGTLLP
SRNTDETFFGVQWVRPGGSQRFAQAQQQLPLESLGWDVAELQLNHTGPQQDPRLYWQGGP
ALGRSFLHGPELDKGQLRIHRDGIYMVHIQVTLAICSSTTASRHHPTTLAVGICSPASRSISLLRL
SFHQGCTIASQRLTPLARGDTLCTNLTGTLLPSRNTDETFFGVQWVRPGGGGSGGGGSCEAI
KAAAAELGKAGISSEEILELLRAAHELGLDPEAIKAAAELGKAGISSEEILELLRAAHELGLDPEAIK
AAAELGKAGISSEEILELLRAAHELGLDPEAIKAAAELGKAGISSEEILELLRAAHELGLDPEAIKA
AAELGKAGISSEEILELLRAAHELGLDPECIKAAAELGKAGISSEEILELLRAAHELGLGGSHHHH
HH (SEQ ID NO: 7)

FIG. 8B cont'd

Sequence Subcomponents:

IgK_SP: METDTLLLWVLLLWVPGSTG (SEQ ID NO: 6)

hsCD70:
QRFAQAQQQLPLESLGWDVAELQLNHTGPQQDPRLYWQGGPALGRSFLHGPELDKGQLRIH
RDGIYMVHIQVTLAICSSTTASRHHPTTLAVGICSPASRSISLLRLSFHQGCTIASQRLTPLARGD
TLCTNLTGTLLPSRNTDETFFGVQWVRP (SEQ ID NO: 4)

Linker: GGS

Linker: GGGGSGGGGS (SEQ ID NO: 24)

cTRP Scaffold:
CEAIKAAAELGKAGISSEEILELLRAAHELGLDPEAIKAAAELGKAGISSEEILELLRAAHELGLDP
EAIKAAAELGKAGISSEEILELLRAAHELGLDPEAIKAAAELGKAGISSEEILELLRAAHELGLDPE
AIKAAAELGKAGISSEEILELLRAAHELGLDPECIKAAAELGKAGISSEEILELLRAAHELGL (SEQ
ID NO: 25)

cTRP cysteine-modified N-terminal α-helix forming b segment:
CEAIKAAAELGKA (SEQ ID NO: 26)

cTRP linker a segment: GIS cTRP internal α-helix forming b and y segments: SEEILELLRAAHEL (SEQ ID NO: 27)

cTRP linker x segment: GLD cTRP cysteine-modified C-terminal α-helix forming b segment:
PECIKAAAELGKA (SEQ ID NO: 28)

His tag: HHHHHH (SEQ ID NO: 9)

FIG. 8B cont'd hsCD70_SC-Toroidx6_SS_tetramer-His:
ATGGAGACCGATACACTGCTGCTGTGGGTGCTGCTGCTGTGGGTGCCTGGCAGCACCGG
ACAGCGGTTCGCACAGGCACAGCAGCAGCTGCCACTGGAGTCCCTGGGATGGGACGTGG
CAGAGCTGCAGCTGAACCACACAGGCCCCAGCAGGACCCCAGGCTGTACTGGCAGGGC
GGCCCCGCCCTGGGCCGCTCCTTTCTGCACGGCCCTGAGCTGGACAAGGGCCAGCTGAG
AATCCACAGAGATGGCATCTATATGGTGCACATCCAGGTGACCCTGGCCATCTGCAGCTC
CACCACAGCCTCTCGGCACCACCCAACCACACTGGCCGTGGGCATCTGTAGCCCAGCCA
GCAGGTCCATCTCTCTGCTGCGCCTGTCTTTCCACCAGGGATGCACCATCGCCAGCCAGC
GGCTGACACCACTGGCCAGAGGCGACACCCTGTGCACAAACCTGACCGGCACACTGCTG
CCCAGCCGGAATACCGATGAGACATTCTTTGGCGTGCAGTGGGTGAGGCCAGGAGGCTCT
CAGCGGTTCGCCCAGGCCCAGCAGCAGCTGCCTCTGGAGAGCCTGGGCTGGGACGTGG
CCGAGCTGCAGCTGAATCACACCGGCCCACAGCAGGACCCCAGACTGTATTGGCAGGGC
GGCCCTGCCCTGGGCCGGAGCTTCCTGCACGGCCCCGAGCTGGACAAGGGACAGCTGA
GAATCCACCGCGACGGAATCTATATGGTCCATATTCAAGTGACCCTGGCCATCTGCTCTAG
CACCACAGCCTCCAGGCATCATCCTACCACACTGGCCGTCGGCATCTGTTCTCCTGCCAG
CCGGTCCATCTCTCTGCTGAGACTGTCCTTTCACCAGGGCTGCACCATCGCCTCTCAGAG
GCTGACACCTCTGGCCCGCGGCGACACTCTGTGCACCAACCTGACTGGCACACTGCTGCC
ATCCCGCAACACTGATGAGACATTCTTTGGAGTGCAGTGGGTGCGGCCAGGAGGCTCCCA
GAGATTCGCCCAGGCTCAGCAGCAGCTGCCCCTGGAGTCTCTGGGCTGGGACGTGGCTG
AACTGCAGCTGAACCATACCGGCCCTCAGCAGGACCCCGCTTATACTGGCAGGGCGGC
CCAGCCCTGGGCCGCAGCTTTCTGCACGGCCCCGAACTGGATAAAGGGCAGCTGAGAAT
CCACAGGGACGGAATCTATATGGTGCATATTCAGGTGACCCTGGCCATCTGCTCCTCTACC
ACAGCCAGCAGGCACCACCCTACCACACTGGCCGTTGGCATCTGTTCTCCCGCCAGCAGG
TCCATCTCTCTGTTACGCCTGAGCTTCCATCAGGGCTGTACTATCGCCTCCCAGCGGCTGA
CACCCCTGGCCAGAGGCGACACTCTGTGCACTAACCTGACTGGCACACTGTTACCCTCCC
GGAACACTGACGAGACATTCTTTGGGGTCCAGTGGGTGAGACCTGGAGGAGGAGGATCC
GGCGGAGGAGGCTCCTGCGAGGCCATCAAGGCTGCCGCCGAGCTGGGCAAGGCAGGCA
TCAGCTCCGAGGAGATCCTGGAGCTGCTGAGGGCAGCACACGAGCTGGGCCTGGACCCC
GAAGCCATCAAGGCTGCCGCCGAACTGGGCAAGGCCGGCATCTCTAGCGAAGAAATCCT
GGAGCTGCTGAGAGCCGCCCATGAACTGGGCCTGGACCCCGAGGCCATCAAGGCTGCCG
CCGAGTTAGGCAAGGCAGGCATCTCCTCTGAAGAGATCCTGGAGTTATTAAGAGCCGCCC
ATGAGCTGGGCCTGGACCCAGAGGCCATCAAGGCTGCCGCCGAGCTAGGCAAGGCCGGC
ATCAGCTCCGAAGAAATCCTGGAGTTACTGAGAGCCGCCCACGAATTAGGCCTGGACCCC
GAGGCCATCAAGGCTGCCGCCGAGCTTGGCAAGGCAGGCATCTCTAGCGAAGAGATCCT
GGAGCTTTTAAGAGCCGCCCACGAACTGGGCCTGGACCCTGAGTGTATCAAGGCTGCCGC
CGAGCTCGGCAAGGCCGGCATCTCCTCTGAGGAAATCCTGGAGTTGTTACGCGCCGCCCA
CGAGCTGGGCCTGGGCGGCAGCCACCACCACCACCACCAC (SEQ ID NO: 29)

aCD3 (5μg/mL) pb +/- cTRP70 (x μg/mL) sol

>set cTRP70 [c] = 0.1 μg/mL

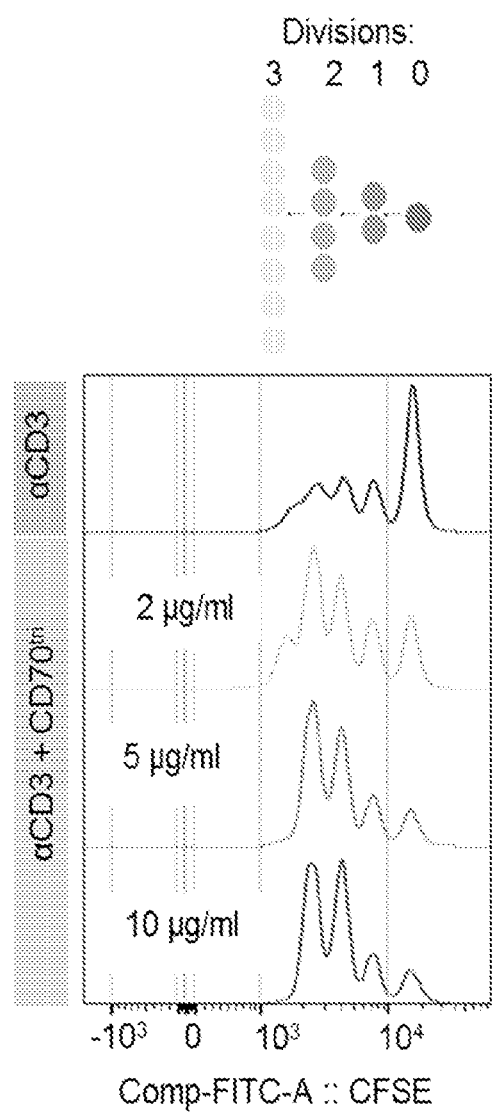

FIG. 12A
| | $T_N$ | $T_{SCM}$ | $T_{CM}$ | $T_{EM}$ | $T_{EFF}$ |
|---|---|---|---|---|---|
| Maintenance | +++ | ++ | + | (+) | - |
| Recall Response | | ++++ | ++ | + | - |
| Anti-tumor Response | | +++ | ++ | +/- | - |
| Stemness | | ++++ | ++ | (+) | - |
| Proliferative Potential | ++++ | +++ | ++ | + | - |
| Senescence | - | - | (+) | + | ++ |
| Cytotoxicity | - | - | - | + | +++ |
| Differentiation | - | (+) | + | ++ | ++++ |
| | | | | | |
|---|---|---|---|---|---|
| CD45RO | - | - | + | + | - |
| CD45RA | + | + | - | - | + |
| CD62L | +++ | +++ | ++ | - | - |
| CCR7 | + | + | + | +/- | - |
| CD27 | +++ | +++ | ++ | +/- | - |
| CD28 | + | + | + | +/- | - |
FIG. 12B
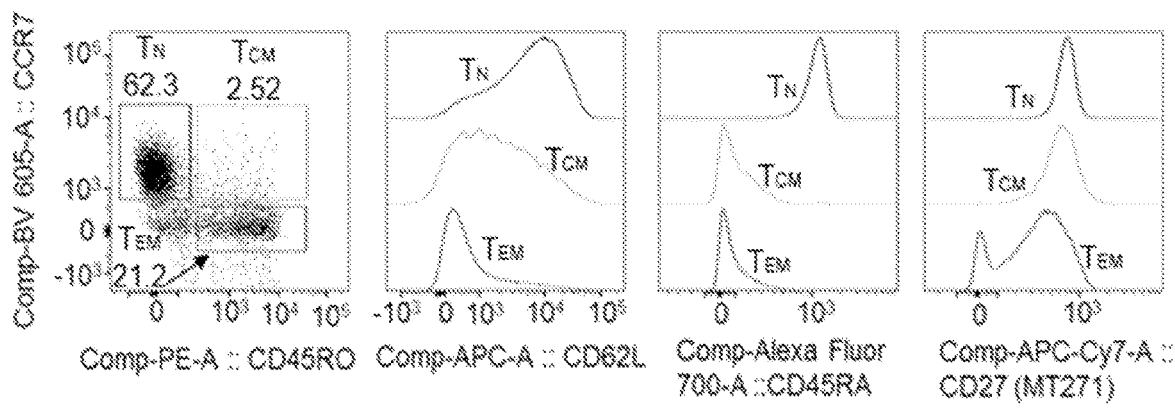

FIG. 15A
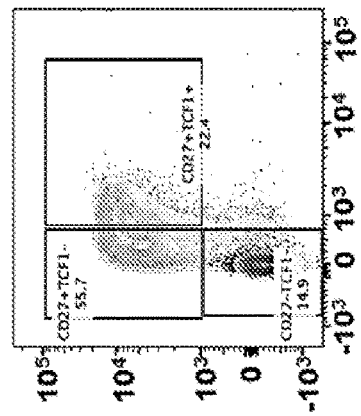
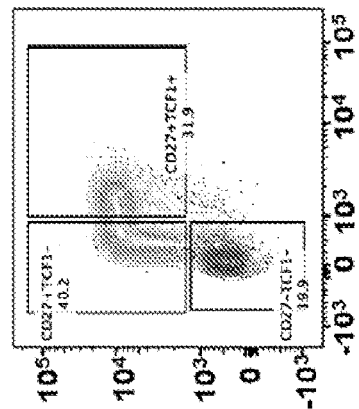
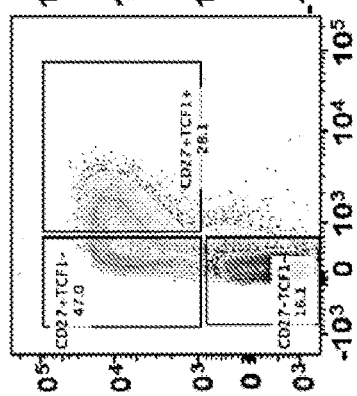
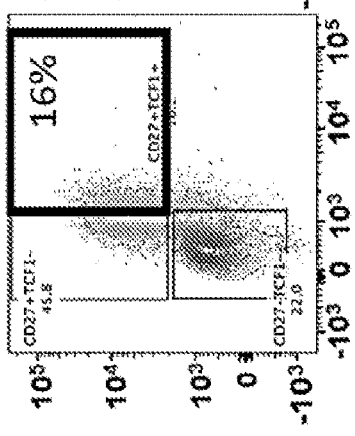
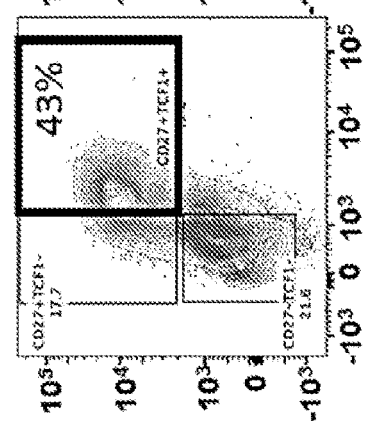

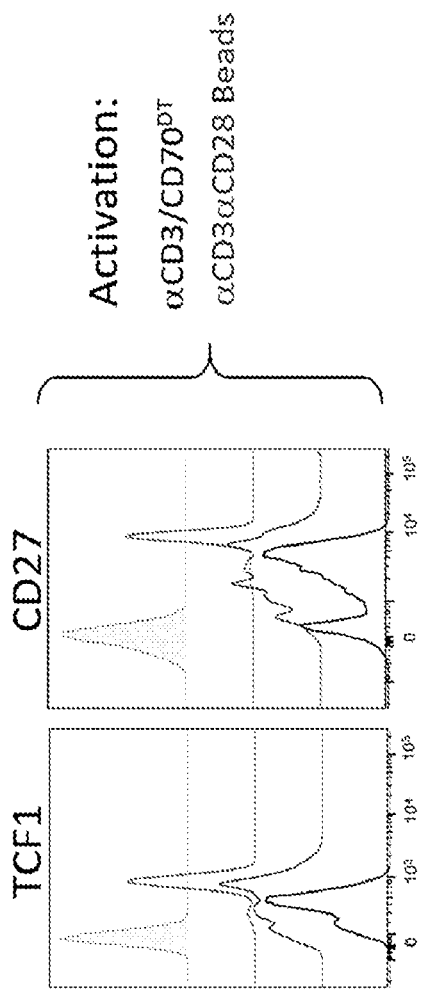
FIG. 16A
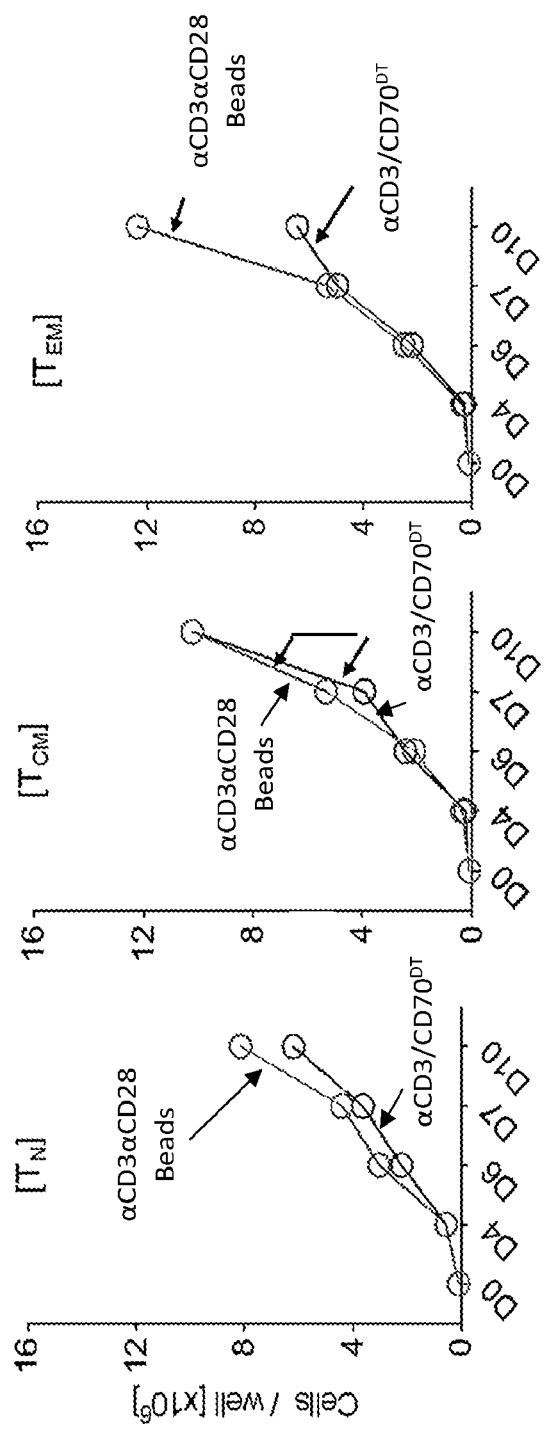
FIG. 16B
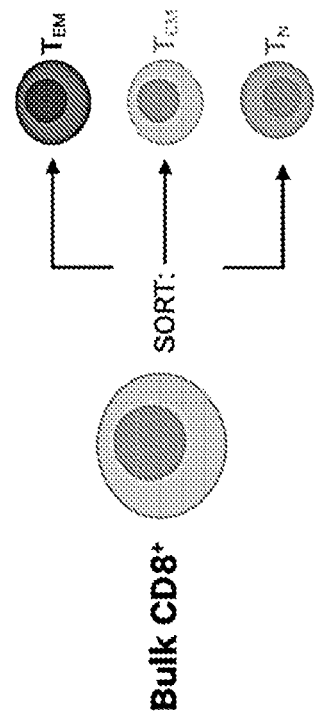

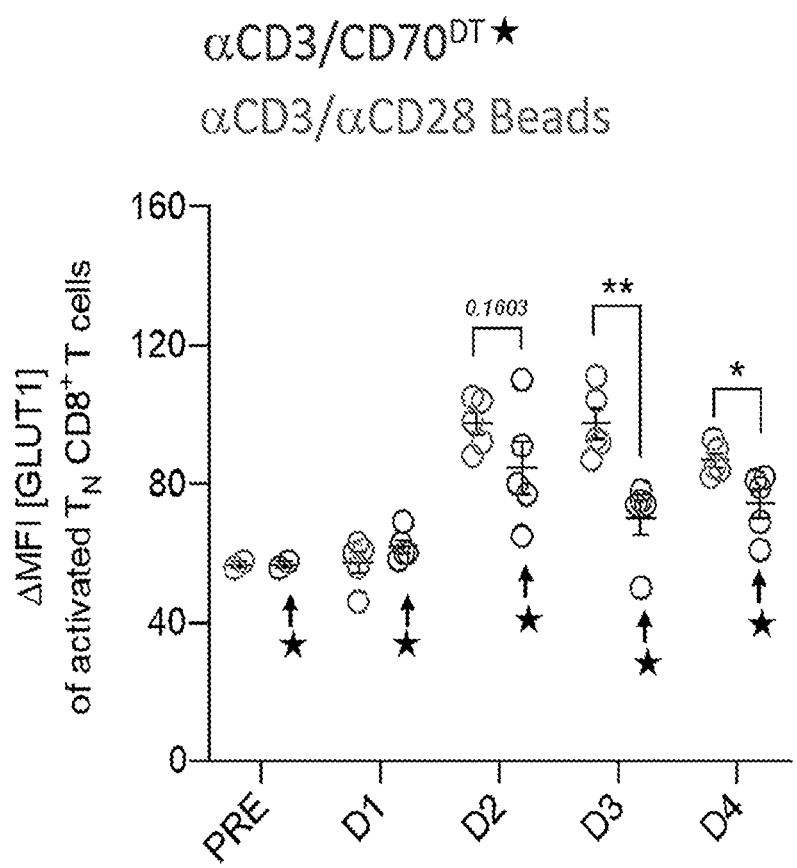

days post injection of
Raji ffluc+ tumor cells days post injection of
Raji ffluc+ tumor cells

FIG. 27

CD70 Extracellular Domain:
QRFAQAQQQLPLESLGWDVAELQLNHTGPQQDPRLYWQGGPALGRSFLHGPELDKGQLRIH
RDGIYMVHIQVTLAICSSTTASRHHPTTLAVGICSPASRSISLLRLSFHQGCTIASQRLTPLARGD
TLCTNLTGTLLPSRNTDETFFGVQWVRP (SEQ ID NO: 4)

hsIgG1:
EPKSSDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK (SEQ ID NO: 12)

hsTetranectin_TD: EPPTQKPKKIVNAKKDVVNTKMFEELKSRLDTLAQEVALLKEQQALQTV
(SEQ ID NO: 30)

hsTetranectin trimer (PDB ID 4C47):
EPPTQKPKKIVNAKKDVVNTKMFEELKSRLDTLAQEVALLKEQQALQTVCLK (SEQ ID NO: 19)

Collagen_TD: NLVTAFSNMDDMLQKAHLVIEGTFIYLRDSTEFFIRVRDGWKKLQLGELIPIPA
(SEQ ID NO: 20)

Mature Human Tetranectin Polypeptide Chain:
EPPTQKPKKIVNAKKDVVNTKMFEELKSRLDTLAQEVALLKEQQALQTVCLKGTKVHMKCFLAF
TQTKTFHEASEDCISRGGTLSTPQTGSENDALYEYLRQSVGNEAEIWLGLNDMAAEGTWVDM
TGARIAYKNWETEITAQPDGGKTENCAVLSGAANGKWFDKRCRDQLPYICQFGIV (SEQ ID
NO: 31)

Collagen XV trimerization domain:
VTAFSNMDDMLQKAHLVIEGTFIYLRDSTEFFIRVRDGWKKLQLGELIPIPADSPPPPALSSNP
(SEQ ID NO: 32)

Collagen XVIII trimerization domain:
SGVRLWATRQAMLGQVHEVPEGWLIFVAEQEELYVRVQNGFRKVQLEARTPLPRGTDNE
(SEQ ID NO: 33)

Clathrin (PDB ID 3QIL):
MGSSHHHHHHSSGLVPRGSHMWKQSVELAKKDSLYKDAMQYASESKDTELAEELLQWFLQE
EKRECFGACLFTCYDLLRPDVVLELAWRHNIMDFAMPYFIQVMKEYLTKVDKLDASESLRKEEE
(SEQ ID NO: 34)

FIG. 27 cont'd

SadB or Salmonella enterica trimeric lipoprotein (PDB ID 4C47):
MSDYFADKHLVEEMKEQQKEQETKINLLEKQQKEQEAKINLLEKQQATIINTTKKVTEVVGRVE
RKQRLFDYTELDPSQTHYFIINNGNIGLAGRILSIEPIDNGSVIHLDLVNLLSIPVSNLAFNMTWGT
KKPSEAKDLPRWKQLLLNTKMDSTIELLPGAWTNVTLTLKGVSPNNLKYLKIGIDMENVIFDSIQ
PINDTKKKPKK (SEQ ID NO: 35)

EML4 (PDB ID 4CGC):
GSLDDSISAASTSDVQDRLSALESRVQQQEDEMTVLKAALADVLRRLAISEDHVASVKK (SEQ
ID NO: 36)

Wildtype Matrilin-1 (CMP trimerization domain):
CACESLVKFQAKVEGLLQALTRKLEAVSKRLAILENTVV (SEQ ID NO: 37)

Matrilin1 variant: CACESLVKFQAKVEGLIQALTRKLEAVSKRIAILENTVV (SEQ ID NO: 38)

Wildtype DMPK:
EAEAEVTLRELQEALEEEVLTRQSLSREMEAIRTDNQNFASQLREAEARNRDLEAHVRQLQER
MELLQAE (SEQ ID NO: 39)

DMPK variant:
IAEIEVTIRELQEAIEEEVLTRQSLSREIEAIRTDIQNIASQLREIEARIRDLEAHVRQLQERMELLQ
AE (SEQ ID NO: 40)

Wildtype Langerin: ASALNTKIRALQGSLENMSKLLKRQNDILQVVS (SEQ ID NO: 41)

Variant of Langerin: ISALNTKIRAIQGSIENMSKLIKRQNDIIQVVS (SEQ ID NO: 42)

Coronin 1a wildtype: VSRLEEEMRKLQATVQELQKRLDRLEETVQAK (SEQ ID NO: 43)

Coronin 1a variant: VSRLEEEIRKLQATVQELQKRLDRLEETVQAK (SEQ ID NO: 44)

Coronin 1a variant: VSRIEEEIRKLQATVQELQKRLDRLEETVQAK (SEQ ID NO: 45)

Coronin 1a variant: ISRIEEEIRKLQATVQELQKRLDRLEETVQAK (SEQ ID NO: 46)

Coronin 1a variant: ISRIEEEIRKIQATVQELQKRLDRLEETVQAK (SEQ ID NO: 47)

Coronin 1a variant: ISRIEEEIRKIQATVQELQKRIDRLEETVQAK (SEQ ID NO: 48)

Coronin 1a variant: ISRIEEEIRKINATVQELQKRIDRLEETVQAK (SEQ ID NO: 49)

Coronin 1a variant: ISRIEEEIRKINATIQELQKRIDRLEETVQAK (SEQ ID NO: 50)

FIG. 27 cont'd

Full length human CMP:
MRVLSGTSLMLCSLLLLLQALCSPGLAPOSRGHLCRTRPIDLVFVVDSSRSVRPVEFEKVKVFL
SQVIESLDVGPNATRVGMVNYASTVKQEFSLRAHVSKAALLQAVRRIQPLSTGTMTGLAIQFAIT
KAFGDAEGGRSRSPDISKVVIVTDGRPODSVQDVSARARASGVELFAIGVGSVDKATLROIASE
PQDEHVDYVESYSVIEKLSRKFQEAFCVVSDLCATGDHDCEQVCISSPGSYTCACHEGFTLNS
DGKTCNVCSGGGGSSATDLVFLIDGSKSVRPENFELVKKFISQIVDTLDVSDKLAQVGLVQYSS
SVROEFPLGRFHTKKDIKAAVRNMSYMEKGTMTGAALKYLIDNSFTVSSGARPGAOKVGIVFID
GRSODYINDAAKKAKDLGFKMFAVGVGNAVEDELREIASEPVAEHYFYTADFKTINQIGKKLOK
KICVEEDPCACESLVKFQAKVEGLLQALTRKLEAVSKRLAILENTVV (SEQ ID NO: 51)

Cartilage matrix protein precursor [Homo sapiens]:
MRVLSGTSLMLCSLLLLLQALCSPGLAPQSRGHLCRTRPTDLVFVVDSSRSVRPVEFEKVKVFL
SQVIESLDVGPNATRVGMVNYASTVKQEFSLRAHVSKAALLQAVRRIQPLSTGTMTGLAIQFAIT
KAFGDAEGGRSRSPDISKVVIVVTDGRPQDSVQDVSARARASGVELFAIGVGSVDKATLRQIAS
EPQDEHVDYVESYSVIEKLSRKFQEAFCVVSDLCATGDHDCEQVCISSPGSYTCACHEGFTLN
SDGKTCNVCSGGGGSSATDLVFLIDGSKSVRPENFELVKKFISQIVDTLDVSDKLAQVGLVQYS
SSVRQEFPLGRFHTKKDIKAAVRNMSYMEKGTMTGAALKYLIDNSFTVSSGARPGAQKVGIVF
TDGRSQDYINDAAKKAKDLGFKMFAVGVGNAVEDELREIASEPVAEHYFYTADFKTINQIGKKL
QKKICVEEDPCACESLVKFQAKVEGLLQALTRKLEAVSKRLAILENTVV (SEQ ID NO: 52)

T4 fibritin:
MTDIVLNDLPFVDGPPAEGQSRISWIKNGEEILGADTQYGSEGSMNRPTVSVLRNVEVLDKNIG
ILKTSLETANSDIKTIQGILDVSGDIEALAQIGINKKDISDLKTLTSEHTEILNGTNNTVDSILADIGPF
NAEANSVYRTIRNDLLWIKRELGQYTGQDINGLPVVGNPSSGMKHRIINNTDVITSQGIRLSELE
TKFIESDVGSLTIEVGNLREELGPKPPSFSQNVYSRLNEIDTKQTTVESDISAIKTSIGYPGNNSII
TSVNTNTDNIASINLELNQSGGIKQRLTVIETSIGSDDIPSSIKGQIKDNTTSIESLNGIVGENTSSG
LRANVSWLNQIVGTDSSGGQPSPHGSLLNRVSTIETSVSGLNNAVQNLQVEIGNNSAGIKGQV
VALNTLVNGTNPNGSTVEERGLTNSIKANETNIASVTQEVNTAKGNISSLQGDVQALQEAGYIP
EAPRDGQAYVRKDGEWVLLSTFLSPA (SEQ ID NO: 53)

Trimerization domain of T4 fibritin:
GYIPEAPRDGQAYVRKDGEWVLLSTFL (SEQ ID NO: 54)

RB69 fibritin:
MIELKSLPYVDGPPDEGQKRLNWIKNSEEITGADTLYGSEGVMNRPITEVQRNVETINDNVKTIA
ESLDTANADIVTIKSILDVSGDVDALAQIGHNTDDIEVLKHTVNSHGVDILNTEEKLDDTIANIGVV
NPETDSVYRTVRNDLLWIKTELGQYTGQDINGVPTEGNESTGMKRRIITNSSVLVDQGVRLTEL
ENKFADSDVGALTTEVENLRQEIGPRPSLTVPVYTRLSGIDSSISIQTRDIAALKDFVGYPNSTAI
KTQVEANRLSISTINSDINSPGGIKPRLTTLETTIGSPDLPTTLQGKIKLNTDSISGINTVLGVDSSS
GLRFNVAWLNQVVGVDSNGGQPEPAGSLLYRTRILETGVTDLGNNIQNVQTELGTNSSGIKGQ
VTSLNKLISGTNPNGQTIEERGILPTVKNHDTSIMALTTRVTTLETDLAAAEAEIQALKEAGYIEDA
PSDGKFYVRKDGAWVELPTA (SEQ ID NO: 55)

FIG. 27 cont'd

Trimerization domain of RB69 fibritin:
GYIEDAPSDGKFYVRKDGAWVELPTA (SEQ ID NO: 56)

TNF receptor-associated factor-2 (TRAF2) (GENBANK® Accession No. Q12933.2):
MAAASVTPPGSLELLQPGFSKTLLGTKLEAKYLCSACRNVLRRPFQAQCGHRYCSFCLASILSS
GPQNCAACVHEGIYEEGISILESSSAFPDNAARREVESLPAVCPSDGCTWKGTLKEYESCHEG
RCPLMLTECPACKGLVRLGEKERHLEHECPERSLSCRHCRAPCCGADVKAHHEVCPKFPLTC
DGCGKKKIPREKFQDHVKTCGKCRVPCRFHAIGCLETVEGEKQQEHEVQWLREHLAMLLSSV
LEAKPLLGDQSHAGSELLQRCESLEKKTATFENIVCVLNREVERVAMTAEACSRQHRLDQDKIE
ALSSKVQQLERSIGLKDLAMADLEQKVLEMEASTYDGVFIWKISDFARKRQEAVAGRIPAIFSPA
FYTSRYGYKMCLRIYLNGDGTGRGTHLSLFFVVMKGPNDALLRWPFNQKVTLMLLDQNNREH
VIDAFRPDVTSSSFQRPVNDMNIASGCPLFCPVSKMEAKNSYVRDDAIFIKAIVDLTGL (SEQ ID
NO: 57)

Thrombospondin 1 (Accession No. P07996 [gi:135717]:
MGLAWGLGVLFLMHVCGTNRIPESGGDNSVFDIFELTGAARKGSGRRLVKGPDPSSPAFRIED
ANLIPPVPDDKFQDLVDAVRAEKGFLLLASLRQMKKTRGTLLALERKDHSGQVFSVVSNGKAG
TLDLSLTVQGKQHVVSVEEALLATGQWKSITLFVQEDRAQLYIDCEKMENAELDVPIQSVFTRD
LASIARLRIAKGGVNDNFQGVLQNVRFVFGTTPEDILRNKGCSSSTSVLLTLDNNVVNGSSPAIR
TNYIGHKTKDLQAICGISCDELSSMVLELRGLRTIVTTLQDSIRKVTEENKELANELRRPPLCYHN
GVQYRNNEEWTVDSCTECHCQNSVTICKKVSCPIMPCSNATVPDGECCPRCWPSDSADDGW
SPWSEWTSCSTSCGNGIQQRGRSCDSLNNRCEGSSVQTRTCHIQECDKRFKQDGGWSHWS
PWSSCSVTCGDGVITRIRLCNSPSPQMNGKPCEGEARETKACKKDACPINGGWGPWSPWDI
CSVTCGGGVQKRSRLCNNPTPQFGGKDCVGDVTENQICNKQDCPIDGCLSNPCFAGVKCTSY
PDGSWKCGACPPGYSGNGIQCTDVDECKEVPDACFNHNGEHRCENTDPGYNCLPCPPRFTG
SQPFGQGVEHATANKQVCKPRNPCTDGTHDCNKNAKCNYLGHYSDPMYRCECKPGYAGNGI
ICGEDTDLDGWPNENLVCVANATYHCKKDNCPNLPNSGQEDYDKDGIGDACDDDDDNDKIPD
DRDNCPFHYNPAQYDYDRDDVGDRCDNCPYNHNPDQADTDNNGEGDACAADIDGDGILNER
DNCQYVYNVDQRDTDMDGVGDQCDNCPLEHNPDQLDSDSDRIGDTCDNNQDIDEDGHQNNL
DNCPYVPNANQADHDKDGKGDACDHDDDNDGIPDDKDNCRLVPNPDQKDSDGDGRGDACK
DDFDHDSVPDIDDICPENVDISETDFRRFQMIPLDPKGTSQNDPNWVVRHQGKELVQTVNCDP
GLAVGYDEFNAVDFSGTFFINTERDDDYAGFVFGYQSSSRFYVVMWKQVTQSYWDTNPTRA
QGYSGLSVKVVNSTTGPGEHLRNALWHTGNTPGQVRTLWHDPRHIGWKDFTAYRWRLSHRP
KTGFIRVVMYEGKKIMADSGPIYDKTYAGGRLGLFVFSQEMVFFSDLKYECRDP (SEQ ID NO:
58)

Matrilin-4 (Accession No. O95460 [gi:14548117]:
MRGLLCWPVLLLLLQPWETQLQLTGPRCHTGPLDLVFVIDSSRSVRPFEFETMRQFLMGLLRG
LNVGPNATRVGVIQYSSQVQSVFPLRAFSRREDMERAIRDLVPLAQGTMTGLAIQYAMNVAFS
VAEGARPPEERVPRVAVIVTDGRPQDRVAEVAAQARARGIEIYAVGVQRADVGSLRAMASPPL
DEHVFLVESFDLIQEFGLQFQSRLCGKDQCAEGGHGCQHQCVNAWAMFHCTCNPGYKLAAD
NKSCLAIDLCAEGTHGCEHHCVNSPGSYFCHCQVGFVLQQDQRSCRAIDYCSFGNHSCQHEC
VSTPGGPRCHCREGHDLQPDGRSCQVRDLCNGVDHGCEFQCVSEGLSYRCLCPEGRQLQA
DGKSCNRCREGHVDLVLLVDGSKSVRPQNFELVKRFVNQIVDFLDVSPEGTRVGLVQFSSRV

FIG. 27 cont'd

RTEFPLGRYGTAAEVKQAVLAVEYMERGTMTGLALRHMVEHSFSEAQGARPRALNVPRVGLV
FTDGRSQDDISVWAARAKEEGIVMYAVGVGKAVEAELREIASEPAELHVSYAPDFGTMTHLLE
NLRGSICPEEGISAGTELRSPCECESLVEFQGRTLGALESLTLNLAQLTARLEDLENQLANQK
(SEQ ID NO: 59)

Heat shock transcription factor (HSF) (Accession No. AAX42211 [gi:61362386]:
MDLPVGPGAAGPSNVPAFLTKLWTLVSDPDTDALICWSPSGNSFHVFDQGQFAKEVLPKYFK
HNNMASFVRQLNMYGFRKVVHIEQGGLVKPERDDTEFQHPCFLRGQEQLLENIKRKVTSVSTL
KSEDIKIRQDSVTKLLTDVQLMKGKQECMDSKLLAMKHENEALWREVASLRQKHAQQQKVVN
KLIQFLISLVQSNRILGVKRKIPLMLNDSGSAHSMPKYSRQFSLEHVHGSGPYSAPSPAYSSSSL
YAPDAVASSGPIISDITELAPASPMASPGGSIDERPLSSSPLVRVKEEPPSPPQSPRVEEASPGR
PSSVDTLLSPTALIDSILRESEPAPASVTALTDARGHTDTEGRPPSPPPTSTPEKCLSVACLDKN
ELSDHLDAMDSNLDNLQTMLSSHGFSVDTSALLDLFSPSVTVPDMSLPDLDSSLASIQELLSPQ
EPPRPPEAENSSPDSGKQLVHYTAQPLFLLDPGSVDTGSNDLPVLFELGEGSYFSEGDGFAED
PTISLLTGSEPPKAKDPTVS (SEQ ID NO: 60)

Cubilin (Accession No. NP001072 [gi:4557503]:
MMNMSLPFLWSLLTLLIFAEVNGEAGELELQRQKRSINLQQPRMATERGNLVFLTGSAQNIEFR
TGSLGKIKLNDEDLSECLHQIQKNKEDIIELKGSAIGLPQNISSQIYQLNSKLVDLERKFQGLQQT
VDKKVCSSNPCQNGGTCLNLHDSFFCICPPQWKGPLCSADVNECEIYSGTPLSCQNGGTCVN
TMGSYSCHCPPETYGPQCASKYDDCEGGSVARCVHGICEDLMREQAGEPKYSCVCDAGWM
FSPNSPACTLDRDECSFQPGPCSTLVQCFNTQGSFYCGACPTGWQGNGYICEDINECEINNG
GCSVAPPVECVNTPGSSHCQACPPGYQGDGRVCTLTDICSVSNGGCHPDASCSSTGSLPLC
TCLPGYTGNGYGPNGCVQLSNICLSHPCLNGQCIDTVSGYFCKCDSGWTGVNCTENINECLS
NPCLNGGTCVDGVDSFSCECTRLWTGALCQVPQQVCGESLSGINGSFSYRSPDVGYVHDVN
CFWVIKTEMGKVLRITFTFFRLESMDNCPHEFLQVYDGDSSSAFQLGRFCGSSLPHELLSSDN
ALYFHLYSEHLRNGRGFTVRWETQQPECGGILTGPYGSIKSPGYPGNYPPGRDCVWIVVTSPD
LLVTFTFGTLSLEHHDDCNKDYLEIRDGPLYQDPLLGKFCTTFSVPPLQTTGPFARIHFHSDSQI
SDQGFHITYLTSPSDLRCGGNYTDPEGELFLPELSGPFTHTRQCVYMMKQPQGEQIQINFTHV
ELQCQSDSSQNYIEVRDGETLLGKVCGNGTISHIKSITNSVWIRFKIDASVEKASFRAVYQVACG
DELTGEGVIRSPFFPNVYPGERTCRWTIHQPQSQVILLNFTVFEIGSSAHCETDYVEIGSSSILG
SPENKKYCGTDIPSFITSVYNFLYVTFVKSSSTENHGFMAKFSAEDLACGEILTESTGTIQSPGH
PNVYPHGINCTWHILVQPNHLIHLMFETFHLEFHYNCTNDYLEVYDTDSETSLGRYCGKSIPPSL
TSSGNSLMLVFVTDSDLAYEGFLINYEAISAATACLQDYTDDLGTFTSPNFPNNYPNNWECIYRI
TVRTGQLIAVHFTNFSLEEAIGNYYTDFLEIRDGGYEKSPLLGIFYGSNLPPTIISHSNKLWLKFKS
DQIDTRSGFSAYWDGSSTGCGGNLTTSSGTFISPNYPMPYYHSSECYWWLKSSHGSAFELEF
KDFHLEHHPNCTLDYLAVYDGPSSNSHLLTQLCGDEKPPLIRSSGDSMFIKLRTDEGQQGRGF
KAEYRQTCENVVIVNQTYGILESIGYPNPYSENQHCNWTIRATTGNTVNYTFLAFDLEHHINCST
DYLELYDGPRQMGRYCGVDLPPPGSTTSSKLQVLLLTDGVGRREKGFQMQWFVYGCGGELS
GATGSFSSPGFPNRYPPNKECIWYIRTDPGSSIQLTIHDFDVEYHSRCNFDVLEIYGGPDFHSP
RIAQLCTQRSPENPMQVSSTGNELAIRFKTDLSINGRGFNASWQAVTGGCGGIFQAPSGEIHS
PNYPSPYRSNTDCSWVIRVDRNHRVLLNFTDFDLEPQDSCIMAYDGLSSTMSRLARTCGREQL
ANPIVSSGNSLFLRFQSGPSRQNRGFRAQFRQACGGHILTSSFDTVSSPRFPANYPNNQNCS

FIG. 27 cont'd

WIIQAQPPLNHITLSFTHFELERSTTCARDFVEILDGGHEDAPLRGRYCGTDMPHPITSFSSALT
LRFVSDSSISAGGFHTTVTASVSACGGTFYMAEGIFNSPGYPDIYPPNVECVWNIVSSPGNRLQ
LSFISFQLEDSQDCSRDFVEIREGNATGHLVGRYCGNSFPLNYSSIVGHTLWVRFISDGSGSGT
GFQATFMKIFGNDNIVGTHGKVASPFWPENYPHNSNYQWTVNVNASHVVHGRILEMDIEEIQN
CYYDKLRIYDGPSIHARLIGAYCGTQTESFSSTGNSLTFHFYSDSSISGKGFLLEWFAVDAPDG
VLPTIAPGACGGFLRTGDAPVFLFSPGWPDSYSNRVDCTWLIQAPDSTVELNILSLDIESHRTC
AYDSLVIRDGDNNLAQQLAVLCGREIPGPIRSTGEYMFIRFTSDSSVTRAGFNASFHKSCGGYL
HADRGIITSPKYPETYPSNLNCSWHVLVQSGLTIAVHFEQPFQIPNGDSSCNQGDYLVLRNGPD
ICSPPLGPPGGNGHFCGSHASSTLFTSDNQMFVQFISDHSNEGQGFKIKYEAKSLACGGNVYI
HDADSAGYVTSPNHPHNYPPHADCIWILAAPPETRIQLQFEDRFDIEVTPNCTSNYLELRDGVD
SDAPILSKFCGTSLPSSQWSSGEVMYLRFRSDNSPTHVGFKAKYSIAQCGGRVPGQSGVVESI
GHPTLPYRDNLFCEWHLQGLSGHYLTISFEDFNLQNSSGCEKDFVEIWDNHTSGNILGRYCGN
TIPDSIDTSSNTAVVRFVTDGSVTASGFRLRFESSMEECGGDLQGSIGTFTSPNYPNPNHGRI
CEWRITAPEGRRITLMFNNLRLATHPSCNNEHVIVFNGIRSNSPQLEKLCSSVNVSNEIKSSGNT
MKVIFFTDGSRPYGGFTASYTSSEDAVCGGSLPNTPEGNFTSPGYDGVRNYSRNLNCEWTLS
NPNQGNSSISIHFEDFYLESHQDCQFDVLEFRVGDADGPLMWRLCGPSKPTLPLVIPYSQVWI
HFVTNERVEHIGFHAKYSFTDCGGIQIGDSGVITSPNYPNAYDSLTHCSSLLEAPQGHTITLTFS
DFDIEPHTTCAWDSVTVRNGGSPESPIIGQYCGNSNPRTIQSGSNQLVVTFNSDHSLQGGGFY
ATWNTQTLGCGGIFHSDNGTIRSPHWPQNFPENSRCSWTAITHKSKHLEISFDNNFLIPSGDG
QCQNSFVKVWAGTEEVDKALLATGCGNVAPGPVITPSNTFTAVFQSQEAPAQGFSASFVSRC
GSNFTGPSGYIISPNYPKQYDNNMNCTYVIEANPLSVVLLTFVSFHLEARSAVTGSCVNDGVHII
RGYSVMSTPFATVCGDEMPAPLTIAGPVLLNFYSNEQITDFGFKFSYRIISCGGVFNFSSGIITSP
AYSYADYPNDMHCLYTITVSDDKVIELKFSDFDVVPSTSCSHDYLAIYDGANTSDPLLGKFCGS
KRPPNVKSSNNSMLLVFKTDSFQTAKGWKMSFRQTLGPQQGCGGYLTGSNNTFASPDSDSN
GMYDKNLNCVWIIAPVNKVIHLTFNTFALEAASTRQRCLYDYVKLYDGDSENANLAGTFCGST
VPAPFISSGNFLTVQFISDLTLEREGFNATYTIMDMPCGGTYNATWTPQNISSPNSSDPDVPFSI
CTWVIDSPPHQQVKITVWALQLTSQDCTQNYLQLQDSPQGHGNSRFQFCGRNASAVPVFYSS
MSTAMVIFKSGVVNRNSRMSFTYQIADCNRDYHKAFGNLRSPGWPDNYDNDKDCTVTLTAPQ
NHTISLFFHSLGIENSVECRNDFLEVRNGSNSNSPLLGKYCGTLLPNPVFSQNNELYLRFKSDS
VTSDRGYEIIWTSSPSGCGGTLYGDRGSFTSPGYPGTYPNNTYCEWVLVAPAGRLVTINFYFIS
IDDPGDCVQNYLTLYDGPNASSPSSGPYCGGDTSIAPFVASSNQVFIKFHADYARRPSAFRLT
WDS (SEQ ID NO: 61)

Lipocalin:
QDSTSDLIPAPPLSKVPLQQNFQDNQFQGKWYVVGLAGNAILREDKDPQKMYATIYELKEDKS
YNVTSVLFRKKKCDYWIRTFVPGCQPGEFTLGNIKSYPGLTSYLVRVVSTNYNQHAMVFFKKV
SQNREYFKITLYGRTKELTSELKENFIRFSKSLGLPENHIVFPVPIDQCIDG (SEQ ID NO: 62)

cTRP Scaffold:
CEAIKAAAELGKAGISSEEILELLRAAHELGLDPEAIKAAAELGKAGISSEEILELLRAAHELGLDP
EAIKAAAELGKAGISSEEILELLRAAHELGLDPEAIKAAAELGKAGISSEEILELLRAAHELGLDPE
AIKAAAELGKAGISSEEILELLRAAHELGLDPECIKAAAELGKAGISSEEILELLRAAHELGL (SEQ ID NO: 25)

FIG. 27 cont'd

Linker: GS
Linker: GGS
Linker: GGGS (SEQ ID NO: 8)
Linker: GGGGS (SEQ ID NO: 21)
Linker: GGGGSGGGGS (SEQ ID NO: 24)

His: HHHHHH (SEQ ID NO: 9)
Avi: GLNDIFEAQKIEWHE (SEQ ID NO: 10)
Tev: ENLYFQG (SEQ ID NO: 11)
sFLAG: DYKDE (SEQ ID NO: 22)

Signal Peptide: METDTLLLWVLLLWVPGSTG (SEQ ID NO: 6)

Signal Peptide: MELWGAYLLLCLFSLLTQVTT (SEQ ID NO: 18)

CD3z
RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 205)

CD3z
ELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 206)

4-1BB cytoplasmic domain: VKRGRKKLLYIFKQPFMRPVQTTQEEDGCSCRFPEEEEGGCEL (SEQ ID NO: 207)

4-1BB cytoplasmic domain: VKRGRKKLLYIFKQPFMRPVQTTQEEDGCSCRFPEEEEGGC (SEQ ID NO: 208)

CD28_Transmembrane domain: MFWVLVVVGGVLACYSLLVTVAFIIFW (SEQ ID NO: 209)

CD28_Transmembrane domain: FWVLVVVGGVLACYSLLVTVAFIIFW (SEQ ID NO: 210)

P2A: GSGATNFSLLKQAGDVEENPGPGASG (SEQ ID NO: 211)

T2A: GSGEGRGSLLTCGDVEENPGP (SEQ ID NO: 212)

E2A: GSGQCTNYALLKLAGDVESNPGPP (SEQ ID NO: 213)

F2A: GSGVKQTLNFDLLKLAGDVESNPGP (SEQ ID NO: 214)

ENGINEERED TRIMERIC CD70 PROTEINS AND USES THEREOF

CROSS REFERENCE TO RELATED APPLICATIONS

This application is a U.S. National Phase Patent Application based on International Patent Application No. PCT/US2020/054855, filed on Oct. 8, 2020, which claims priority to U.S. Provisional Patent Application No. 62/912,510 filed Oct. 8, 2019; to U.S. Provisional Patent Application No. 62/971,712 filed Feb. 7, 2020; and to U.S. Provisional Patent Application No. 62/984,695 filed Mar. 3, 2020, the entire contents of each of which are incorporated by reference herein in their entirety.

STATEMENT REGARDING FEDERALLY SPONSORED RESEARCH OR DEVELOPMENT

This invention was made with government support under CA114536, awarded by the National Institutes of Health. The government has certain rights in the invention.

REFERENCE TO SEQUENCE LISTING

The Sequence Listing associated with this application is provided in text format in lieu of a paper copy, and is hereby incorporated by reference into the specification. The name of the text file containing the Sequence Listing is 2087870.txt. The text file is 176 KB, was created on Mar. 31, 2022, and is being submitted electronically via EFS-Web.

FIELD OF THE DISCLOSURE

The current disclosure provides engineered trimeric CD70 proteins and their use in ex vivo T cell manufacturing. Use of the proteins during manufacturing creates expanded bulk T cell populations that: proliferate more and earlier in culture; selectively expand naïve and memory T cell subsets; persist longer in vivo following administration to a subject; and provide improved therapeutic effects.

BACKGROUND OF THE DISCLOSURE

Significant progress has been made in genetically engineering T cells of the immune system to target and kill unwanted cell types, such as cancer cells. For example, T cells have been genetically engineered to express molecules having extracellular components that bind particular target antigens and intracellular components that direct actions of the T cell when the extracellular component has bound the target antigen. As an example, the extracellular component can be designed to bind target antigens found on cancer cells and, when bound, the intracellular component activates the T cell to destroy the bound cancer cell. Examples of such molecules include chimeric antigen receptors (CAR).

Clinical trials with CAR-expressing T cells (CAR-T) have shown positive responses in patients with refractory large B-cell lymphoma when conventional treatments had failed. However, while CAR-T cells result in cancer cell destruction, they have failed to provide prolonged anti-cancer activity in vivo for some patients and in some indications. For example, in some cases, T cells have not received a strong enough activation signal when the binding domain of an extracellular component binds a targeted cancer cell marker, resulting in a failure to kill the bound cell. Further, administered T cell populations often do not proliferate sufficiently or persist in vivo for sufficient periods of time following administration to maintain on-going anti-cancer effects.

CD27 is a molecule that is expressed constitutively on naïve activated and memory T cells, natural killer (NK) and NKT cells, regulatory T cells (Treg), and B lymphocytes. It is a member of the tumor necrosis factor superfamily of cellular receptors (TNFRSF) and acts as a potent costimulatory molecule.

CD70 (TNFRSF7 or CD27L) is the ligand for CD27. Binding of CD70 to CD27 is important in the priming phase of T cell activation, in the acquisition of effector functions, and in the formation of long-lived T cell memory as well as plasma and memory B-cell generation. During T cell activation, engagement of CD27 leads to reduced surface expression of CD27, reported to be due to extracellular cleavage. Terminal T cell differentiation is associated with a loss of CD27 surface expression.

CD27 signaling can be induced by ligand-based or agonistic antibody-based methods during T cell manufacturing. However, TNFR superfamily-based signal transmission is a structurally-complex event that takes place when the surface-expressed, homotrimeric TNFR superfamily ligands contact their corresponding receptors, expressed on the surface of other cells. This interaction of multi-trimer-based clustering is essential for agonistic signaling. Because of these clustering requirements for activation of CD27 agonistic signaling, many attempts to stimulate CD27 during cell manufacturing with monovalent and bivalent approaches have not been sufficiently effective.

SUMMARY OF THE DISCLOSURE

The current disclosure provides engineered trimeric CD70 proteins and their use in ex vivo T cell manufacturing. Use of the proteins during manufacturing creates expanded bulk T cell populations that: proliferate more and earlier in culture; selectively expand naïve and memory T cell subsets; exhibit enhanced markers of metabolism; persist longer in vivo following administration to a subject; and provide improved therapeutic effects.

In particular embodiments, the trimeric CD70 protein is expressed as a single chain with three CD70 extracellular domains and the Fc portion of an antibody. The Fc portion serves as a dimerization domain to link the single chain protein with a similar (or identical) single chain protein to create an engineered "dimer-trimer" CD70 protein (also referred to herein interchangeably as a CD70DT). An exemplary form of this protein is depicted in FIG. 3A, and a particular example includes MDT-000762-2.

In particular embodiments, the trimeric CD70 protein includes a CD70 molecule expressed within a single chain, including a trimerization domain (e.g., tetranectin, collagen, and other trimerization domains provided herein). The trimerization domain serves to link the single chain with two similar (or identical) single chain proteins to create a monotrimer. Forms of this protein are depicted in FIGS. 3B and 3C and particular examples include MDT-000763 and MDT-00764-2.

In particular embodiments, the trimeric CD70 protein includes trimeric CD70 molecules anchored to a circular-tandem repeat protein (cTRP). In particular embodiments, the trimeric CD70 protein includes a CD70 molecule expressed as a single chain anchored to a circular-tandem repeat protein (cTRP). The cTRP may enable the display of single chain CD70 trimers in trimeric, tetrameric, and pentameric arrangements and in multiple orientations. A form of this protein is depicted in FIG. 3D and a particular example includes MDT-001100.

In particular embodiments, these engineered trimeric binding proteins are coated onto one or more surfaces during T cell manufacturing. The trimeric proteins can also be utilized as soluble factors during T cell manufacturing. MDT-001100 is particularly well-suited for use as a soluble factor.

BRIEF DESCRIPTION OF THE FIGURES

Some of the figures submitted herein are better understood in color. Applicant considers the color versions of the drawings as part of the original submission and reserves the right to present color images of the drawings in later proceedings.

FIGS. 1A-1C. CD70 domain architecture. (1A) Surface representation of CD70 modeled antigen structure. Top view looking down towards cell membrane. (1B) Ribbon representation of CD70 modeled structure. View is looking from the cell membrane to the extracellular domain. Structural model by SWISS-MODEL using PDB ID 2000, tumor necrosis factor (TNF) superfamily ligand TL1A (TNFSF15) (27.14% sequence identity) shows a trimeric arrangement of CD70 ectodomain, and the predicted structure reveals the presence of one disulfide bond. The N- and C-termini are located in close proximity with unstructured ends, which can facilitate both fusion to other proteins and/or single trimeric polypeptide CD70 constructs. Multimerization can be facilitated by a single polypeptide linked trimer CD70 (single chain approach) that can be fused with human siderocalin (hsSCN) for expression and with or without a fragment crystallizable (Fc) domain for functionality. (1C) Annotated CD70 sequence.

FIG. 2. The role of providing CD27 signaling using CD27 agonistic proteins during CAR-T cell generation was investigated.

FIGS. 4A-4E. Trimerization can be accomplished using trimerization domains (TDs) which can be N- or C-terminal to CD70. TDs can be selected to be a human sequence from a secreted protein, N- or C-terminal TDs, with size and availability of atomic resolution structures. (4A) Structure of hsTetranectin trimer (PDB ID 4C47) (molecular weight (MW)=5.92 kDa), which is the N-terminal coiled coil domain used for N-terminal trimerization. The wildtype sequence contains a signal peptide (SP) that leads into the TD. (4B) Structure of stSadB trimer (PDB ID 4C47) (MW =5.68 KDa). The TD is the N-terminal coiled coil domain. It can be used for N-terminal trimerization, but it is not a human sequence (*Salmonella typhimurium*). (4C) Structure of hsEML4 TD (PDB ID 4CGC) (MW=6.36 KDa). TD can be used for C-terminal trimerization, but it is not part of a secreted protein. (4D) Structure of hsCollagen TD (PDB ID 3N3F) (MW=6.25 KDa). TD is part of a secreted protein and can be used for C-terminal trimerization. (4E) Structure of btClathrin TD (PDB ID 3QIL) (MW=11.6 KDa). TD can be used for C-terminal trimerization, but it is not a human sequence (*Bos taurus*).

FIGS. 5A-5E. Exemplary dimer trimer design and purification: hsCD70_SC-His-Avi-Tev-FC_hsIgG1 (5A) schematic of MDT-000762-2 design. (5B) associated sequences; (5C) Lentiviral transduction results for a vector which can be described as: SignalP-hsCD70_SC-His-Avi-Tev-FC_hsIgG1-(IRES-GFP) are shown. To produce the protein, the 293F cell line was used, producing a final viable cell density (VCD) of $5.31e^6$ cells/mL and final viability of 98.5%. Post one-step purification yields 133.98 mg (determined by absorbance at 280 nm (A280), abs=1). (5D) Purification by size exclusion chromatography (using a Superdex 200 Increase 10/300 GL column) shows a well-behaved protein of the expected molecular weight. (5E) The sodium dodecyl sulfate (SDS) polyacrylamide gel electrophoresis (PAGE) gel shows the molecular weight of MDT-000762-2 in its non-reduced (NR) and reduced (R) forms. The theoretical molecular weight of the mature peptide is 82,064.72 Da. The raw optical density at 280 nm (OD280) is 3.84 mg/mL, and the total yield is 92.16 mg.

FIGS. 6A-6E. Exemplary trimeric monomer design and purification: hsTetranectin_TD-hsCD70-His-Avi. (5A) schematic of MDT-000763; (5B) associated sequences; (6C) Lentiviral transduction results for a vector which can be described as SignalP-hsTetranectin_TD-hsCD70-His-Avi (IRES-GFP) are shown. To produce the protein, the 293F cell line was used. This produced a final VCD of $3.89 \times 10^6$ cells/mL and final viability of 98.2%. Post one-step purification yielded 96.75 mg (determined by A280, abs=1). (6D) The Superdex 200 Increase 10/300 GL shows that this protein comes off the size-exclusion chromatography (SEC) column between 10 and 15 mL, indicating that it is a single species and has a higher molecular weight compared to its protein sequence. (6E) The SDS PAGE gel shows that this protein runs at 55 kDa and the fuzziness of the band is an indication of glycosylation as well as the shift when treated with peptide: N-glycosidase F (PNGase F) for 1 hr at 37° C. The theoretical molecular weight of the mature peptide is 28,129 Da. The raw OD280 is 2.93 mg/mL, and the total yield is 73.25 mg.

FIGS. 7A-7E. Exemplary trimeric monomer design and purification: hsCD70-Collagen_TD-His-Avi. (7A) schematic of MDT-000764-2; (7B) associated sequences; (7C) Lentiviral transduction results for a vector which can be described as IgK-hsCD70-Collagen_TD-His-Avi (IRES-GFP) are shown. To produce the protein, the 293F cell line was used, and the protein was purified on a 2L run on one 5 ml Ni HiTrap. This produced a final VCD of $4.64 \times 10^6$ cells/mL and a final viability of 97.6%. Post one-step purification yielded 3.8 mg (determined by A280, abs=1). (7D) Purification by size exclusion chromatography (using a Superdex 200 Increase 10/300 GL column) shows a well-behaved protein of the expected molecular weight. (7E) The SDS PAGE gel shows the molecular weight of MDT-000764-2 in its R and NR forms. The theoretical molecular weight of the mature peptide is 26,493 Da. The molecule runs largely on SEC, suggesting trimerization. On the gel the PNGase F treatment shows a shift down in the molecular weight, however, the band does not tighten. Contaminating band on the gel at 38 kDa is PNGase. Freeze-thaw showed no signs of degradation. The raw OD280 is 1.4 mg/mL, and the total yield is 2.1 mg.

FIGS. 8A-8F. Exemplary cTRP design, purification and functional testing: hsCD70_SC-Toroidx6_SS_tetramer-His. (8A) schematic of MDT-00110; (8B) associated sequences; (8C) Lentiviral transduction results for a vector which can be described as IgK_SP-hsCD70_SC-Toroidx6_SS_tetramer-His (IRES-GFP) are shown. To produce the protein, the 293F cell line was used. This produced a final VCD of $4.61 \times 10^6$ cells/mL and a final viability of 83.65%. Post-one-step purification yielded 100.6 mg (determined by A280). (8D) Purification by size exclusion chromatography (using a Superdex 200 Increase 10/300 GL column) shows a well-behaved protein of the expected molecular weight. (8E) The SDS PAGE gel shows the molecular weight of MDT-001100 in its R and NR forms. The theoretical molecular weight of the mature peptide is 294,896.42 Da. The raw OD280 is 2.86 mg/mL, and the total yield is 60.10 mg. (8F) The functionality of the cTRP246SS-scTrimerCD7° was assessed using a CFSE-dilution-based T-cell proliferation assay using activated human CD8$^+$ T-cells with plate-bound OKT3 (middle panel, 5 µg/mL) alone and in combination with soluble cTRP246SS-scTrimerCD70 (bottom panel, 1 µg/mL). Non-activated CD8+ T cells were considered as a CFSEhi non-proliferating controls (top panel). The addition of soluble cTRP246SS-scTrimerCD70 increased OKT3-induced proliferation of CD8+ T cells in vitro, consistent with its function as a costimulatory ligand.

FIGS. 10A-10D. Providing CD27 co-stimulation during αCD3-based CD8$^+$ T cell activation allows robust expansion and enhances acquisition of memory gene signature. In vitro validation and functional analysis of bulk CD8$^+$ T cells. A non-tissue culture-treated 96 well plate was pre-coated with mAb αCD3 (OKT3) with or without CD70 dimer-trimer (CD70tri; MDT-000762-2 (also referred to as CD70DT) in PBS. After 4 h of incubation at 37° C., the plate was flicked off, and bulk CD8$^+$ T cells were added. (10A) Experimental design. (10B) CD8$^+$ T cells were carboxyfluorescein N-hydroxysuccinimidyl ester (CFSE) labeled before culture start. On day 3 of activation, CFSE dilution was measured by flow cytometry. Comparative proliferation of αCD3 (5 µg/ml) versus αCD3/CD70tri (2,5,10 µg/ml) is shown. Greater cell proliferation is observed in all αCD3/CD70tri conditions over αCD3 alone. (10C) 100,000 cells were plated on D0. Cell growth was assessed by cell counts on D3, D5, D7, and D10 post activation. Absolute numbers of αCD3/CD70tri or αCD3 activated cells for each individual timepoint are shown. Stimulation with αCD3/CD70tri leads to more T cell proliferation at earlier time points (see D3, D5) than stimulation with αCD3. (10D) RNA was extracted from D10 cell culture, and gene expression analysis of selected signature genes was performed. The αCD3/CD70$^{tri}$ expanded T cell population is enriched for cells expressing a memory cell signature—the αCD3 expanded T cell population is enriched for cells expressing an effector cell signature.

FIGS. 12A-12C. CD27 co-stimulation is important for the expansion of naïve and central memory CD8$^+$ T cell subsets. (12A) CD8$^+$ T cell subset marker panel and functional specification. (12B) Gating strategy for CD8$^+$ T cell sorting: naïve T cells ($T_N$) (CCR7$^+$CD45RO$^-$), central memory T cells ($T_{CM}$) (CCR7$^+$CD45RO$^+$), and effector memory T cells ($T_{EM}$) (CCR7$^-$CD45RO$^+$) according to the described marker panel. Subset-specific CD62L, CD45RA, and CD27 expression are also depicted. (12C) Role of CD27 stimulation on T cell sub-populations. Images of D4 proliferation clusters of $T_N$ (CCR7+CD45RO$^-$), $T_{CM}$ (CCR7$^-$CD45RO$^+$), and $T_{EM}$ (CCR7$^-$CD45RO+) cells activated under αCD3 and αCD3/CD70$^{tri}$ culture conditions were assessed. The cell growth of individual conditions over 10 days is shown at the bottom.

FIGS. 15A-15D. CD27 co-stimulation leads to higher abundance of CD27$^+$ TCF1$^+$ T cells early after activation (day 4-day 6), which is indicative of a stem cell memory phenotype. CD27 and TCF1 expression of bulk or purified $T_N$ CD8$^+$ T cells were assessed at diverse timepoints after activation with αCD3/αCD28 DynaBeads or CD3/CD70$^{DT}$. Representative dot plots with isotype control overlay (bottom left quadrant of each dot plot chart) are shown for (15A) bulk CD8+ T cells and (15B) purified $T_N$ CD8$^+$ T cells. (15C) Frequency of TCF1$^+$ CD27$^+$ cells at indicated timepoints after activation with αCD3/αCD28 DynaBeads, αCD3/αCD28 TransAct polymers, plate coated αCD3 [5 μg/mL]/CD70$^{DT}$ [5 μg/mL] (3/70) or plate coated αCD3 [5 μg/mL]/αCD28 [1 μg/mL] (3/28 Ab). (15D) $T_N$-derived CD8$^+$ T cells (representative for n=2-3 different donors) after activation with αCD3/αCD28 DynaBeads or plate coated αCD3 [5 μg/mL]/CD70$^{DT}$ [5 μg/mL] (3/70) or plate coated αCD3 [5 μg/mL]/αCD28 [1 μg/mL] (3/28 Ab). FIGS. 15A-15D demonstrate that CD27 co-stimulation mediates fast and superior TCF1 recovery in activated CD8$^+$ $T_N$ cells.

FIGS. 16A-16C. CD27 co-stimulation preferentially maintains $T_N$-derived CD27$^+$ TCF1$^+$ T cells throughout the in vitro culture, improving the stem cell memory quality of the product. (16A) A schematic of the methodology shows that 0.1×10$^6$ FACS-sorted $T_N$ (CCR7$^+$ CD45RO$^-$), $T_{CM}$ (CCR7$^+$ CD45RO$^+$), and $T_{EM}$ (CCR7$^-$CD45RO$^+$) CD8$^+$ T cells were activated with either αCD3/αCD28 DynaBeads or αCD3/CD70$^{DT}$ and (16B) cell numbers were enumerated throughout the expansion for each of $T_N$, $T_{CM}$, and $T_{EM}$ cells. Within the (16A) histogram overlays: line 1 (isotype), line 2 ($T_N$), line 3 ($T_{CM}$), and line 4 ($T_{EM}$). (16C) Representative dot plot shows the frequencies of CD27$^+$ TCF1$^+$/total CD8$^+$ T cells from 9 days activated $T_N$, $T_{CM}$, and $T_{EM}$ CD8$^+$ T cells. On day 9 of culture, CD27$^+$ TCF1$^+$ T cells are mainly derived from $T_N$ cells, and αCD3/CD70$^{DT}$ activated $T_N$ cells maintained a significantly higher CD27$^+$ TCF 1$^+$ cell fraction. $T_{CM}$ and $T_{EM}$ strongly down-regulated TCF1 and CD27 expression, compared to their initial expression level.

FIGS. 19A-19C. MYC gene expression and MYC-dependent glucose metabolism are more upregulated in αCD3/αCD28 vs. αCD3/CD70 activated CD8$^+$ $T_N$ cells, which is indicative for a more pronounced switch to an effector metabolic phenotype. (19A) Scheme of key metabolic pathways with relevant membrane transporters, enzymatic steps, and degradation products. (19B) GLUT1 expression is reduced in αCD3/CD70 activated T cells compared with αCD3/αCD28 activated T cells. Data shows the delta MFI of GLUT1 receptor expression above isotype control on non-activated (PRE) and activated (D1-D4) CD8$^+$ $T_N$ cells. (19C) Log2 Fold Change (DynaBead vs. αCD3/CD70$^{DT}$) of MYC, HK2, LDHA, and SLC16A3 gene expression in activated $T_N$ cells at indicated timepoints after activation.

FIG. 27. Sequences supporting the disclosure.

DETAILED DESCRIPTION

Significant progress has been made in genetically engineering T cells of the immune system to target and kill unwanted cell types, such as cancer cells. For example, T cells have been genetically engineered to express molecules having extracellular components that bind particular target antigens and intracellular components that direct actions of the T cell when the extracellular component has bound the target antigen. As an example, the extracellular component can be designed to bind target antigens found on cancer cells and, when bound, the intracellular component activates the T cell to destroy the bound cancer cell. Examples of such molecules include chimeric antigen receptors (CAR).

Clinical trials with CAR-expressing T cells (CAR-T) have shown positive responses in patients with refractory large B-cell lymphoma when conventional treatments had failed. However, while CAR-T cells result in cancer cell destruction, they have failed to provide prolonged anti-cancer activity in vivo for some indications. For example, in some cases, T cells have not received a strong enough activation signal when the binding domain of the extracellular component binds a targeted cancer cell marker, resulting in a failure to kill the bound cell. Further, administered T cell populations often do not persist in vivo for sufficient periods of time following administration to maintain on-going anti-cancer effects.

CD27 is a molecule that is expressed constitutively on naïve, activated, and memory T cells, natural killer (NK) and NKT cells, regulatory T cells (Treg), and B lymphocytes. It is a member of the tumor necrosis factor superfamily of cellular receptors (TNFRSF) and acts as a potent costimulatory molecule.

Figure 1A:
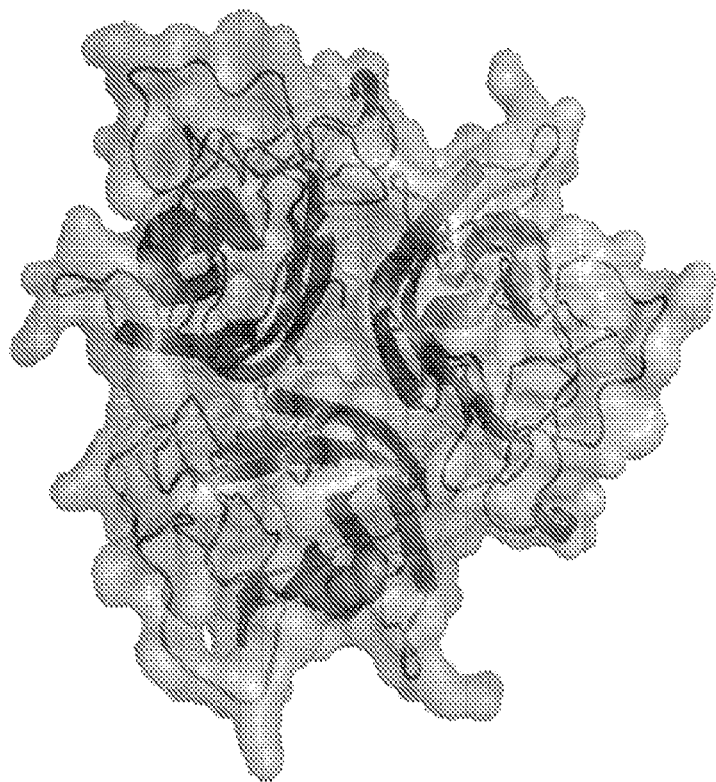
Figure 1B:

CD70 (TNFRSF7 or CD27L (FIGS. 1A-1C)) is the ligand for CD27. Binding of CD70 to CD27 is involved in priming, effector functions, differentiation, and memory formation of T-cells as well as plasma and memory B-cell generation. During T cell activation, engagement of CD27 leads to reduced surface expression, reported to be due to extracellular cleavage. However, terminal differentiation is associated with loss of CD27 surface expression.

CD27 signaling can be induced by ligand-based or agonistic antibody-based methods during T cell manufacturing. However, TNFR superfamily-based signal transmission is a structurally-complex event that takes place when the surface-expressed, homotrimeric TNFR superfamily ligands contact their corresponding receptors, expressed on the surface of other cells. This interaction of multi-trimer-based clustering is essential for agonistic signaling. Because of these clustering requirements for activation of CD27 agonistic signaling, many attempts to stimulate CD27 during cell manufacturing with monovalent and bivalent approaches have not been sufficiently effective.

The current disclosure provides engineered trimeric CD70 proteins for use in ex vivo T cell manufacturing. Use of the proteins during manufacturing provides a number of benefits. These benefits include, for example, an increase in T cell expansion, an increase in T cell proliferation, a decrease in T cell exhaustion, selective expansion of less differentiated T cell populations, selective expansion of naïve and memory T cells, a decrease in glucose metabolism, a decrease in glycolytic switch capacity, a weaker induction of mTORC1/S6K signaling, a decrease in mTORC1-dependent protein translation during the late expansion phase, an increase in T cell survival ex vivo and following administration, an increase in expansion ex vivo and following administration, an increase in engraftment following administration, an increase in killing capacity, an increase in serial killing capacity, and an increase in the targeting of tumor cells. In some embodiments, these benefits are exhibited when the engineered CD70 proteins of the disclosure are used in conjunction with αCD3 stimulating molecule. In some embodiments, the benefits are realized as when compared to T cell activation under comparable control conditions using αCD28/CD3 stimulating molecule (e.g., DynaBeads).

Figure 10A:
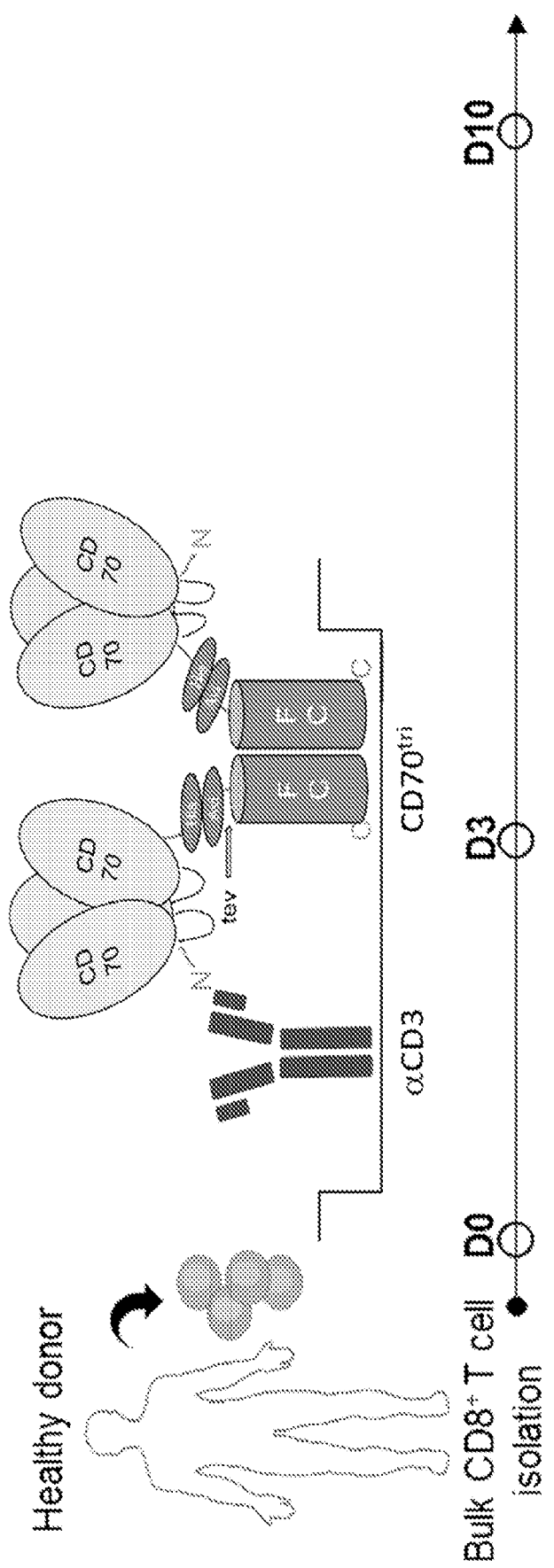
Figure 10C:
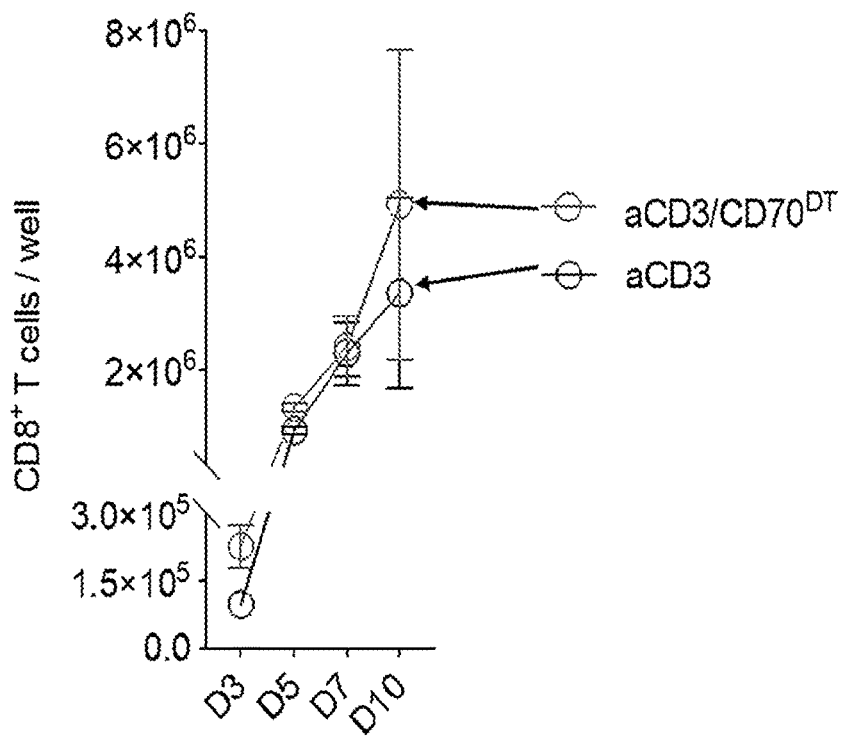
Figure 10D:
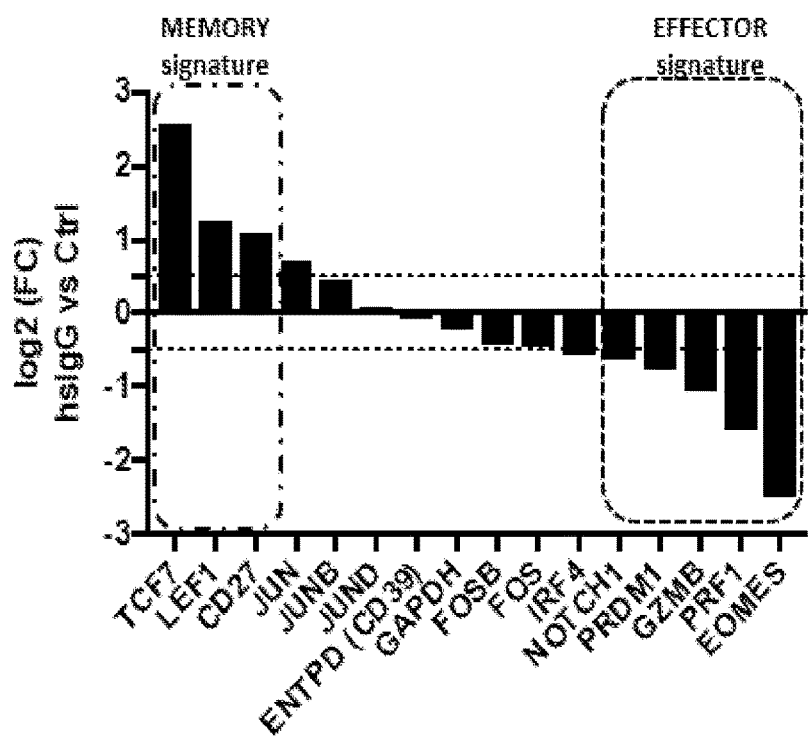
Figure 11A:
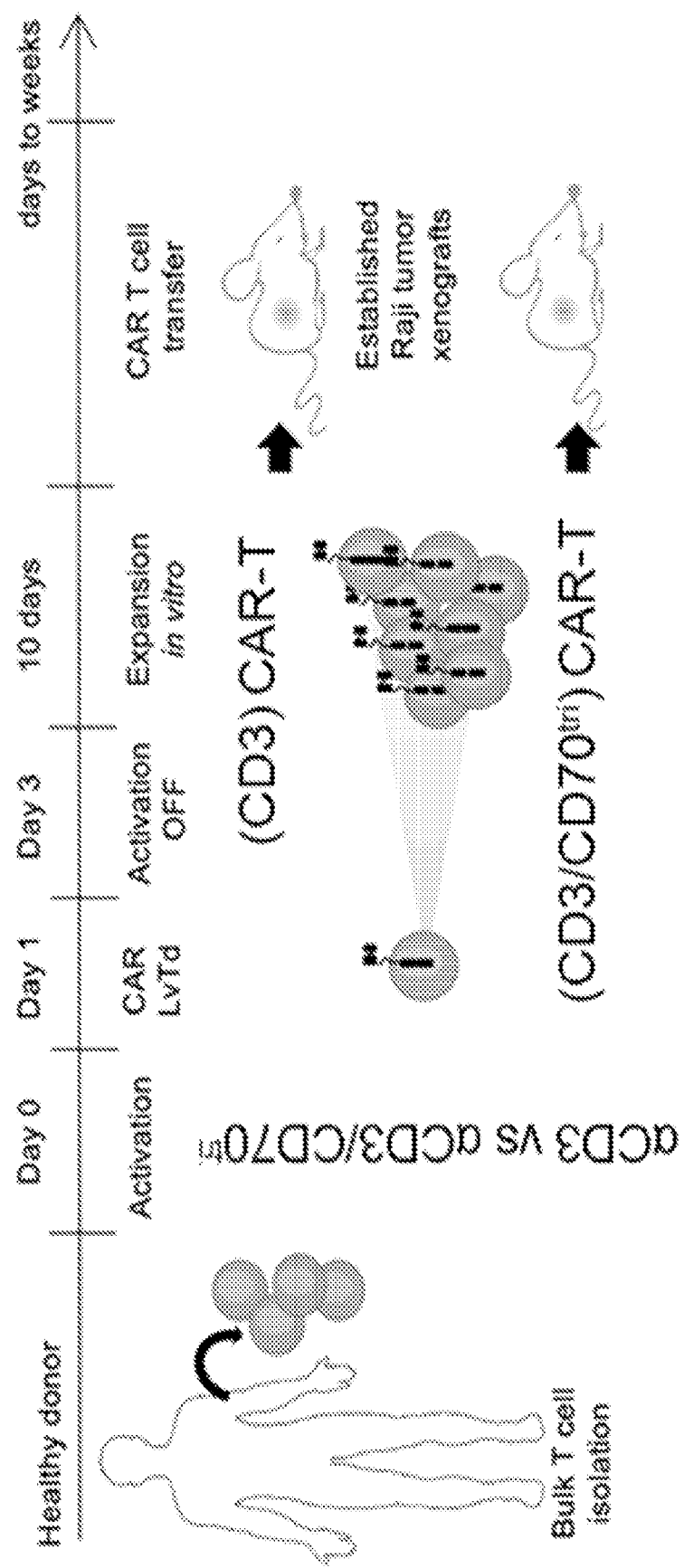
FIGS. 11A-11G. Providing CD27 co-stimulation during CAR T cell manufacturing reduces the expression of Tigit and Lag 3 inhibitory receptors on T cells in vitro and results in improved therapeutic efficiency in vivo. (11A) A chimeric antigen receptor (CAR) T cell generation protocol and scheme are shown. CAR T cells were injected on D10 post-activation into previously (7 days) established Raji (CD19 expressing human lymphoma cell line) tumor-bearing NOD scid gamma (NSG®, The Jackson Laboratory, Bar Harbor, ME) mice. (11B) In vitro CAR T cell expansion, D7 phenotype. CD8$^+$ T cell surface marker expression was assessed on D7 post T cell activation and CAR T cell generation. Phenotype markers include CD28, CD45RO, CD127, CD122, CD62L, CD45RA, CD69, CCR7, CD95, CD27. Inhibitory markers include TIGIT, LAG-3, TIM-3, PD1. For inhibitory markers and CD27, isotype controls were used (dim lines). (11C)-(11E) In vivo expansion and persistence of CAR-T cells. In vitro generated CAR T cells (epidermal growth factor receptor ((EGFRt) marked) were injected at a dose of 0.8×10e$^6$ cells per mouse. All mice were inoculated with 0.5×10e$^6$ Raji tumor cells that expressed firefly luciferase (ffluc) 7 days before. (11C) The frequency (percentage) of EGFRt$^+$ hCD45$^+$ CAR T cells per total blood mononuclear cells. (11D) The tumor burden measured by live imaging of ffluc+ tumor cells after injection of luciferin is shown for D63. (11E) Overall survival of mice treated with αCD3 or αCD3/CD70$^{tri}$ CAR T cells is shown. (11F, 11G) In vivo re-expansion capacity of CAR-T cells. Mice were re-challenged with Raji ROR1 ffluc tumor cells on day 112 post primary tumor inoculation. (11F) The frequency of EGFRt$^+$ hCD45$^+$ CAR T cells per total blood is shown (% of blood mononuclear cells expressing hCD45 and EGFRt) and only increased in mice previously treated with αCD3/CD70$^{tri}$ CAR T cells compared to mice treated with αCD3 CAR T cells. (11G) Flow cytometry plots showing the percentage of CAR T cells (EGFRt+, huCD45+) in blood from mice treated with αCD3 and αCD3/CD70$^{tri}$ CAR T cells and then rechallenged with Raji tumor cells. Data for D7 and D37 post rechallenge are shown.
Figure 11B:
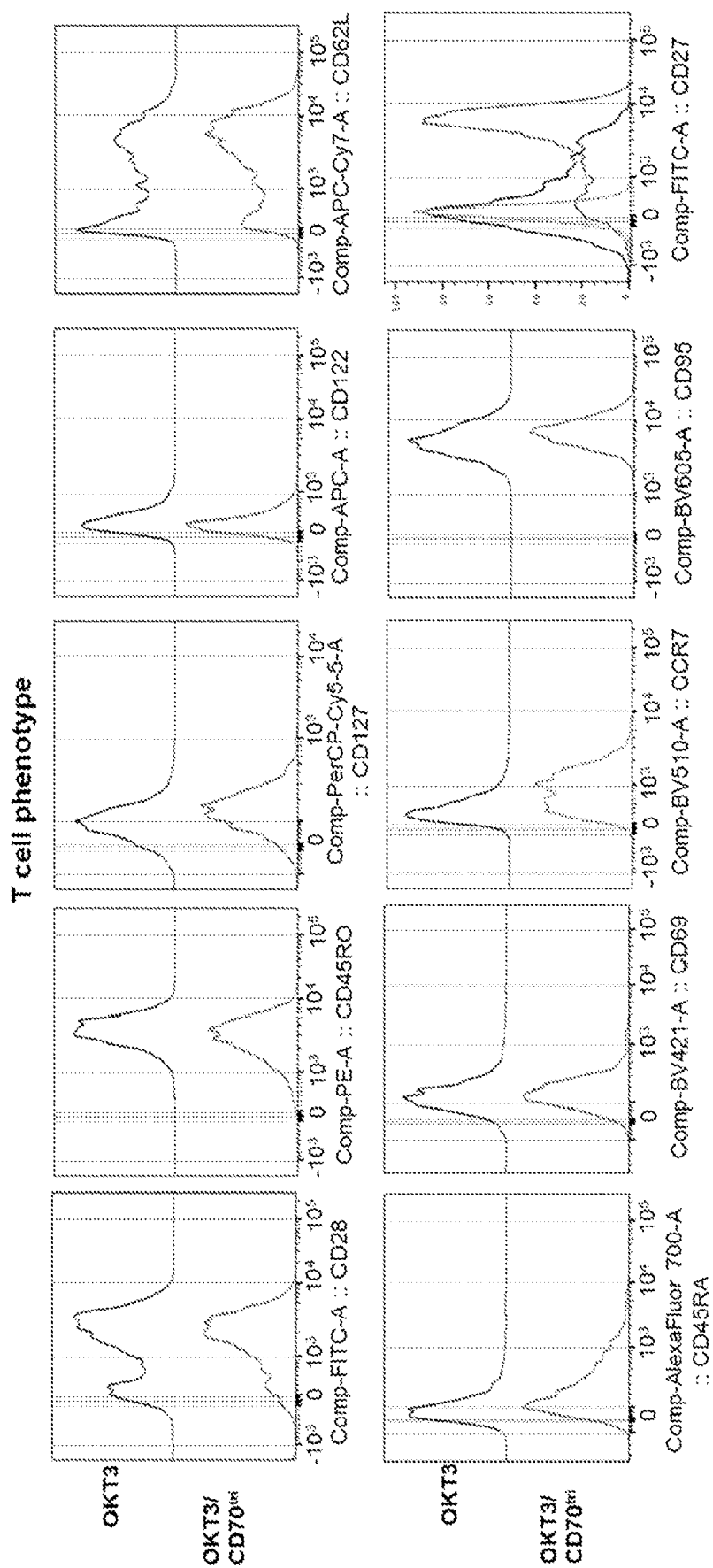
Figure 11B:
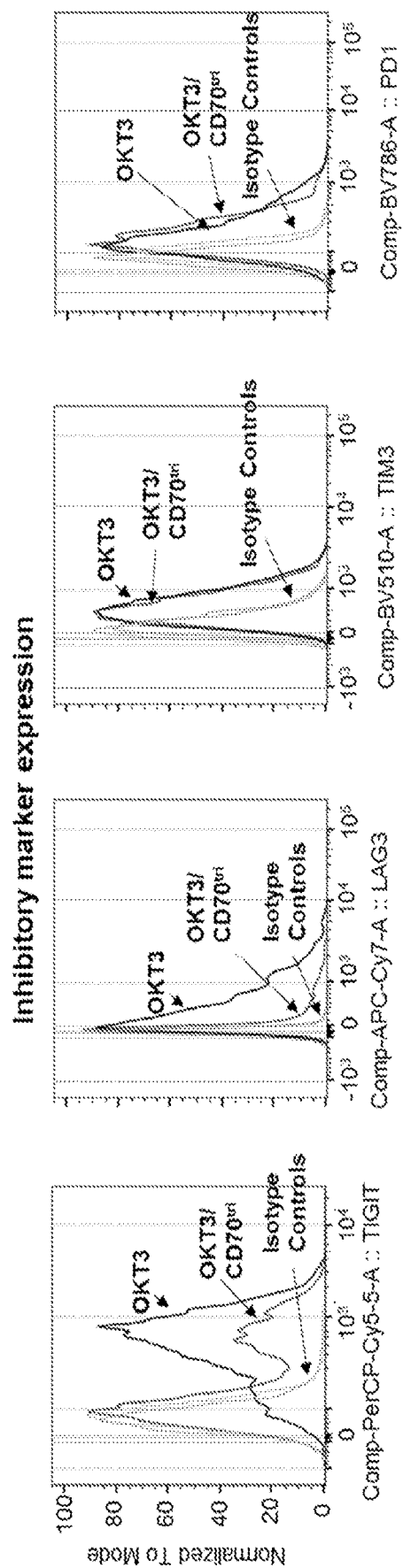
Figure 11C:
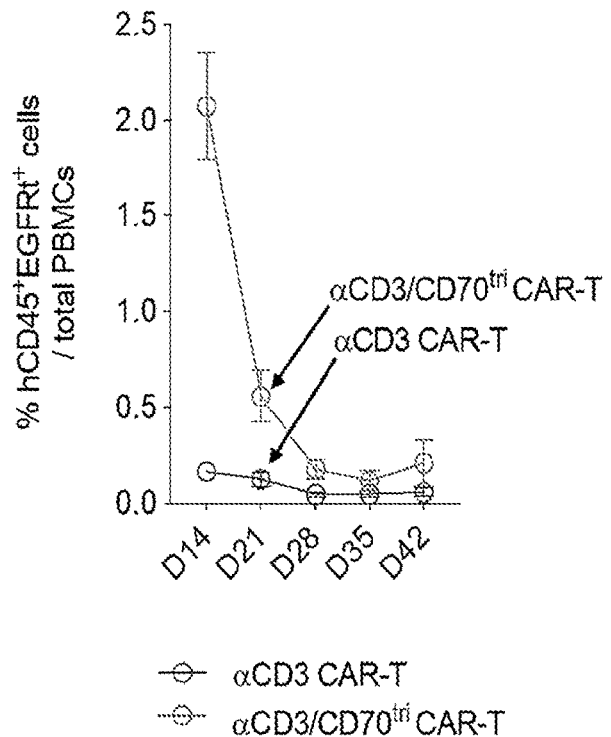
Figure 11D:
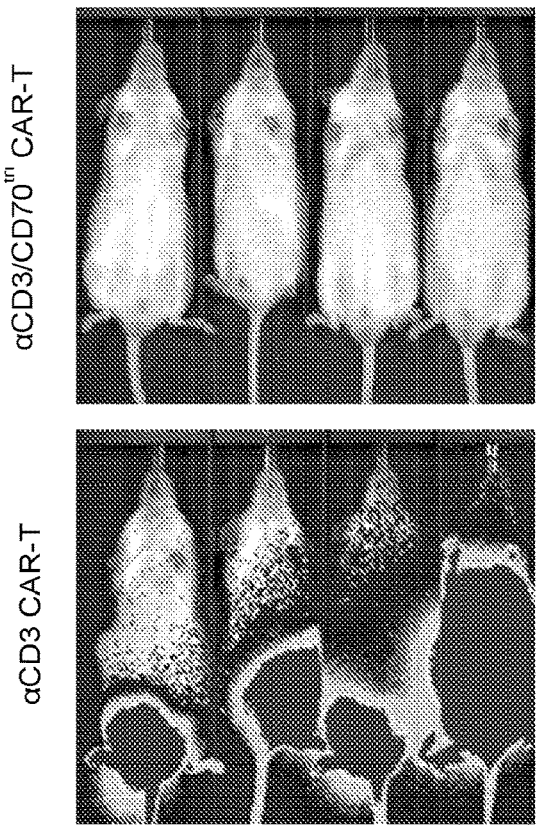
Figure 11E:
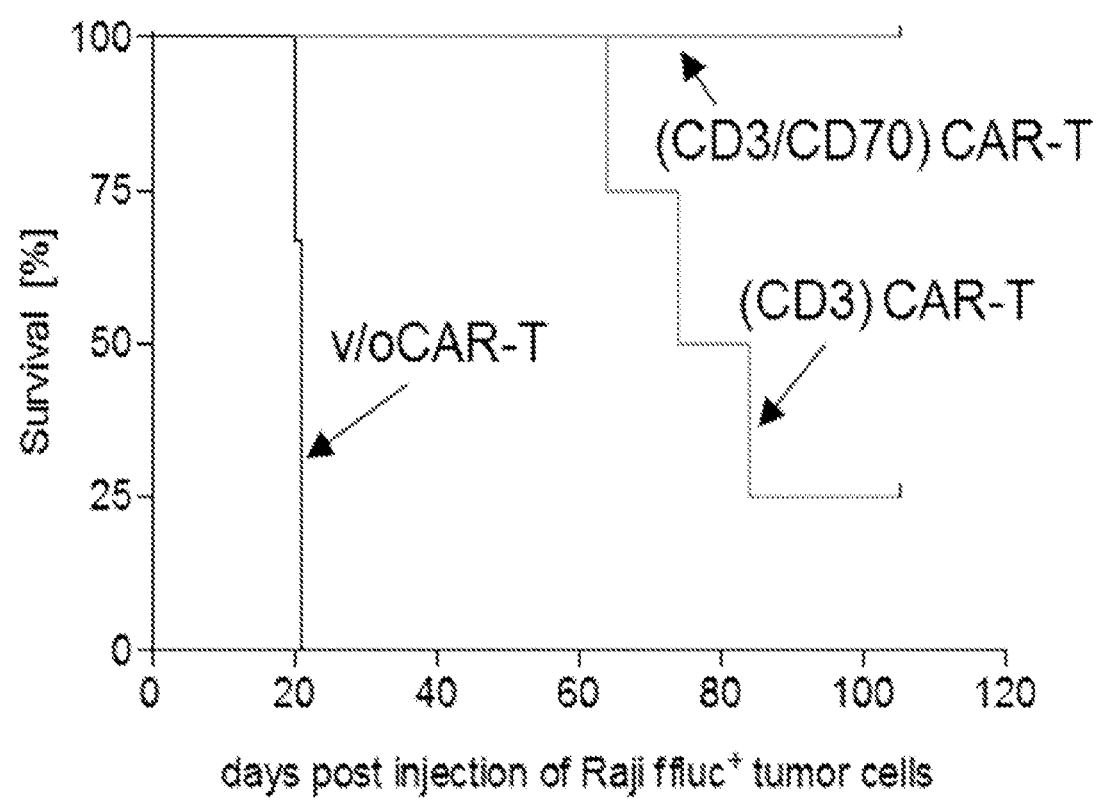
Figure 11F:
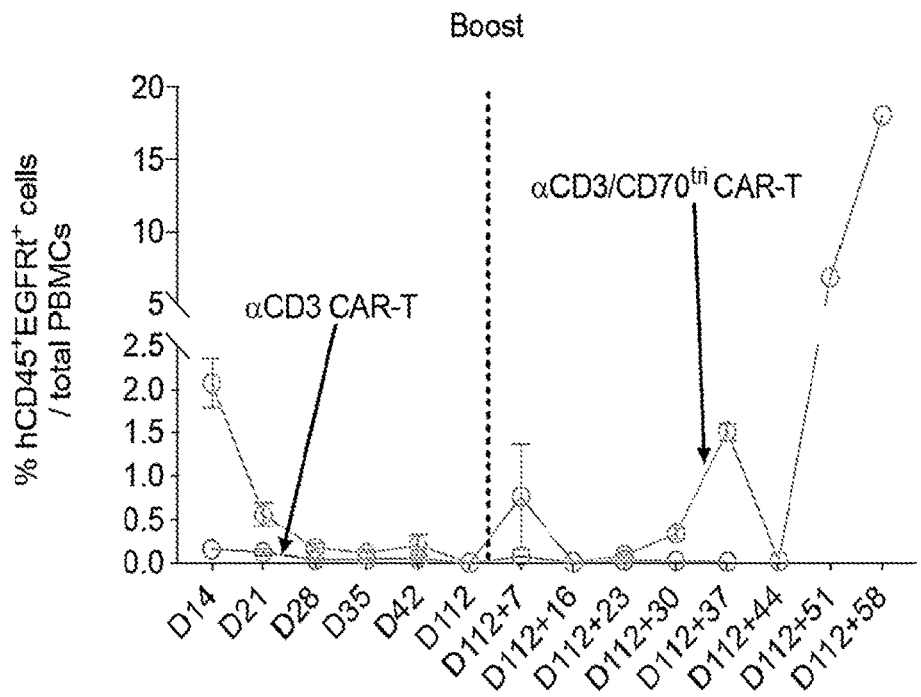
Figure 11G:
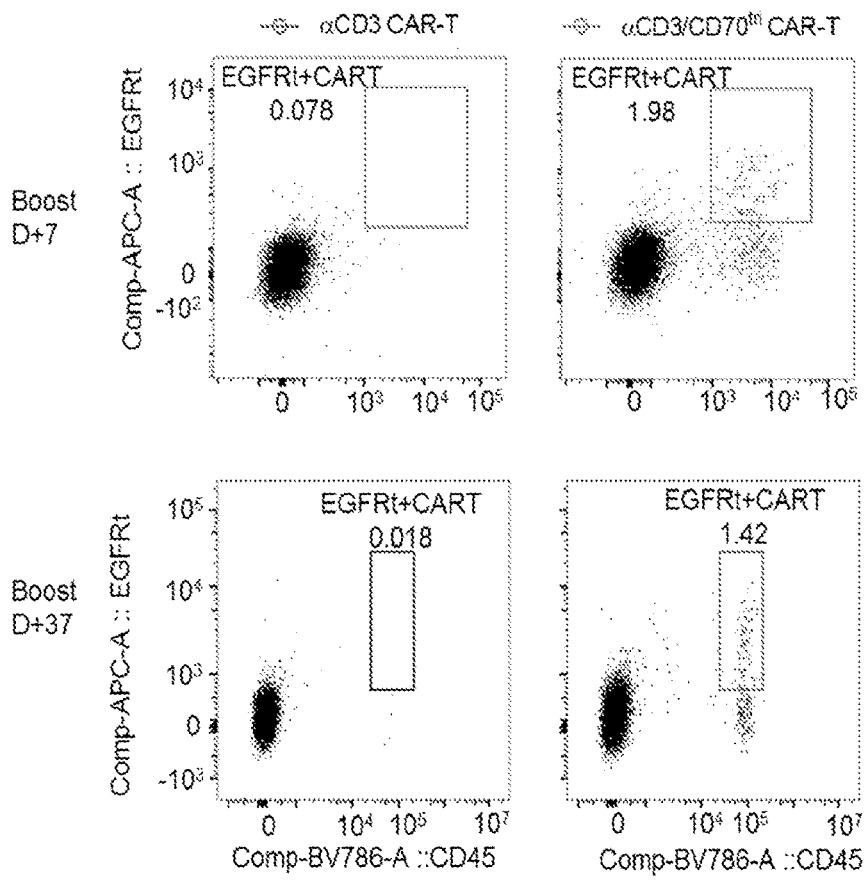

More specifically use of the engineered trimeric CD70 proteins of the disclosure in ex vivo T cell manufacturing creates expanded T cell populations that: proliferate more and earlier in culture (FIGS. 10B and 10C). Accordingly, in some embodiments, use of the proteins during culture can result in 10% more T cell proliferation, 20% more T cell proliferation, 30% more T cell proliferation, 40% more T cell proliferation, or up to 50% more T cell proliferation, on days 2, 3, 4, 5, or 6 of culture. In some embodiments, use of the proteins during culture can result in expanded T cell populations that proliferate earlier in culture, e.g., as early as 1-2 days in culture. Use of the engineered trimeric CD70 proteins of the disclosure during T cells (e.g., bulk-derived or bulk derived CD8$^+$ T cells) manufacturing selectively expands less differentiated cell populations and leads to an increase in the percentage of memory T cells in the expansion product (FIGS. 10D, 11A and 11B). Accordingly, in some embodiments, there is at least a 10% more, 20% more, 30% more, 40% more, or 50% more selective expansion of memory T cells in the expansion product. Such populations are desirable because they show improved long-term survival, expansion, and/or engraftment following administration. Terakura et al. (2012) Blood. 1:72-82; Wang et al. (2012) J Immunother. 35 (9): 689-701; Gattinoni et al. (2009) Nat Med. 15 (7): 808-13. An increased percent of memory T cells can be observed by having an increased percentage of cells within a culture with a memory signature (e.g., CCR7$^+$/CD45RO$^+$; upregulated TCF7, LEF1 and CD27 and/or down-regulated NOTCH1, PRDM1, GZMB, PRF1, and EOMES) as compared to a cell population of a relevant control culture. Accordingly, in some embodiments, there is an associated change in the memory signature in the expansion product.

In some embodiments, use of the engineered trimeric CD70 proteins of the disclosure in ex vivo T cell manufacturing leads to decreases in effector metabolism, e.g., a weaker induction of mTORC1/S6K signaling (day 2), a decrease in glucose uptake (day 2-4), a decrease in glycolytic switch capacity (day 5), and/or a late decrease in mTORC1-dependent protein translation (day 6-day 10), allowing for an expansion product (day 10) that experienced reduced metabolic exhaustion over time. In some embodiments, the use of the proteins leads to at least a 10%, at least a 20%, at least a 30%, at least a 40%, or even at least a 50% decrease in the metabolism of T cells.

Use of the proteins during manufacturing also results in T cell populations that persist longer (e.g., at least 10% longer, at least 20% longer, at least 30% longer, at least 40% longer, or at least 50% longer) in vivo following administration to a subject. The T cell populations lead to an increase in engraftment following administration (e.g., at least 10% increase, at least 20% increase, at least 30% increase, at least 40% increase, or at least 50% increase), an increase in killing capacity (e.g., at least 10% increase, at least 20% increase, at least 30% increase, at least 40% increase, or at least 50% increase), an increase in serial killing capacity (e.g., at least 10% increase, at least 20% increase, at least 30% increase, at least 40% increase, or at least 50% increase), and/or least to an increase in the targeting of tumor cells (e.g., at least 10% increase, at least 20% increase, at least 30% increase, at least 40% increase, or at least 50% increase) and provide improved therapeutic effects (FIGS. 11C-11G). The persistence of administered cells can be increased at least from 1.5-fold to 500-fold, 600-fold, 700-fold, 800-fold, 1000-fold, or more following administration. In some embodiments, the persistence of administered cells can be increased at least 1.5-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 60-fold, 70-fold, 80-fold, 90-fold, 100-fold or more following administration. Improved therapeutic effects can be demonstrated through increased or prolonged survival and/or through increased anti-cancer or anti-infection effects as described in more detail elsewhere herein.

Figure 3A:
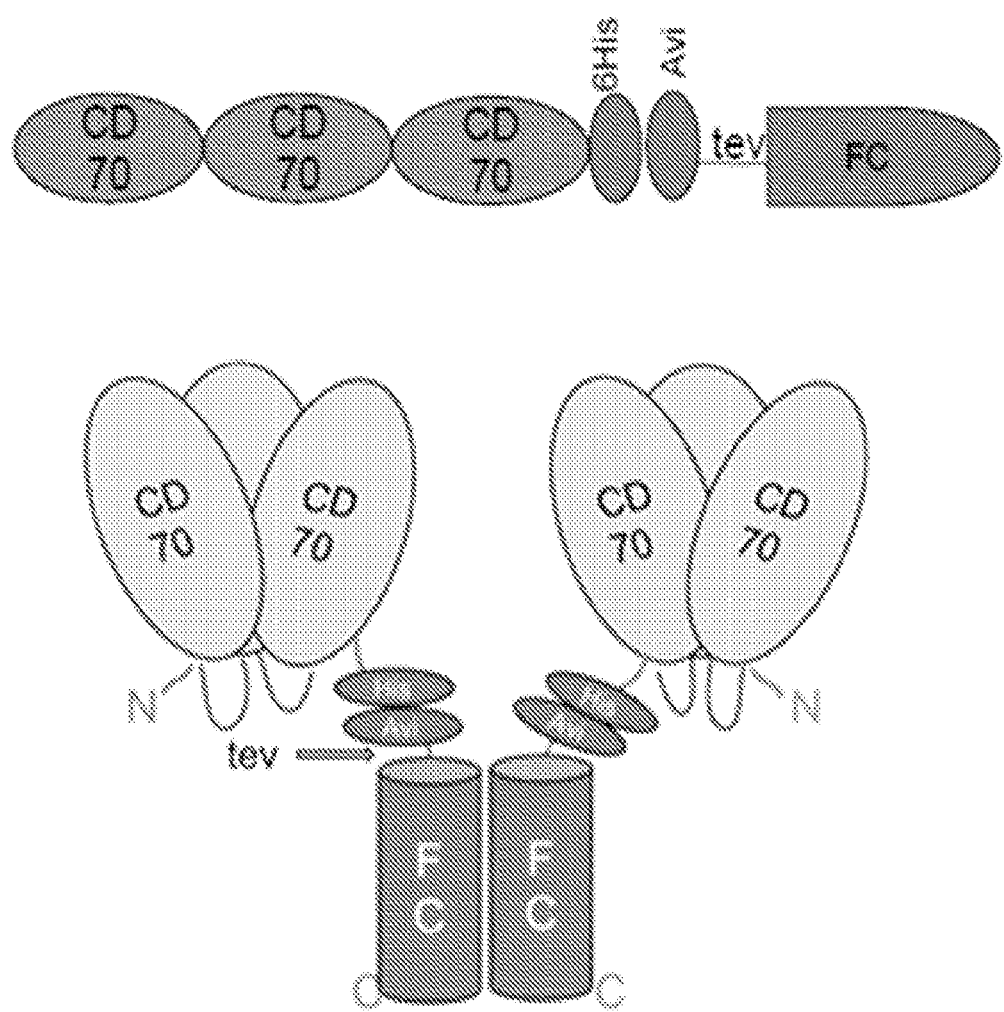
FIGS. 3A-3D. Schematics of CD27 agonistic proteins including (3A) dimer-trimer design; (3B, 3C) trimeric monomer design; and (3D) tetrameric circular tandem repeat protein (cTRP) design.

In particular embodiments, the engineered trimeric CD70 protein is expressed as a single chain with three CD70 extracellular domains and the Fc portion of an antibody. The Fc portion serves as a dimerization domain to link the single chain protein with a similar (or identical) single chain protein to create a "dimer-trimer." An exemplary form of this protein is depicted in FIG. 3A, and a particular example includes MDT-000762-2.

Figure 3B:
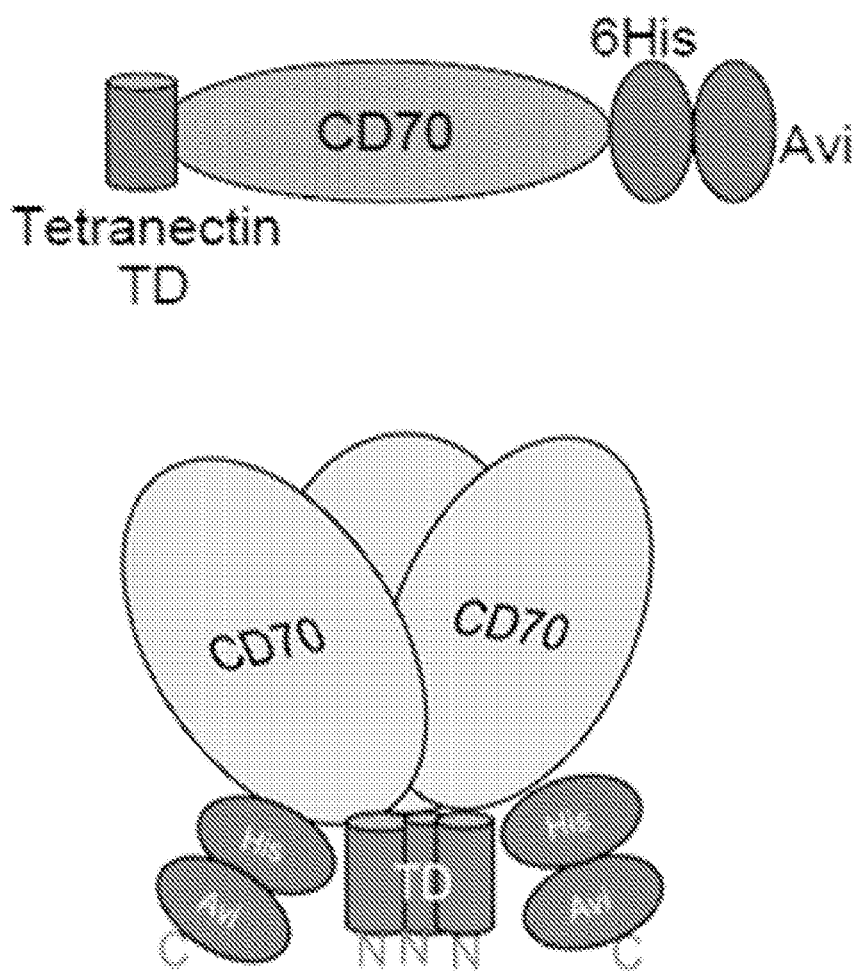
Figure 3C:
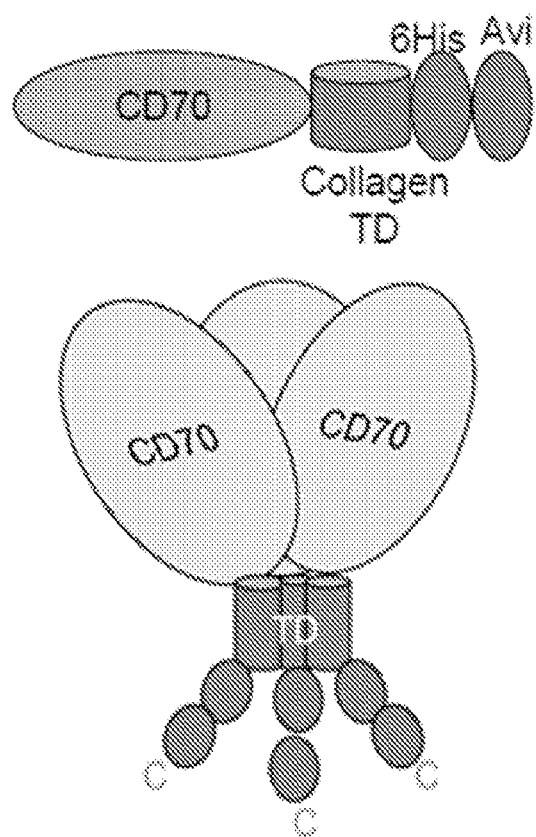

In particular embodiments, the trimeric CD70 protein includes a CD70 extracellular domain expressed within a single chain, including a trimerization domain, such as tetranectin or collagen. The trimerization domain serves to link the single chain with two similar (or identical) single chain proteins to create a mono-trimer. Forms of this protein are depicted in FIGS. 3B and 3C and particular examples include MDT-000763 and MDT-00764-2.

Figure 3D:
Figure 4A:
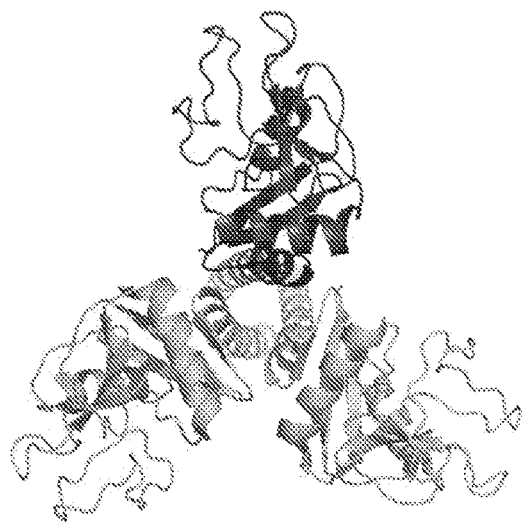
Figure 4B:
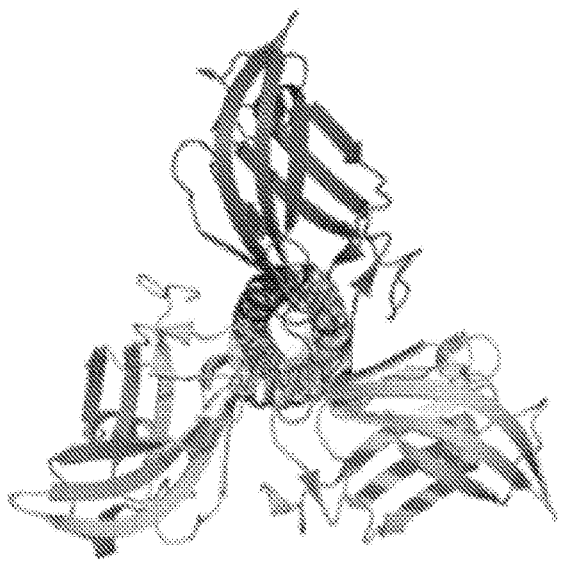
Figure 4C:
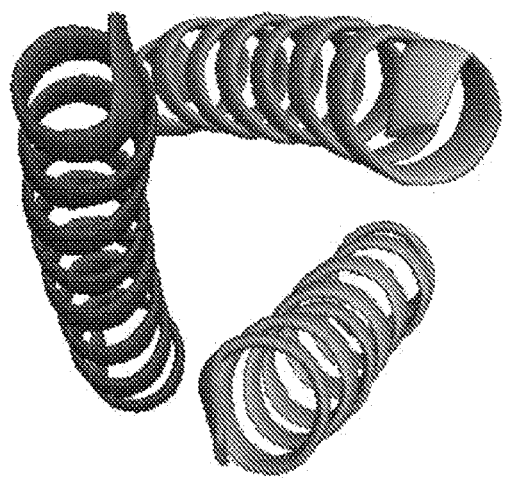
Figure 4D:

In particular embodiments, the engineered trimeric CD70 protein includes trimeric CD70 extracellular domains anchored to a circular-tandem repeat protein (cTRP). The cTRP enables the display of single chain TNFRSF binding trimers in trimeric, tetrameric, and pentameric arrangements and in multiple orientations. A form of this protein is depicted in FIG. 3D and a particular example includes MDT-001100.

An exemplary sequence for an extracellular domain of CD70 of the disclosure is provided in SEQ ID NO: 4. Accordingly, in some embodiments, a trimeric CD70 protein of the disclosure includes the amino acid sequence set forth in SEQ ID NO: 4, or an amino acid sequence including a sequence having at least 70%, at least 75%, at least 80%, at least 85%, at least 90%, at least 95%, or even at least 99% sequence identity thereto, and retaining the signaling properties of CD70.

In some embodiments, the engineered trimeric CD70 of the disclosure is a single chain with three CD70 extracellular domains and the Fc portion of an antibody, wherein the extracellular domain of CD70 includes the amino acid sequence set forth in SEQ ID NO: 4, or an amino acid sequence including a sequence having at least 70%, at least 75%, at least 80%, at least 85%, at least 90%, at least 95%, or even at least 99% sequence identity thereto.

In some embodiments, the engineered trimeric CD70 of the disclosure is a CD70 extracellular domain expressed with a single chain including a trimerization domain, wherein the extracellular domain of CD70 includes the amino acid sequence set forth in SEQ ID NO: 4, or an amino acid sequence including a sequence having at least 70%, at least 75%, at least 80%, at least 85%, at least 90%, at least 95%, or even at least 99% sequence identity thereto.

In some embodiments, the engineered trimeric CD70 protein includes trimeric CD70 extracellular domains anchored to a circular-tandem repeat protein (cTRP), wherein the extracellular domain of CD70 includes the amino acid sequence set forth in SEQ ID NO: 4, or an amino acid sequence including a sequence having at least 70%, at least 75%, at least 80%, at least 85%, at least 90%, at least 95%, or even at least 99% sequence identity thereto.

In particular embodiments, one or more types of these trimeric proteins are coated onto one or more surfaces during T cell manufacturing. Such surfaces include, for example, solid surfaces, porous surfaces, semi-porous surfaces, polymeric surfaces, spherical surfaces, non-spherical surfaces, rod-like surfaces, and the like. In other embodiments, trimeric proteins can also be utilized as soluble factors during T cell manufacturing. MDT-001100 is particularly well-suited for use as a soluble factor.

In particular embodiments, the engineered trimeric CD27 binding proteins can be formulated into pharmaceutical compositions for administration to a subject.

Aspects of the current disclosure are now described in additional detail as follows: (i) Engineered Trimeric CD70 Proteins; (ii) T Cell Classes; (iii) Cell Sample Collection and T Cell Enrichment; (iv) T Cell Activating & Expansion Culture Conditions; (v) Genetically Modifying T Cell Populations to Express Recombinant Molecules; (vi) Ex Vivo Manufactured Cell Formulations; (vii) Compositions for Administration; (viii) Methods of Use; (ix) Examples; (x) Exemplary Embodiments; (xi) Sequence Listing Summary; and (xii) Closing Paragraphs. These headings do not limit the interpretation of the disclosure and are provided for organizational purposes only.

(i) Engineered Trimeric CD70 Proteins. The current disclosure provides trimeric CD70 proteins designed to activate CD27 during T cell manufacturing. The disclosed proteins adopt numerous configurations based upon the underlying selected architecture. The proteins include at least three extracellular CD70 domains (FIGS. 1A-1C) and a supporting architecture that stimulates CD27 signaling. Supporting architectures include dimerization domains, trimerization domains, cTRP scaffolds, linkers, and tags.

(i-a) Dimerization Domains. Dimerization domains result in the binding of two monomers to form a dimer. Particular embodiments utilize the Fc portion of an antibody (e.g., IgG1, IgG2, IgG3, IgG4, IgM, IgA, IgD) as a dimerization domain. This approach is depicted in relation to the MDT-000762-2 dimer-trimer design (FIG. 3A).

In particular embodiments, dimerization domains can be derived from an FcεRI chain. In particular embodiments, one monomer can include a part of an FcεRI α chain and another monomer can include a part of an FcεRI β chain such that said FcεRI chains spontaneously dimerize to form a dimer.

Dock and Lock (DNL) dimerization domains can also be used. In particular embodiments, complementary binding domains can be derived from binding events such as those between an enzyme and its substrate/inhibitor, for example, cutinase and phosphonates (Hodneland, et al. Proc Natl Acd Sci USA. 2002; 99:5048-5052), may be utilized to generate the two associating components (the "docking" step), which are subsequently stabilized covalently (the "lock" step).

In particular embodiments, dimerization domains can include protein sequence motifs such as coiled coils, acid patches, zinc fingers, calcium hands, a CH1-CL pair, an "interface" with an engineered "knob" and/or "protuberance" (U.S. Pat. No. 5,821,333).

(i-b) Trimerization Domains. Trimerization domains can be used to form stable homotrimeric and/or heterotrimeric complexes when attached by a peptide bond or suitable linker to other proteins. Accordingly, polypeptide sequences may be placed amino-terminally or carboxy-terminally to the trimerization domain allowing for the formation of a trimeric molecular assembly.

In particular embodiments, the trimerization domain is derived from tetranectin. In humans, tetranectin is a homotrimer, forming a triple α-helical coiled coil. Each monomer consists of a carbohydrate recognition domain (CRD) connected to a long α-helix. The mature human tetranectin polypeptide chain (SEQ ID NO: 31) of 181 amino acid residues is encoded in three exons, as shown by molecular cloning and characterization of the gene. In particular embodiments, the tetranectin trimerization domain is the hsTetranectin trimerization domain (SEQ ID NOs: 14 or 30). In various aspects of the disclosure, the trimerization domain is derived from human tetranectin, murine tetranectin, bovine tetranectin, Atlantic salmon tetranectin, chicken tetranectin, C-type lectin of bovine cartilage, or C-type lectin of shark cartilage.

In particular embodiments, the trimerization domain is a collagen xv trimerization domain (PDB ID 3N3F) (SEQ ID NO: 20). Collagens contain large numbers of Gly-Xaa-Yaa peptide repeats that form the characteristic triple helix, where the individual chains fold into a polyproline II helix, and three of these helices form a right-handed triple helix. These domains ensure a single starting point for triple helix formation and are also responsible for the chain selection in heterotrimeric collagens. The size of trimerization domains varies from 35 residues in type IX collagen to 250 residues for the fibrillar collagens (Boudko, et al., 2012. The International Journal of Biochemistry & Cell Biology. 44 (1): 21-32). In particular embodiments, the trimerization domain is derived from collagen XV (SEQ ID NO: 32). In particular embodiments, the trimerization domain is derived from collagen XVIII (SEQ ID NO: 33).

In particular embodiments, the trimerization domain is from the clathrin trimerization domain (PDB ID 3QIL) (SEQ ID NO: 34). Clathrin is a trimer of three heavy chains, each with an associated light chain. In general, the three Clathrin heavy chains are joined at their C-termini, extending into proximal and distal leg domains ending in globular N-terminal domain elements, which are responsible for peptide binding. The Clathrin heavy chain terminal domains provide multiple interaction sites for a variety of adaptor proteins (AP) that can bind multiple receptors occupied by ligands. The heavy chain N-terminal domain elements each include a seven-bladed beta-propeller connected to a flexible linker region, respectively. The propeller domain is followed by a long filamentous segment, which is interrupted by a bent region between the distal and proximal domains and ends in the trimerization domain at the C-terminus.

In particular embodiments, the trimerization domain is derived from the inner membrane lipoprotein SadB (PDB ID 4C47) (SEQ ID NO: 35). SadB is derived from the organism *Salmonella typhimurium* and forms a homotrimer.

In particular embodiments, the trimerization domain is derived from echinoderm microtubule-associated protein-like 4 (EML4) (PDB ID 4C4G) (SEQ ID NO: 36).

In particular embodiments, the trimerization domain includes a useful alpha-helical coiled coil domain. Useful alpha-helical coiled coll domains include those derived from Matrilin 1 (SEQ ID NOs: 37 and 38; also referred to as cartilage matrix protein or CMP). DMPK (SEQ ID NOs: 39 and 40). Langerin (SEQ ID NOs: 41 and 42), and Coronin 1a (SEQ ID NOs: 43-50). Coronin 1a proteins are also referred to as any of Coronin-like protein A, Clipin-A, Coronin-like protein p57, Tryptophan aspartate-containing coat protein, and the HUGO name CORO1A.

Matrilin 1 trimerization is mediated through ionic bonds and other non-covalent bonds formed between adjacent charged amino acids of the polypeptide chains. This trimerization domain is described, e.g., in Beck et al., J. Mol. Biol. (1996) 256. 909-923. In particular embodiments, the trimerization domain derived from matrilin-1 include the amino acids 463-496 of SEQ ID NO: 52.

In particular embodiments, the trimerization domain includes a fibritin trimerization domain. In particular embodiments, the fibritin trimerization domain includes a fibritin trimerization domain from bacteriophage T4, bacteriophage RB69, or related bacteriophages. The T4 fibritin trimerization domain is, e.g., described in U.S. Pat. No. 6,911,205 and WO 01/19958. T4 fibritin has the sequence of SEQ ID NO: 53, and its trimerization domain is set forth in SEQ ID NO: 54 and at residues 458-484 of SEQ ID NO: 53. RB69 fibritin has the sequence of SEQ ID NO: 55, and its trimerization domain is set forth in SEQ ID NO: 56 and at residues 455-480 of SEQ ID NO: 55.

In particular embodiments, the trimerization domain includes a leucine zipper domain. An exemplary leucine zipper domain is the engineered yeast GCN4 leucine variant described by Harbury et al. (1993) Science 262:1401-1407.

In particular embodiments, the trimerization domain can be derived from the polypeptide FcεRI chain. In particular embodiments, the monomers can include a part of a FcεRI α chain and a part of a FcεRI γ chain such that said FcεRI chains spontaneously trimerize together to form a trimer.

Additional trimerization domains include: the trimerization domain derived from amino acids $310^{-349}$ of TNF receptor-associated factor-2 (TRAF2) (SEQ ID NO: 57), the trimerization domain derived from amino acids 291-314 of Thrombospondin 1 (SEQ ID NO: 58), the trimerization domain derived from amino acids 594-618 of Matrilin-4 (SEQ ID NO: 59), the trimerization domain derived from amino acids 165-191 of heat shock transcription factor (HSF) (SEQ ID NO: 60), and the trimerization domain derived from amino acids $10^4$-138 of cubilin (SEQ ID NO: 61). In certain aspects, the trimerization domain includes amino acids 310 to 349 of human TRAF2 (SEQ ID NO: 57).

(i-c) cTRP Scaffolds. In particular embodiments, the supporting architecture is based on a cTRP scaffold. cTRPs are repeat proteins designed purely by geometric criteria defining the inter-repeat geometry. cTRPs have a repetitive alpha (α)-helical structures joined by linkers. The particular structure of the proteins is based on the formula $(a-b-x-y)_n$ wherein a and x represent linkers; b represents an amino acid sequence that forms an a helix; y represents an amino acid sequence that forms a second a helix; n=3 or more; and wherein each (a-b-x-y) unit is structurally repetitive to an adjacent (a-b-x-y) unit; the protein is handed; and the N-termini ("first segment") and C-termini ("last segment") of the protein create a circular architecture or a closed stapled architecture, depending on whether precise cysteine modifications are provided in the N-terminal and C-terminal b segments of the protein. WO2017 096236 provides exemplary cTRP proteins, and its contents are incorporated by reference in their entirety herein.

cTRPs can further include functional domains (here, trimeric CD70) inserted adjacent to or within the a and/or x linkers. If all functional domains are inserted adjacent to or within "a" linker sequences only, the functional domains appear either on the "top" or the "bottom" of the cTRP protein. If functional domains are inserted adjacent to or within "a" and "x" linker sequences, the functional domains appear on the "top" and the "bottom" of the cTRP protein.

An exemplary cTRP of MDT-001100 includes GIS as an "a" linker segment; CEAIKAAAELGKA (SEQ ID NO: 26) as a cysteine modified-N-terminal α-helix forming "b" segment; GLD as an "x" linker segment; SEEILELLRAAHEL (SEQ ID NO: 27) as internal "b" and "y" α-helix forming segments; and PECIKAAAELGKA (SEQ ID NO: 28) as cysteine-modified C-terminal α-helix forming "b" segment. The cysteine modifications in the N- and C-terminal b segments create a closed, stapled cTRP architecture. With an n of 6, this cTRP scaffold creates the sequence: CEAIKAAAELGKAGISSEEILELLRAAHELGLDPEAI-KAAAELGKAGISSEEILELLRAAHELGLDP EAI-KAAAELGKAGISSEEILELLRAAHELGLDPEAI-KAAAELGKAGISSEEILELLRAAHELGLDPE AIKAAAELGKAGISSEEILELLRAAHELGLDPECI-KAAAELGKAGISSEEILELLRAAHELGL (SEQ ID NO: 25).

Figure 8C:
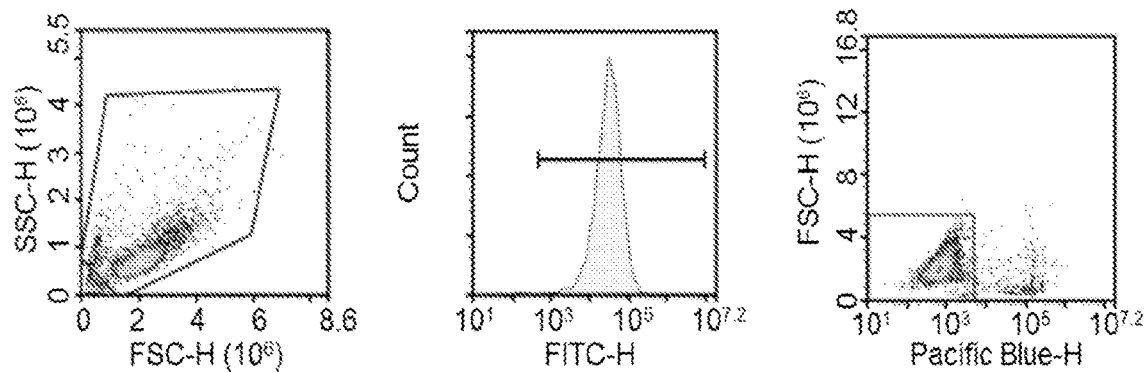
Figure 8D:
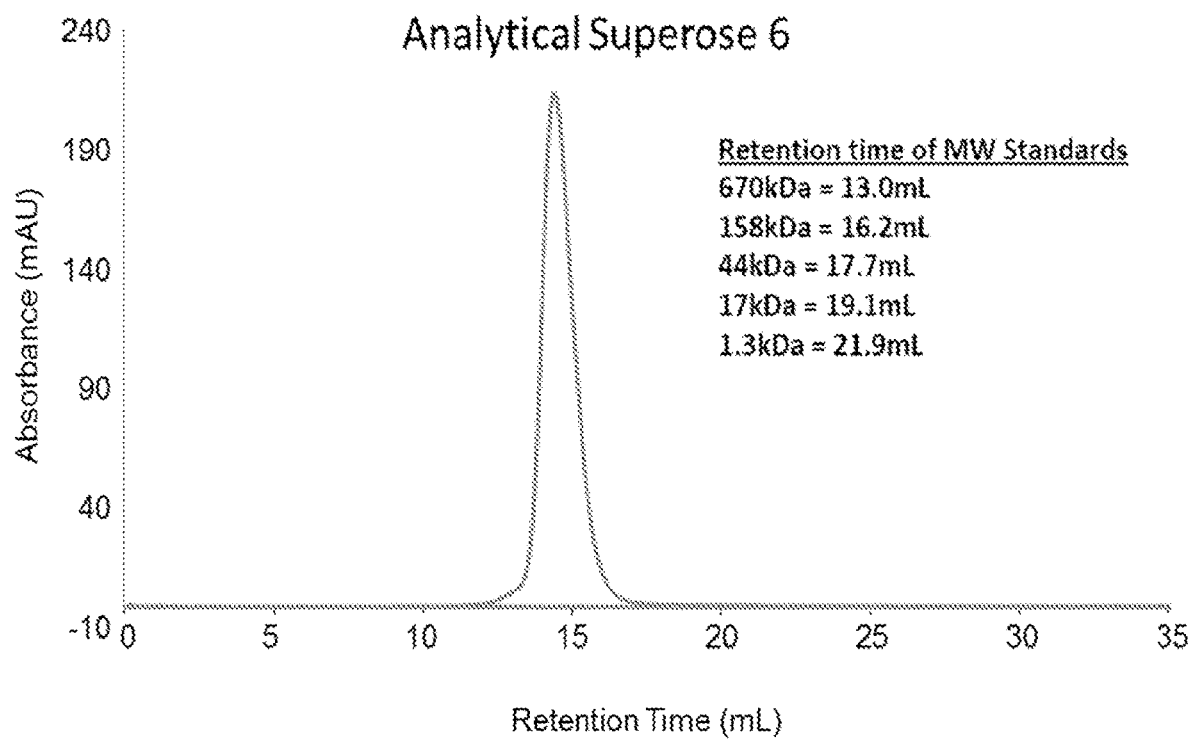
Figure 8E:
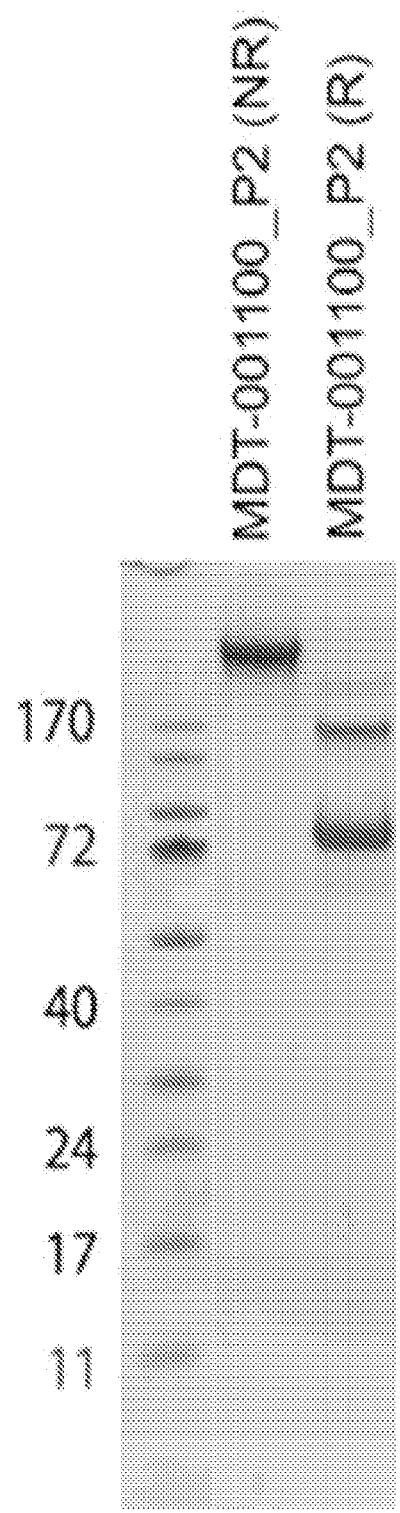
Figure 8F:
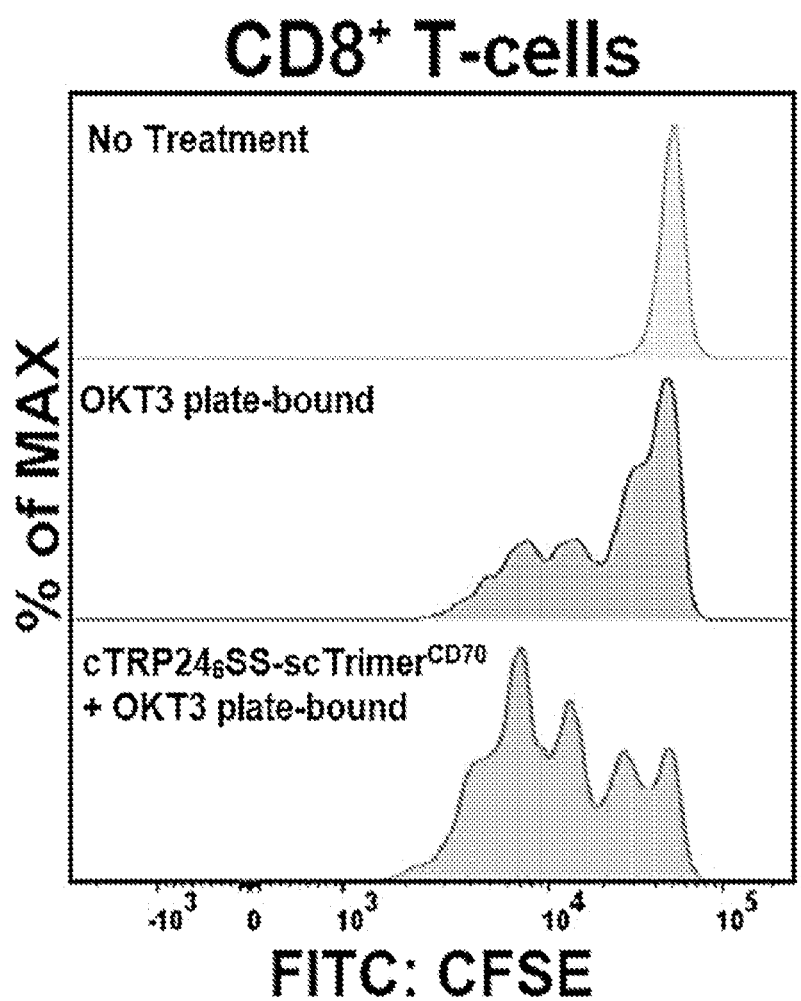

CD70 functional domains may be inserted within or adjacent to the "a" and "x" linker segments as depicted in FIG. 8B (SEQ ID NO: 7).

(i-d) Linkers. Particular embodiments can include linkers between different subcomponents of an engineered trimeric CD70 protein disclosed herein. Examples of linkers can be found in Chen et al., Adv Drug Deliv Rev. 2013 Oct. 15; 65 (10): 1357-1369. Linkers can be flexible, rigid, or semi-rigid, depending on the desired CD70 presentation.

Commonly used flexible linkers include Gly-Ser linkers such as GS, GGS, GGGS (SEQ ID NO: 8), GGGGS (SEQ ID NO: 21), GGGGSGGGGS (SEQ ID NO: 24), GGSGGGSGGSG (SEQ ID NO: 63), GGSGGGSGSG (SEQ ID NO: 64), GGSGGGSG (SEQ ID NO: 65), and GGSGGS (SEQ ID NO: 66). Particular embodiments utilize GS, GGS, GGGS (SEQ ID NO: 8), GGGGS (SEQ ID NO: 21), and GGGGSGGGGS (SEQ ID NO: 24) as linkers. Additional examples of linkers include GD, GN, GT, LPHD (SEQ ID NO: 67), NPND (SEQ ID NO: 68), DPKD (SEQ ID NO: 69), GLEPD (SEQ ID NO: 70), GVSLD (SEQ ID NO: 71), and GVLPD (SEQ ID NO: 72).

In some situations, flexible linkers may be incapable of maintaining a distance or positioning of CD70 functional domains needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs).

The rigidity of protein linkers refers to the degree of flexibility of the protein backbone over the entire length of a short, single chain protein as measured by the average root-mean-square (RMS) ($RMS^{fluct}$) of all internal torsion angles ($\Phi$, $\psi$) over the length of a given single chain protein linker.

$RMS^{fluct}$ of a torsion angle is the standard deviation of the torsion angle value about the time-averaged value in a CHARMM molecular dynamics simulation, wherein $RMS^{fluct}$ is calculated as follows:

$$\text{RMS}^{fluct} = \sqrt{\frac{1}{N_f}\sum_f (\theta^f - \theta^{ave})^2}$$

where f refers to the frame number, N is the total number of frames in the trajectory file, and $\theta^r$ and $\theta^{ave}$ are the current value and the average value for the torsion angle, respectively. "CHARMM" (Chemistry at Harvard Macromolecular Mechanics) refers to a computer simulation engine (see Brooks et al., (1983) J Comp Chem 4:187-217; Mackerell, et al., (1998) J. Phys. Chem. B 102 (18): 3586-3616; and "CHARMM: The Energy Function and Its Parameterization with an Overview of the Program," by Mackerell et al., in The Encyclopedia of Computational Chemistry, Volume 1, 271-277, by Paul von Raque Schleyer et al., editors (John Wiley & Sons: Chichester, United Kingdom (1998)); and Brooks, et al., (2009) J. Comp. Chem., 30:1545-1615 (2009).

In particular embodiments, the average $\text{RMS}^{fluct}$ can be calculated using the formula: (average RMSfluct phi (Φ)+ average $\text{RMS}^{fluct}$ psi (ψ))/2. The average RMS fluctuation of all internal backbone torsion angles over the length of the protein can be used to quantify the rigidity of the protein linker. The more rigid the protein is, the smaller the average RMS fluctuation should be due to a more limited conformational space accessible to the protein.

In particular embodiments, a rigid protein linker refers to a linker having an average RMSfluct of 25 or less, 20 or less, 15 or less when measured using CHARMM modeling over a production run of 200 picoseconds (ps). In particular embodiments, a semi-rigid protein linker refers to a linker having an average RMSfluct of 45-25 when measured using CHARMM modeling over a production run of 200 picoseconds (ps).

(i-e) Tags. In particular embodiments, engineered trimeric CD70 proteins can include one or more tags for use during production or use of the proteins. "Tags" refer to a peptide sequence that is part of a single chain protein that forms an engineered trimeric CD70 protein wherein the tag can be used to detect, enrich for, isolate, and track proteins, including the tag.

Exemplary tags include His tag (SEQ ID NO: 9), Avi tag (SEQ ID NO: 10), Flag tag (DYKDDDDK, SEQ ID NO: 195), Xpress tag (DLYDDDDK, SEQ ID NO: 196), Calmodulin tag (KRRWKKNFIAVSAANRFKKISSSGAL, SEQ ID NO: 197), Polyglutamate tag, HA tag (YPYDVPDYA, SEQ ID NO: 198), Myc tag (EQKLISEEDL, SEQ ID NO: 199), Softag 1 (SLAELLNAGLGGS, SEQ ID NO: 200), Softag 3 (TQDPSRVG, SEQ ID NO: 201), Strep tag (which refers the original STREP® tag (WRHPQFGG, SEQ ID NO: 202), STREP® tag II (WSHPQFEK, SEQ ID NO: 203) (IBA Institut fur Bioanalytik, Germany); see, e.g., U.S. Pat. No. 7,981,632), and V5 tag (GKPIPNPLLGLDST, SEQ ID NO: 204).

Conjugate binding molecules that specifically bind tag sequences disclosed herein are commercially available. For example, His tag antibodies are commercially available from suppliers including Life Technologies, Pierce Antibodies, and GenScript. Avi tag antibodies are commercially available from suppliers including Pierce Antibodies, IsBio, and Genecopoeia. Flag tag antibodies are commercially available from suppliers, including Pierce Antibodies, GenScript, and Sigma-Aldrich. Xpress tag antibodies are commercially available from suppliers, including Pierce Antibodies, Life Technologies, and GenScript. Calmodulin tag antibodies are commercially available from suppliers including Santa Cruz Biotechnology, Abcam, and Pierce Antibodies. HA tag antibodies are commercially available from suppliers, including Pierce Antibodies, Cell Signal, and Abcam. Myc tag antibodies are commercially available from suppliers, including Santa Cruz Biotechnology, Abcam, and Cell Signal. Strep tag antibodies are commercially available from suppliers including Abcam, Iba, and Qiagen.

(ii) T Cell Classes. Several different subsets of T-cells have been discovered, each with a distinct function. For example, a majority of T-cells have a T-cell receptor (TCR) existing as a complex of several proteins. The actual T-cell receptor is composed of two separate peptide chains, which are produced from the independent T-cell receptor alpha and beta (TCRa and TCRB) genes and are called α- and β-TCR chains.

γδ T-cells represent a small subset of T-cells that possess a distinct T-cell receptor (TCR) on their surface. In γδ T-cells, the TCR is made up of one γ-chain and one δ-chain. This group of T-cells is much less common (2% of total T-cells) than the αβ T-cells.

CD3 is expressed on all mature T cells. Activated T-cells express 4-1BB (CD137), CD69, and CD25.

T-cells can further be classified into helper cells ($CD4^+$ T-cells) and cytotoxic T-cells (CTLs, $CD8^+$ T-cells), which include cytolytic T-cells. T helper cells assist other white blood cells in immunologic processes, including maturation of B cells into plasma cells and activation of cytotoxic T-cells and macrophages, among other functions. These cells are also known as $CD4^+$ T-cells because they express the CD4 protein on their surface. Helper T-cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T-cells destroy virally infected cells and tumor cells and are also implicated in transplant rejection. These cells are also known as $CD8^+$ T-cells because they express the CD8 glycoprotein on their surface. These cells recognize their targets by binding to antigen associated with MHC class I, which is present on the surface of nearly every cell of the body.

"Central memory" T-cells (or "$T_{CM}$") as used herein refers to an antigen experienced CTL that expresses CD62L or CCR7 and CD45RO on the surface thereof and does not express or has decreased expression of CD45RA as compared to naive cells. In particular embodiments, central memory cells are positive for expression of CD62L, CCR7, CD25, CD127, CD45RO, and CD95 and have decreased expression of CD45RA as compared to naive cells. $T_{CM}$ can also be identified based on a $CCR7^+/CD45RO^+$ marker profile.

"Effector memory" T-cell (or "$T_{EM}$") as used herein refers to an antigen experienced T-cell that does not express or has decreased expression of CD62L on the surface thereof as compared to central memory cells and does not express or has decreased expression of CD45RA as compared to a naive cell. In particular embodiments, effector memory cells are negative for expression of CD62L and CCR7, compared to naive cells or central memory cells, and have a variable expression of CD28 and CD45RA. Effector T-cells are positive for granzyme B and perforin as compared to memory or naive T-cells. $T_{EM}$ can also be identified based on a $CCR7-/CD45RO^+$ marker profile.

"Naive" T-cells as used herein refers to a non-antigen experienced T cell that expresses CD62L and CD45RA and does not express CD45RO as compared to central or effector memory cells. In particular embodiments, naive CD8$^+$ T lymphocytes are characterized by the expression of phenotypic markers of naive T-cells, including CD62L, CCR7, CD28, CD127, and CD45RA. Naïve T cells can also be identified based on a CCR7$^+$/CD45RO$^-$ marker profile.

In particular embodiments, memory T cells show up-regulated gene expression of TCF7, LEF1, and CD27. In particular embodiments, memory T cells show down-regulated gene expression of NOTCH1, PRDM1, GZMB, PRF1, and EOMES.

As described herein, expansion of T cells utilizing the trimeric CD70 proteins disclosed herein results in a T cell population with an increased percentage of T cells expressing a memory signature and/or a decreased percentage of cells expressing an effector signature. In these embodiments, a memory signature can include up-regulated expression of TCF7, LEF1, and CD27 and/or down-regulated expression of NOTCH1, PRDM1, GZMB, PRF1, and EOMES. An effector signature can include normal and/or upregulated expression of NOTCH1, PRDM1, GZMB, PRF1, and EOMES.

A statement that a cell or population of cells is "positive" for or expressing a particular marker refers to the detectable presence on or in the cell of the particular marker. When referring to a surface marker, the term can refer to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

A statement that a cell or population of cells is "negative" for a particular marker or lacks expression of a marker refers to the absence of substantial detectable presence on or in the cell of a particular marker. When referring to a surface marker, the term can refer to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

(iii) Cell Sample Collection and T Cell Enrichment. Methods of sample collection and enrichment are known by those skilled in the art. In some embodiments, cells are derived from T cell lines. The cells in some embodiments are obtained from a xenogeneic source, for example, from mouse, rat, non-human primate, or pig. In particular embodiments, T cells are derived from humans.

In some embodiments, T cells are derived or isolated from samples such as whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organs, and/or cells derived therefrom. In some aspects, the T cells are derived or isolated from blood or a blood-derived sample or are derived from an apheresis or leukapheresis product. In relation to a particular subject, T cells can be autologous or allogeneic.

In some embodiments, blood cells collected from a subject are washed, e.g., to remove the plasma fraction and to place the cells in an appropriate buffer or media for subsequent processing steps. In particular embodiments, the cells are washed with phosphate buffered saline (PBS). In some embodiments, the wash solution lacks calcium and/or magnesium and/or many or all divalent cations. Washing can be accomplished using a semi-automated "flow-through" centrifuge (for example, the Cobe 2991 cell processor, Baxter) according to the manufacturer's instructions. Tangential flow filtration (TFF) can also be performed. In particular embodiments, cells can re-suspended in a variety of biocompatible buffers after washing, such as Ca$^{++}$/Mg$^{++}$ free PBS.

In particular embodiments, a sample can be enriched for T cells by using density-based cell separation methods and related methods. For example, white blood cells can be separated from other cell types in the peripheral blood by lysing red blood cells and centrifuging the sample through a Percoll or Ficoll gradient.

In particular embodiments, a bulk T cell population can be used that has not been enriched for a particular T cell type. In particular embodiments, a selected T cell type can be enriched for and/or isolated based on cell-marker based positive and/or negative selection. In positive selection, cells having bound cellular markers are retained for further use. In negative selection, cells not bound by a capture agent, such as an antibody to a cellular marker, are retained for further use. In some examples, both fractions can be retained for further use.

The separation need not result in 100% enrichment or removal of a particular cell population or cells expressing a particular marker. For example, positive selection of or enrichment for cells of a particular type refers to increasing the number or percentage of such cells but need not result in a complete absence of cells not expressing the marker. Likewise, negative selection, removal, or depletion of cells of a particular type refers to decreasing the number or percentage of such cells but need not result in a complete removal of all such cells.

In some examples, multiple rounds of separation steps are carried out, where the positively or negatively selected fraction from one step is subjected to another separation step, such as a subsequent positive or negative selection.

In some embodiments, an antibody or binding domain for a cellular marker is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ); see also U.S. Pat. Nos. 4,452,773; 4,795,698; 5,200,084; and EP 452342.

In some embodiments, the affinity-based selection is via magnetic-activated cell sorting (MACS) (Miltenyi Biotec, Auburn, CA). MACS systems are capable of a high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labeled and depleted from the heterogeneous population of cells.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1 (5): 355-376). In both cases, cells can be labeled with multiple markers, allowing for the isolation of well-defined T cell subsets at high purity.

Cell-markers for different T cell subpopulations are described above. In particular embodiments, specific subpopulations of T cells, such as cells positive or expressing high levels of one or more surface markers, e.g., CCR7, CD45RO, CD8, CD27, CD28, CD62L, CD127, CD4, and/or CD45RA T cells, are isolated by positive or negative selection techniques.

$CD3^+$, $CD28^+$ T cells can be positively selected for and expanded using anti-CD3/anti-CD28 conjugated magnetic beads (e.g., DYNABEADS® M-450 CD3/CD28 T Cell Expander).

In particular embodiments, a $CD8^+$ or $CD4^+$ selection step is used to separate $CD4^+$ helper and $CD8^+$ cytotoxic T cells. Such $CD8^+$ and $CD4^+$ populations can be further sorted into sub-populations by positive or negative selection for markers expressed or expressed to a relatively higher degree on one or more naive, memory, and/or effector T cell subpopulations.

In some embodiments, enrichment for central memory T ($T_{CM}$) cells is carried out. In particular embodiments, memory T cells are present in both CD62L subsets of $CD8^+$ peripheral blood lymphocytes. PBMC can be enriched for or depleted of CD62L, CD8, and/or $CD62L+CD8^+$ fractions, such as by using anti-CD8 and anti-CD62L antibodies.

In some embodiments, the enrichment for central memory T ($T_{CM}$) cells is based on positive or high surface expression of CCR7, CD45RO, CD27, CD62L, CD28, CD3, and/or CD127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CCR7, CD45RO, and/or CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously, and in other aspects are carried out sequentially, in either order. In some aspects, the same CD4 expression-based selection step used in preparing the $CD8^+$ cell population or subpopulation also is used to generate the $CD4^+$ cell population or sub-population, such that both the positive and negative fractions from the CD4-based separation are retained, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or RORI, and positive selection based on a marker characteristic of central memory T cells, such as CCR7, CD45RO, and/or CD62L, where the positive and negative selections are carried out in either order.

In particular embodiments, cell enrichment results in a bulk $CD8^+$ FACs-sorted cell population.

(iv) T Cell Activating & Expansion Culture Conditions. Cell populations can be incubated in a culture-initiating composition to expand T cell populations. The incubation can be carried out in a culture vessel, such as a bag, cell culture plate, flask, chamber, chromatography column, cross-linked gel, cross-linked polymer, column, culture dish, hollow fiber, microtiter plate, silica-coated glass plate, tube, tubing set, well, vial, or other container for culture or cultivating cells.

Culture conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate and/or expand the cells.

In some aspects, incubation is carried out in accordance with techniques such as those described in US 6,040, 177, Klebanoff et al. (2012) J Immunother. 35 (9): 651-660, Terakura et al. (2012) Blood. 1:72-82, and/or Wang et al. (2012) J Immunother. 35 (9): 689-701.

Exemplary culture media for culturing T cells include (i) RPMI supplemented with non-essential amino acids, sodium pyruvate, and penicillin/streptomycin; (ii) RPMI with HEPES, 5-15% human serum, 1-3% L-Glutamine, 0.5-1.5% penicillin/streptomycin, and $0.25 \times 10^{-4}$-$0.75 \times 10^{-4}$ M β-MercaptoEthanol; (iii) RPMI-1640 supplemented with 10% fetal bovine serum (FBS), 2 mM L-glutamine, 10 mM HEPES, 100 U/ml penicillin and 100 m/mL streptomycin; (iv) DMEM medium supplemented with 10% FBS, 2 mM L-glutamine, 10 mM HEPES, 100 U/ml penicillin and 100 m/mL streptomycin; and (v) X-Vivo 15 medium (Lonza, Walkersville, MD) supplemented with 5% human AB serum (Gemcell, West Sacramento, CA), 1% HEPES (Gibco, Grand Island, NY), 1% Pen-Strep (Gibco), 1% GlutaMax (Gibco), and 2% N-acetyl cysteine (Sigma-Aldrich, St. Louis, MO). T cell culture media are also commercially available from Hyclone (Logan, UT) and Stemcell Technologies (e.g., ImmunoCult™ (ImmC). CTL-Test™ Medium (ImmunoSpot®, Cellular Technology, Ltd; Cleveland, OH) may also be used. Additional T cell culture components that can be added to such culture media are described in more detail below.

In some embodiments, the T cells are cultured by adding to the culture-initiating composition feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g., for a time sufficient to expand the numbers of T cells). In some aspects, the non-dividing feeder cells can include gamma-irradiated PBMC feeder cells. In some embodiments, the PBMC are irradiated with gamma rays in the range of 3000 to 3600 rads to prevent cell division. In some aspects, the feeder cells are added to the culture medium prior to the addition of the populations of T cells.

Optionally, the incubation may further include adding non-dividing EBV-transformed lymphoblastoid cells (LCL) as feeder cells. LCL can be irradiated with gamma rays in the range of 6000 to 10,000 rads. The LCL feeder cells in some aspects are provided in any suitable amount, such as a ratio of LCL feeder cells to initial T lymphocytes of at least 10:1.

In some embodiments, the culture conditions include temperature suitable for the growth of human T lymphocytes, for example, at least 25° C., at least 30° C., or 37° C.

As used herein, cell activation or activating occurs in the presence of at least an engineered trimeric CD70 protein disclosed herein and optionally in combination with another stimulating molecule (such as αCD3, CD28, 4-1BB, and/or other activation molecules described herein). In one embodiment, expansion refers to a period following activation wherein the CD3, CD27, or CD28 binding molecule is no longer present. In particular embodiments, expansion refers to a period following activation wherein activating αCD3 molecules and CD27 binding molecules are no longer present. This expansion period can last until the end of culture, when, for example, the cells are formulated for administration. In certain embodiments, expansion may take place in the presence of αCD3 molecules, CD27 binding molecules, such as the engineered CD70 molecules herein, other co-stimulatory molecules, and/or cytokines.

CD3 is a primary signal transduction element of T cell receptors. As indicated previously, CD3 is expressed on all mature T cells.

In exemplary embodiments, the CD3 stimulating molecule (e.g., CD3 binding domain) can be an anti-CD3 antibody, e.g., by way of example, only in some embodiments, the CD3 stimulating molecule is an OKT3 antibody or a binding domain thereof. The OKT3 antibody is described in detail in U.S. Pat. No. 5,929,212; see also U.S. Pat. No. 4,361,549; ATCC® CRL-8001™; and Arakawa et al., J. Biochem. 120, 657-662 (1996).

In particular embodiments, the variable light chain of huOKT3 includes:

(SEQ ID NO: 73)
DIQMTQSPSSLSASVGDRVTITCSASSSVSYMNWYQQTPGKAPKRWIYD
TSKLASGVPSRFSGSGSGTDYTFTISSLQPEDIATYYCQQWSSNPFTFG
QGTKLQITR.

In particular embodiments, the variable heavy chain of huOKT3 includes:
(SEQ ID NO: 74)
QVQLVQSGGGVVQPGRSLRLSCKASGYTFTRYTMHWVRQAPGKGLEWIG
YINPSRGYTNYNQKFKDRFTISRDNSKNTAFLQMDSLRPEDTGVYFCAR
YYDDHYSLDYWGQGTPVTVSS.

In particular embodiments, the CDR regions of huOKT3 include:
CDRH1:
(SEQ ID NO: 75)
GYTFTRYTMH;

CDRH2:
(SEQ ID NO: 76)
INPSRGYTNYNQKFKD;

CDRH3:
(SEQ ID NO: 77)
YYDDHYSLDY;

CDRL1:
(SEQ ID NO: 78)
SASSSVSYMN;

CDRL2:
(SEQ ID NO: 79)
DTSKLAS; and

CDRL3:
(SEQ ID NO: 80)
QQWSSNPFT.

In particular embodiments, the CD3 binding domain
is derived from the OKT3 antibody with the
following CDRs:
CDRH1 (KASGYTFTRYTMH (SEQ ID NO: 81)), CDRH2 (INPSRGYTNYNQKFKD (SEQ ID NO: 76)), and

CDRH3 (YYDDHYCLDY (SEQ ID NO: 82)),

CDRL1 (SASSSVSYMN (SEQ ID NO: 78)),

CDRL2 (RWIYDTSKLAS (SEQ ID NO: 83)), and

CDRL3 (QQWSSNPFT (SEQ ID NO: 80)).

The following sequence is an scFv derived from
OKT3 which retains the capacity to bind
CD3:
(SEQ ID NO: 84)
QVQLQQSGAELARPGASVKMSCKASGYTFTRYTMHWVKQRPGQGLEWIG
YINPSRGYTNYNQKFKDKATLTTDKSSSTAYMQLSSLTSEDSAVYYCAR
YYDDHYCLDYWGQGTTLTVSSSGGGGSGGGGSGGGGSQIVLTQSPAIMS
ASPGEKVTMTCSASSSVSYMNWYQQKSGTSPKRWIYDTSKLASGVPAHF
RGSGSGTSYSLTISGMEAEDAATYYCQQWSSNPFTFGSGTKLEINR.

In particular embodiments, the CD3 binding domain
is derived from the 20G6-F3 antibody with the
following CDRs:
CDRL1 (QSLVHNNGNTY (SEQ ID NO: 85)),

CDRL2 (KVS), CDRL3 (GQGTQYPFT (SEQ ID NO: 86));

CDRH1 (GFTFTKAW (SEQ ID NO: 87)),

CDRH2 (IKDKSNSYAT (SEQ ID NO: 88)), and

CDRH3 (RGVYYALSPFDY (SEQ ID NO: 89)).

In particular embodiments, the CD3 binding domain
is an scFv derived from the 4B4-D7 antibody with
the following CDRs:
CDRL1 (QSLVHDNGNTY (SEQ ID NO: 90)),

CDRL2 (KVS), CDRL3 (GQGTQYPFT (SEQ ID NO: 86)),

CDRH1 (GFTFSNAW (SEQ ID NO: 91)),

CDRH2 (IKARSNNYAT (SEQ ID NO: 92)), and

CDRH3 (RGTYYASKPFDY (SEQ ID NO: 93)).

In particular embodiments, the CD3 binding domain
is derived from the 4E7-C9 antibody with the
following CDRs:
CDRL1 (QSLEHNNGNTY (SEQ ID NO: 94)),

CDRL2 (KVS), CDRL3 (GQGTQYPFT (SEQ ID NO: 86)),

CDRH1 (GFTFSNAW (SEQ ID NO: 91)),

CDRH2 (IKDKSNNYAT (SEQ ID NO: 95)), and

CDRH3 (RYVHYGIGYAMDA (SEQ ID NO: 96)).

-continued

In particular embodiments, the CD3 binding domain is derived from the 18F5-H10 antibody with the following CDRs:
CDRL1 (QSLVHTNGNTY (SEQ ID NO: 97)),

CDRL2 (KVS), CDRL3 (GQGTHYPFT (SEQ ID NO: 98)),

CDRH1 (GFTFTNAW (SEQ ID NO: 99)),

CDRH2 (KDKSNNYAT (SEQ ID NO: 100)), and

CDRH3 (RYVHYRFAYALDA (SEQ ID NO: 101)).

Additional examples of anti-CD3 antibodies, binding domains, and CDRs can be found in WO2016/116626. TR66 may also be used.

In particular embodiments, CD3 stimulating molecules can be included within culture media at a concentration of at least 0.25 or 0.5 ng/ml or a concentration of 2.5-10 µg/ml. Particular embodiments utilize a CD3 stimulating molecule (e.g., OKT3) at 3, 4, 5, 6, 7, 8, or 9 µg/ml. Particular embodiments utilize a CD3 stimulating molecule (e.g., OKT3) at 5 µg/ml.

Engineered trimeric CD70 proteins to be included within the activating T cell culture conditions are described above in section (i). Engineered trimeric proteins can be included within a culture media at, for example, 0.5-20 µg/ml (e.g., 2 µg/ml, 5 µg/ml, or 10 µg/ml). In particular embodiments, 5 µg/ml of a dimer-trimer is preferred. In particular embodiments, engineered trimer proteins can be included within a culture media at 0.01-20 µg/ml. Particular embodiments utilize 0.1 µg/ml, 0.2 µg/ml, 0.5 µg/ml, 1 µg/ml, 2 µg/ml, 5 µg/ml or 10 µg/ml of a cTRP anchored trimeric CD70 molecule.

Engineered trimeric CD70 proteins to be included within the activating T cell culture conditions are described above in section (i). Engineered trimeric proteins can be included within a culture media at, for example, 0.5-20 µg/ml (e.g., 2 µg/ml, 5 µg/ml, or 10 µg/ml). In particular embodiments, 5 µg/ml of a dimer-trimer is preferred. In particular embodiments, engineered trimer proteins can be included within a culture media at 0.01-20 µg/ml. Particular embodiments utilize 0.1 µg/ml, 0.2 g/ml, 0.5 µg/ml, 1 µg/ml, 2 µg/ml, 5 g/ml or 10 µg/ml of a cTRP anchored trimeric CD70 molecule.

In some examples, CD3 stimulating molecules and engineered trimeric CD70 proteins are provided at a concentration range of 100 µg/ml-0.1 µg/ml. In some examples, CD3 stimulating molecules and engineered trimeric CD70 proteins are provided at a ratio, for example a 1:1 CD3: CD27 ratio of 50:1, 40:1, 30:1, 20:1, 10:1-1:10 (e.g., 5 µg/ml: 5 µg/ml: Dimer-Trimer) or for example a 50:1 ratio (e.g., 5 µg/ml: 0.1 µg/ml; cTRP).

In particular embodiments, activating molecules associated with avi-tags or other similar systems (see, e.g., Methods Mol Biol 2015; 1266:171-184) can be biotinylated and bound to streptavidin beads or other surfaces. This approach can be used to create, for example, a removable CD3 and/or CD27 activation system. Thus, in certain embodiments, activating and costimulatory molecules as described herein, such as anti-CD3 antibodies, engineered CD70 molecules, and the like, may be adsorbed via affinity pairing or chemical coupling to a surface. Non-limiting examples of affinity pairs include biotin-streptavidin pair, an antibody-antigen pair, and an Fc receptor-IgG pair.

Molecules that stimulate other T cell activating epitopes may also be included within T cell activating culture conditions. Examples of additional T cell stimulating epitopes in addition to CD3 and CD27 include CD2, CD4, CD5, CD7, CD8, CD28, CD30, CD40, CD56, CD83, CD90, CD95, 4-1BB (CD 137), B7-H3, CTLA-4, Frizzled-1 (FZD1), FZD2, FZD3, FZD4, FZD5, FZD6, FZD7, FZD8, FZD9, FZD10, HVEM, ICOS, IL-1R, LAT, LFA-1, LIGHT, MHCI, MHCII, NKG2D, OX40, ROR2 and RTK.

An exemplary binding domain for CD28 can include or be derived from TGN1412. In particular embodiments, the variable heavy chain of TGN1412 includes:

(SEQ ID NO: 102)
QVQLVQSGAEVKKPGASVKVSCKASGYTFTSYYIHWVRQAPGQGLEWIG

CIYPGNVNTNYNEKFKDRATLTVDTSISTAYMELSRLRSDDTAVYFCTR

SHYGLDWNFDVWGQGTTVTVSS.

In particular embodiments, the variable light chain of TGN1412 includes:

(SEQ ID NO: 103)
DIQMTQSPSSLSASVGDRVTITCHASQNIYVWLNWYQQKPGKAPKLLIY

KASNLHTGVPSRFSGSGSGTDFTLTISSLQPEDFATYYCQQGQTYPYTF

GGGTKVEIK.

In particular embodiments, the CDR regions of TGN1412 include: CDRL1 (HASQNIYVWLN (SEQ ID NO: 104)), CDRL2 (KASNLHT (SEQ ID NO: 105)), CDRL3 (QQGQTYPYT (SEQ ID NO: 106)), CDRH1 (GYTFTSYYIH (SEQ ID NO: 107) or SYYIH (SEQ ID NO: 108)), CDRH2 (CIYPGNVNTNYNEK (SEQ ID NO: 109)), and CDRH3 (SHYGLDWNFDV (SEQ ID NO: 110)).

In particular embodiments, a CD28 binding domain (e.g., scFv) is derived from CD80, CD86, or the 9D7 antibody. Additional antibodies that bind CD28 include 9.3, KOLT-2, 15E8, 248.23.2, EX5.3D10, and CD28.3 (deposited as a synthetic single chain Fv construct under GenBank Accession No. AF451974.1; see also Vanhove et al., BLOOD, 15 Jul. 2003, Vol. 102, No. 2, pages 564-570). Further, 1YJD provides a crystal structure of human CD28 in complex with the Fab fragment of a mitogenic antibody (5.11A1). In particular embodiments, antibodies that do not compete with 9D7 are selected.

In particular embodiments, a CD80/CD86 binding domain includes the CDRs: CDRL1 (SVSSSISSSNLH (SEQ ID NO: 111)), CDRL2 (GTSNLAS (SEQ ID NO: 112)), CDRL3 (QQWSSYPLT (SEQ ID NO: 113)), CDRH1 (DYYMH (SEQ ID NO: 114)), CDRH2 (WIDPENGNTLYDPKFQG (SEQ ID NO: 115)), and CDRH3 (EGLFFAY (SEQ ID NO: 116)). In particular embodiments a CD80/CD86 binding domain is derived from one or more monoclonal antibodies described in U.S. Pat. No. 7,531,175.

In particular embodiments, a 4-1BB binding domain includes the CDRs: CDRL1 (RASQSVS (SEQ ID NO: 117)), CDRL2 (ASNRAT (SEQ ID NO: 118)), CDRL3 (QRSNWPPALT (SEQ ID NO: 119)), CDRH1 (YYWS (SEQ ID NO: 120)), CDRH2 (INH), and CDRH3 (YGPGNYDWYFDL (SEQ ID NO: 121)).

In particular embodiments, a 4-1BB binding domain includes the CDRs: CDRL1 (SGDNIGDQYAH (SEQ ID NO: 122)), CDRL2 (QDKNRPS (SEQ ID NO: 123)), CDRL3 (ATYTGFGSLAV (SEQ ID NO: 124)), CDRH1 (GYSFSTYWIS (SEQ ID NO: 125)), CDRH2 (KIYPGDSYTNYSPS (SEQ ID NO: 126)), and CDRH3 (GYGIFDY (SEQ ID NO: 127)).

Additional 4-1BB binding domains can be derived from LOB12, IgG2a, LOB12.3, or IgG1 as described in Taraban et al. Eur J Immunol. 2002 December; 32 (12): 3617-27.

In particular embodiments, a 4-1BB binding domain is derived from a monoclonal antibody described in U.S. Pat. No. 9,382,328. Additional 4-1BB binding domains are described in U.S. Pat. Nos. 6,569,997, 6,303,121, and Mittler et al. Immunol Res. 2004; 29 (1-3): 197-208.

OX40 (CD134) and/or ICOS activation may also be used. OX40 binding domains are described in US20100196359, US20150307617, WO 2015/153513, WO2013/038191, and Melero et al. Clin Cancer Res. 2013 Mar. 1; 19 (5): 1044-53. Exemplary binding domains that can bind and activate ICOS are described in, e.g., US20080279851 and Deng et al. Hybrid Hybridomics. 2004 June; 23 (3): 176-82.

T cell culture conditions can additionally include one or more cytokines, for example, interleukin (IL)-2, IL-7, IL-15, and/or IL-21. IL-2 can be included at a range of 10-1,000 IU/ml (e.g., 50 U/ml); IL-7 at a range of 5-100 ng/ml (e.g., 10 ng/ml); IL-15 at a range of 5-100 ng/ml (e.g., 10 ng/ml); and IL-21 at a range of 5-100 ng/ml. Particular embodiments utilize only IL-2. Particular embodiments utilize IL-7 in combination with IL-15. Particular embodiments utilize IL-2 in combination with IL-7 and IL-15. Particular embodiments utilize IL-2 in combination with IL-15 and IL-21.

In particular embodiments, the engineered trimeric proteins of the disclosure and or the T cell stimulating agents are immobilized on a surface. Such surfaces include, for example, solid surfaces, porous surfaces, semi-porous surfaces, lipid, membrane or membrane-like surfaces, polymeric surfaces, spherical surfaces, non-spherical surfaces, rod-like surfaces, and the like. In particular embodiments, the surface is a solid phase and is a surface of the culture vessel (e.g., bag, cell culture plate, chamber, chromatography column, cross-linked gel, cross-linked polymer, column, culture dish, hollow fiber, microtiter plate, silica-coated glass plate, tube, tubing set, well, vial, other structure or container for culture or cultivation of cells).

In particular embodiments, a surface can be added to a culture media, or the media may be added to a culture container or vessel, including a surface. Such surfaces can include, for example, solid surfaces, porous surfaces, semi-porous surfaces, lipid, membrane or membrane-like surfaces, polymeric surfaces, spherical surfaces, non-spherical surfaces, rod-like surfaces, beads, hollow fibers, resins, membranes, and polymers.

Exemplary beads include magnetic beads, polymeric beads, and resin beads (e.g., Strep-Tactin® Sepharose, Strep-Tactin® Superflow, and Strep-Tactin® MacroPrep IBA GmbH, Gottingen)). Anti-CD3/anti-CD28 beads are commercially available reagents for T cell expansion (Invitrogen). These beads are uniform, 4.5 µm superparamagnetic, sterile, non-pyrogenic polystyrene beads coated with a mixture of affinity purified monoclonal antibodies against the CD3 and CD28 cell surface molecules on human T cells. Hollow fibers are available from TerumoBCT Inc. (Lakewood, Colo., USA). Resins include metal affinity chromatography (IMAC) resins (e.g., TALON® resins (Westburg, Leusden)). Membranes include paper as well as the membrane substrate of a chromatography matrix (e.g., a nitrocellulose membrane or a polyvinylidene difluoride (PVDF) membrane).

Exemplary polymers include polysaccharides, such as polysaccharide matrices. Such matrices include agarose gels (e.g., Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare.

Synthetic polymers that may be used include polyacrylamide, polymethacrylate, a co-polymer of polysaccharide and agarose (e.g., a polyacrylamide/agarose composite) or a polysaccharide and N,N'-methylenebisacrylamide. An example of a copolymer of a dextran and N,N'-methylenebisacrylamide is the Sephacryl® (Pharmacia Fine Chemicals, Inc., Piscataway, NJ) series of materials.

Particular embodiments may utilize silica particles coupled to a synthetic or to a natural polymer, such as polysaccharide grafted silica, polyvinylpyrrolidone grafted silica, polyethylene oxide grafted silica, poly(2-hydroxyethylaspartamide) silica, and poly(N-isopropylacrylamide) grafted silica.

T-cell activating agents can be attached to a surface of choice through covalent bonds or can be reversibly immobilized through non-covalent attachments. In certain embodiments, activating and costimulatory molecules as described herein, such as anti-CD3 antibodies, engineered CD70 molecules, and the like, may be adsorbed via affinity pairing or chemical coupling to a surface. Non-limiting examples of affinity pairs include biotin-streptavidin pair, an antibody-antigen pair, and an Fc receptor-IgG pair.

In particular embodiments, T-cell activating agents can be added to a culture media in soluble form. That is, the T-cell activating agent is not bound to a surface. In soluble form, trimeric CD70 proteins may be provided at concentrations of, for example, 0.001-5 µg/ml (e.g., 0.001 µg/ml, 0.005 µg/ml, 0.01 µg/ml, 0.05 µg/ml, 0.1 µg/ml, or 0.2 µg/ml. Additional exemplary concentrations include, for example, 1 µg/ml, 5 µg/ml, 6 µg/ml, 7 µg/ml, 8 µg/ml, 9 g/ml, 10 µg/ml, 15 µg/ml, 20 µg/ml, 25 µg/ml, 30 µg/ml, 35 µg/ml, 40 µg/ml, 45 µg/ml, 50 µg/ml, 55 µg/ml, 60 µg/ml, or more.

When in soluble form, T-cell activating agents can be coupled with another molecule, such as polyethylene glycol (PEG) molecule. Any suitable PEG molecule can be used. Typically, PEG molecules up to a molecular weight of 1000 Da are soluble in water or culture media. In some cases, such PEG based reagent can be prepared using commercially available activated PEG molecules (for example, PEG-NHS derivatives available from NOF North America Corporation, Irvine, Calif., USA, or activated PEG derivatives available from Creative PEGWorks, Chapel Hills, N.C., USA).

In particular embodiments, a T-cell activating culture media includes a FACS-sorted T cell population cultured within RPMI with HEPES, 5-15% human serum, 1-3% L-Glutamine, 0.5-1.5% Pen/strep, $0.25 \times 10^{-4}$-$0.75 \times 10^{-4}$ M β-MercaptoEthanol, and αCD3$^+$ CD70$^{tri}$ with 25-75 U/ml rhIL-2. The culture is carried out on a flat-bottom well plate with $0.1$-$0.5 \times 10e^6$ plated cells/well. On Day 3, post activation cells are transferred to a TC-treated plate (>αCD3 or αCD3$^+$ CD70$^{tri}$ stimulation OFF).

In particular embodiments, a T-cell activating culture media includes a FACS-sorted CD8$^+$ T population cultured within RPMI with HEPES, 10% human serum, 2% L-Glutamine, 1% Pen/strep, $0.5 \times 10^{-4}$ M β-MercaptoEthanol, and αCD3$^+$ CD70$^{tri}$ with 50 U/ml rhIL-2. The culture is carried out on a flat-bottom non-tissue culture (TC)-treated 96/48-well plate with $0.1$-$0.5 \times 10e^6$ plated cells/well. On Day 3, post activation cells are transferred to TC-treated plate (>αCD3/αCD3$^+$ CD70$^{tri}$ stimulation OFF).

In particular embodiments, for soluble cTRP activating conditions, cells can simply be washed and resuspended in fresh media before transfer into a new plate.

In some examples, durations of a cell activation period are 1, 2, 3, 4, or 5 days and durations of a cell expansion period are 5, 6, 7, 8, 9, or 10 days. In more particular examples, a cell activation period can be 3 days, and an expansion period can be 5, 6, 7, 8, 9, or 10 days. In other examples, a cell activation period can be 1, 2, 3, 4, or 5 days and an expansion period can be 7 days. In certain embodiments, the cell activation period is 3 days and the expansion period is 7 days. Within these examples of time periods, αCD3 (e.g., OKT3) and an engineered protein disclosed herein can be present at a 1:1 ratio (e.g., 5 µg/ml: 5 µg/ml).

(v) Genetically Modifying T Cell Populations to Express Recombinant Molecules. In particular embodiments, T cell populations are genetically modified to express chimeric antigen receptors (CAR) or other molecules, such as engineered TCR or TCR/CAR hybrids. Accordingly, in some embodiments, the T cells manufactured ex vivo with the use of the trimeric CD70 proteins herein may further be genetically modified to express CARs, TCRs, or TCR/CAR hybrids.

As described previously, CAR proteins include several distinct subcomponents that allow the genetically modified T cells to recognize and kill unwanted cells, such as cancer cells or virally-infected. The subcomponents include at least an extracellular component and an intracellular component. The extracellular component includes a binding domain that specifically binds a marker that is preferentially present on the surface of unwanted cells. When the binding domain binds such markers, the intracellular component activates the T cell to destroy the bound cell. CAR additionally include a transmembrane domain that links the extracellular component to the intracellular component and other subcomponents that can increase the CAR's function. For example, the inclusion of one or more linkers, such as a spacer region, can allow the CAR to have additional conformational flexibility, often increasing the binding domain's ability to bind the targeted cell marker.

(v-a) Binding Domains of Extracellular Components. Binding domains that can be expressed on the T cells include any substance that binds to a cellular marker to form a complex. The choice of binding domain can depend upon the type and number of cellular markers that define the surface of a target cell. Examples of binding domains include cellular marker ligands, receptor ligands, antibodies, peptides, peptide aptamers, receptors (e.g., T cell receptors), or combinations and engineered fragments or formats thereof.

Antibodies are one example of binding domains and include whole antibodies or binding fragments of an antibody, e.g., Fv, Fab, Fab', F(ab')2, and single chain (sc) forms and fragments thereof that bind specifically to a cellular marker. Antibodies or antigen binding fragments can include all or a portion of polyclonal antibodies, monoclonal antibodies, human antibodies, humanized antibodies, synthetic antibodies, non-human antibodies, recombinant antibodies, chimeric antibodies, bispecific antibodies, mini bodies, and linear antibodies. Functional fragments thereof, include a single-domain antibody such as a heavy chain variable domain (VH), a light chain variable domain (VL), and a variable domain (VHH) of camelid derived nanobody and the like.

In some instances, scFvs can be prepared according to methods known in the art (see, for example, Bird et al., (1988) Science 242:423-426 and Huston et al., (1988) Proc. Natl. Acad. Sci. USA 85:5879-5883). ScFv molecules can be produced by linking VH and VL regions of an antibody together using flexible polypeptide linkers. If a short polypeptide linker is employed (e.g., between 5-10 amino acids), intrachain folding is prevented. Interchain folding is also required to bring the two variable regions together to form a functional epitope binding site. For examples of linker orientations and sizes, see, e.g., Hollinger et al. 1993 Proc Natl Acad. Sci. U.S.A. 90:6444-6448, US 2005/0100543, US 2005/0175606, US 2007/0014794, and WO2006/020258 and WO2007/024715.

An scFv can include a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. In particular embodiments, the linker may include any naturally occurring amino acid. Generally, linkers that are used to connect the VH and VL of an scFv are five to 35 amino acids in length. In particular embodiments, a VH-VL linker includes from five to 35, ten to 30 amino acids, or from 15 to 25 amino acids. Variation in the linker length may retain or enhance activity, giving rise to superior efficacy in activity studies.

In some embodiments, the linker includes the amino acids glycine and serine. In particular embodiments, the linker includes sets of glycine and serine repeats such as from one to ten repeats of (GlyxSery) n, wherein x and y are independently an integer from 0 to 10 provided that x and y are not both 0 and wherein n is an integer of 1, 2, 3, 4, 5, 6, 7, 8, 9 or 10) and wherein linked VH-VL regions form a functional immunoglobulin-like binding domain (e.g., scFv, scTCR). Particular examples include (Gly4Ser)n (SEQ ID NO: 128), (Gly3Ser)n (Gly4Ser)n (SEQ ID NO: 129), (Gly3Ser)n(Gly2Ser)n (SEQ ID NO: 130), (Gly3Ser)n (Gly4Ser) 1 (SEQ ID NO: 131), (Gly4Ser) 1 (SEQ ID NO: 21), (Gly3Ser) 1 (SEQ ID NO: 8), or (Gly2Ser) 1. In particular embodiments, the linker is (Gly4Ser) 4 (SEQ ID NO: 132) or (Gly4Ser) 3 (SEQ ID NO: 133). Such linkers can also be used to link T cell receptor Vα/β and Cα/β chains (e.g., Vα-Cα, Vβ-Cβ, Vα-Vβ).

Additional examples include scFv-based grababodies and soluble VH domain antibodies. These antibodies form binding regions using only heavy chain variable regions. See, for example, Jespers et al., Nat. Biotechnol. 22:1161, 2004; Cortez-Retamozo et al., Cancer Res. 64:2853, 2004; Baral et al., Nature Med. 12:580, 2006; and Barthelemy et al., J. Biol. Chem. 283:3639, 2008.

In some instances, it is beneficial for the binding domain to be derived from the same species it will ultimately be used in. For example, for use in humans, it may be beneficial for the antigen binding domain to include a human antibody, humanized antibody, or a fragment or engineered form thereof. Antibodies from human origin or humanized antibodies have lowered, or no immunogenicity in humans and have a lower number of non-immunogenic epitopes compared to non-human antibodies. Antibodies and their engineered fragments will generally be selected to have a reduced level or no antigenicity in human subjects.

In particular embodiments, the binding domain includes a humanized antibody or an engineered fragment thereof. In some aspects, a non-human antibody is humanized, where one or more amino acid residues of the antibody are modified to increase similarity to an antibody naturally produced in a human or fragment thereof. These nonhuman amino acid residues are often referred to as "import" residues, which are typically taken from an "import" variable domain. As provided herein, humanized antibodies or antibody fragments include one or more CDRs from nonhuman immunoglobulin molecules and framework regions wherein the amino acid residues, including the framework, are derived completely or mostly from human germline. In one aspect, the antigen binding domain is humanized. A humanized antibody can be produced using a variety of techniques known in the art, including CDR-grafting (see, e.g., EP 239,400; WO 91/09967; and U.S. Pat. Nos. 5,225,539, 5,530,101, and 5,585,089), veneering or resurfacing (see, e.g., EP 592, 106 and EP 519,596; Padlan, 1991, Molecular Immunology, 28 (4/5): 489-498; Studnicka et al., 1994, Protein Engineering, 7 (6): 805-814; and Roguska et al., 1994, PNAS, 91:969-973), chain shuffling (see, e.g., U.S. Pat. No. 5,565,332), and techniques disclosed in, e.g., US 2005/0042664, US 2005/0048617, U.S. Pat. Nos. 6,407,213, 5,766,886, WO 9317105, Tan et al., J. Immunol., 169:1119-25 (2002), Caldas et al., Protein Eng., 13 (5): 353-60 (2000), Morea et al., Methods, 20 (3): 267-79 (2000), Baca et al., J. Biol. Chem., 272 (16): 10678-84 (1997), Roguska et al., Protein Eng., 9 (10): 895-904 (1996), Couto et al., Cancer Res., 55 (23 Supp): 5973s-5977s (1995), Couto et al., Cancer Res., 55 (8): 1717-22 (1995), Sandhu J S, Gene, 150 (2): 409-10 (1994), and Pedersen et al., J. Mol. Biol., 235 (3): 959-73 (1994). Often, framework residues in the framework regions will be substituted with the corresponding residue from the CDR donor antibody to alter, for example, improve, cellular marker binding. These framework substitutions are identified by methods well-known in the art, e.g., by modeling of the interactions of the CDR and framework residues to identify framework residues important for cellular marker binding and sequence comparison to identify unusual framework residues at particular positions. (See, e.g., U.S. Pat. No. 5,585,089; and Riechmann et al., 1988, Nature, 332:323).

Antibodies that specifically bind a particular cellular marker can be prepared using methods of obtaining monoclonal antibodies, methods of phage display, methods to generate human or humanized antibodies, or methods using a transgenic animal or plant engineered to produce antibodies as is known to those of ordinary skill in the art (see, for example, U.S. Pat. Nos. 6,291,161 and 6,291,158). Phage display libraries of partially or fully synthetic antibodies are available and can be screened for an antibody or fragment thereof that can bind to a cellular marker. For example, binding domains may be identified by screening a Fab phage library for Fab fragments that specifically bind to a cellular marker of interest (see Hoet et al., Nat. Biotechnol. 23:344, 2005). Phage display libraries of human antibodies are also available. Additionally, traditional strategies for hybridoma development using a cellular marker of interest as an immunogen in convenient systems (e.g., mice, HuMAb mouse® (GenPharm Int'l. Inc., Mountain View, CA), TC mouse® (Kirin Pharma Co. Ltd., Tokyo, JP), KM-mouse® (Medarex, Inc., Princeton, NJ), llamas, chicken, rats, hamsters, rabbits, etc.) can be used to develop binding domains. In particular embodiments, antibodies specifically bind to a cellular marker preferentially expressed by a particular unwanted cell type and do not cross react with nonspecific components or unrelated targets. Once identified, the amino acid sequence of the antibody and gene sequence encoding the antibody can be isolated and/or determined.

An alternative source of binding domains includes sequences that encode random peptide libraries or sequences that encode an engineered diversity of amino acids in loop regions of alternative non-antibody scaffolds, such as scTCR (see, e.g., Lake et al., Int. Immunol. 11:745, 1999; Maynard et al., J. Immunol. Methods 306:51, 2005; U.S. Pat. No. 8,361,794), fibrinogen domains (see, e.g., Weisel et al., Science 230:1388, 1985), Kunitz domains (see, e.g., U.S. Pat. No. 6,423,498), designed ankyrin repeat proteins (DARPins; Binz et al., J. Mol. Biol. 332:489, 2003 and Binz et al., Nat. Biotechnol. 22:575, 2004), fibronectin binding domains (adnectins or monobodies; Richards et al., J. Mol. Biol. 326:1475, 2003; Parker et al., Protein Eng. Des. Selec. 18:435, 2005 and Hackel et al. (2008) J. Mol. Biol. 381: 1238-1252), cysteine-knot miniproteins (Vita et al., 1995, Proc. Nat'l. Acad. Sci. (USA) 92:6404-6408; Martin et al., 2002, Nat. Biotechnol. 21:71, 2002 and Huang et al. (2005) Structure 13:755, 2005), tetratricopeptide repeat domains (Main et al., Structure 11:497, 2003 and Cortajarena et al., ACS Chem. Biol. 3:161, 2008), leucine-rich repeat domains (Stumpp et al., J. Mol. Biol. 332:471, 2003), lipocalin domains (see, e.g., WO 2006/095164, Beste et al., Proc. Nat'l. Acad. Sci. (USA) 96:1898, 1999 and Schönfeld et al., Proc. Nat'l. Acad. Sci. (USA) $10^6$:8198, 2009), V-like domains (see, e.g., US 2007/0065431), C-type lectin domains (Zelensky and Gready, FEBS J. 272:6179, 2005; Beavil et al., Proc. Nat'l. Acad. Sci. (USA) 89:753, 1992 and Sato et al., Proc. Nat'l. Acad. Sci. (USA) 100:7779, 2003), mAb2 or Fc-region with antigen binding domain (Fcab™ (F-Star Biotechnology, Cambridge UK; see, e.g., WO 2007/098934 and WO 2006/072620), armadillo repeat proteins (see, e.g., Madhurantakam et al., Protein Sci. 21:1015, 2012; WO 2009/040338), affilin (Ebersbach et al., J. Mol. Biol. 372:172, 2007), affibody, avimers, knottins, fynomers, atrimers, cytotoxic T-lymphocyte associated protein-4 (Weidle et al., Cancer Gen. Proteo. 10:155, 2013), or the like (Nord et al., Protein Eng. 8:601, 1995; Nord et al., Nat. Biotechnol. 15:772, 1997; Nord et al., Euro. J. Biochem. 268:4269, 2001; Binz et al., Nat. Biotechnol. 23:1257, 2005; Boersma and Plückthun, Curr. Opin. Biotechnol. 22:849, 2011).

Peptide aptamers include a peptide loop (which is specific for a cellular marker) attached at both ends to a protein scaffold. This double structural constraint increases the binding affinity of peptide aptamers to levels comparable to antibodies. The variable loop length is typically 8 to 20 amino acids, and the scaffold can be any protein that is stable, soluble, small, and non-toxic. Peptide aptamer selection can be made using different systems, such as the yeast two-hybrid system (e.g., Gal4 yeast-two-hybrid system) or the LexA interaction trap system.

In particular embodiments, a binding domain is a scT cell receptor (scTCR) including Vα/β and Cα/β chains (e.g., Vα-Cα, Vβ-Cβ, Vα-Vβ) or including a Vα-Cα, Vβ-Cβ, Vα-Vβ pair specific for a cellular marker of interest (e.g., peptide-MHC complex).

Binding domains can be selected to bind numerous cellular markers associated with unwanted cell types, such as cancer cell markers or markers associated with virally-infected cells. Exemplary cellular markers include A33; BAGE; Bcl-2; β-catenin; BCMA; B7H4; BTLA; CA125; CA19-9; CD3, CD5; CD19; CD20; CD21; CD22; CD25; CD28; CD30; CD33; CD37; CD38; CD40; CD52; CD44v6; CD45; CD56; CD79*b*; CD80; CD81; CD86; CD123; CD134; CD137; CD151; CD171; CD276; CEA; CEACAM6; c-Met; CS-1; CTLA-4; cyclin B1; DAGE; EBNA; EGFR; EGFRvIII; ephrinB2; ErbB2; ErbB3; ErbB4; EphA2; estrogen receptor; FAP; ferritin; α-fetoprotein (AFP); FLT1; FLT4; folate-binding protein; Frizzled; GAGE; G250; GD-2; GHRHR; GHR; GITR; GM2; GPRC5D; gp75; gp100 (Pmel 17); gp130; HLA; HER-2/neu; HPV E6; HPV E7; hTERT; HVEM; IGF1R; IL6R; KDR; Ki-67; Lewis A; Lewis Y; LIFRB; LRP; LRP5; LTBR; MAGE; MART; mesothelin; MUC; MUC1; MUM⁻

1-B; myc; NYESO-1; O-acetyl GD-2; O-acetyl GD3; OSMRß; p53; PD1; PD-L1; PD-L2; PRAME; progesterone receptor; PSA; PSMA; PTCH1; RANK; ras; Robo1; RORI; survivin; TCRa; TCRB; tenascin; TGFBR1; TGFBR2; TLR7; TLR9; TNFR1; TNFR2; TNFRSF4; TWEAK-R; TSTA tyrosinase; VEGF; and WT1.

Also contemplated are binding domains specific for infectious disease agents, for instance, by binding to an infectious agent antigen. These include, for instance, viral antigens or other viral markers, for instance, which are expressed by virally-infected cells. Exemplary viruses include adenoviruses, arenaviruses, bunyaviruses, coronaviruses, flaviviruses, hantaviruses, hepadnaviruses, herpesviruses, papillomaviruses, paramyxoviruses, parvoviruses, picornaviruses, poxviruses, orthomyxoviruses, retroviruses, reoviruses, rhabdoviruses, rotaviruses, spongiform viruses, or togaviruses. In additional embodiments, viral antigen markers include peptides expressed by CMV, cold viruses, Epstein-Barr viruses, flu viruses, hepatitis A, B, and C viruses, herpes simplex, HIV, influenza, Japanese encephalitis, measles, polio, rabies, respiratory syncytial, rubella, smallpox, varicella zoster or West Nile virus.

As further particular examples, cytomegaloviral antigens include envelope glycoprotein B and CMV pp65; Epstein-Barr antigens include EBV EBNAI, EBV P18, and EBV P23; hepatitis antigens include the S, M, and L proteins of HBV, the pre-S antigen of HBV, HBCAG DELTA, HBV HBE, hepatitis C viral RNA, HCV NS3 and HCV NS4; herpes simplex viral antigens include immediate early proteins and glycoprotein D; HIV antigens include gene products of the gag, pol, and env genes such as HIV gp32, HIV gp41, HIV gp120, HIV gp160, HIV P17/24, HIV P24, HIV P55 GAG, HIV P66 POL, HIV TAT, HIV GP36, the Nef protein and reverse transcriptase; influenza antigens include hemagglutinin and neuraminidase; Japanese encephalitis viral antigens include proteins E, M-E, M-E-NS1, NS1, NS1-NS2A and 80% E; measles antigens include the measles virus fusion protein; rabies antigens include rabies glycoprotein and rabies nucleoprotein; respiratory syncytial viral antigens include the RSV fusion protein and the M2 protein; rotaviral antigens include VP7sc; rubella antigens include proteins E1 and E2; and varicella zoster viral antigens include gpl and gpll.

Additional particular exemplary viral antigen sequences include:

| Source | Sequence |
| --- | --- |
| Nef (66-97): | VGFPVTPQVPLRPMTYKAAVDLSHFLKEKGGL (SEQ ID NO: 134) |
| Nef (116-145) | HTQGYFPDWQNYTPGPGVRYPLTFGWLYKL (SEQ ID NO: 135) |
| Gag p17 (17-35) | EKIRLRPGGKKKYKLKHIV (SEQ ID NO: 136) |
| Gag p17-p24 (253-284) | NPPIPVGEIYKRWIILGLNKIVRMYSPTSILD (SEQ ID NO: 137) |
| Pol 325-355 (RT 158-188) | AIFQSSMTKILEPFRKQNPDIVIYQYMDDLY (SEQ ID NO: 138) |

See Fundamental Virology, Second Edition, eds. Fields, B. N. and Knipe, D. M. (Raven Press, New York, 1991) for additional examples of viral antigens.

Binding domains for CD19 include FMC63, SJ25C1 (Bejcek et al. Cancer Res 2005, PMID 7538901) and HD37 (Pezutto et al. JI 1987, PMID 2437199).

In particular embodiments, an scFV sequence that binds human CD19 includes:

```
                                     (SEQ ID NO: 139)
MALPVTALLLPLALLLHAEVKLQQSGAELVRPGSSVKISCKASGYAFSS

YWMNWVKQRPGQGLEWIGQIYPGDGDTNYNGKFKGQATLTADKSSSTAY

MQLSGLTSEDSAVYFCARKTISSVVDFYFDYWGQGTTVTVSSGGGGSGG

GGSGGGGSDIELTQSPKFMSTSVGDRVSVTCKASQNVGTNVAWYQQKPG

QSPKPLIYSATYRNSGVPDRFTGSGSGTDFTLTITNVQSKDLADYFCQQ

YNRYPYTSGGGTKLEIKRAAAIEVMYPPPYLDNEKSNGTIIHVKGKHLC

PSPLFPGPSKPFW.
```

An scFV sequence that binds human ROR1 includes:

```
                                     (SEQ ID NO: 140)
MLLLVTSLLLCELPHPAFLLIPQEQLVESGGRLVTPGGSLTLSCKASGF

DFSAYYMSWVRQAPGKGLEWIATIYPSSGKTYYATWVNGRFTISSDNAQ

NTVDLQMNSLTAADRATYFCARDSYADDGALFNIWGPGTLVTISSGGGG

SGGGGSGGGGSELVLTQSPSVSAALGSPAKITCTLSSAHKTDTIDWYQQ

LQGEAPRYLMQVQSDGSYTKRPGVPDRFSGSSSGADRYLIIPSVQADDE

ADYYCGADYIGGYVFGGGTQLTVTGESKYGPPCPPCPMFWVLVVVGGVL

ACYSLLV.
```

In particular embodiments, the CDR regions binding ROR1 include a variable light chain including a CDRL1 sequence including ASGFDFSAYYM (SEQ ID NO: 141), a CDRL2 sequence including TIYPSSG (SEQ ID NO: 142), and a CDRL3 sequence including ADRATYFCA (SEQ ID NO: 143). In particular embodiments, the CDR regions binding ROR1 include a variable heavy chain including a CDRH1 sequence including DTIDWY (SEQ ID NO: 144), a CDRH2 sequence including VQSDGSYTKRPGVPDR (SEQ ID NO: 145), and a CDRH3 sequence including YIGGYVFG (SEQ ID NO: 146).

In particular embodiments, the binding domain of the R11 antibody is a human or humanized binding domain (e.g., scFv) including a variable light chain including a CDRL1 sequence including QASQSIDSNLA (SEQ ID NO: 147), a CDRL2 sequence including RASNLAS (SEQ ID NO: 148), and a CDRL3 sequence including LGGVGNVSYRTS (SEQ ID NO: 149). In particular embodiments, the binding domain of the R11 antibody is a human or humanized binding domain (e.g., scFv) including a variable heavy chain including a CDRH1 sequence including DYPIS (SEQ ID NO: 150), a CDRH2 sequence including FINSGGSTWY-ASWVKG (SEQ ID NO: 151), and a CDRH3 sequence including GYSTYYCDFNI (SEQ ID NO: 152).

In particular embodiments, the binding domain of the R12 antibody is a human or humanized binding domain (e.g., scFv) including a variable light chain including a CDRL1 sequence including TLSSAHKTDTID (SEQ ID NO: 153), a CDRL2 sequence including GSYTKRP (SEQ ID NO: 154), and a CDRL3 sequence including GADYIGGYV (SEQ ID NO: 155). In particular embodiments, the binding domain of the R12 antibody is a human or humanized binding domain (e.g., scFv) including a variable heavy chain including a CDRH1 sequence including AYYMS (SEQ ID NO: 156), a CDRH2 sequence including TIYPSSGKTYYATWVNG (SEQ ID NO: 157), and a CDRH3 sequence including DSYADDGALFNI (SEQ ID NO: 158).

A number of additional antibodies specific for ROR1 are known to those of skill in the art and can be readily characterized for sequence, epitope binding, and affinity. See, for example, WO2008076868, WO/2008103849, WO201008069, WO2010124188, WO2011079902, WO2011054007, WO2011159847, WO2012076066, WO2012076727, WO 2012045085, and WO2012097313. Additional examples of antibodies that bind ROR1 include the Y31 antibody and 2A2 antibody.

In particular embodiments, an scFV sequence that binds human CD33 includes a variable light chain region including sequence (SEQ ID NO: 159)
DIVLTQSPTIMSASPGERVTMTCTASSSVNYIHWYQQKSGDSPKRWIFD

TSKVASGVPARFSGSGSGTSYSLTISTMEAEDAATYYCQQWRSYPLTFG

DGTRLELKRADAAPTVS, and a variable heavy chain region including sequence (SEQ ID NO: 160)
DIVLTQSPAIMSASPGEKVTMTCSANSSVSYIHWYQQKSGTSPKRWIFD

TSKLASGVPARFSGSGSGTSYSLTISTMEAEDAATYYCQQWTSHPLTFG

TGTKLQLKRADAAPTVS.

An exemplary binding domain for PD-L1 can include or be derived from Avelumab or Atezolizumab. In particular embodiments, the variable heavy chain of Avelumab includes:

(SEQ ID NO: 161)
EVQLLESGGGLVQPGGSLRLSCAASGFTFSSYIMMWVRQAPGKGLEWVS

SIYPSGGITFYADTVKGRFTISRDNSKNTLYLQMNSLRAEDTAVYYCAR

IKLGTVTTVDYWGQGTLVTVSS.

In particular embodiments, the variable light chain of Avelumab includes:

(SEQ ID NO: 162)
QSALTQPASVSGSPGQSITISCTGTSSDVGGYNYVSWYQQHPGKAPKLM

IYDVSNRPSGVSNRFSGSKSGNTASLTISGLQAEDEADYYCSSYTSSST

RVFGTGTKVTVL.

In particular embodiments, the CDR regions of Avelumab include: CDRH1: SGFTFSSYIMM (SEQ ID NO: 163); CDRH2: SIYPSGGITFYADTVKG (SEQ ID NO: 164); CDRH3: IKLGTVTTVDY (SEQ ID NO: 165); CDRL1: TGTSSDVGGYNYVS (SEQ ID NO: 166); CDRL2: DVSNRPS (SEQ ID NO: 167); and CDRL3: SSYTSSSTRV (SEQ ID NO: 168).

In particular embodiments, the variable heavy chain of Atezolizumab includes:

(SEQ ID NO: 169)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSS.

In particular embodiments, the variable light chain of Atezolizumab includes:

(SEQ ID NO: 170)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIK.

In particular embodiments, the CDR regions of Atezolizumab include: CDRH1: SGFTFSDSWIH (SEQ ID NO: 171); CDRH2: WISPYGGSTYYADSVKG (SEQ ID NO: 172); CDRH3: RHWPGGFDY (SEQ ID NO: 173); CDRL1: RASQDVSTAVA (SEQ ID NO: 174); CDRL2: SASFLYS (SEQ ID NO: 175); and CDRL3: QQYLYHPAT (SEQ ID NO: 176).

Binding domains for CD123 are described in WO2013173820A2; PCT/IB2008/002930; PCT/US2015/031580; PCT/US1988/000011; EP19890907981; PCT/US2014/028961; U.S. Ser. No. 12/082,940; U.S. Ser. No. 11/271,381; U.S. Pat. No. 7,763,242; EP2063907; JP5550905; and U.S. Pat. No. 8,188,231.

Binding domains for CLL-1 are described in U.S. Pat. Nos. 9,914,777; 9,908,946; 9,145,588; 9,248,181; 9,248,182; PCT/NL2016/050507; PCT/NL2013/050693; EP2147594B1; JP5749161; EP20170170370; and PCT/EP2016/051470.

In particular embodiments, the binding domain of a CAR binds the cellular marker MUC16. In particular embodiments, the binding domain is human or humanized and includes a variable light chain including a CDRL1 sequence including SEDIYSG (SEQ ID NO: 177), a CDRL2 sequence including GAS, a CDRL3 sequence including GYSYSSTL (SEQ ID NO: 178). In particular embodiments, the binding domain is human or humanized and includes a variable heavy chain including a CDRH1 sequence including TLGMGVG (SEQ ID NO: 179), a CDRH2 sequence including HIWWDDDKYYNPALKS (SEQ ID NO: 180), and a CDRH3 sequence including IGTAQATDALDY (SEQ ID NO: 181).

In particular embodiments, the binding domain of a CAR binds the cellular marker FOLR. In particular embodiments, the binding domain that binds FOLR is derived from farletuzumab. In particular embodiments, the binding domain includes a variable light chain including a CDRL1 sequence including KASQSVSFAGTSLMH (SEQ ID NO: 182), a CDRL2 sequence including RASNLEA (SEQ ID NO: 183), and a CDRL3 sequence including QQSREYPYT (SEQ ID NO: 184), and a variable heavy chain including a CDRH1 sequence including GYFMN (SEQ ID NO: 185), a CDRH2 sequence including RIHPYDGDTFYNQKFQG (SEQ ID NO: 186), and a CDRH3 sequence including YDGSRAMDY (SEQ ID NO: 187).

An exemplary binding domain for mesothelin can include or be derived from Amatuximab.

In particular embodiments, the variable heavy chain of Amatuximab includes (SEQ ID NO: 188)
QVQLQQSGPELEKPGASVKISCKASGYSFTGYTMNWVKQSHGKSLEWIG

LITPYNGASSYNQKFRGKATLTVDKSSSTAYMDLLSLTSEDSAVYFCAR

GGYDGRGFDYWGSGTPVTVSS.

In particular embodiments, the variable light chain of Amatuximab includes:
DIELTQSPAIM-SASPGEKVTMTCSASSSVSYMHWYQQKSGTSPKR-WIYDTSKLASGVP GRFSGSGSGNSYSLTISSVEAED-DATYYCQQWSKHPLTFGSGTKVEIK (SEQ ID NO: 189).

In particular embodiments, the CDR regions of Amatuximab include:

CDRH1:
GYSFTGYTMN; (SEQ ID NO: 190)

CDRH2:
LITPYNGASSYNQ; (SEQ ID NO: 191)

CDRH3:
GGYDGRGFDY; (SEQ ID NO: 192)

CDRL1:
SASSSVSYM; (SEQ ID NO: 193)

CDRL2:
DTSKLAS; and (SEQ ID NO: 79)

CDRL3:
QQWSKHPLT. (SEQ ID NO: 194)

In particular embodiments, a binding domain of a CAR includes or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region (VL) or to a heavy chain variable region (VH), or both, wherein each CDR includes zero changes or at most one, two, or three changes, from a monoclonal antibody or fragment or derivative thereof that specifically binds to a cellular marker of interest.

In particular embodiments, a binding domain VH region of the present disclosure can be derived from or based on a VH of a known monoclonal antibody and can contain one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the VH of a known monoclonal antibody. An insertion, deletion, or substitution may be anywhere in the VH region, including at the amino- or carboxy-terminus or both ends of this region, provided that each CDR includes zero changes or at most one, two, or three changes and provided a binding domain containing the modified VH region can still specifically bind its target with an affinity similar to the wild type binding domain.

In particular embodiments, a VL region in a binding domain of the present disclosure is derived from or based on a VL of a known monoclonal antibody and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the VL of the known monoclonal antibody. An insertion, deletion, or substitution may be anywhere in the VL region, including at the amino- or carboxy-terminus or both ends of this region, provided that each CDR includes zero changes or at most one, two, or three changes and provided a binding domain containing the modified VL region can still specifically bind its target with an affinity similar to the wild type binding domain.

In particular embodiments, engineered CAR include a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a known or identified TCR Vα, Vβ, Cα, or Cβ, wherein each CDR includes zero changes or at most one, two, or three changes, from a TCR or fragment or derivative thereof that specifically binds to the targeted cellular marker.

In particular embodiments, engineered CAR include Vα, Vβ, Cα, or Cβ regions derived from or based on a Vα, Vβ, Cα, or Cβ of a known or identified TCR (e.g., a high-affinity TCR) and includes one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the Vα, Vβ, Cα, or Cβ of a known or identified TCR. An insertion, deletion or substitution may be anywhere in a Vα, Vβ, Cα, or Cβ region, including at the amino- or carboxy-terminus or both ends of these regions, provided that each CDR includes zero changes or at most one, two, or three changes and provides a target binding domain containing a modified Vα, Vβ, Cα, or Cβ region can still specifically bind its target with an affinity and action similar to wild type.

The precise amino acid sequence boundaries of a given CDR or FR can be readily determined using any of a number of well-known schemes, including those described by: Kabat et al. (1991) "Sequences of Proteins of Immunological Interest," 5th Ed. Public Health Service, National Institutes of Health, Bethesda, Md. (Kabat numbering scheme); Al-Lazikani et al. (1997) J Mol Biol 273:927-948 (Chothia numbering scheme); Maccallum et al. (1996) J Mol Biol 262:732-745 (Contact numbering scheme); Martin et al. (1989) Proc. Natl. Acad. Sci., 86:9268-9272 (AbM numbering scheme); Lefranc M P et al. (2003) Dev Comp Immunol 27 (1): 55-77 (IMGT numbering scheme); and Honegger and Pluckthun (2001) J Mol Biol 309 (3): 657-670 ("Aho" numbering scheme). The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. In particular embodiments, the antibody CDR sequences disclosed herein are according to Kabat numbering.

CAR/TCR hybrids refer to proteins having an element of a TCR and an element of a CAR. For example, a CAR/TCR hybrid could have a naturally occurring TCR binding domain with an effector domain that the TCR binding domain is not naturally associated with. A CAR/TCR hybrid could have a mutated TCR binding domain and an ITAM signaling domain. A CAR/TCR hybrid could have a naturally occurring TCR with an inserted non-naturally occurring spacer region or transmembrane domain.

Particular CAR/TCR hybrids include TRUC® (T Cell Receptor Fusion Construct) hybrids; TCR2 Therapeutics, Cambridge, MA. By way of example, the production of TCR fusion proteins is described in International Patent Publications WO 2018/026953 and WO 2018/067993, and in US 2017/0166622.

In particular embodiments, CAR/TCR hybrids include a "T-cell receptor (TCR) fusion protein" or "TFP." A TFP includes a recombinant polypeptide derived from the various polypeptides, including the TCR that is generally capable of i) binding to a surface antigen on target cells and ii) interacting with other polypeptide components of the intact TCR complex, typically when co-located in or on the surface of a T-cell.

(v-b) Intracellular Signaling Components. The intracellular or otherwise the cytoplasmic signaling components of a CAR are responsible for activation of the cell in which the CAR is expressed. The term "intracellular signaling components" or "intracellular components" is thus meant to include any portion of the intracellular domain sufficient to transduce an activation signal. Intracellular components of expressed CAR can include effector domains. An effector domain is an intracellular portion of a fusion protein or receptor that can directly or indirectly promote a biological or physiological response in a cell when receiving the appropriate signal. In certain embodiments, an effector domain is part of a protein or protein complex that receives a signal when bound, or it binds directly to a target molecule, which triggers a signal from the effector domain. An effector domain may directly promote a cellular response when it contains one or more signaling domains or motifs, such as an immunoreceptor tyrosine-based activation motif (ITAM). In other embodiments, an effector domain will indirectly promote a cellular response by associating with one or more other proteins that directly promote a cellular response, such as co-stimulatory domains.

Effector domains can provide for activation of at least one function of a modified cell upon binding to the cellular marker expressed on an unwanted cell. Activation of the modified cell can include one or more of differentiation, proliferation and/or activation, or other effector functions. In particular embodiments, an effector domain can include an intracellular signaling component including a T cell receptor and a co-stimulatory domain which can include the cytoplasmic sequence from co-receptor or co-stimulatory molecule.

An effector domain can include one, two, three or more receptor signaling domains, intracellular signaling components (e.g., cytoplasmic signaling sequences), co-stimulatory domains, or combinations thereof. Exemplary effector domains include signaling and stimulatory domains selected from: 4-1BB (CD137), CARD11, CD3γ, CD3δ, CD3ε, CD3ζ, CD27, CD28, CD79A, CD79B, DAP10, FcRα, FcRβ (FcεR1b), FcRγ, Fyn, HVEM (LIGHTR), ICOS, LAG3, LAT, Lck, LRP, NKG2D, NOTCH1, pTα, PTCH2, OX40, ROR2, Ryk, SLAMF1, Slp76, TCRα, TCRβ, TRIM, Wnt, Zap70, or any combination thereof. In particular embodiments, exemplary effector domains include signaling and co-stimulatory domains selected from: CD86, FcγRIIa, DAP12, CD30, CD40, PD-1, lymphocyte function-associated antigen-1 (LFA-1), CD2, CD7, LIGHT, NKG2C, B7-H3, a ligand that specifically binds with CD83, CDS, ICAM⁻¹, GITR, BAFFR, SLAMF7, NKp80 (KLRF1), CD127, CD160, CD19, CD4, CD8α, CD8β, IL2R β, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (CD150, IPO-3), BLAME (SLAMF8), SELPLG (CD162), LTBR, GADS, PAG/Cbp, NKp44, NKp30, or NKp46.

Intracellular signaling component sequences that act in a stimulatory manner may include signaling motifs which are known as immunoreceptor tyrosine-based activation motifs or iTAMs. Examples of iTAM including primary cytoplasmic signaling sequences include those derived from CD3γ, CD3δ, CD3ε, CD3ζ, CD5, CD22, CD66d, CD79a, CD79b, and common FcRγ (FCER1G), FcγRIIa, FcRβ (Fcε Rib), DAP10, and DAP12. In particular embodiments, variants of CD3ζ retain at least one, two, three, or all ITAM regions.

In particular embodiments, an effector domain includes a cytoplasmic portion that associates with a cytoplasmic signaling protein, wherein the cytoplasmic signaling protein is a lymphocyte receptor or signaling domain thereof, a protein including a plurality of ITAMs, a co-stimulatory domain, or any combination thereof.

Additional examples of intracellular signaling components include the cytoplasmic sequences of the CD3ζ chain and/or co-receptors that act in concert to initiate signal transduction following binding domain engagement.

A co-stimulatory domain is a domain whose activation can be required for an efficient lymphocyte response to cellular marker binding. Some molecules are interchangeable as intracellular signaling components or co-stimulatory domains. Examples of costimulatory domains include CD27, CD28, 4-1BB (CD 137), OX40, CD30, CD40, PD-1, ICOS, lymphocyte function-associated antigen-1 (LFA-1), CD2, CD7, LIGHT, NKG2C, B7-H3, and a ligand that specifically binds with CD83. For example, CD27 co-stimulation has been demonstrated to enhance expansion, effector function, and survival of human CAR T cells in vitro and augments human T cell persistence and anti-cancer activity in vivo (Song et al. Blood., 2012; 119 (3): 696-706). Further examples of such co-stimulatory domain molecules include CDS, ICAM⁻¹, GITR, BAFFR, HVEM (LIGHTR), SLAMF7, NKp80 (KLRF1), NKp44, NKp30, NKp46, CD160, CD19, CD4, CD8α, CD8B, IL2RB, IL2Rγ, IL7Rα, ITGA4, VLA1, CD49a, ITGA4, IA4, CD49D, ITGA6, VLA-6, CD49f, ITGAD, CDIId, ITGAE, CD103, ITGAL, CDIIa, LFA-1, ITGAM, CDI Ib, ITGAX, CDIIc, ITGBI, CD29, ITGB2, CD18, LFA-1, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, and CD19a.

In particular embodiments, the amino acid sequence of the intracellular signaling component including a variant of CD3ζ (SEQ ID NOs: 205 and 206) and a portion of the 4-1BB (SEQ ID NOs: 207 and 208) intracellular signaling component.

In particular embodiments, the intracellular signaling component includes (i) all or a portion of the signaling domain of CD3ζ, (ii) all or a portion of the signaling domain of 4-1BB, or (iii) all or a portion of the signaling domain of CD3ζ and 4-1BB.

Intracellular components may also include one or more of a protein of a Wnt signaling pathway (e.g., LRP, Ryk, or ROR2), NOTCH signaling pathway (e.g., NOTCH1, NOTCH2, NOTCH3, or NOTCH4), Hedgehog signaling pathway (e.g., PTCH or SMO), receptor tyrosine kinases (RTKs) (e.g., epidermal growth factor (EGF) receptor family, fibroblast growth factor (FGF) receptor family, hepatocyte growth factor (HGF) receptor family, insulin receptor (IR) family, platelet-derived growth factor (PDGF) receptor family, vascular endothelial growth factor (VEGF) receptor family, tropomycin receptor kinase (Trk) receptor family, ephrin (Eph) receptor family, AXL receptor family, leukocyte tyrosine kinase (LTK) receptor family, tyrosine kinase with immunoglobulin-like and EGF-like domains 1 (TIE) receptor family, receptor tyrosine kinase-like orphan (ROR) receptor family, discoidin domain (DDR) receptor family, rearranged during transfection (RET) receptor family, tyrosine-protein kinase-like (PTK7) receptor family, related to receptor tyrosine kinase (RYK) receptor family, or muscle specific kinase (MuSK) receptor family); G-protein-coupled receptors, GPCRs (Frizzled or Smoothened); serine/threonine kinase receptors (BMPR or TGFR); or cytokine receptors (IL1R, IL2R, IL7R, or IL15R).

(v-c) Linkers. As used herein, a linker can be any portion of a CAR molecule that serves to connect two other subcomponents of the molecule. Some linkers serve no purpose other than to link other components, while many linkers serve an additional purpose. Linkers in the context of linking VH and VL of an antibody derived binding domains of scFv are described above. Linkers can also include spacer regions, transmembrane domains (which serve to connect extracellular and intracellular components), and junction amino acids.

Spacer regions are a type of linker region that are used to create appropriate distances and/or flexibility from other linked components. In particular embodiments, the length of a spacer region can be customized for individual cellular markers on unwanted cells to optimize unwanted cell recognition and destruction. The spacer can be of a length that provides for increased responsiveness of the cell following antigen binding, as compared to in the absence of the spacer. In particular embodiments, a spacer region length can be selected based upon the location of a cellular marker epitope, affinity of a binding domain for the epitope, and/or the ability of the modified cells expressing the molecule to proliferate in vitro and/or in vivo in response to cellular marker recognition. Spacer regions can also allow for high expression levels in modified cells.

Exemplary spacers include those having 10 to 250 amino acids, 10 to 200 amino acids, 10 to 150 amino acids, 10 to 100 amino acids, 10 to 50 amino acids, or 10 to 25 amino acids. In particular embodiments, a spacer region is 12 amino acids, 20 amino acids, 21 amino acids, 26 amino acids, 27 amino acids, 45 amino acids, or 50 amino acids.

In particular embodiments, the spacer region is selected from the group including all or a portion of a hinge region sequence from IgG1, IgG2, IgG3, IgG4, or IgD alone or in combination with all or a portion of a CH2 region; all or a portion of a CH3 region; or all or a portion of a CH2 region and all or a portion of a CH3 region.

Exemplary spacers include IgG4 hinge alone, IgG4 hinge linked to CH2 and CH3 domains, or IgG4 hinge linked to the CH3 domain. In particular embodiments, the spacer includes an IgG4 linker of the amino acid sequence: ESKYGPPCPPC (SEQ ID NO: 215). Hinge regions can be modified to avoid undesirable structural interactions such as dimerization with unintended partners.

In particular embodiments, a spacer region includes a hinge region that a type II C-lectin interdomain (stalk) region or a cluster of differentiation (CD) molecule stalk region. As used herein, a "wild type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody.

A "stalk region" of a type II C-lectin or CD molecule refers to the portion of the extracellular domain of the type II C-lectin or CD molecule that is located between the C-type lectin-like domain (CTLD; e.g., similar to CTLD of natural killer cell receptors) and the hydrophobic portion (transmembrane domain). For example, the extracellular domain of human CD94 (GenBank Accession No. AAC50291.1) corresponds to amino acid residues 34-179, but the CTLD corresponds to amino acid residues 61-176, so the stalk region of the human CD94 molecule includes amino acid residues 34-60, which are located between the hydrophobic portion (transmembrane domain) and CTLD (see Boyington et al., Immunity 10:15, 1999; for descriptions of other stalk regions, see also Beavil et al., Proc. Nat'l. Acad. Sci. USA 89:153, 1992; and Figdor et al., Nat. Rev. Immunol. 2:11, 2002). These type II C-lectin or CD molecules may also have junction amino acids between the stalk region and the transmembrane region or the CTLD. In another example, the 233 amino acid human NKG2A protein (GenBank Accession No. P26715.1) has a hydrophobic portion (transmembrane domain) ranging from amino acids 71-93 and an extracellular domain ranging from amino acids 94-233. The CTLD includes amino acids 119-231, and the stalk region includes amino acids 99-116, which may be flanked by additional junction amino acids. Other type II C-lectin or CD molecules, as well as their extracellular ligand-binding domains, stalk regions, and CTLDs, are known in the art (see, e.g., GenBank Accession Nos. NP 001993.2; AAH07037.1; NP 001773.1; AAL65234.1; CAA04925.1; for the sequences of human CD23, CD69, CD72, NKG2A, and NKG2D and their descriptions, respectively).

(v-d) As indicated, transmembrane domains serve to connect the extracellular component and intracellular component through the cell membrane. The transmembrane domain can anchor the expressed molecule in the modified cell's membrane.

The transmembrane domain can be derived either from a natural and/or a synthetic source. When the source is natural, the transmembrane domain can be derived from any membrane-bound or transmembrane protein. Transmembrane domains can include at least the transmembrane region(s) of the α, β or ζ chain of a T-cell receptor, CD28, CD27, CD3 epsilon, CD45, CD4, CD5, CD8, CD9, CD16, CD22; CD33, CD37, CD64, CD80, CD86, CD134, CD137 and CD154. In particular embodiments, a transmembrane domain may include at least the transmembrane region(s) of, e.g., KIRDS2, OX40, CD2, CD27, LFA-1 (CD 11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2RB, IL2Rγ, IL7R a, ITGA1, VLA1, CD49a, ITGA4, IA4, CD49D, ITGA6, VLA-6, CD49f, ITGAD, CDI Id, ITGAE, CD103, ITGAL, CDI Ia, LFA-1, ITGAM, CDI Ib, ITGAX, CDI Ic, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Lyl08), SLAM (SLAMF1, CD150, IPO-3), BLAME (SLAMF8), SELPLG (CD162), LTBR, PAG/Cbp, NKG2D, or NKG2C. In particular embodiments, a variety of human hinges can be employed as well, including the human Ig (immunoglobulin) hinge (e.g., an IgG4 hinge, an IgD hinge), a GS linker (e.g., a GS linker described herein), a KIR2DS2 hinge or a CD8a hinge.

In particular embodiments, a transmembrane domain has a three-dimensional structure that is thermodynamically stable in a cell membrane and generally ranges in length from 15 to 30 amino acids. The structure of a transmembrane domain can include an alpha helix, a beta barrel, a beta sheet, a beta helix, or any combination thereof.

A transmembrane domain can include one or more additional amino acids adjacent to the transmembrane region, e.g., one or more amino acid within the extracellular region of the CAR (e.g., up to 15 amino acids of the extracellular region) and/or one or more additional amino acids within the intracellular region of the CAR (e.g., up to 15 amino acids of the intracellular components). In one aspect, the transmembrane domain is from the same protein that the signaling domain, co-stimulatory domain, or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins to minimize interactions with other unintended members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell. In particular embodiments, the transmembrane domain includes the amino acid sequence of the CD28 transmembrane domain (SEQ ID NOs: 209 and 210).

(v-e) Junction amino acids can be a linker which can be used to connect the sequences of CAR domains when the distance provided by a spacer is not needed and/or wanted. Junction amino acids are short amino acid sequences that can be used to connect co-stimulatory intracellular signaling components. In particular embodiments, junction amino acids are 9 amino acids or less.

Junction amino acids can be a short oligo- or protein linker, preferably between 2 and 9 amino acids (e.g., 2, 3, 4, 5, 6, 7, 8, or 9 amino acids) in length to form the linker. In particular embodiments, a glycine-serine doublet can be used as a suitable junction amino acid linker. In particular embodiments, a single amino acid, e.g., an alanine, a glycine, can be used as a suitable junction amino acid.

(v-f) Control Features Including Tag Cassettes, Transduction Markers, and Suicide Switches. In particular embodiments, CAR can include one or more tag cassettes and/or transduction markers. Tag cassettes and transduction markers can be used to activate, promote proliferation of, detect, enrich for, isolate, track, deplete and/or eliminate genetically modified cells in vitro, in vivo, and/or ex vivo. "Tag cassette" refers to a unique synthetic peptide sequence affixed to, fused to, or that is part of a CAR, to which a cognate binding molecule (e.g., ligand, antibody, or other binding partner) is capable of specifically binding where the binding property can be used to activate, promote proliferation of, detect, enrich for, isolate, track, deplete and/or eliminate the tagged protein and/or cells expressing the tagged protein. Transduction markers can serve the same purposes but are derived from naturally occurring molecules and are often expressed using a skipping element (e.g., SEQ ID NOs: 211-214) that separates the transduction marker from the rest of the CAR molecule.

Tag cassettes that bind cognate binding molecules include, for example, Strep tag (which refers to the original STREP® tag (SEQ ID NO: 202), STREP® tag II (SEQ ID NO: 203) (IBA Institut fur Bioanalytik, Germany); see, e.g., U.S. Pat. No. 7,981,632), His tag (SEQ ID NO: 9), Flag tag (SEQ ID NO: 195), Xpress tag (SEQ ID NO: 196), Avi tag (SEQ ID NO: 10), Calmodulin tag (SEQ ID NO: 197), Polyglutamate tag, HA tag (SEQ ID NO: 198), Myc tag (SEQ ID NO: 199), Softag 1 (SEQ ID NO: 200), Softag 3 (SEQ ID NO: 201), and V5 tag (SEQ ID NO: 204).

Conjugate binding molecules that specifically bind tag cassette sequences disclosed herein are commercially available. For example, Strep tag antibodies are commercially available from suppliers including Abcam, Iba, and Qiagen. His tag antibodies are commercially available from suppliers, including Life Technologies, Pierce Antibodies, and GenScript. Flag tag antibodies are commercially available from suppliers, including Pierce Antibodies, GenScript, and Sigma-Aldrich. Xpress tag antibodies are commercially available from suppliers, including Pierce Antibodies, Life Technologies, and GenScript. Avi tag antibodies are commercially available from suppliers including Pierce Antibodies, IsBio, and Genecopoeia. Calmodulin tag antibodies are commercially available from suppliers including Santa Cruz Biotechnology, Abcam, and Pierce Antibodies. HA tag antibodies are commercially available from suppliers, including Pierce Antibodies, Cell Signal, and Abcam. Myc tag antibodies are commercially available from suppliers, including Santa Cruz Biotechnology, Abcam, and Cell Signal.

Transduction markers may be selected from at least one of a truncated CD19 (tCD19; see Budde et al., Blood 122:1660, 2013); a truncated human EGFR (EGFRt; see Wang et al., Blood 118:1255, 2011); an extracellular domain of human CD34; and/or RQR8 which combines target epitopes from CD34 (see Fehse et al., Mol. Therapy 1 (5 Pt 1); 448-456, 2000) and CD20 antigens (see Philip et al., Blood 124:1277-1278).

In particular embodiments, a polynucleotide encoding an iCaspase9 construct (iCasp9) may be inserted into a CAR construct as a suicide switch.

Control features may be present in multiple copies in a CAR or can be expressed as distinct molecules with the use of a skipping element (e.g., SEQ ID NOs: 211-214). For example, a CAR can have one, two, three, four, or five tag cassettes (e.g., Strep tag), and/or one, two, three, four, or five transduction markers could also be expressed. Exemplary embodiments include a CAR having two His tag cassettes, or a His tag and a Myc tag cassette, or a HA tag and a Calmodulin tag cassette, or a Myc tag and a Strep tag cassette. In particular embodiments, a transduction marker includes EGFRt.

One advantage of including at least one control feature in a CAR is that CAR expressing cells administered to a subject can be depleted using the cognate binding molecule to a tag cassette. In certain embodiments, the present disclosure provides a method for depleting a modified cell expressing a CAR by using an antibody specific for the tag cassette, using a cognate binding molecule specific for the control feature, or by using a second modified cell expressing a CAR and having specificity for the control feature. Elimination of modified cells may be accomplished using depletion agents specific for a control feature. For example, if a Myc tag is used, then an anti-Myc tag antibody or anti-Myc tag scFv fused to or conjugated to a cell-toxic reagent (such as a toxin, radiometal) may be used, or an anti-Myc tag/anti-CD3 bispecific scFv, or an anti-Myc tag CAR T cell may be used.

In certain embodiments, modified cells expressing an engineered molecule may be detected or tracked in vivo by using antibodies that bind with specificity to a control feature (e.g., anti-Tag antibodies) or by other cognate binding molecules that specifically bind the control feature (e.g., binding to Myc tag), which binding partners for the control feature are conjugated to a fluorescent dye, radio-tracer, iron-oxide nanoparticle or other imaging agent known in the art for detection by X-ray, CT-scan, MRI-scan, PET-scan, ultrasound, flow-cytometry, near infrared imaging systems, or other imaging modalities (see, e.g., Yu, et al., Theranostics 2:3, 2012).

Thus, modified cells expressing at least one control feature with a CAR can be, e.g., more readily identified, isolated, sorted, induced to proliferate, tracked, and/or eliminated as compared to a modified cell without a tag cassette.

For additional information regarding CAR, see WO2000/014257; WO2012/129514; WO2013/126726; WO2013/166321; WO2013/071154; WO2013/123061; WO2014/055668; WO2014/031687; US2002131960; US2013287748; US20130149337; U.S. Pat. Nos. 6,410,319; 6,451,995; 7,070,995; 7,265,209; 7,354,762; 7,446,179; 7,446,190; 7,446,191; 8,252,592; 8,324,353; 8,339,645; 8,398,282; 8,479,118; EP2537416; Brentjens et al., Sci Transl Med. 2013 5 (177); Davila et al. (2013) PLOS ONE 8 (4): e$^{61338}$; Kochenderfer et al., 2013, Nature Reviews Clinical Oncology, 10, 267-276 (2013); Sadelain et al., Cancer Discov. 2013 April; 3 (4): 388-398; Turtle et al., Curr. Opin. Immunol., 2012 October; 24 (5): 633-39; Wang et al. (2012) J. Immunother. 35 (9): 689-701; and Wu et al., Cancer, 2012 Mar. 18 (2): 160-75.

(v-g) Modification Protocols & Agents. Desired genes encoding CAR, TCR, CAR/TCR hybrids, or other molecules disclosed herein can be introduced into cells by any method known in the art, including transfection, electroporation, microinjection, lipofection, calcium phosphate mediated transfection, infection with a viral or bacteriophage vector including the gene sequences, cell fusion, chromosome-mediated gene transfer, microcell-mediated gene transfer, spheroplast fusion, in vivo nanoparticle-mediated delivery, etc. Numerous techniques are known in the art for the introduction of foreign genes into cells (see, e.g., Loeffler and Behr, 1993, Meth. Enzymol. 217:599-618; Cohen, et al., 1993, Meth. Enzymol. 217:618-644; Cline, 1985, Pharmac. Ther. 29:69-92) and may be used, provided that the necessary developmental and physiological functions of the recipient cells are not unduly disrupted. The technique can provide for the stable transfer of the gene to the cell so that the gene is expressible by the cell and, in certain instances, preferably heritable and expressible by its cell progeny.

The term "gene" refers to a nucleic acid sequence (used interchangeably with polynucleotide or nucleotide sequence) that encodes a molecule described herein. This definition includes various sequence polymorphisms, mutations, and/or sequence variants wherein such alterations do not substantially affect the function of the encoded CAR. The term "gene" may include not only coding sequences but also regulatory regions such as promoters, enhancers, and termination regions. The term further can include all introns and other DNA sequences spliced from an mRNA transcript, along with variants resulting from alternative splice sites. Gene sequences encoding the molecule can be DNA or RNA that directs the expression of a molecule. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Portions of complete gene sequences are referenced throughout the disclosure as is understood by one of ordinary skill in the art.

Gene sequences encoding molecules can be readily prepared by synthetic or recombinant methods from the relevant amino acid sequences and other descriptions provided herein. In embodiments, the gene sequence encoding any of these sequences can also have one or more restriction enzyme sites at the 5' and/or 3' ends of the coding sequence in order to provide for easy excision and replacement of the gene sequence encoding the sequence with another gene sequence encoding a different sequence. In embodiments, the gene sequence encoding the sequences can be codon optimized for expression in mammalian cells.

"Encoding" refers to the property of specific sequences of nucleotides in a gene, such as a cDNA, or an mRNA, to serve as templates for synthesis of other macromolecules such as a defined sequence of amino acids. Thus, a gene code for a protein if transcription and translation of mRNA corresponding to that gene produces the protein in a cell or other biological system. A "gene sequence encoding a protein" includes all nucleotide sequences that are degenerate versions of each other and that code for the same amino acid sequence or amino acid sequences of substantially similar form and function.

Polynucleotide gene sequences encoding more than one portion of an expressed molecule can be operably linked to each other and relevant regulatory sequences. For example, there can be a functional linkage between a regulatory sequence and an exogenous nucleic acid sequence resulting in expression of the latter. For another example, a first nucleic acid sequence can be operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary or helpful, join coding regions into the same reading frame.

A "vector" is a nucleic acid molecule that is capable of transporting another nucleic acid. Vectors may be, e.g., plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

Retroviral vectors (see Miller, et al., 1993, Meth. Enzymol. 217:581-599) can be used. In such embodiments, the gene to be expressed is cloned into the retroviral vector for its delivery into cells. In particular embodiments, a retroviral vector includes all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail about retroviral vectors can be found in Boesen, et al., 1994, Biotherapy 6:291-302; Clowes, et al., 1994, J. Clin. Invest. 93:644-651; Kiem, et al., 1994, Blood 83:1467-1473; Salmons and Gunzberg, 1993, Human Gene Therapy 4:129-141; and Grossman and Wilson, 1993, Curr. Opin. in Genetics and Devel. 3:110$^{-114}$. Adenoviruses, adena-associated viruses (AAV), and alphaviruses can also be used. See Kozarsky and Wilson, 1993, Current Opinion in Genetics and Development 3:499-503, Rosenfeld, et al., 1991, Science 252:431-434; Rosenfeld, et al., 1992, Cell 68:143-155; Mastrangeli, et al., 1993, J. Clin. Invest. 91:225-234; Walsh, et al., 1993, Proc. Soc. Exp. Bioi. Med. 204:289-300; and Lundstrom, 1999, J. Recept. Signal Transduct. Res. 19:673-686. Other methods of gene delivery include use of mammalian artificial chromosomes (Vos, 1998, Curr. Op. Genet. Dev. 8:351-359); liposomes (Tarahovsky and Ivanitsky, 1998, Biochemistry (Mosc) 63:607-618); ribozymes (Branch and Klotman, 1998, Exp. Nephrol. 6:78-83); and triplex DNA (Chan and Glazer, 1997, J. Mol. Med. 75:267-282).

"Lentivirus" refers to a genus of retroviruses that are capable of infecting dividing and non-dividing cells. Several examples of lentiviruses include HIV (human immunodeficiency virus: including HIV type 1 and HIV type 2); equine infectious anemia virus; feline immunodeficiency virus (FIV); bovine immune deficiency virus (BIV); and simian immunodeficiency virus (SIV).

There are a large number of available viral vectors suitable within the current disclosure, including those identified for human gene therapy applications (see Pfeifer and Verma, 2001, Ann. Rev. Genomics Hum. Genet. 2:177). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles including CAR transgenes are described in, e.g., U.S. Pat. No. 8,119,772; Walchli, et al., 2011, PLOS One 6:327930; Zhao, et al., 2005, J. Immunol. 174:4415; Engels, et al., 2003, Hum. Gene Ther. 14:1155; Frecha, et al., 2010, Mol. Ther. 18:1748; and Verhoeyen, et al., 2009, Methods Mol. Biol. 506:97. Retroviral and lentiviral vector constructs and expression systems are also commercially available.

Targeted genetic engineering approaches may also be utilized. The CRISPR (Clustered Regularly Interspaced Short Palindromic Repeats)/Cas (CRISPR-associated protein) nuclease system is an engineered nuclease system used for genetic engineering that is based on a bacterial system. Information regarding CRISPR-Cas systems and components thereof are described in, for example, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Particular embodiments utilize zinc finger nucleases (ZFNs) as gene editing agents. ZFNs are a class of site-specific nucleases engineered to bind and cleave DNA at specific positions. ZFNs are used to introduce double stranded breaks (DSBs) at a specific site in a DNA sequence which enables the ZFNs to target unique sequences within a genome in a variety of different cells.

For additional information regarding ZFNs and ZFNs useful within the teachings of the current disclosure, see, e.g., U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; US 2003/0232410 and US 2009/0203140 as well as Gaj et al., Nat Methods, 2012, 9 (8): 805-7; Ramirez et al., Nucl Acids Res, 2012, 40 (12): 5560-8; Kim et al., Genome Res, 2012, 22 (7): 1327-33; Urnov et al., Nature Reviews Genetics, 2010, 11:636-646; Miller, et al. Nature biotechnology 25, 778-785 (2007); Bibikova, et al. Science 300, 764 (2003); Bibikova, et al. Genetics 161, 1169-1175 (2002); Wolfe, et al. Annual review of biophysics and biomolecular structure 29, 183-212 (2000); Kim, et al. Proceedings of the National Academy of Sciences of the United States of America 93, 1156-1160 (1996); and Miller, et al. The EMBO journal 4, 1609-1614 (1985).

Particular embodiments can use transcription activator like effector nucleases (TALENs) as gene editing agents. TALENs refer to fusion proteins, including a transcription activator-like effector (TALE) DNA binding protein and a DNA cleavage domain. TALENs are used to edit genes and genomes by inducing double DSBs in the DNA, which induce repair mechanisms in cells. Generally, two TALENs must bind and flank each side of the target DNA site for the DNA cleavage domain to dimerize and induce a DSB. For additional information regarding TALENs, see U.S. Pat. Nos. 8,440,431; 8,440,432; 8,450,471; 8,586,363; and 8,697,853; as well as Joung and Sander, Nat Rev Mol Cell Biol, 2013, 14 (I): 49-55; Beurdeley et al., Nat Commun, 2013, 4:1762; Scharenberg et al., Curr Gene Ther, 2013, 13 (4): 291-303; Gaj et al., Nat Methods, 2012, 9 (8): 805-7; Miller, et al. Nature biotechnology 29, 143-148 (2011); Christian, et al. Genetics 186, 757-761 (2010); Boch, et al. Science 326, 1509-1512 (2009); and Moscou, & Bogdanove, Science 326, 1501 (2009).

Particular embodiments can utilize MegaTALs as gene editing agents. MegaTALs have a sc rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

In particular embodiments, the isolating, incubating, expansion, and/or engineering steps are carried out in a sterile or contained environment and/or in an automated fashion, such as controlled by a computer attached to a device in which the steps are performed.

(vi) Ex Vivo Manufactured Cell Formulations. In particular embodiments, activated, expanded, and/or genetically-modified cells can be harvested from a culture medium and washed and concentrated into a carrier in a therapeutically-effective amount. Exemplary carriers include saline, buffered saline, physiological saline, water, Hanks' solution, Ringer's solution, Nonnosol-R (Abbott Labs), PLASMA-LYTE AR (Baxter Laboratories, Inc., Morton Grove, IL), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols, including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinositol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose, and glucose; disaccharides such as lactose, maltose and sucrose; trisaccharides such as raffinose, and polysaccharides such as dextran.

Where necessary or beneficial, compositions or formulations can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within compositions or formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

In compositions and formulations disclosed herein, cells are generally in a volume of a liter or less, 500 mls or less, 250 mls or less, or 100 mls or less. Hence the density of administered cells is typically greater than $10^4$ cells/ml, $10^7$ cells/ml, or $10^8$ cells/ml.

The cell-based compositions disclosed herein can be prepared for administration by, e.g., injection, infusion, perfusion, or lavage. The compositions can further be formulated for bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous injection.

(vii) Compositions for Administration. The engineered proteins described herein can be formulated for administration to a subject. Compositions include one or more engineered proteins described herein and one or more pharmaceutically acceptable carriers.

In particular embodiments, the protein compositions include active ingredients of at least 0.1% w/v or w/w of the composition; at least 1% w/v or w/w of the composition; at least 10% w/v or w/w of the composition; at least 20% w/v or w/w of the composition; at least 30% w/v or w/w of the composition; at least 40% w/v or w/w of the composition; at least 50% w/v or w/w of the composition; at least 60% w/v or w/w of the composition; at least 70% w/v or w/w of the composition; at least 80% w/v or w/w of the composition; at least 90% w/v or w/w of the composition; at least 95% w/v or w/w of the composition; or at least 99% w/v or w/w of the composition.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents, or co-solvents, stabilizers, surfactants, and/or delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and/or trimethylamine salts.

An exemplary chelating agent is EDTA.

Exemplary isotonic agents include polyhydric sugar alcohols, including trihydric or higher sugar alcohols, such as glycerin, erythritol, arabitol, xylitol, sorbitol, or mannitol.

Exemplary preservatives include phenol, benzyl alcohol, meta-cresol, methyl paraben, propyl paraben, octadecyldimethylbenzyl ammonium chloride, benzalkonium chloride, hexamethonium chloride, alkyl parabens such as methyl or propyl paraben, catechol, resorcinol, cyclohexanol, and 3-pentanol.

Stabilizers refer to a broad category of excipients which can range in function from a bulking agent to an additive which solubilizes the active ingredients or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinositol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose, and glucose; disaccharides such as lactose, maltose and sucrose; trisaccharides such as raffinose, and polysaccharides such as dextran. Stabilizers are typically present in the range of from 0.1 to 10,000 parts by weight based on therapeutic weight.

The compositions disclosed herein can be formulated for administration by, for example, injection. For injection, compositions can be formulated as aqueous solutions, such as in buffers including Hanks' solution, Ringer's solution, or physiological saline, or in culture media, such as Iscove's Modified Dulbecco's Medium (IMDM). The aqueous solutions can include formulatory agents such as suspending, stabilizing, and/or dispersing agents. Alternatively, the composition can be in lyophilized and/or powder form for constitution with a suitable vehicle, e.g., sterile pyrogen-free water, before use.

Any compositions disclosed herein can advantageously include any other pharmaceutically acceptable carriers, which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, compositions can be prepared to meet sterility, pyrogenicity, general safety, and purity standards as required by the US FDA Office of Biological Standards and/or other relevant foreign regulatory agencies.

(viii) Methods of Use. Methods disclosed herein include treating subjects (primates, humans, non-human primates, veterinary animals (dogs, cats, reptiles, birds, etc.), livestock (horses, cattle, goats, pigs, chickens, etc.), and research animals (monkeys, rats, mice, fish, etc.) with formulations and compositions disclosed herein. Treating subjects includes delivering therapeutically effective amounts. Therapeutically effective amounts include those that provide effective amounts, prophylactic treatments, and/or therapeutic treatments.

An "effective amount" is the amount of a composition necessary to result in a desired physiological change in the subject. For example, an effective amount can provide an immunogenic anti-cancer or anti-infection effect. Effective amounts are often administered for research purposes. Effective amounts disclosed herein can cause a statistically-significant effect in an animal model or in vitro assay relevant to the assessment of a cancer or infection's development or progression. An immunogenic composition can be provided in an effective amount, wherein the effective amount stimulates an immune response.

A "prophylactic treatment" includes a treatment administered to a subject who does not display signs or symptoms of a cancer or infection or displays only early signs or symptoms of a cancer or infection such that treatment is administered for the purpose of diminishing or decreasing the risk of developing the cancer or infection further. Thus, a prophylactic treatment functions as a preventative treatment against a cancer or infection. In particular embodiments, prophylactic treatments reduce, delay, or prevent metastasis from a primary a cancer tumor site from occurring.

A "therapeutic treatment" includes a treatment administered to a subject who displays symptoms or signs of a cancer or infection and is administered to the subject for the purpose of diminishing or eliminating those signs or symptoms of the cancer or infection. The therapeutic treatment can reduce, control, or eliminate the presence or activity of the cancer or infection and/or reduce control or eliminate side effects of the cancer or infection.

Function as an effective amount, prophylactic treatment, or therapeutic treatment are not mutually exclusive, and in particular embodiments, administered dosages may accomplish more than one treatment type.

In particular embodiments, therapeutically effective amounts provide anti-cancer effects. Anti-cancer effects include a decrease in the number of cancer cells, decrease in the number of metastases, a decrease in tumor volume, an increase in life expectancy, induced chemo- or radiosensitivity in cancer cells, inhibited angiogenesis near cancer cells, inhibited cancer cell proliferation, inhibited tumor growth, prevented or reduced metastases, prolonged subject life, reduced cancer-associated pain, and/or reduced relapse or re-occurrence of cancer following treatment.

A "tumor" is a swelling or lesion formed by an abnormal growth of cells (called neoplastic cells or tumor cells). A "tumor cell" is an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be benign, pre-malignant, or malignant.

Types of cancer that can be treated using ex vivo manufactured T cells include prostate cancer, breast cancer, stem cell cancer, ovarian cancer, mesothelioma, renal cell carcinoma melanoma, pancreatic cancer, lung cancer, HBV-induced hepatocellular carcinoma, and multiple myeloma. Further exemplary cancers that may be treated include medulloblastoma, oligodendroglioma, ovarian clear cell adenocarcinoma, ovarian endometrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epitheloid sarcoma, renal medullo carcinoma, diffuse large B-cell lymphoma, follicular lymphoma and not otherwise specified (NOS) sarcoma.

Acute myeloid leukemia (AML), blastic plasmacytoid dendritic cell neoplasm (BPDCN), myelodysplastic syndromes (MDS), natural killer cell lymphomas, hairy cell leukemia, acute lymphocytic leukemia (ALL; also known as acute lymphoblastic lymphoma), chronic myelocytic leukemia (CML), other leukemias, hematological cancers or tumors, Hodgkin's lymphoma (HL), B-cell HL, non-Hodgkin lymphoma (NHL), mantle cell lymphoma (MCL), T cell lymphoma, multiple myeloma (refractory, relapsed, etc.), systemic mastocytosis (SM), hypereosinophilic syndrome (HES), myelofibrosis, anemia, systemic lupus erythematosus (SLE), psoriasis, and systemic sclerosis (scleroderma) may also be treated with formulations and compositions disclosed herein.

Formulations and compositions described herein can also be used to target and destroy other unwanted cell types, such as cells infected with adenoviruses, arenaviruses, bunyaviruses, coronaviruses, flaviviruses, hantaviruses, hepadnaviruses, herpesviruses, papillomaviruses, paramyxoviruses, parvoviruses, picornaviruses, poxviruses, orthomyxoviruses, retroviruses, reoviruses, rhabdoviruses, rotaviruses, spongiform viruses or togaviruses. In additional embodiments, viral antigen markers include peptides expressed by CMV, cold viruses, Epstein-Barr, flu viruses, hepatitis A, B, and C viruses, herpes simplex, HIV, influenza, Japanese encephalitis, measles, polio, rabies, respiratory syncytial, rubella, smallpox, varicella zoster or West Nile virus.

In particular embodiments, therapeutically effective amounts provide anti-pathogen effects. Anti-pathogen effects can include anti-infection effects. Anti-infection effects can include a decrease in the occurrence of infections, a decrease in the severity of infections, a decrease in the duration of infections, a decrease in the number of infected cells, a decrease in volume of infected tissue, an increase in life expectancy, induced sensitivity of infected cells to immune clearance, reduced infection-associated pain, and/or reduction or elimination of a symptom associated with the treated infection.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian, or researcher, taking into account parameters such as physical and physiological factors including target, body weight, severity of the condition, type of cancer or infection, stage of cancer or infection, previous or concurrent therapeutic interventions, idiopathy of the subject and route of administration.

Therapeutically effective amounts of cells to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$. Administered cells can be autologous or allogeneic to the recipient.

Therapeutically effective amounts of proteins to administer can include 0.5 μg or mg/kg, 1 μg or mg/kg, 2 μg or mg/kg, 3 μg or mg/kg, 4 μg or mg/kg, 5 μg or mg/kg, 6 μg or mg/kg, 7 μg or mg/kg, 8 μg or mg/kg, 9 μg or mg/kg, 10 μg or mg/kg, 11 μg or mg/kg, 12 μg or mg/kg, 13 μg or mg/kg, 14 μg or mg/kg, 15 μg or mg/kg, 16 μg or mg/kg, 17 μg or mg/kg, 18 μg or mg/kg, 19 μg or mg/kg, 20 μg or mg/kg, or more.

Therapeutically effective amounts can be achieved by administering single or multiple doses during the course of a treatment regimen.

As indicated, the formulations and compositions disclosed herein can be administered by, e.g., injection, infusion, perfusion, or lavage and can more particularly include administration through one or more bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous infusions and/or bolus injections.

In certain embodiments, formulations and/or compositions are administered to a patient in conjunction with (e.g., before, simultaneously, or following) any number of relevant treatment modalities. In particular embodiments, formulations and/or compositions may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies, or other antibody therapies, cytoxin, fludaribine, cyclosporin, FK506, rapamycin, mycoplienolic acid, steroids, FR901228, cytokines, and irradiation.

EXAMPLES

Figure 9A:
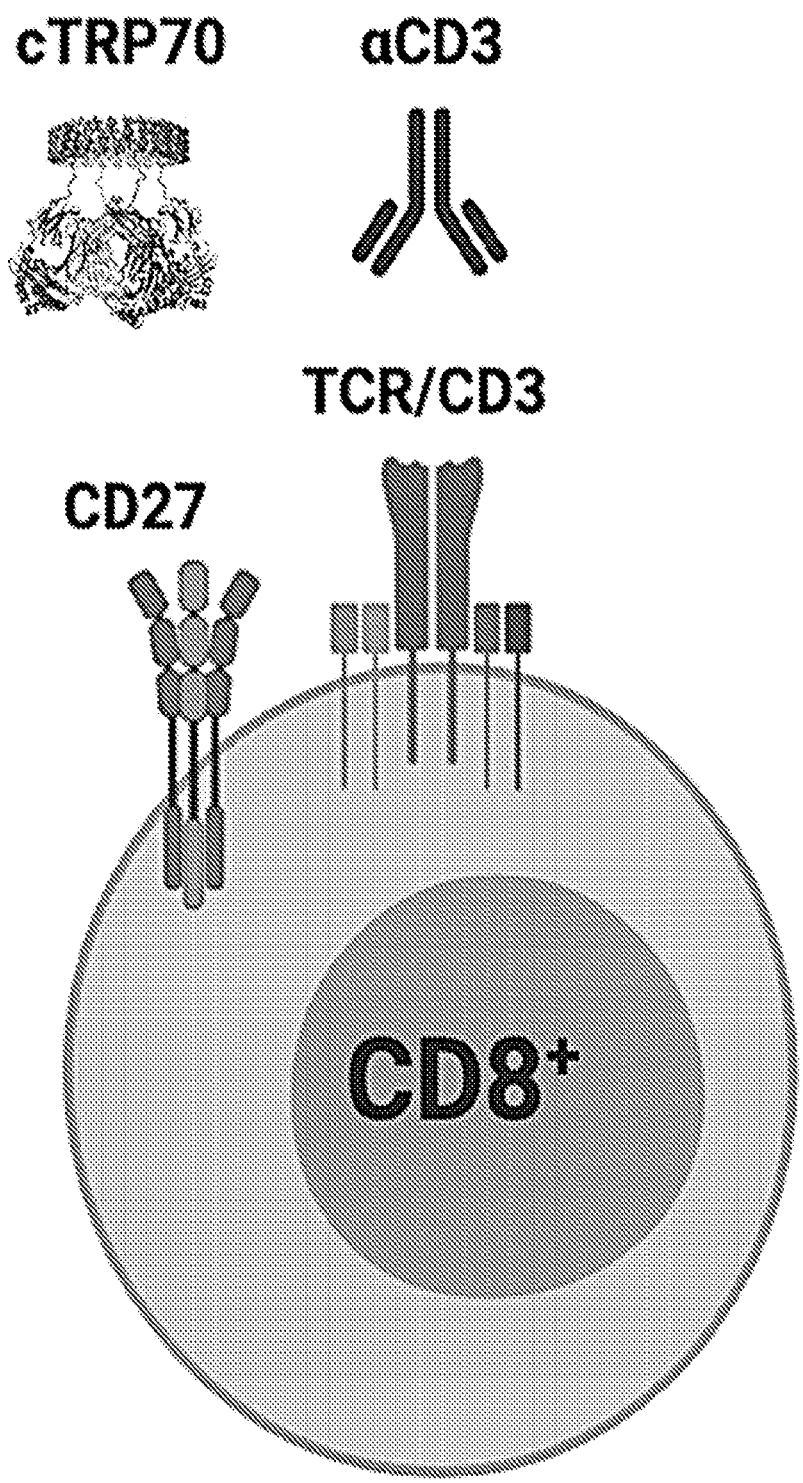
FIGS. 9A-9D. The cTRP with tetrameric CD70 mediates potent co-stimulation at low doses when provided in soluble form. (9A) Schematic of cTRP with tetrameric CD70 (native trimer structure; MDT-001100). (9B) cTRP70 test titrations. CFSE labeled cells were activated with plate-bound (pb) αCD3, in the presence or absence of titrated doses of soluble (sol) or plate-bound (pb) cTRP70. (9C) Representative CFSE dilution peak distribution of activated CD8$^+$ T cells (frequency of undivided, D1, D2, D3, D4). (9D) Proliferation peaks distribution of αCD3 activated cells in the presence or absence of titrated amounts of soluble cTRP70 (0.0001-5 µg/ml).
Figure 9B:
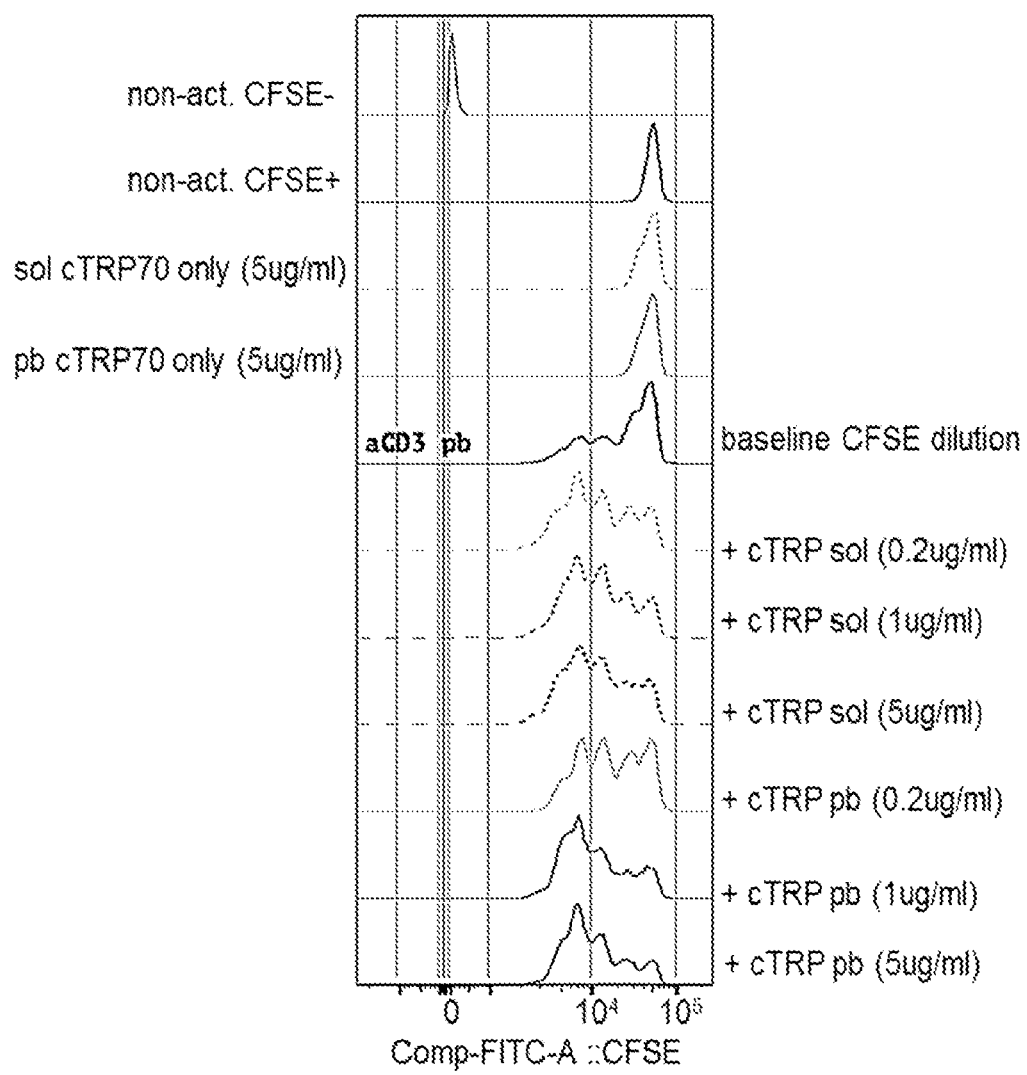
Figure 9C:
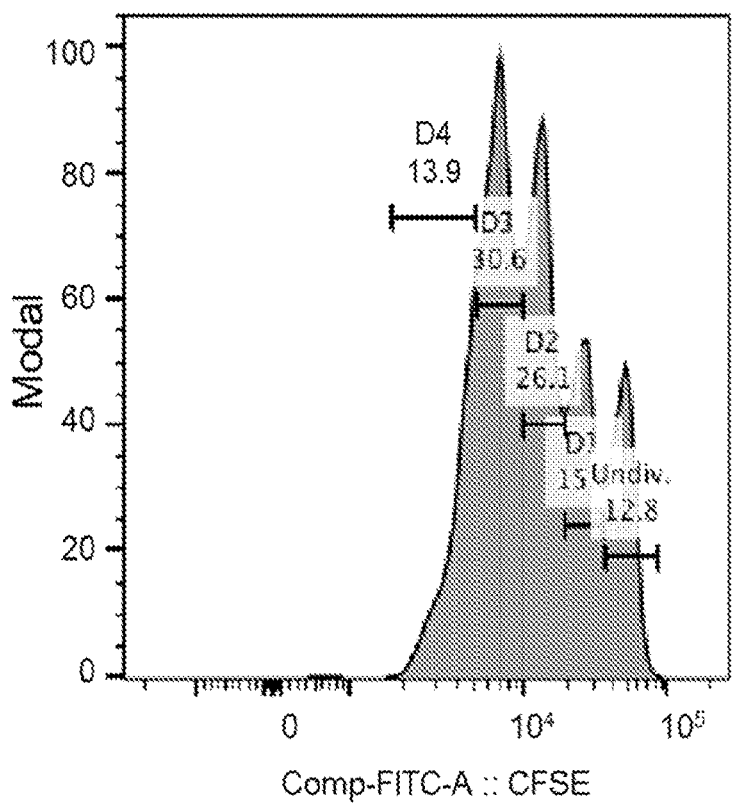
Figure 9D:
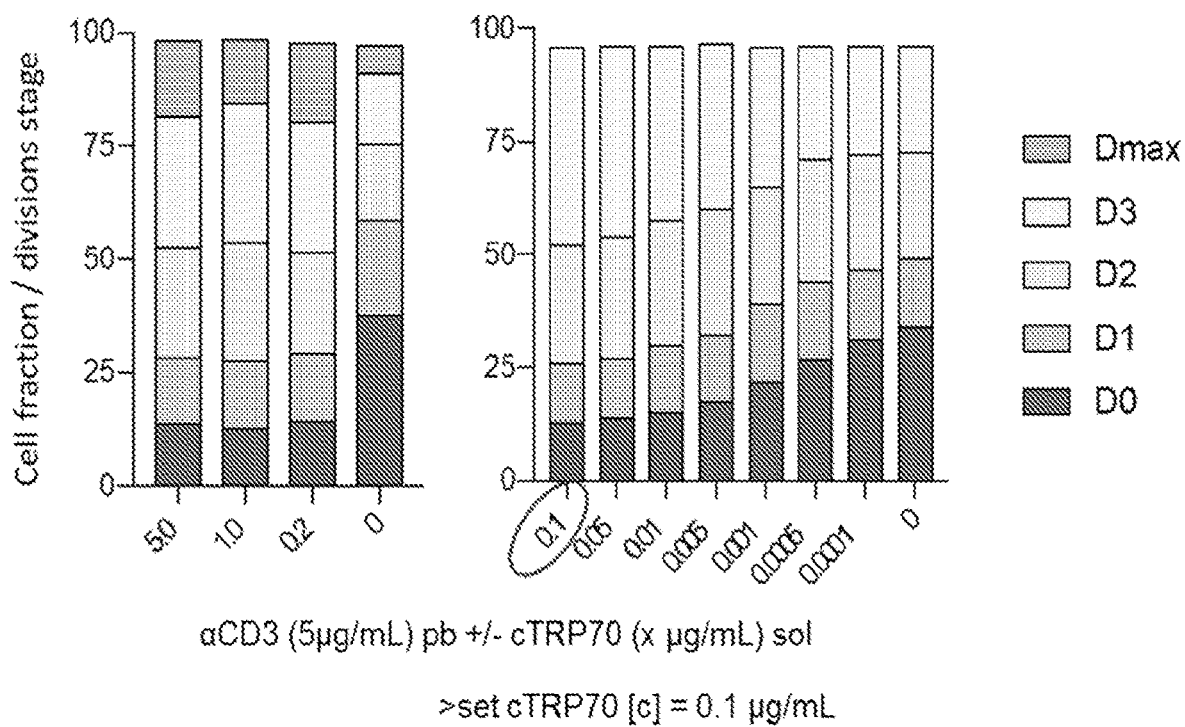

Example 1. The cTRP with tetrameric CD70 mediates potent co-stimulation at low doses when provided in soluble form. (FIG. 9A) Schematic of cTRP with tetrameric CD70 (native trimer structure; MDT-001100). (FIG. 9B) cTRP70 test titrations. CFSE labeled cells were activated with plate-bound (pb) αCD3, in the presence or absence of titrated doses of soluble (sol) or plate-bound (pb) cTRP70. (FIG. 9C) Representative CFSE dilution peak distribution of activated CD8$^+$ T cells (frequency of undivided, D1, D2, D3, D4). (9D) Proliferation peaks distribution of αCD3 activated cells in the presence or absence of titrated amounts of soluble cTRP70 (0.0001-5 μg/ml).

Example 2. Providing CD27 co-stimulation during αCD3-based CD8$^+$ T cell activation allows robust expansion and enhances acquisition of memory gene signature. In vitro validation and functional analysis of bulk CD8$^+$ T cells. A non-tissue culture-treated 96 well plate was pre-coated with mAb αCD3 (OKT3) with or without CD70 dimer-trimer (CD70$^{tri}$; MDT-000762-2 (also referred to as CD70$^{DT}$) in PBS. After 4 h of incubation at 37° C., the plate was flicked off, and bulk CD8$^+$ T cells were added. (FIG. 10A) Experimental design. (FIG. 10B) CD8$^+$ T cells were carboxyfluorescein N-hydroxysuccinimidyl ester (CFSE) labeled before culture start. On day 3 of activation, CFSE dilution was measured by flow cytometry. Comparative proliferation of αCD3 (5 μg/ml) versus αCD3/CD70$^{tri}$ (2,5,10 μg/ml) is shown. Greater cell proliferation is observed in all αCD3/CD70$^{tri}$ conditions over αCD3 alone. (FIG. 10C) 100,000 cells were plated on D0. Cell growth was assessed by cell counts on D3, D5, D7, and D10 post activation. Absolute numbers of αCD3/CD70$^{tri}$ or αCD3 activated cells for each individual timepoint are shown. Stimulation with αCD3/CD70$^{tri}$ leads to more T cell proliferation at earlier time points (see D3, D5) than stimulation with αCD3. (FIG. 10D) RNA was extracted from D10 cell culture, and gene expression analysis of selected signature genes was performed. The αCD3/CD70$^{tri}$ expanded T cell population is enriched for cells expressing a memory cell signature—the αCD3 expanded T cell population is enriched for cells expressing an effector cell signature.

Providing CD27 co-stimulation during CAR T cell manufacturing reduces the expression of Tigit and Lag 3 inhibitory receptors on T cells in vitro and results in improved therapeutic efficiency in vivo. (FIG. 11A) A chimeric antigen receptor (CAR) T cell generation protocol and scheme are shown. CAR T cells were injected on D10 post activation into previously (7 days) established Raji (CD19 expressing human lymphoma cell line) tumor bearing NOD scid gamma (NSG®, The Jackson Laboratory, Bar Harbor, ME) mice. (FIG. 11B) In vitro CAR T cell expansion, D7 phenotype. CD8$^+$ T cell surface marker expression was assessed on D7 post T cell activation and CAR T cell generation. Phenotype markers include CD28, CD45RO, CD127, CD122, CD62L, CD45RA, CD69, CCR7, CD95, CD27. Inhibitory markers include TIGIT, LAG-3, TIM-3, PD1. For inhibitory markers and CD27, isotype controls were used (dim lines). (FIG. 11C)-(FIG. 11E) In vivo expansion and persistence of CAR T cells. In vitro generated CAR T cells (epidermal growth factor receptor (EGFRt) marked) were injected at a dose of 0.8×10e$^6$ cells per mouse. All mice were inoculated with 0.5×10e$^6$ Raji tumor cells that expressed firefly luciferase (ffluc) 7 days before. (FIG. 11C) The frequency (percentage) of EGFRt$^+$hCD45$^+$ CAR T cells per total blood mononuclear cells. (11D) The tumor burden measured by live imaging of ffluc+ tumor cells after injection of luciferin is shown for D63. (FIG. 11E) Overall survival of mice treated with αCD3 or αCD3/CD70$^{tri}$ CAR T cells is shown. (FIG. 11F, FIG. 11G) In vivo re-expansion capacity of CAR-T cells. Mice were re-challenged with Raji ROR1 ffluc tumor cells on day 112 post primary tumor inoculation. (FIG. 11F) The frequency of EGFRt+ hCD45+ CAR T cells per total blood is shown (% of blood mononuclear cells expressing hCD45 and EGFRt) and only increased in mice previously treated with αCD3/CD70$^{tri}$ CAR T cells compared to mice treated with αCD3 CAR T cells. (FIG. 11G) Flow cytometry plots showing the percentage of CAR T cells (EGFRt+, huCD45+) in blood from mice treated with αCD3 and αCD3/CD70$^{tri}$ CAR T cells and then rechallenged with Raji tumor cells. Data for D7 and D37 post rechallenge are shown.

Figure 12C:
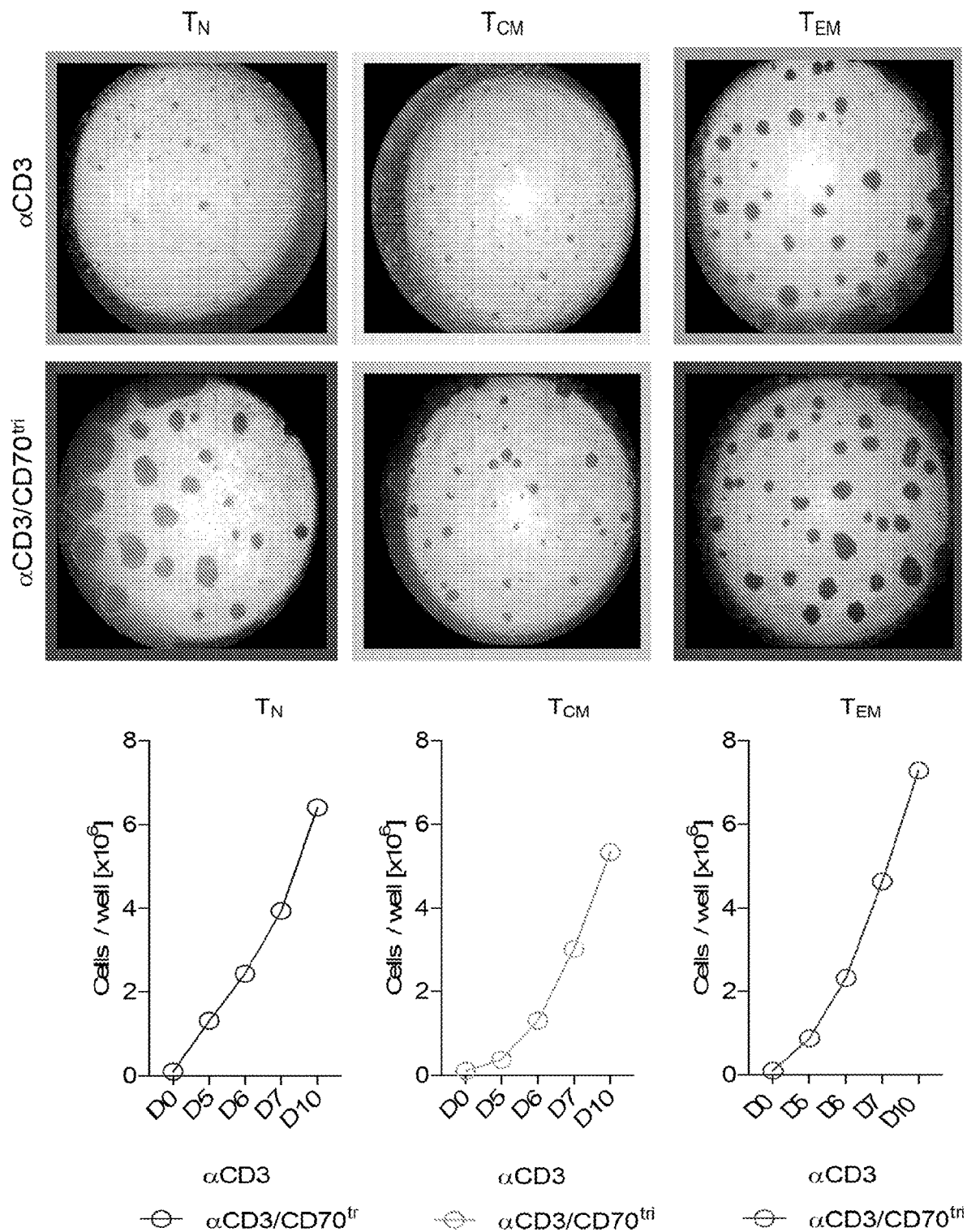

Example 3. CD27 co-stimulation is important for the expansion of naïve and central memory CD8+ T cell subsets. (FIG. 12A) CD8+ T cell subset marker panel and functional specification. (FIG. 12B) Gating strategy for CD8+ T cell sorting: naïve T cells ($T_N$) (CCR7+ CD45RO−), central memory T cells ($T_{CM}$) (CCR7+ CD45RO+), and effector memory T cells ($T_{EM}$) (CCR7−CD45RO+) according to the described marker panel. Subset-specific CD62L, CD45RA, and CD27 expression are also depicted. (FIG. 12C) Role of CD27 stimulation on T cell sub-populations. Images of D4 proliferation clusters of $T_N$ (CCR7+ CD45RO−), $T_{CM}$ (CCR7+ CD45RO+), and $T_{EM}$ (CCR7−CD45RO+) cells activated under αCD3 and αCD3/CD70$^{tri}$ culture conditions were assessed. The cell growth of individual conditions over 10 days is shown at the bottom.

Figure 13A:
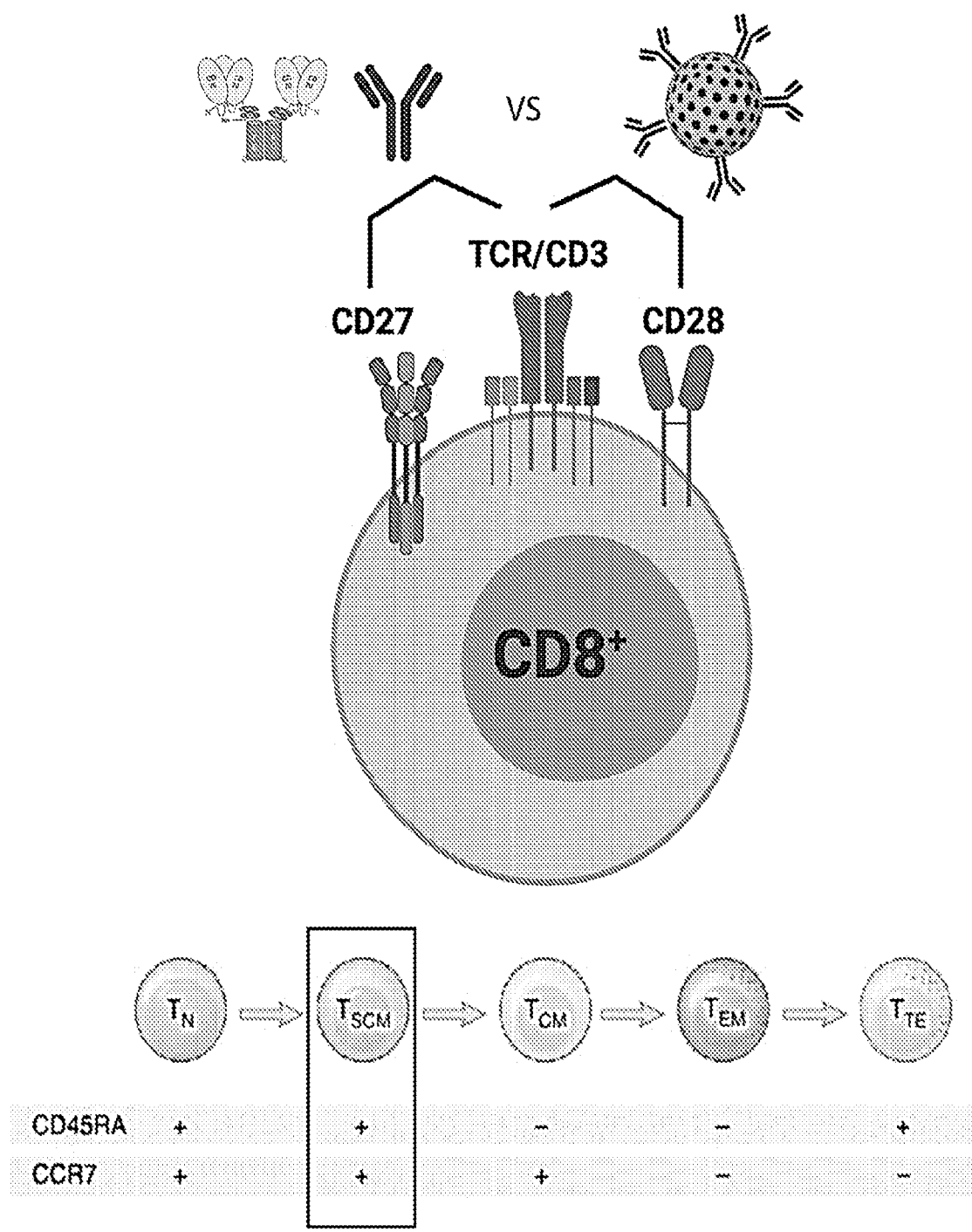
FIGS. 13A-13D. CD27 co-stimulation mediates superior acquisition of $T_{SCM}$-like T cell phenotype compared to CD28 co-stimulation. (13A) Scheme of T cell differentiation with highlighted $T_{SCM}$ surface marker expression. (13B) Healthy donor-derived bulk CD8$^+$ T cells were activated with either plate-bound αCD3 and CD70$^{DT}$ (also referred to as CD70$^{tri}$) or CD3/CD28 DynaBeads. Three days after activation, cells were taken OFF the plate or beads, respectively, and expanded for 7 more days in the presence of human IL-2. (13C) Contour plots showing CCR7 and CD45RA expression on D0 (PRE) and D10 activated CD8$^+$ T cells. αCD3/CD70$^{DT}$ activated CD8$^+$ T cells are more (4 to 9-fold) enriched in $T_{SCM}$-like cells after 10 days in culture compared to αCD3/αCD28 bead activated cells. Phenotype of αCD3/αCD28 DynaBead or αCD3 [5 µg/mL]/CD70$^{DT}$ [5 µg/mL] activated bulk CD8$^+$ T cells is shown for T cells stimulated under each condition in either CTL or ImmunoCult™ (ImmC; Stemcell Technologies, Cambridge, MA) media and 50U/mL IL2. (13D) Frequency of CCR7$^+$CD45RA$^+$CD8$^+$ T cells and mean fluorescent intensity (MFI) of each marker are shown (*designates αCD3/CD70$^{DT}$).

Example 4. CD27 co-stimulation mediates superior acquisition of $T_{SCM}$-like T cell phenotype compared to CD28 co-stimulation. (FIG. 13A) Scheme of T cell differentiation with highlighted $T_{SCM}$ surface marker expression. (FIG. 13C) Contour plots showing CCR7 and CD45RA expression on D0 (PRE) and D10 activated CD8+ T cells. αCD3/CD70$^{DT}$ activated CD8+T cells are more (4 to 9-fold) enriched in $T_{SCM}$-like cells after 10 days in culture compared to αCD3/αCD28 bead activated cells. Phenotype of αCD3/αCD28 DynaBead or αCD3 [5 µg/mL]/CD70$^{DT}$ [5 µg/mL] activated bulk CD8+ T cells is shown for T cells stimulated under each condition in either CTL or ImmunoCult™ (ImmC; Stemcell Technologies, Cambridge, MA) media and 50U/mL IL2. (FIG. 13D) Frequency of CCR7+ CD45RA+ CD8+ T cells and mean fluorescent intensity (MFI) of each marker are shown (designates αCD3/CD70$^{DT}$).

Figure 13B:
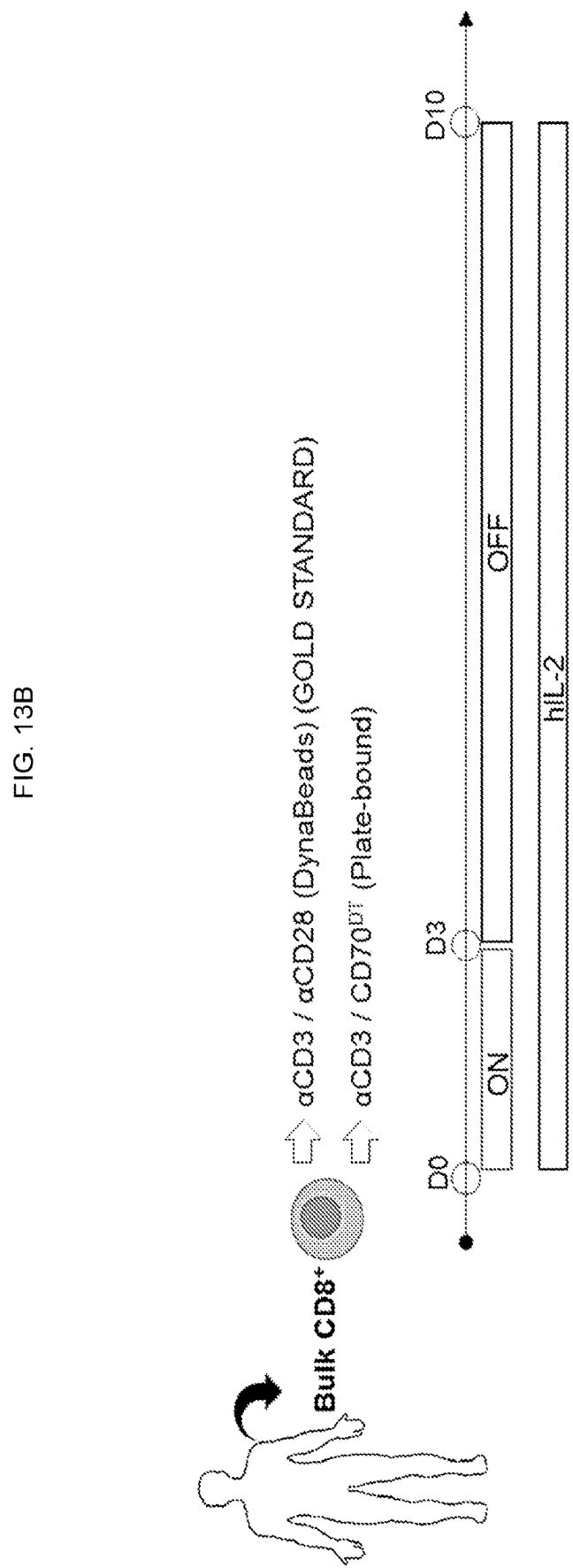
Figure 13C:
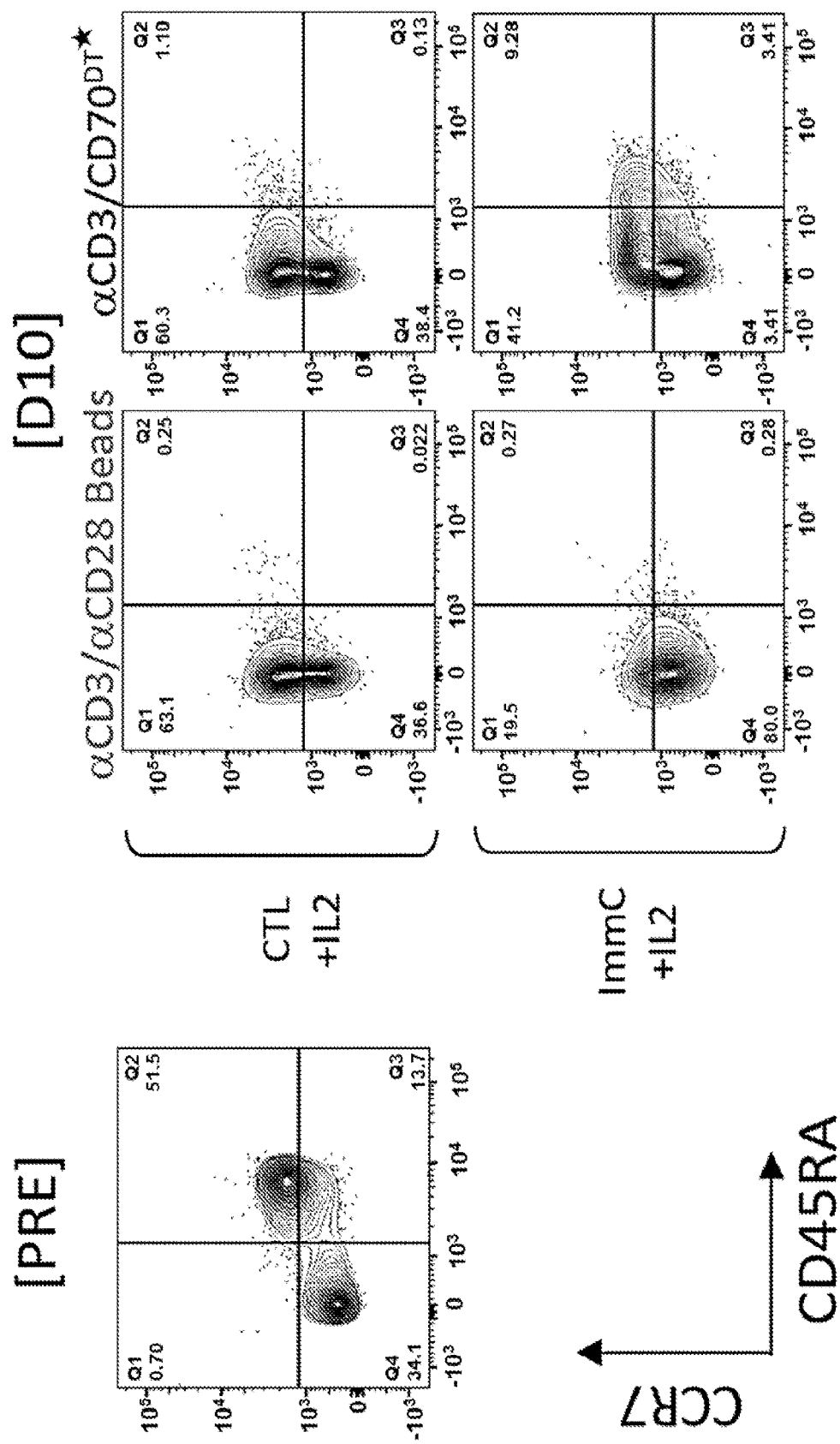
Figure 13D:
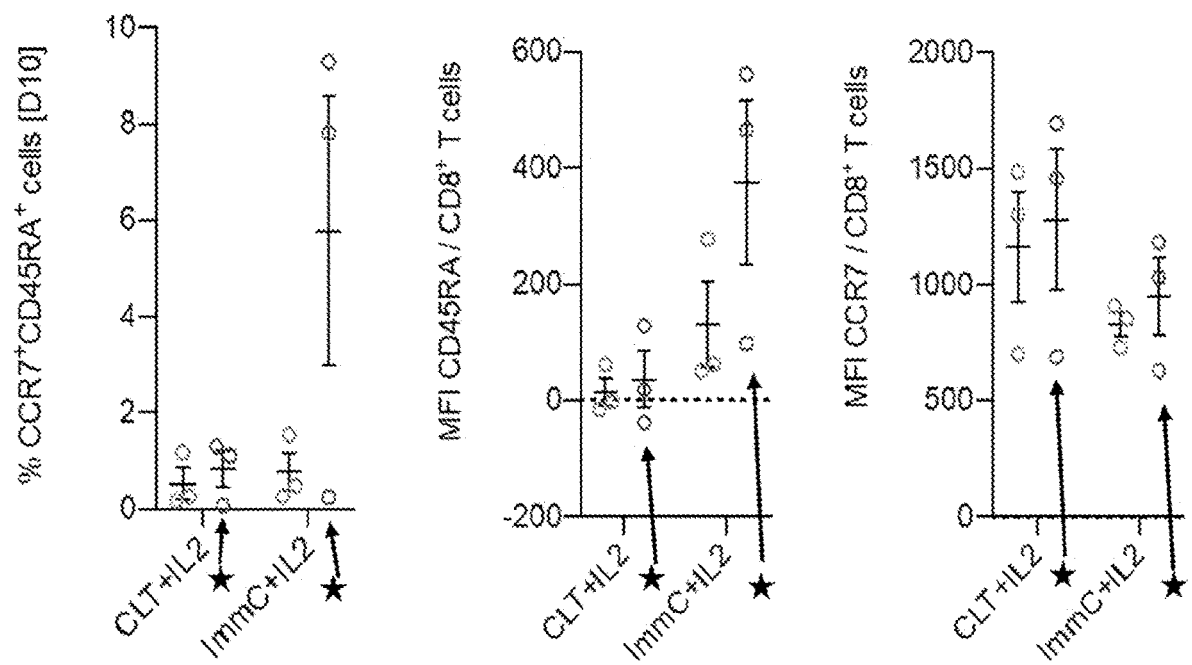

Example 5. αCD3/CD70$^{DT}$ activated CAR T cells elicit better tumor control and expansion capacity compared to the αCD3/αCD28 DynaBead activated T cells. In collaboration with the proteomics core of the Fred Hutchinson Cancer Research Center (FHCRC), an Fc-fused dimer of single chain trimers of CD70 proteins were generated (FIGS. 3A and 13B). These plate-bound αCD3 and CD70$^{DT}$ proteins were used to activate human CD8+ T cells and were compared to the activation of human CD8+ T cells with αCD3/αCD28 DynaBeads, which are currently considered the gold standard in the field. Three days after activation, cells were taken off the plate or beads, respectively, and expanded for seven additional days in the presence of human interleukin-2 (IL-2) (FIG. 13B).

Figure 14A:
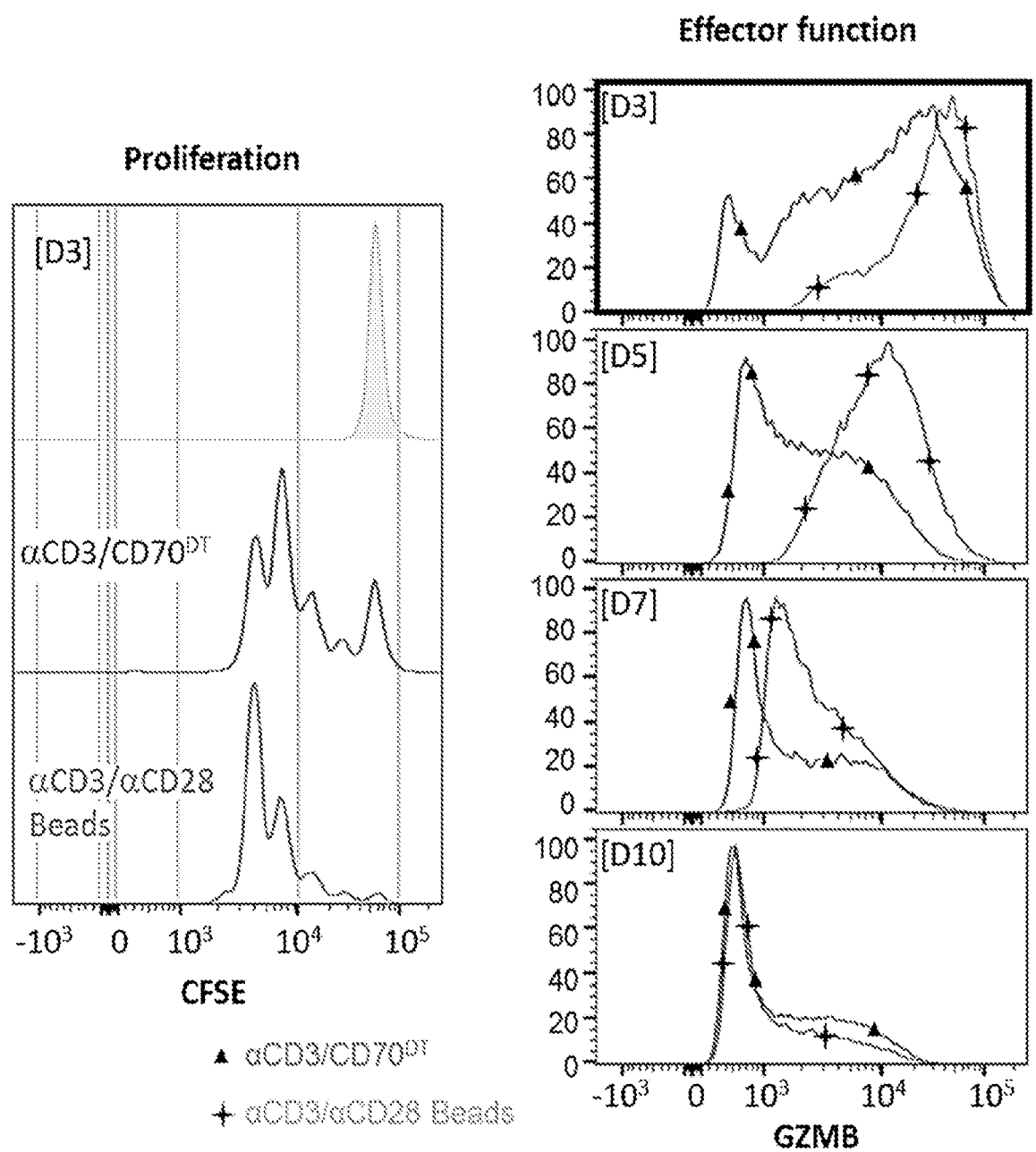
FIGS. 14A, 14B. CD27 co-stimulation reduces the acquisition of effector metabolic phenotype during CD8$^+$ T cell expansion compared to CD28 co-stimulation. (14A) Proliferation capacity was assessed by measuring CFSE dilution 3 days after activation, as shown in the panel on the left. In four right panels, effector function was assessed by measuring intracellular granzyme B (GZMB) expression at days 3, 5, 7, and 10 during CD8$^+$ T cell expansion. (14B) Metabolic phenotype of αCD3/αCD28 DynaBead or αCD3 [5 μg/mL]/CD70$^{DT}$ [5 μg/mL] activated bulk CD8$^+$ T cells under conditioning in either CTL or ImmunoCult™ (ImmC) media and 50 IU/mL IL-2. Long chain fatty acid (FA) uptake assessed using Bodipy500 dye (Day 4); Mitochondrial membrane potential assessed using cationic TMRM dye (Day 5); Glucose uptake measured using fluorescent 2-Deoxy-D-Glucose analog 2-NBDG (Day 4); Mitochondrial content assessed using MitoTracker stain (Day 5). These data are consistent with both CD3/CD28 and αCD3/CD70$^{DT}$ inducing robust proliferation of bulk-derived CD8$^+$ T cells, but shows that CD3/CD28 bead activation induces higher granzyme b expression and higher levels of glucose uptake and fatty acid oxidation early after stimulation indicative of greater effector cell differentiation and loss of stemness compared to the αCD3/CD70$^{DT}$.
Figure 14B:
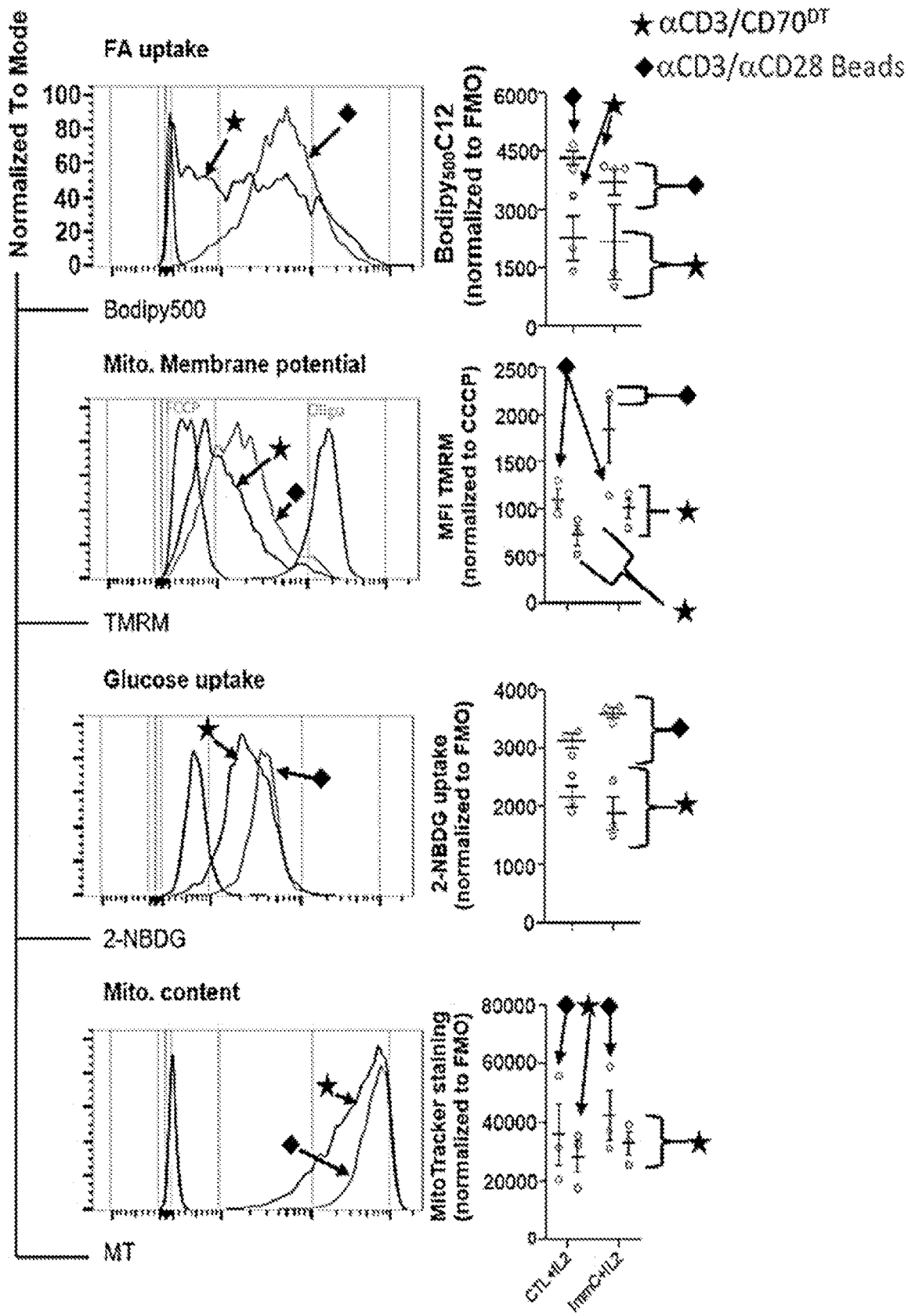

CFSE dilution was used three days post-activation to assess proliferation, and αCD3/CD70$^{DT}$ stimulation showed robust induction of proliferation of bulk-derived CD8+ T cells. αCD3/αCD28 DynaBead activation, however, induced a stronger effector function, which was maintained longer throughout expansion compared to the αCD3/CD70$^{DT}$ activated cells (FIG. 14A). Furthermore, fatty acid (FA)-uptake and mitochondrial membrane potential were higher in αCD3/αCD28 DynaBead activated T cells, suggesting that CD27 signaling restrains the acquisition of effector metabolic program/function at early timepoints after activation (FIG. 14B).

Figure 15B:
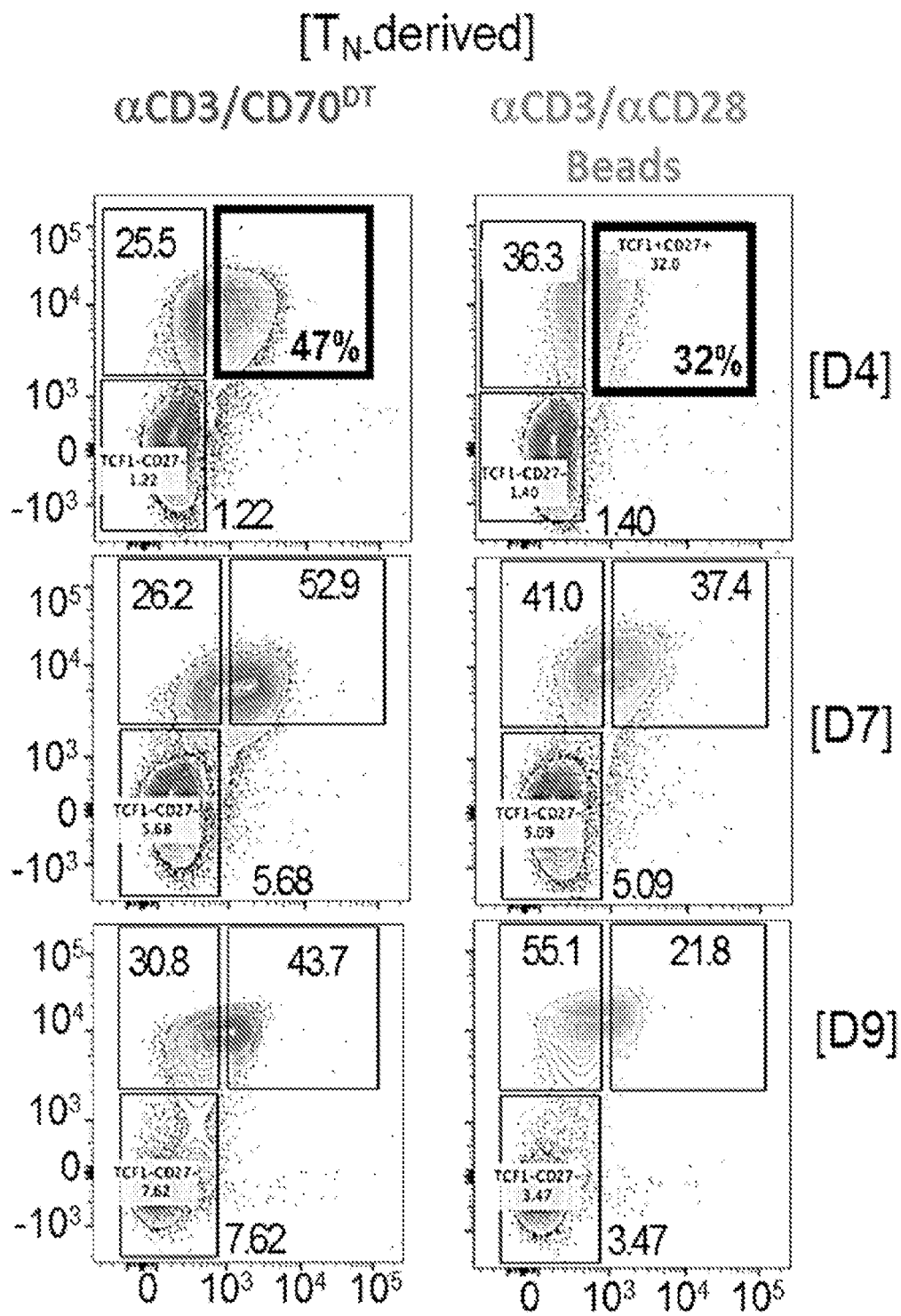
Figure 15C:
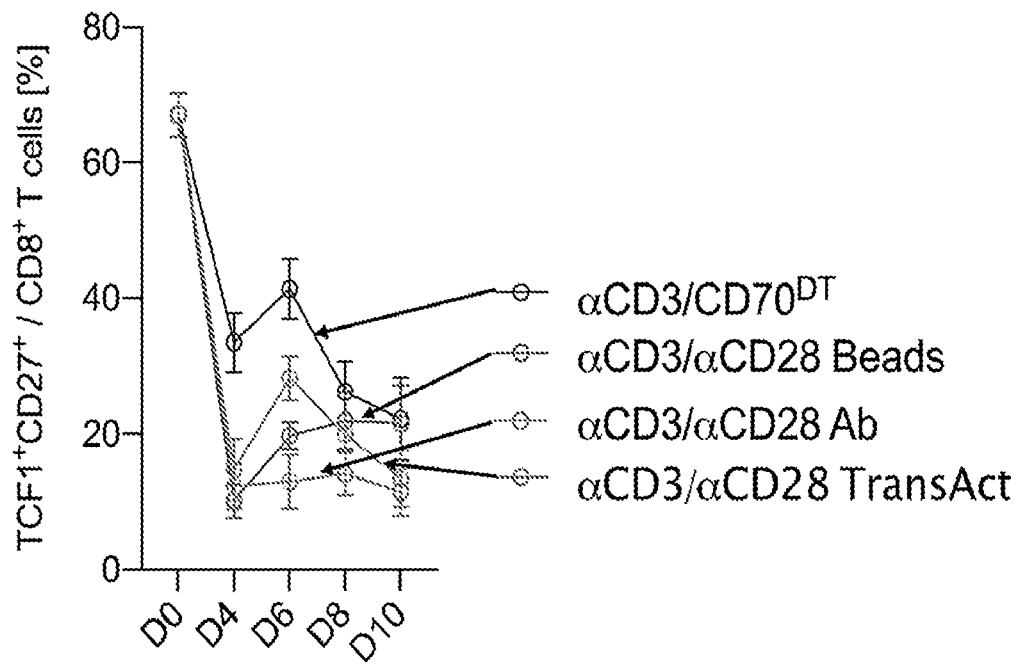
Figure 15D:
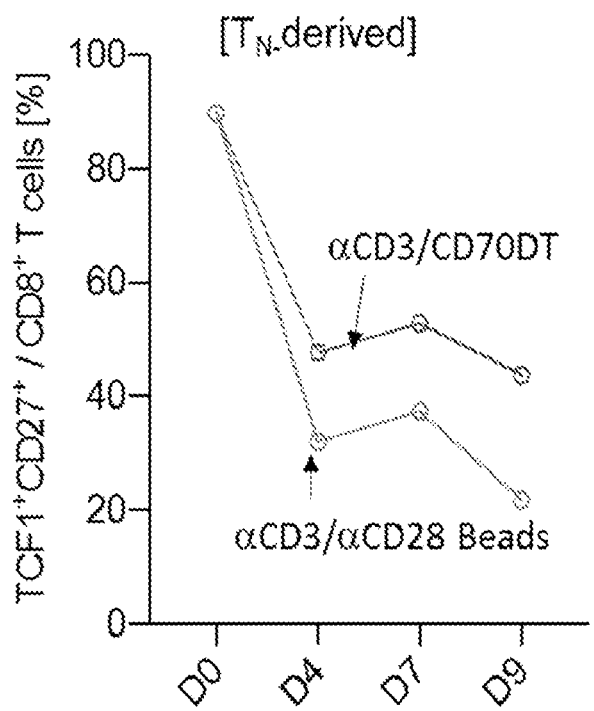

To determine whether CD8+ T cell differentiation capacity in vitro is altered between the αCD3/αCD28 and αCD3/engineered trimeric CD70 proteins co-stimulation systems, CD27 and TCF1 expression were measured (FIG. 15A). CD27 and TCF1 are markers that are associated with a naïve-like/stem-like phenotype. Quantifying the double positive population (CD27+ TCF1+), or the least differentiated population, showed that CD27 co-stimulation (αCD3/CD70$^{DT}$) better maintains CD27+ TCF1+ T cells early after bulk T cell activation. At the end of the culture, however, the fractions of CD27+ TCF1+ T cells were not significantly different between treatment groups (FIG. 15C).

Figure 16C:
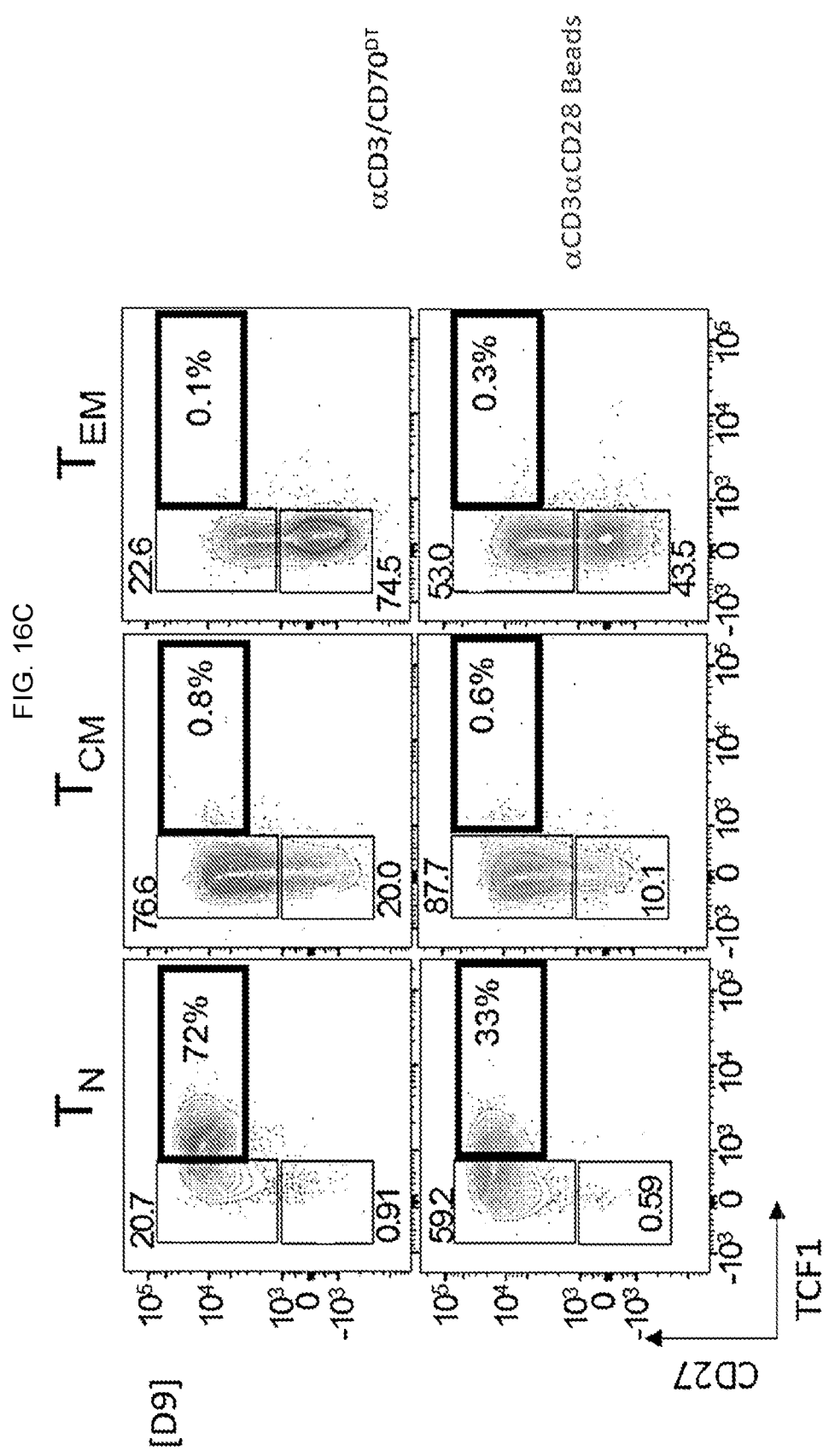

To determine which T cell subsets the CD27+ TCF1+ T cells were derived from, $T_N$, $T_{CM}$, and $T_{EM}$ cells were FACS-sorted from bulk CD8+ T cells, and 0.1×10$^6$ cells per T cell subset were activated with either αCD3/αCD28 or αCD3/CD70$^{DT}$ (FIG. 16A). Within the histogram overlays: line 1 (isotype), line 2 ($T_N$), line 3 ($T_{CM}$), and line 4 ($T_{EM}$). While CD8+ $T_N$, $T_{CM}$ cell expansion was comparable between αCD3/αCD28 or αCD3/CD70$^{DT}$ activated cells, αCD3/CD70$^{DT}$ activation poorly expanded $T_{EM}$ cells (FIG. 16B). On day 9 of culture, CD27+ TCF1+ cells were mainly derived from $T_N$ cells, whereas $T_{CM}$ and $T_{EM}$ strongly down-regulated TCF1 and CD27 expression compared to their initial expression level (FIG. 16C). Importantly, αCD3/CD70$^{DT}$ activated $T_N$ cells maintained a significantly higher CD27+ TCF1+ cell fraction, suggesting that CD27 signaling preferentially maintained $T_N$-derived CD27+ TCF1+ T cells throughout the in vitro culture (FIG. 16C).

Figure 17A:
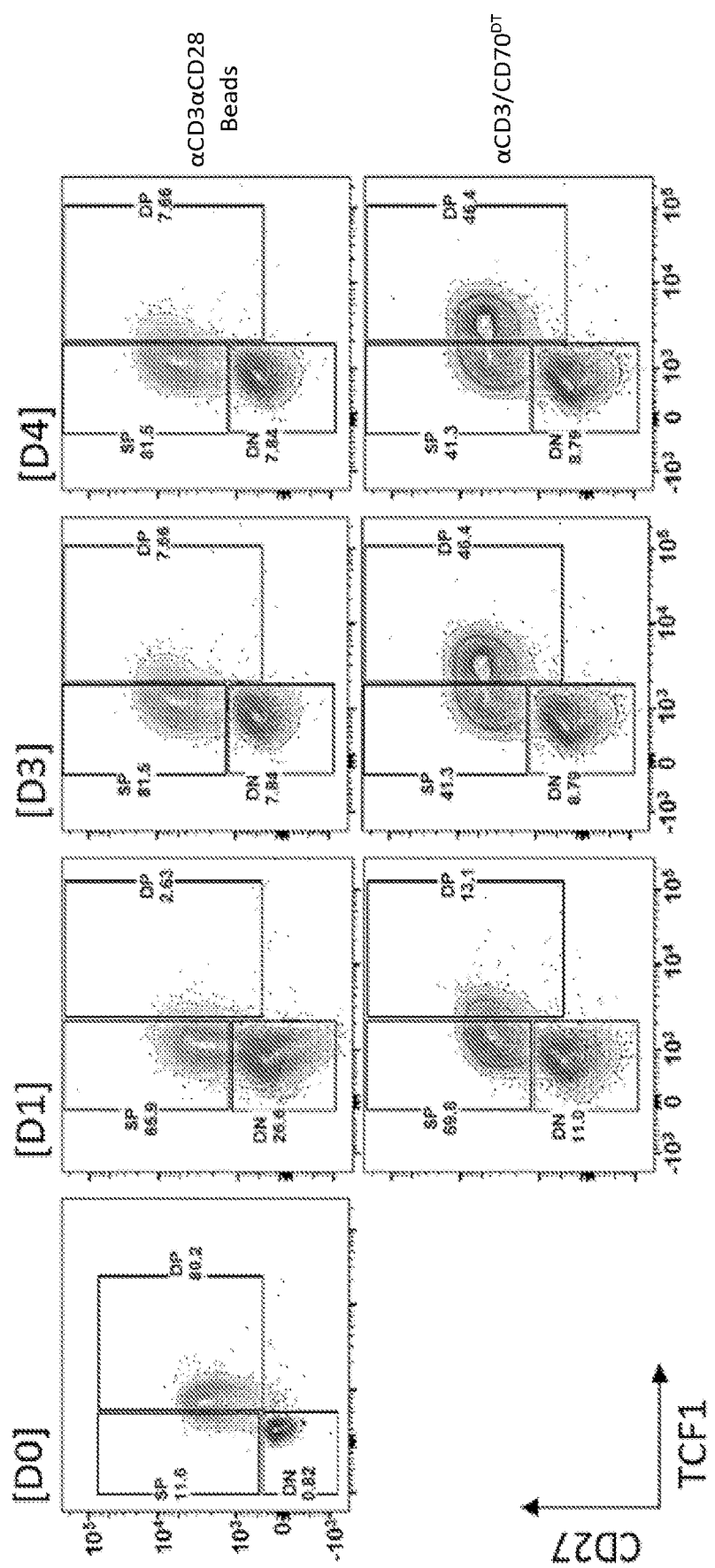
FIGS. 17A-17C. CD27 co-stimulation mediates prompt and superior TCF1 recovery in activated CD8$^+$ $T_N$ cells which is indicative of faster transition into a stem cell memory T cell state. Naïve CD8$^+$ T cells were activated with αCD3/αCD28 DynaBeads [at a 3:1 bead to cell ratio] or plate coated αCD3 [5 μg/mL]/CD70$^{DT}$ [5 μg/mL]. (17A) Assessment of TCF1 and CD27 expression of non-activated [D0] and activated [D1-4] cells by flow cytometry. Gates are set based on isotype control [black, overlayed]. Top row: αCD3/αCD28 DynaBeads; bottom row: CD70$^{DT}$ (17B) Frequency of TCF1$^+$ CD8$^+$ $T_N$ cells measured at indicated timepoints after activation in cultures stimulated with αCD3/αCD28 DynaBeads or with αCD3 [5 μg/mL]/CD70$^{DT}$ [5 μg/mL]. (17C) Log2 fold change (DynaBeads vs αCD3/αCD70$^{DT}$) of TCF7 gene expression of activated T CD8$^+$ $T_N$ cells measured by pPCR is shown.
Figure 17B:
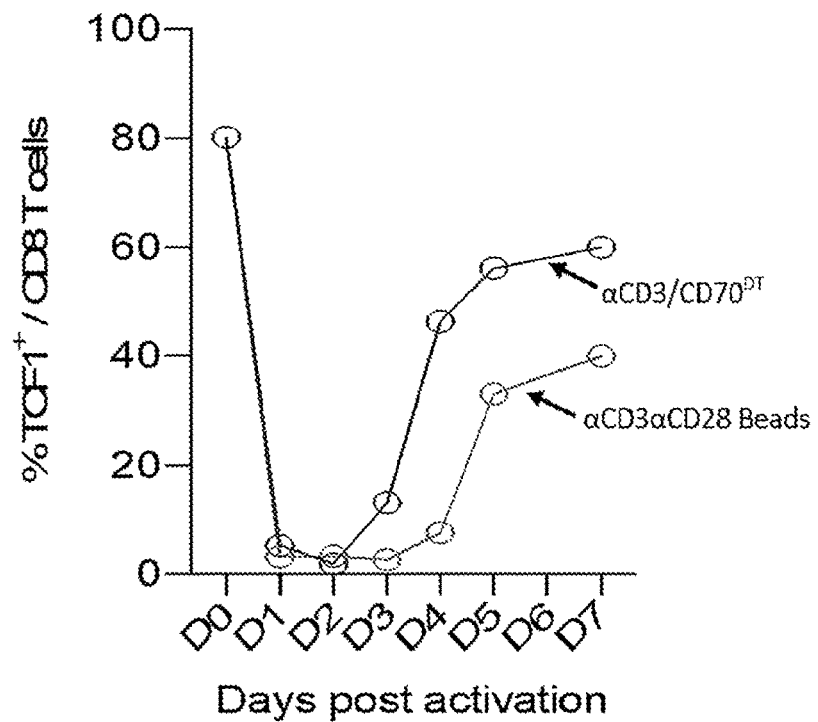
Figure 17C:
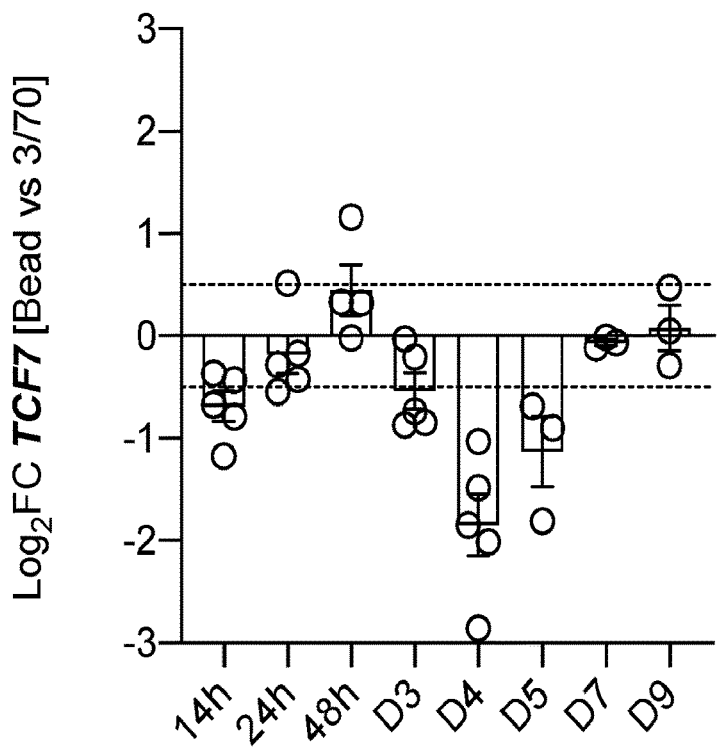

FIGS. 17A-17C show data indicating that CD27 co-stimulation mediates prompt and superior TCF1 recovery in activated CD8+ $T_N$ cells which is indicative of faster transition into a stem cell memory T cell state. Naïve CD8+ T cells were activated with αCD3/αCD28 DynaBeads [at a 3:1 bead to cell ratio] or plate coated αCD3 [5 µg/mL]/CD70$^{DT}$ [5 µg/mL]. (17A) Assessment of TCF1 and CD27 expression of non-activated [D0] and activated [D1-4] cells by flow cytometry. Gates are set based on isotype control [black, overlayed]. (17B) Frequency of TCF1+ CD8+ $T_N$ cells measured at indicated timepoints after activation in cultures stimulated with αCD3/αCD28 DynaBeads or with αCD3 [5 µg/mL]/CD70$^{DT}$ [5 µg/mL. (17C) Log2 fold change (Dyna-Beads vs. αCD3/αCD70$^{DT}$) of TCF7 gene expression of activated T CD8+ $T_N$ cells measured by pPCR is shown.

Figure 18:
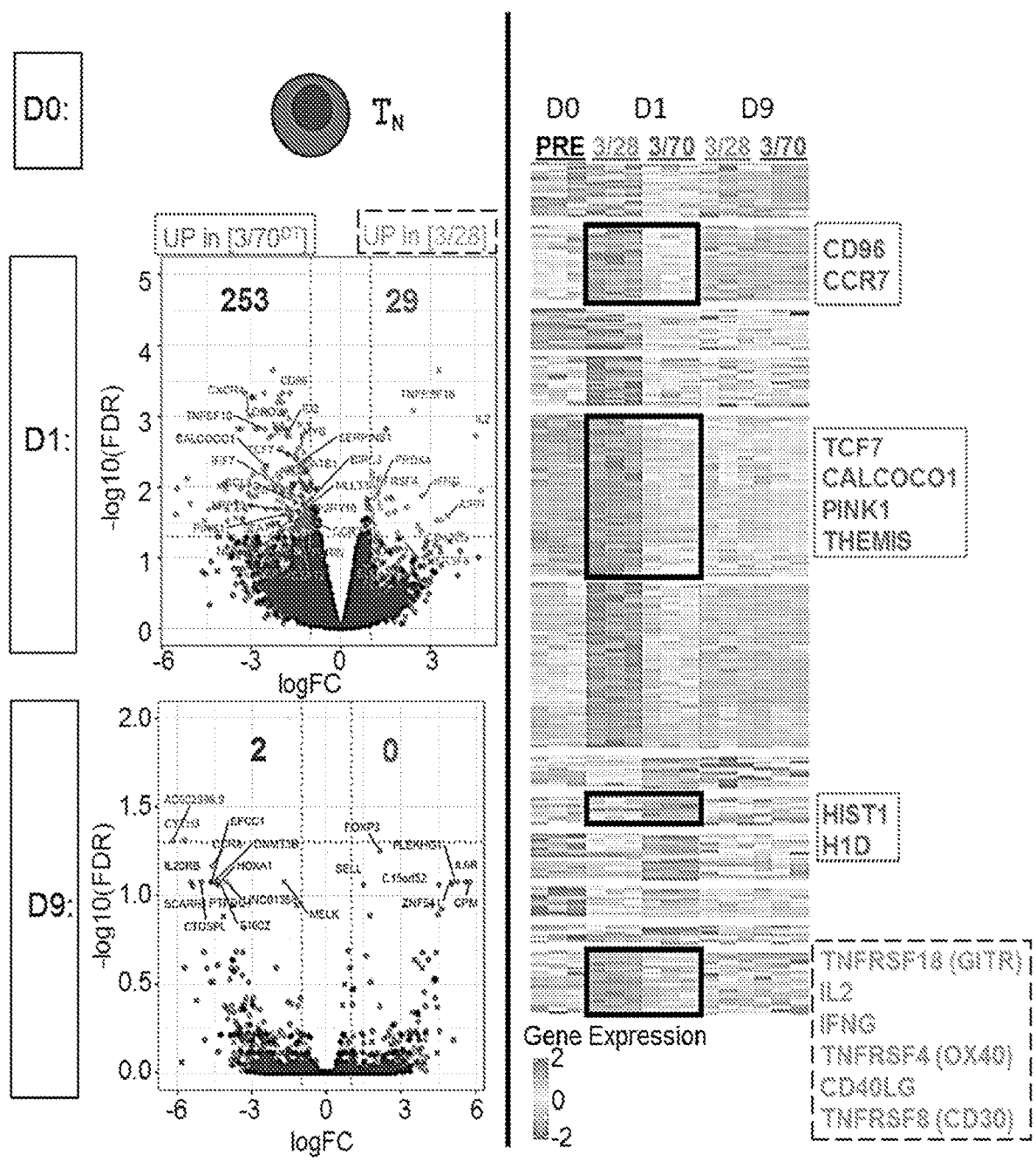
FIG. 18. Transcriptional profile of αCD3/αCD28 vs. αCD3/CD70 activated CD8$^+$ $T_N$ cells diverges early after activation. Bulk RNAseq of FACS-sorted un-activated (D0; PRE) $T_N$ CD8$^+$ T cells or activated (D1, D9) with αCD3/αCD28 beads (3/28) or αCD3/CD70$^{DT}$ (3/70) was performed. (Left) Volcano plots with the indicated number of differentially expressed genes (differentially expressed genes (DEGs), false discovery rate (FDR) 5%) and selected annotated gene names. (Right) Heatmap showing relative expression profiles including all DEGs of D1 and D9 activated $T_N$ CD8$^+$ T cells. Identification of 12 different expression clusters and representative gene names are shown.

Unique transcriptional signatures between αCD3/CD70$^{DT}$ and αCD3/αCD28 activated $T_N$ cells were searched for using RNAseq at early and late timepoints. A large number of differentially expressed genes (DEGs) were found on day 1, however, the transcriptional profiles were relatively similar at the end of the culture, on day 9 (FIG. 18). The heat map showed 12 distinct gene regulation clusters among all the differentially expressed genes. For example, genes such as CD96 or CCR7, which are associated with T cell inhibition and memory, were strongly down-regulated in cells activated by αCD3/αCD28 on day 1 and were better maintained in cells activated by αCD3/CD70$^{DT}$. Genes like TCF7, CALCOCO1, PINK, and THEMIS, are associated with stemness, Wnt-signaling, protection from mitochondrial dysfunction, and TCR signaling modulation. Although they have high expression in non-activated $T_N$ cells, they were strongly down-regulated on day 1 in T cells activated with αCD3/αCD28, and to a lower extent in αCD3/CD70$^{DT}$ activated T cells. HIST1H1D, a Histone/DNA linker responsible for chromosome compaction, was up-regulated in αCD3/CD70$^{DT}$ activated T$_N$ cells on day 1. On the other hand, IL-2, interferon gamma (IFNG), and other TNFRs (TNF receptor family members), genes associated with T cell activation and effector function, were strongly up-regulated in αCD3/αCD28 activated T$_N$ cells on day 1. Nevertheless, these early transcriptional differences were not maintained throughout the expansion of T$_N$ cells.

Figure 19A:
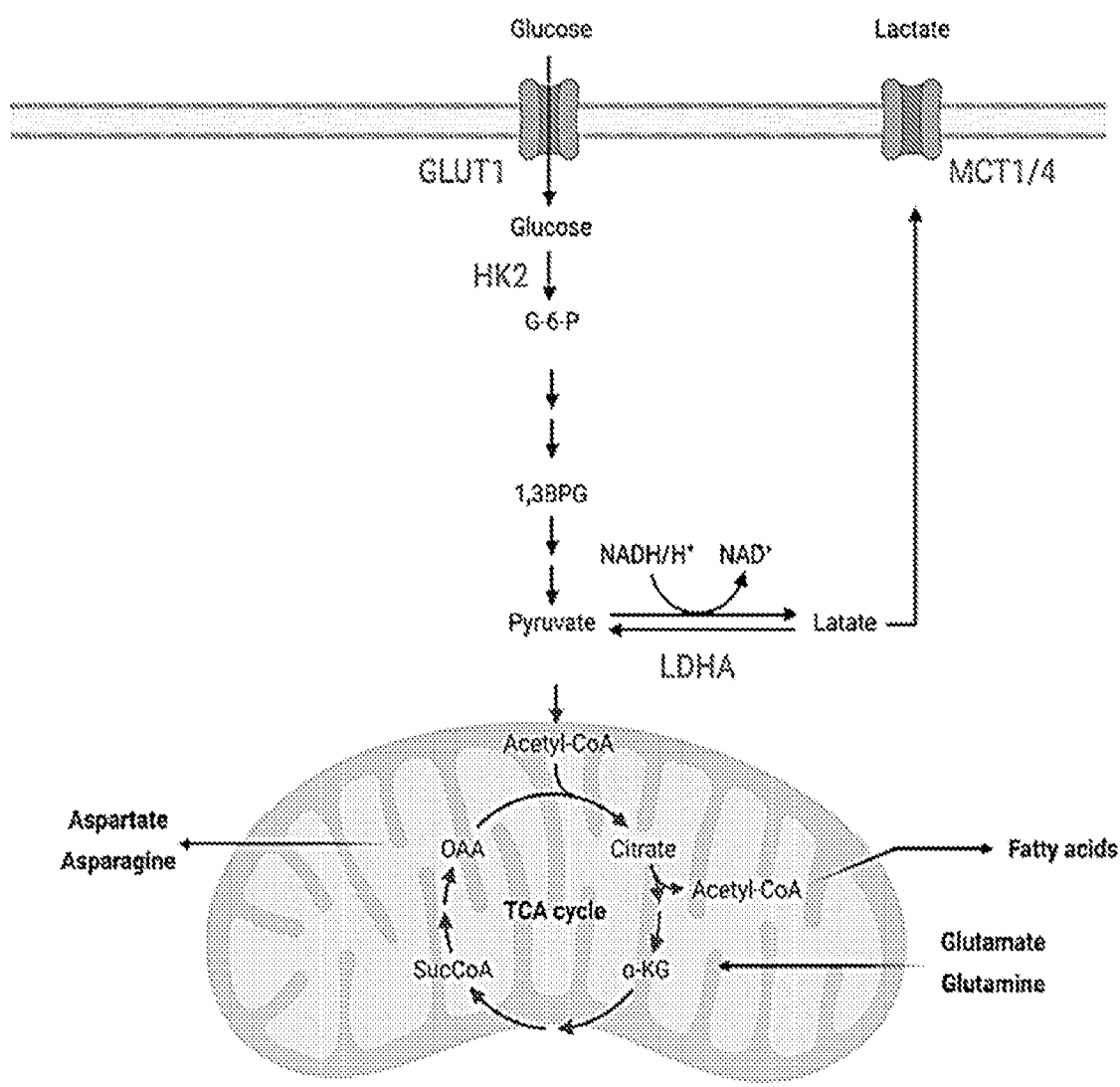
Figure 19C:
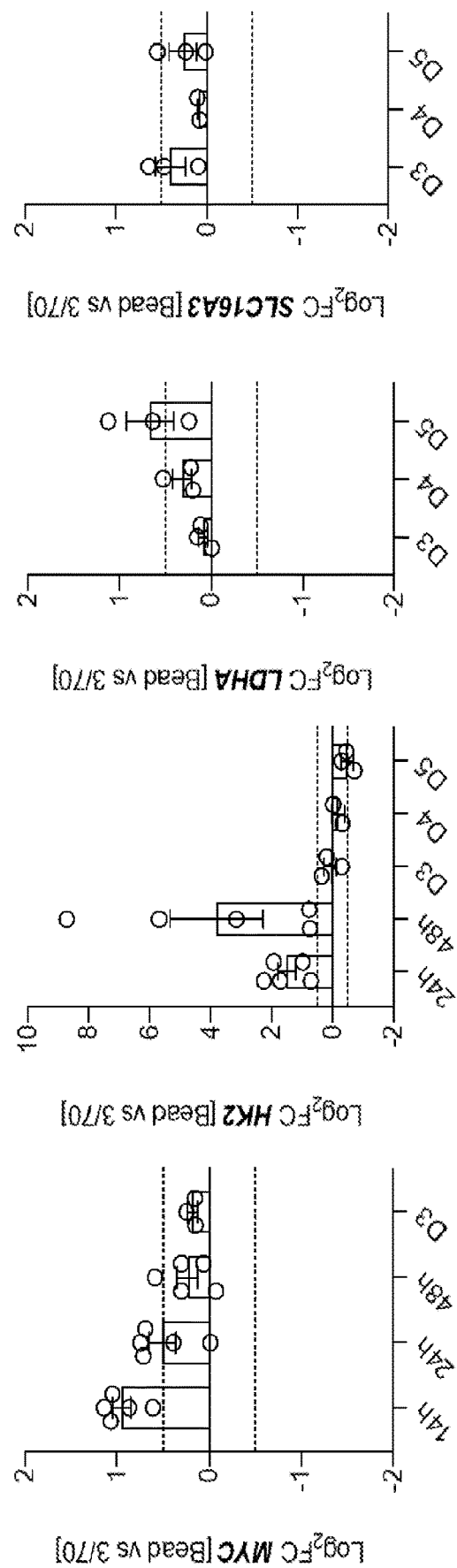

FIGS. 19A-19C show that MYC gene expression and MYC-dependent glucose metabolism are more upregulated in αCD3/αCD28 vs. αCD3/CD70 activated CD8$^+$ T$_N$ cells. This is indicative of a more pronounced switch to an effector metabolic phenotype. (FIG. 19A) Scheme of key metabolic pathways with relevant membrane transporters, enzymatic steps, and degradation products. (FIG. 19B) GLUT1 expression is reduced in αCD3/CD70 activated T cells compared with αCD3/αCD28 activated T cells. Data shows the delta MFI of GLUT1 receptor expression above isotype control on non-activated (PRE) and activated (D1-D4) CD8$^+$ T$_N$ cells. (FIG. 19C) Log2 Fold Change (DynaBead vs. αCD3/CD70$^{DT}$) of MYC, HK2, LDHA, and SLC16A3 gene expression in activated T$_N$ cells at indicated timepoints after activation.

Figure 20A:
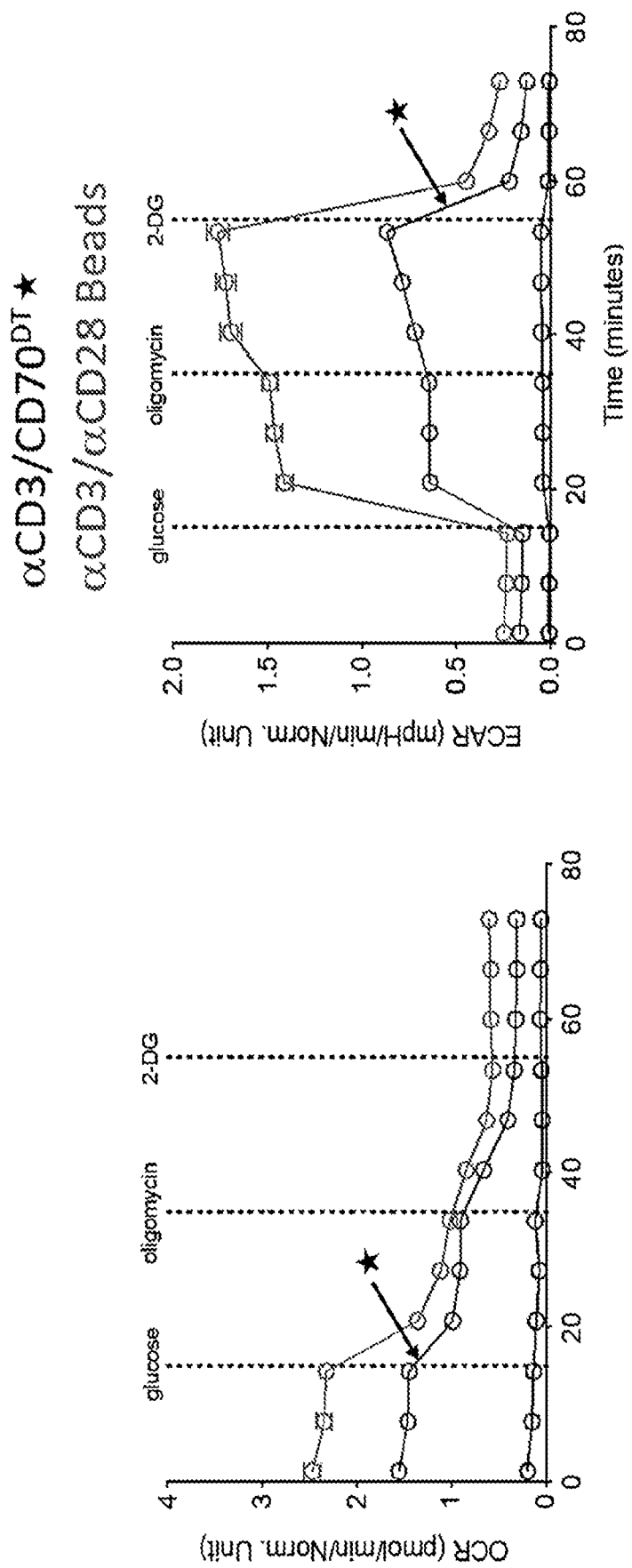
FIGS. 20A, 20B. Difference in cellular respiration and glycolysis of CD8$^+$ $T_N$ cells activated by αCD3/αCD28 vs. αCD3/CD70. Naïve CD8$^+$ $T_N$ cells were activated with αCD3/αCD28 or αCD3/CD70 for 5 or 10 days and then assayed for oxygen consumption rate (OCR) and extracellular acidification rate (ECAR) after addition of glucose, oligomycin, and 2-DG as shown in 20A for cells assayed at day 5. (20B) The differences in glycolysis normalized by day 9, indicating that the strong induction of effector metabolism observed after αCD3/CD28 stimulation was never attained after αCD3/CD70 stimulation.
Figure 20B:
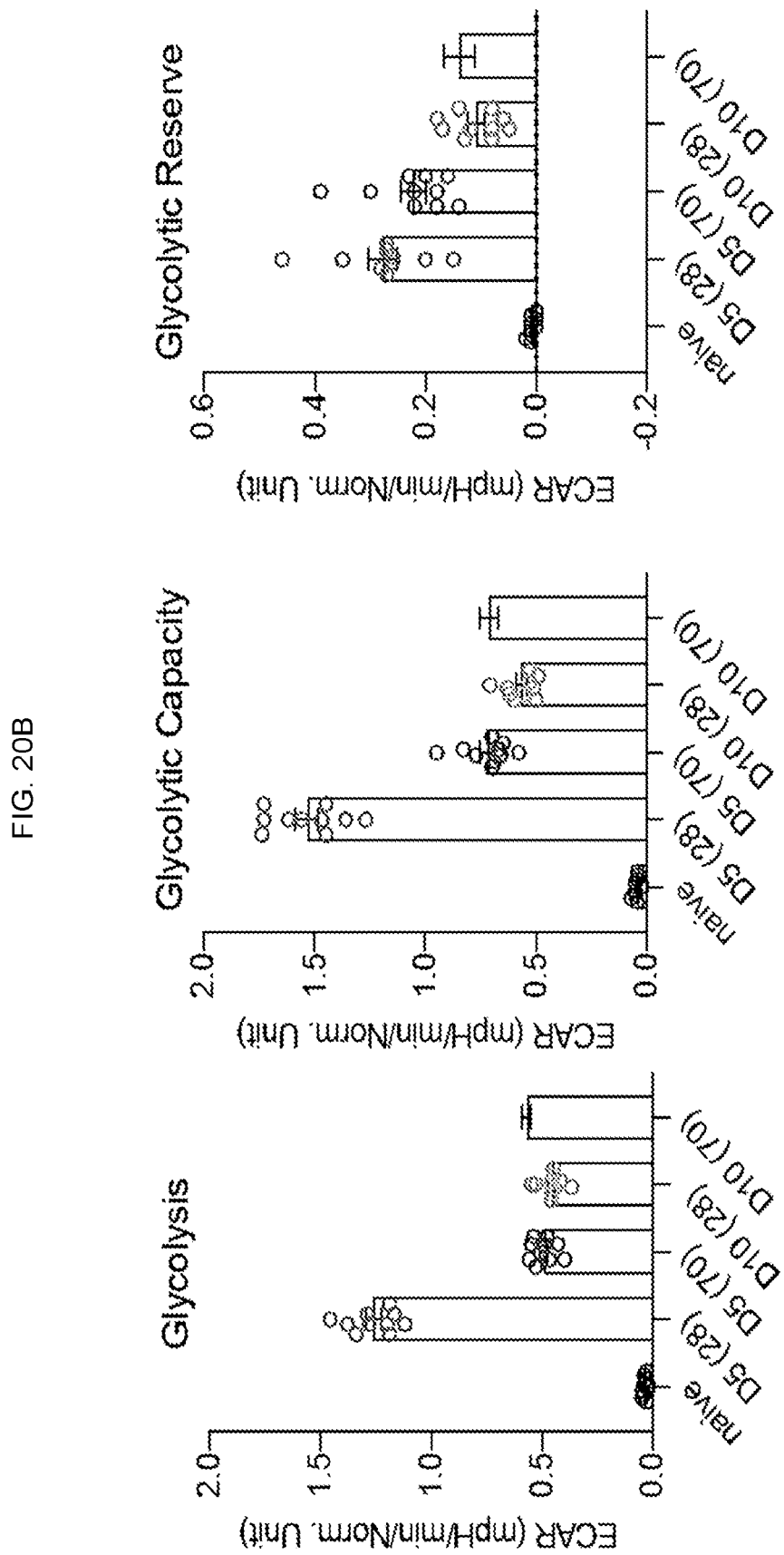

FIGS. 20A, 20B show the difference in cellular respiration and glycolysis of CD8$^+$ T$_N$ cells activated by αCD3/αCD28 vs. αCD3/CD70. Naïve CD8$^+$ T$_N$ cells were activated with αCD3/αCD28 or αCD3/CD70 for 5 or 10 days and then assayed for oxygen consumption rate (OCR) and extracellular acidification rate (ECAR) after addition of glucose, oligomycin, and 2-DG as shown in (20A) for cells assayed at day 5. (20B) The differences in glycolysis normalized by day 9, indicating that the strong induction of effector metabolism observed after αCD3/CD28 stimulation was never attained after αCD3/CD70 stimulation.

Figure 21:
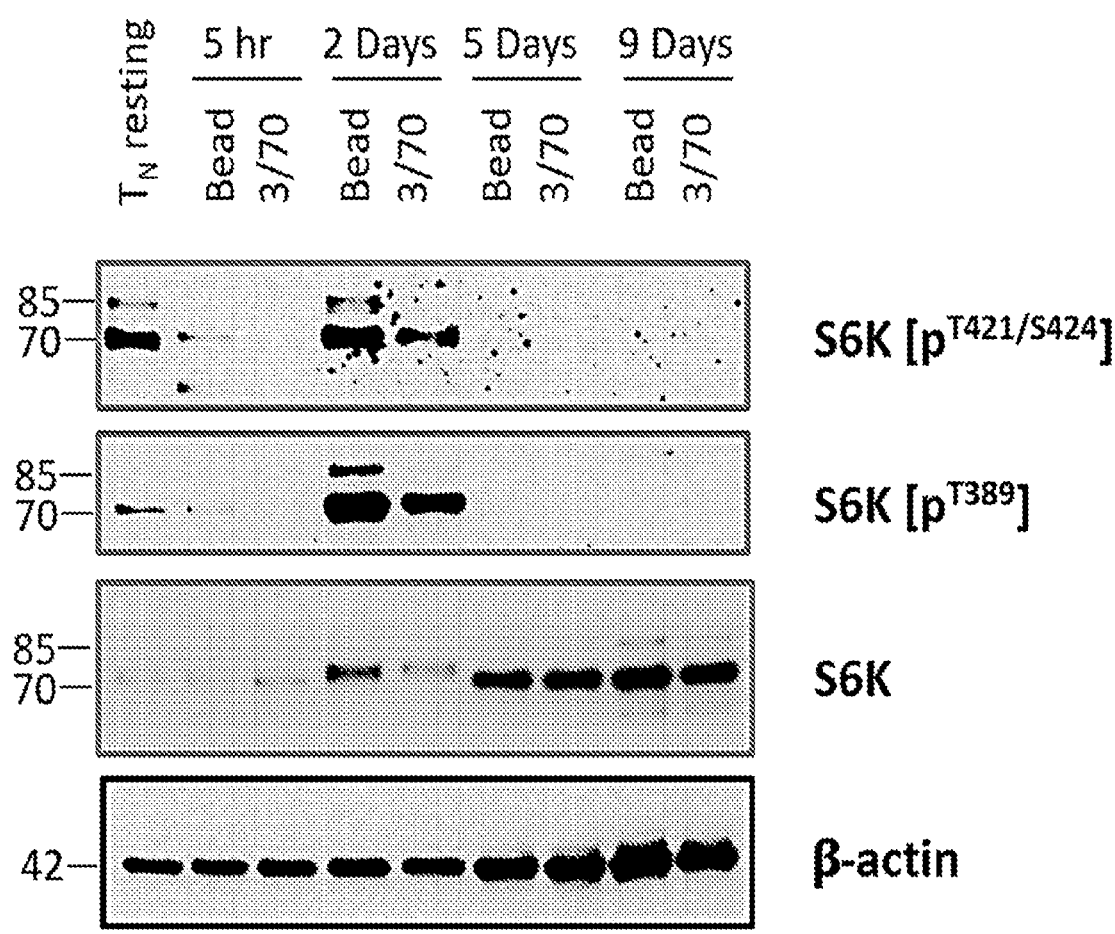
FIG. 21. As of 2 days after activation, mTORC1 signaling is stronger induced in αCD3/αCD28 vs. αCD3/CD70 co-stimulated CD8$^+$ T cells, consistent with enhanced effector metabolic reprogramming. αCD3/αCD28 DynaBead activated cells show stronger induction of mTORC1/S6K signaling compared to αCD3/CD70$^{DT}$ activated cells. Assessment of mTORC1-dependent signaling in αCD3/αCD28 DynaBead or αCD3 [5 μg/mL]/CD70$^{DT}$ [5 μg/mL] activated CD8$^+$ $T_N$ cells using Western Blot. Expression levels of S6K backbone and its active forms (targeted phosphorylation sites: T421/S424 and T389) are shown in naïve, 5h, and 2-9 day activated cells.

FIG. 21 shows that as of 2 days after activation, mTORC1 signaling is more strongly induced in αCD3/αCD28 vs. αCD3/CD70 co-stimulated CD8$^+$ T$_N$ cells, consistent with enhanced effector metabolic reprogramming. αCD3/αCD28 DynaBead activated cells show stronger induction of mTORC1/S6K signaling compared to αCD3/CD70$^{DT}$ activated cells. Assessment of mTORC1-dependent signaling in αCD3/αCD28 DynaBead or αCD3 [5 µg/mL]/CD70$^{DT}$ [5 µg/mL] activated CD8$^+$ T$_N$ cells using Western Blot. Expression levels of S6K backbone and its active forms (targeted phosphorylation sites: T421/S424 and T389) are shown in naïve, 5h, and 2-9 day activated cells.

Figure 22:
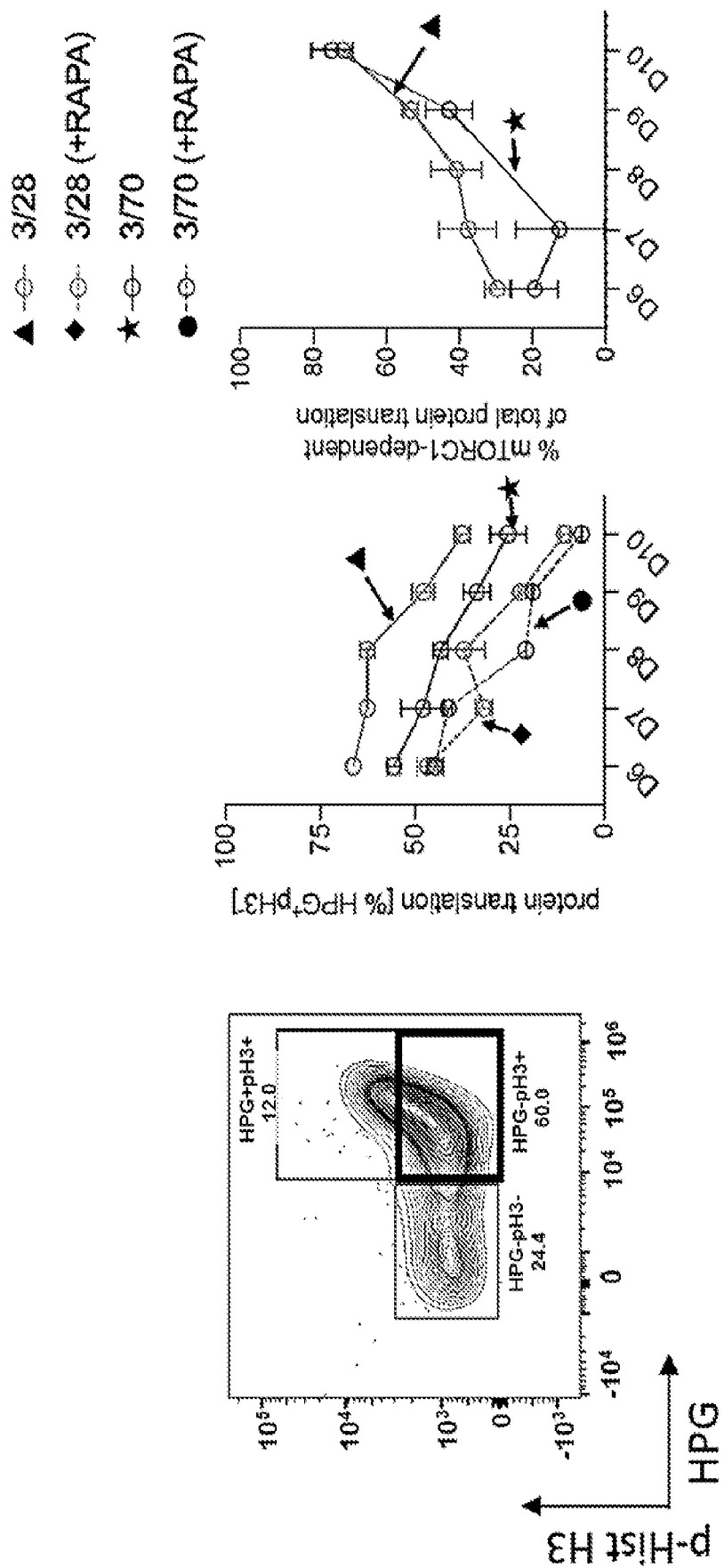
FIG. 22. mTORC1-dependent protein translation is elevated in αCD3/αCD28 vs. αCD3/CD70 co-stimulated CD8$^+$ $T_N$ cells during the late expansion phase, indicative of a constitutively higher metabolic state. αCD3/αCD28. Flow-cytometry based assessment of total and mTORC1-independent protein translation in αCD3/αCD28 DynaBead or αCD3 [5 μg/mL]/CD70$^{DT}$ [5 μg/mL] activated CD8$^+$ $T_N$ cells. L-Methionine analog incorporation (HPG+) in non-mitotic (phospho-Histone H3 negative; p-HistH3⁻) cells is assessed during the late expansion phase (D6-D10 after activation). For transient inhibition of mTORC1 activity, Rapamycin (RAPA) is added to the cell cultures during the HPG-incorporation phase.

FIG. 22 shows that mTORC1-dependent protein translation is elevated in αCD3/αCD28 vs. αCD3/CD70 co-stimulated CD8$^+$ T$_N$ cells during the late expansion phase, indicative of a constitutively higher metabolic state (see, e.g., Seedhom, J. Immunol. Aug. 15, 2016, 197 (4) 1498-1506). αCD3/αCD28. Flow-cytometry based assessment of total and mTORC1-independent protein translation in αCD3/αCD28 DynaBead or αCD3 [5 µg/mL]/CD70$^{DT}$ [5 µg/mL] activated CD8$^+$ T$_N$ cells. L-Methionine analog incorporation (HPG+) in non-mitotic (phospho-Histone H3 negative; p-HistH3$^-$) cells is assessed during the late expansion phase (D6-D10 after activation). For transient inhibition of mTORC1 activity, Rapamycin (RAPA) is added to the cell cultures during the HPG-incorporation phase.

Figure 23:
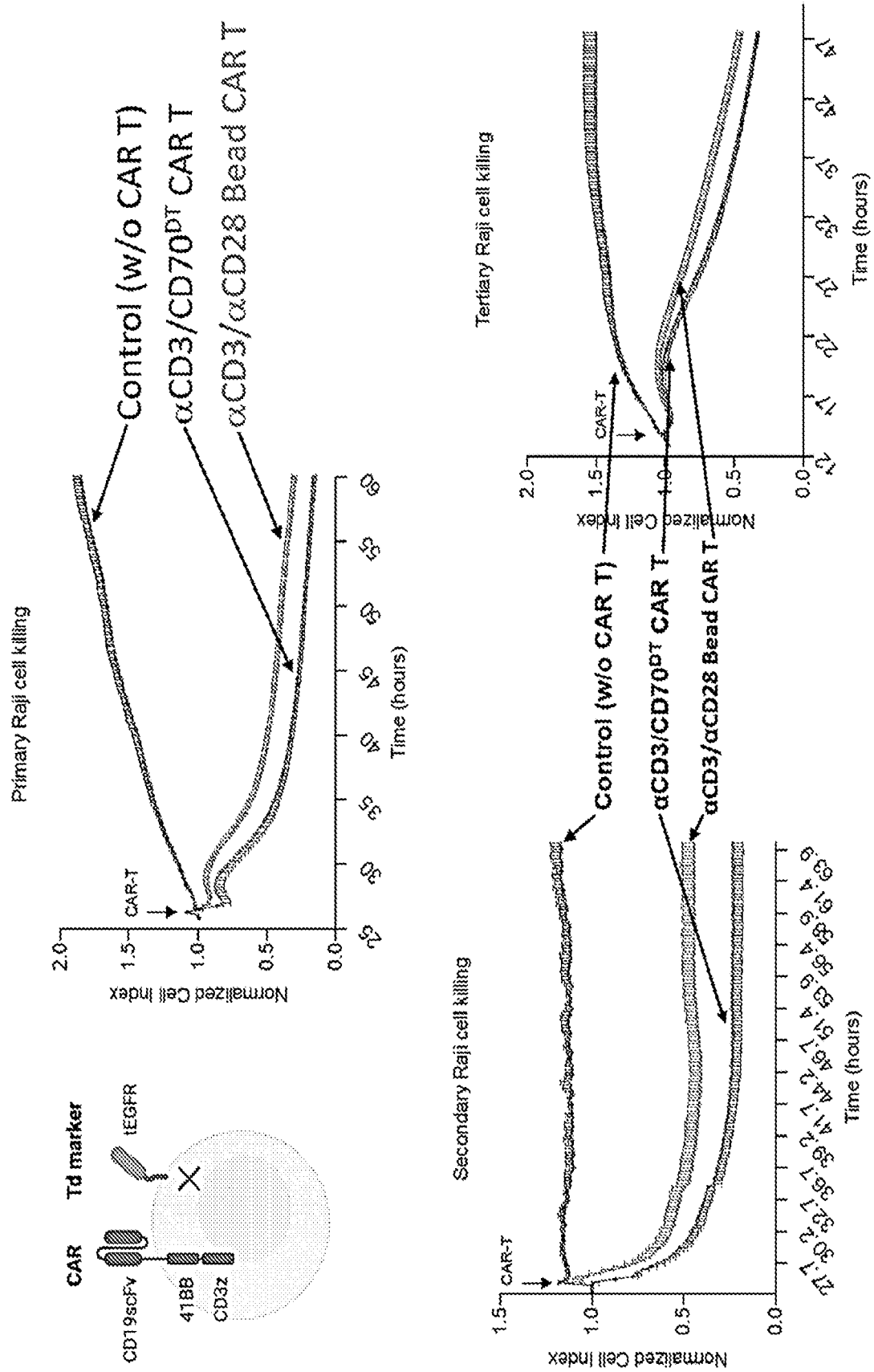
FIG. 23. αCD3/CD70 activated CAR T cells show superior ability to maintain tumor cell killing over serial tumor cell exposure compared with αCD3/αCD28 activated CAR T cells. Impedance-based in vitro serial killing assay of CD8$^+$ bulk-derived CD19 (BBz)-EGFRt CAR T cells targeting CD19$^+$ Raji lymphoma cells. 10 days after activation with αCD3/αCD28 DynaBead or αCD3 [5 μg/mL]/CD70$^{DT}$ [5 μg/mL] CAR T cells were purified using positive EGFR selection and plated at a 10:1 [E:T] ratio with Raji cells. After a 3-day killing period, CAR T cells were cleaned up and further rested for 24 h in CTL containing 5U/mL IL2. The next day CAR T cells were re-plated for secondary killing at a 7:1 ratio for another 3 days. After 24 h of resting, CAR T cells were re-plated for tertiary killing at a 2:1 ratio.

FIG. 23 provides data showing that αCD3/CD70 activated CAR T cells show superior ability to maintain tumor cell killing over serial tumor cell exposure compared with αCD3/αCD28 activated CAR T cells. Impedance based in vitro serial killing assay of CD8$^+$ bulk-derived CD19 (BBz)- EGFRt CAR T cells targeting CD19$^+$ Raji lymphoma cells. 10 days after activation with αCD3/αCD28 DynaBead or αCD3 [5 µg/mL]/CD70$^{DT}$ [5 µg/mL] CAR T cells were purified using positive EGFR selection and plated at a 10:1 [E: T] ratio with Raji cells. After a 3-day killing period, CAR T cells were cleaned up and further rested for 24 h in CTL containing 5U/mL IL2. The next day CAR T cells were re-plated for secondary killing at a 7:1 ratio for another 3 days. After 24 h of resting, CAR T cells were re-plated for tertiary killing at a 2:1 ratio.

Figure 24A:
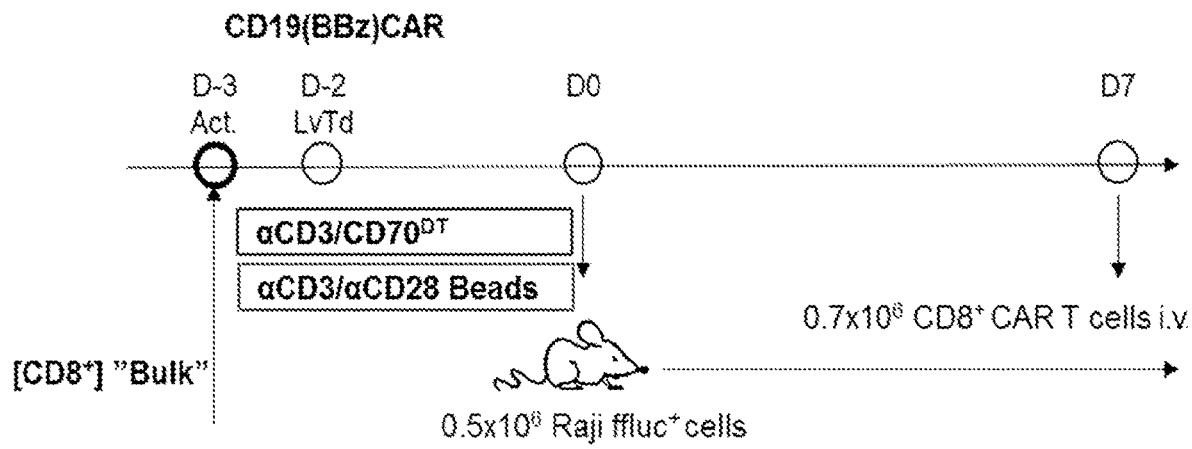
FIGS. 24A-24D. αCD3/CD70 activated bulk-derived CAR T cells have an increased in vivo expansion capacity and show better tumor control compared to αCD3/αCD28 activated CAR T cells. (24A) Schematic depicts a method to test CAR T cell function in vivo using a Raji lymphoma xenograft model. In this experiment, bulk CD8$^+$ T cells were activated with αCD3/αCD28 DynaBeads or αCD3/CD70$^{DT}$ and cells were transduced with a CD19 targeting 4-1BB/CD3ζ (BBz) CAR. A sub-curative dose of CD8$^+$ CAR T cells were injected into the tumor-bearing mice on day 7. (24B) Bioluminescence imaging (BLI) is shown of Raji ffluc$^+$ bearing NSG xenograft mice: Untreated (Ctrl.) or treated with αCD3/αCD28 DynaBead or αCD3/CD70$^{DT}$ activated bulk-derived CD8$^+$ CD19 (BBz) CAR T cells. (24C) Line graphs show average radiance of Raji ffluc$^+$ bearing tumor mice shows that αCD3/CD70$^{DT}$ activated bulk-derived CAR T cells control tumor growth better than control or αCD3/αCD28 DynaBeads. (24D) The expansion capacity was assessed in the peripheral blood by tracking truncated epidermal growth factor receptor-like protein (EGFRt) transduction marker. The percent expansion of EGFRt+ CD45$^+$ CD8$^+$ CAR T cells detected in the peripheral blood of mice (n=9 mice per group) showed that αCD3/CD70$^{DT}$ has a higher expansion capacity compared to the αCD3/αCD28 DynaBeads.
Figure 24B:
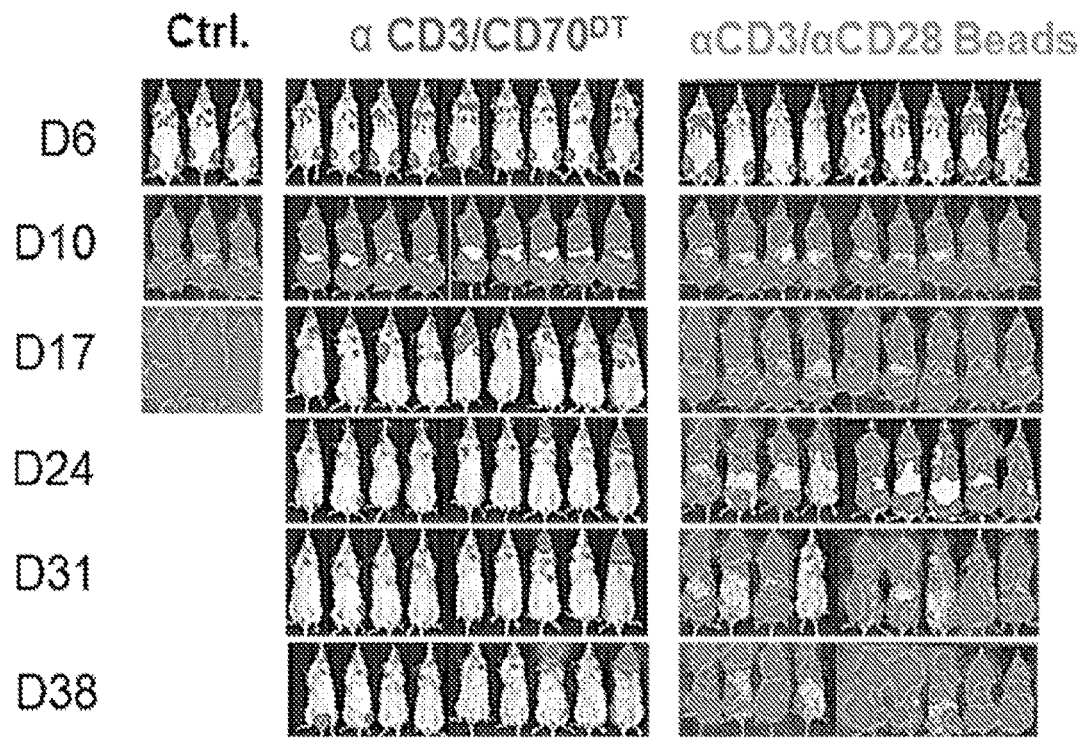
Figure 24C:
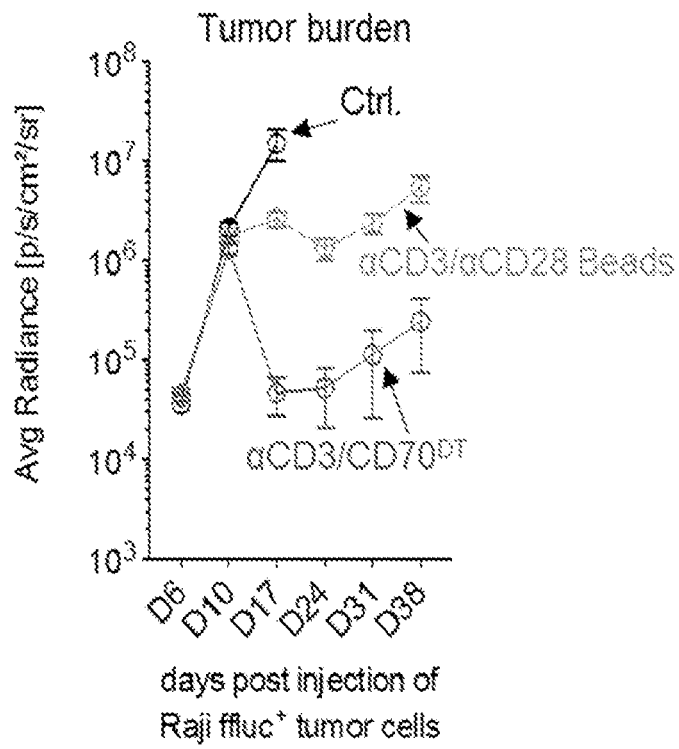
Figure 24D:
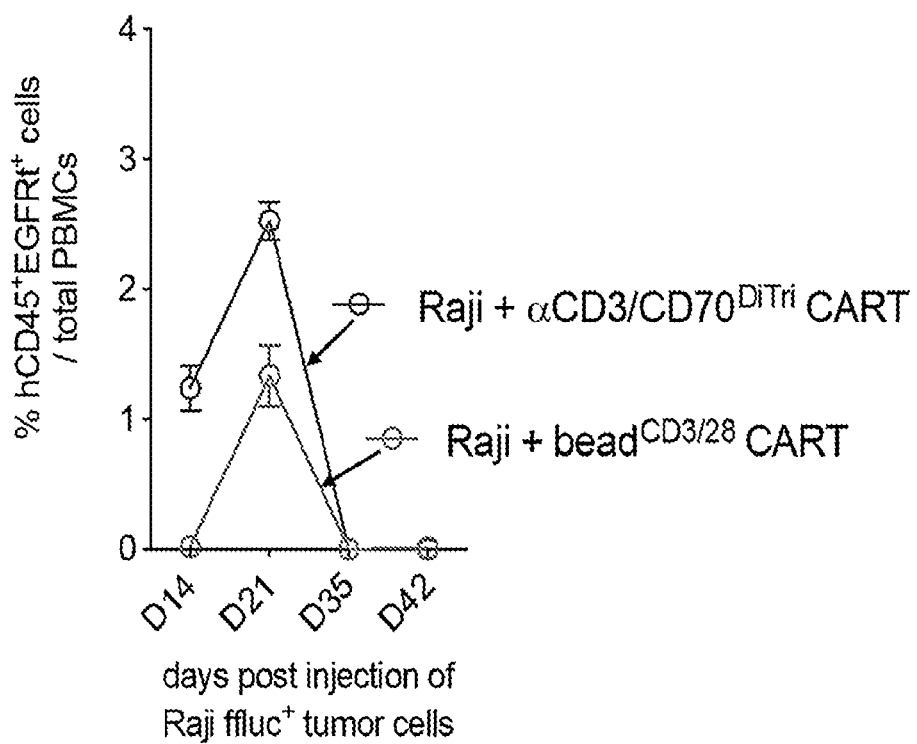

In FIGS. 24A-24D, CAR T cell function was tested in vivo using a Raji lymphoma xenograft model. In this experiment, bulk CD8$^+$ T cells were activated with αCD3/αCD28 or αCD3/CD70$^{DT}$ following the established protocol and transduced with a CD19 targeting BBz CAR (FIG. 24A). A sub-curative dose of these CD8$^+$ CAR T cells were injected into the tumor-bearing mice. The bioluminescence imaging and the quantification of the average radiance demonstrated that αCD3/CD70$^{DT}$ activated bulk-derived CAR T cells have a better capacity to control tumors (FIGS. 24B and 24C). Furthermore, αCD3/CD70$^{DT}$ activated CAR T cells have an increased expansion capacity as assessed in the peripheral blood by tracking truncated EGFR transduction marker (FIG. 24D). These investigations demonstrate that αCD3/CD70$^{DT}$ activated CAR T cells will result in a higher abundance of less differentiated TCF1$^+$ CD27$^+$ T cells which results in a better tumor control and expansion capacity compared to the αCD3/αCD28 DynaBead activated T cells.

Figure 25A:
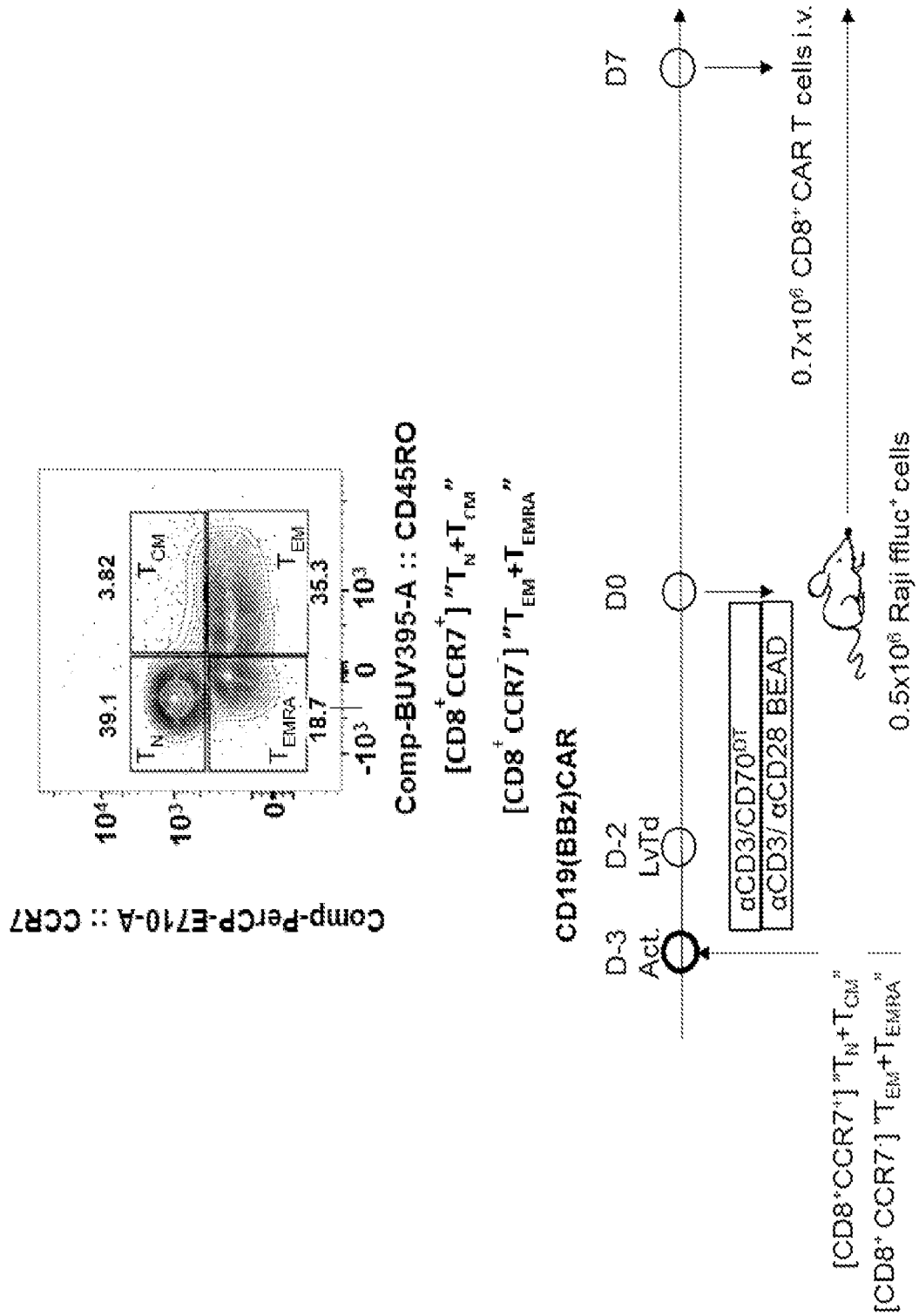
FIGS. 25A-25C. αCD3/CD70 T$_N$ and T$_{CM}$-derived CAR T cells show better tumor control compared to αCD3/αCD28 activated T$_N$ and T$_{CM}$-derived CAR T cells and to T$_{EM}$/TEMRA-derived CAR T cells. αCD3/CD70$^{DT}$ activated CCR7$^+$-derived CAR T cells have a better capacity to control tumors and an increased expansion capacity compared to the αCD3/αCD28 DynaBeads. (25A) Schematic depicts a method to test CAR T cell function in vivo using a Raji lymphoma xenograft model. In this experiment, CD8$^+$ CCR7$^+$ T$_N$+T$_{CM}$ cells and CD8$^+$ CCR7-T$_{EM}$+ TEMRA cells were activated with αCD3/αCD28 DynaBeads or αCD3/CD70$^{DT}$ and cells were transduced with a CD19 targeting BBz CAR. A sub-curative dose of CD8$^+$ CAR T cells were injected into the tumor-bearing mice on day 7. (25B) Line graph shows the average radiance of Raji ffluc$^+$ bearing NSG xenograft mice that were untreated (Ctrl.) or treated with αCD3/αCD28 DynaBeads or αCD3/CD70$^{DT}$ activated CCR7$^+$ or CCR7$^-$-derived CD8$^+$ CD19 (BBz) CAR T cells. αCD3/CD70$^{DT}$ activated CCR7$^+$ cells showed the most tumor growth control. (25C) overall survival is shown (n=5 mice per group).
Figure 25B:
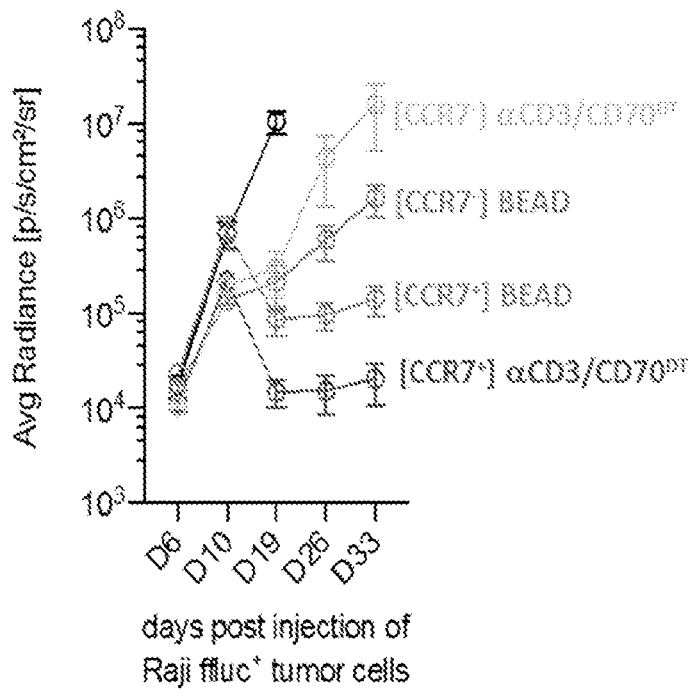
Figure 25C:
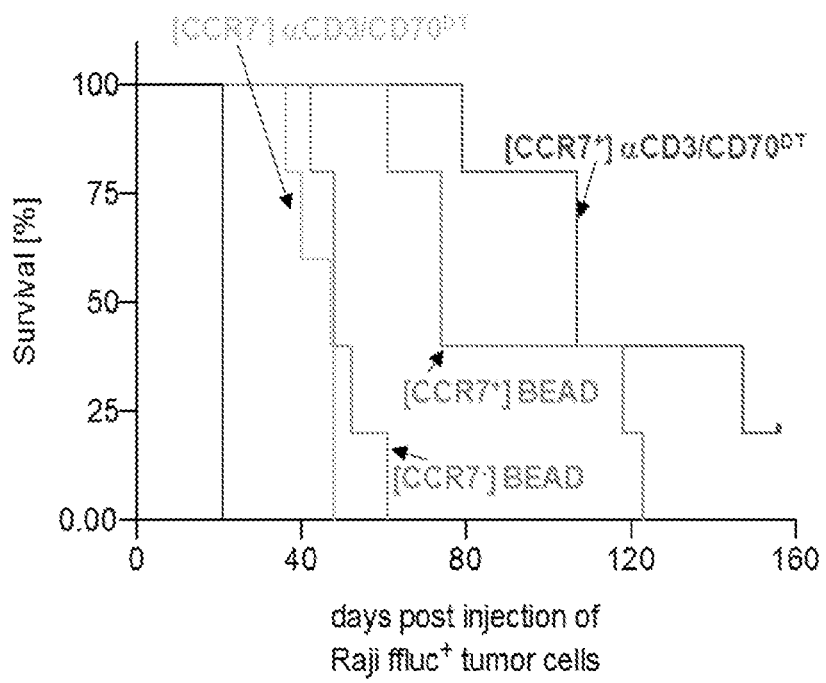

FIGS. 25A, 25B provide data showing that αCD3/CD70 T$_N$ and T$_{CM}$-derived CAR T cells show better tumor control compared to αCD3/αCD28 activated T$_N$ and T$_{CM}$-derived CAR T cells and to T$_{EM}$/TEMRA-derived CAR T cells. αCD3/CD70$^{DT}$ activated CCR7$^+$-derived CAR T cells have a better capacity to control tumors and an increased expansion capacity compared to the αCD3/αCD28 DynaBeads. (FIG. 25A) Schematic depicts a method to test CAR T cell function in vivo using a Raji lymphoma xenograft model. In this experiment, CD8$^+$ CCR7$^+$ T$_N^+$ T$_{CM}$ cells and CD8$^+$ CCR7-T$_{EM}^+$ TEMRA cells were activated with αCD3/αCD28 DynaBeads or αCD3/CD70PT and cells were transduced with a CD19 targeting BBz CAR. A sub-curative dose of CD8$^+$ CAR T cells were injected into the tumor-bearing mice on day 7. (FIG. 25B) Line graph shows the average radiance of Raji ffluc$^+$ bearing NSG xenograft mice that were untreated (Ctrl.) or treated with αCD3/αCD28 Dyna-Beads or αCD3/CD70$^{DT}$ activated CCR7$^+$ or CCR7$^-$-derived CD8$^+$ CD19 (BBz) CAR T cells. αCD3/CD70$^{DT}$ activated CCR7$^+$ cells showed the most tumor growth control. (FIG. 25C) overall survival are shown (n=5 mice per group).

Figure 26:
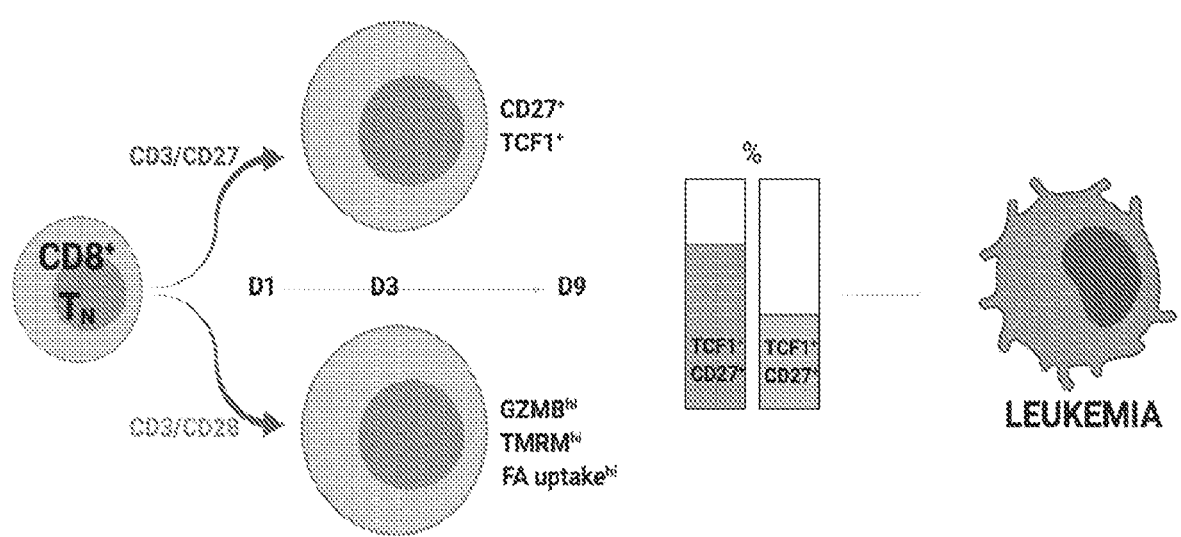
FIG. 26. Partial data summary.

FIG. 26 provides results summarizing that αCD3/CD70$^{DT}$ co-stimulation in vitro results in robust CD8$^+$ T cell proliferation, restrains effector function/metabolism; maintains a high fraction of CD27$^+$ TCF1$^+$ bulk-derived T cells after early activation; transcriptionally preserves early differentiation/activation (D1); mediates accumulation of CD27$^+$ TCF1$^+$ T$_N$-derived cells in the late T cell product (D9); and generates CAR T cells with superior killing capacity.

FIG. 27 provides additional sequences supporting the disclosure.

EXEMPLARY EMBODIMENTS

1. A single chain protein including at least three copies of the extracellular domain of CD70, wherein the extracellular domain of CD70 includes the amino acid sequence of SEQ ID NO: 4 or an amino acid sequence having at least 70% identity thereto and retaining the signaling properties of CD70.

2. The single chain protein of embodiment 1, wherein use of the single chain protein during T cell manufacturing results in a T cell population with enhanced properties.

3. The single chain protein of embodiment 1, wherein the enhanced properties include an increase in T cell expansion, an increase in T cell proliferation, a decrease in T cell exhaustion, selective expansion of less differentiated T cell populations, selective expansion of naïve and memory T cells, a decrease in glucose metabolism, a decrease in glycolytic switch capacity, a weaker induction of mTORC1/S6K signaling, a decrease in mTORC1-dependent protein translation during late expansion phase, an increase in T cell survival ex vivo and following administration, an increase in expansion ex vivo and following administration, an increase in engraftment following administration, an increase in killing capacity, an increase in serial killing capacity, and/or an increase in the targeting of tumor cells when compared to T cell activation under comparable control conditions using αCD28/CD3 stimulating molecule (e.g., DynaBeads).

4. The single chain protein of embodiment 1, wherein the enhanced properties include enhanced acquisition of a memory gene signature (see, e.g., FIG. 10D), superior acquisition of a $T_{SCM}$-like T cell phenotype (see, e.g., FIGS. 13A-13D), reduced expression of Tigit and LAG 3 inhibitory receptors (see, e.g., FIG. 11A-11G), reduced acquisition of an effector metabolic phenotype (see, e.g., 14A, 14B), increased frequency of gene-modified blood mononuclear cells (see, e.g., FIG. 11F), reduced granzyme b expression, glucose uptake, and fatty acid oxidation (see, e.g., 14A, 14B), higher abundance of CD27$^+$ TCF1$^+$ T cells within 4-6 days of activation, indicative of a stem cell memory phenotype (see, e.g., FIGS. 15A-15D), faster transition into a stem cell memory T cell state (see, e.g., 17A-17C), a less pronounced switch to an effector metabolic phenotype as evidenced by decreased MYC gene expression and MYC-dependent glucose metabolism (see, e.g., FIGS. 19A-19C), reduced GLUT1 expression (see, e.g., FIG. 19B), reduced glycolysis as measured by oxygen consumption rate (OCR) and extracellular acidification rate (ECAR) (see, e.g., FIGS. 20A, 20B), less mTORC1 signaling (see, e.g., FIG. 21) and/or less mTORC1-dependent protein translation (see, e.g., FIG. 22) when compared to T cell activation under comparable control conditions using αCD28/CD3 stimulating molecule (e.g., DynaBeads).

5. The single chain protein of any of embodiments 1-4, wherein the single chain protein further includes a dimerization domain.

6. The single chain protein of embodiment 5, wherein the dimerization domain includes the Fc portion of an antibody.

7. The single chain protein of embodiment 5, wherein the dimerization domain includes the Fc portion of an IgG antibody.

8. The single chain protein of any of embodiments 1-7, wherein the single chain protein further includes a tag.

9. The single chain protein of embodiment 8, wherein the tag includes 6His and/or Avi.

10. The single chain protein of embodiment 8, wherein the tag includes Flag tag, Xpress tag, Calmodulin tag, Polyglutamate tag, HA tag, Myc tag, Softag 1, Softag 3, Strep tag, or V5 tag. 11. The single chain protein of any of embodiments 1-10, wherein the single chain protein further includes a linker.

12. The single chain protein of embodiment 11, wherein the linker is selected from GS and GGGS (SEQ ID NO: 8).

13. The single chain protein of any of embodiments 1-12, wherein the single chain protein further includes Tev.

14. The single chain protein of any of embodiments 1-13, having the sequence set forth in SEQ ID NO: 5.

15. The single chain protein of any of embodiments 5-14, dimerized, optionally dimerized with an identical single chain protein.

16. The single chain protein of any of embodiments 5-15, dimerized with a single chain protein that is identical to the single chain protein of any of embodiments 2-12 but for the presence of a dimerization domain that is complementary to the dimerization domain of the single chain of any of embodiments 2-12.

17. The single chain protein of any of embodiments 5-16, dimerized with a single chain protein that shares 98% or 99% sequence identity with the single chain protein of any of embodiments 2-13.

18. The single chain protein of any of embodiments 1-17, further including a circular tandem repeat protein (cTRP) scaffold.

19. The single chain protein of embodiment 18, wherein the cTRP scaffold includes a protein of the formula (a-b-x-y) n wherein a and x represent linkers; b represents an amino acid sequence that forms an a helix; y represents an amino acid sequence that forms a second a helix; and n=3 or more.

20. The single chain protein of embodiment 19, wherein the extracellular domains of CD70 are inserted within or adjacent to the a and x linkers.

21. The single chain protein of embodiment 19 or 20, wherein the linker includes GIS.

22. The single chain protein of any of embodiments 19-21, wherein the N-terminal b segment includes CEAIKAAAELGKA (SEQ ID NO: 26).

23. The single chain protein of any of embodiments 19-22, wherein the x linker includes GLD. 24. The single chain protein of any of embodiments 19-23, wherein n=3 or more and b and y segments that are not N-terminal or C-terminal include SEEILELLRAAHEL (SEQ ID NO: 27).

25. The single chain protein of any of embodiments 19-24, wherein the C-terminal b segment includes PECIKAAAELGKA (SEQ ID NO: 28).

26. The single chain protein of any of embodiments 19-25, wherein n=6.

27. The single chain protein of any of embodiments 19-26, having the sequence set forth in SEQ ID NO: 7.

28. A single chain protein including the extracellular domain of CD70 and a trimerization domain (TD).

29. The single chain protein of embodiment 28, wherein the TD includes tetranectin or collagen. 30. The single chain protein of embodiment 28, wherein the TD includes the SadB TD, the EML4 TD, the clathrin TD, the Collagen XV TD, the Collagen XVIII TD, the Matrilin-1 TD, a Matrilin-1 variant TD, the DMPK TD, a DMPK variant TD, the Langerin TD, a Langerin variant TD, the Coronin 1a TD, or a Coronin 1a variant TD.

31. The single chain protein of any of embodiments 28-30, wherein the single chain protein further includes a tag.

32. The single chain protein of embodiment 31, wherein the tag includes 6His and/or Avi 33. The single chain protein of embodiment 31, wherein the tag includes Flag tag, Xpress tag, Calmodulin tag, Polyglutamate tag, HA tag, Myc tag, Softag 1, Softag 3, Strep tag, or V5 tag. 34. The single chain protein of any of embodiments 28-33, wherein the single chain protein further includes a linker.

35. The single chain protein of embodiment 34, wherein the linker includes GS, GGS, GGGS (SEQ ID NO: 8), or GGGGS (SEQ ID NO: 21).

36. The single chain protein of any of embodiments 28-35, wherein the single chain protein further includes Tev.

37. The single chain protein of any of embodiments 28-36, having the sequence set forth in SEQ ID NO: 13 or SEQ ID NO: 15.

38. The single chain protein of any of embodiments 28-37, trimerized with two identical single chain proteins.

39. The single chain protein of any of embodiments 28-38, trimerized with two single chain proteins that are identical to the single chain protein of any of embodiments 28-38 but for the presence within each of the two of a trimerization domain that is complementary to the trimerization domain of the single chain of any of embodiments 28-38.

40. The single chain protein of any of embodiments 28-39, trimerized with two single chain proteins that share 98%, 99%, or 100% sequence identity with the single chain protein of any of embodiments 28-39.

41. A T cell population expanded within culture conditions including a single chain protein of any of embodiments 1-40.

42. The T cell population of embodiment 41, wherein the T cell population is enriched for CD4$^+$ T cells or CD8$^+$ T cells.

43. A T cell of the population of embodiment 41 or 42, genetically modified to express a recombinant molecule.

44. The T cell of embodiment 43, wherein the recombinant molecule is a chimeric antigen receptor (CAR).

45. The T cell of embodiment 43, wherein the recombinant molecule includes a T cell receptor.

46. The T cell of any of embodiments 43-45, wherein the recombinant molecule specifically binds a marker on a cancer cell or a virally infected cell.

47. The T cell of embodiment 46, wherein the marker includes A33; BAGE; Bcl-2; β-catenin; BCMA; B7H4; BTLA; CA125; CA19-9; CD3, CD5; CD19; CD20; CD21; CD22; CD25; CD28; CD30; CD33; CD37; CD38; CD40; CD52; CD44v6; CD45; CD56; CD79b; CD80; CD81; CD86; CD123; CD134; CD137; CD151; CD171; CD276; CEA; CEACAM6; c-Met; CS-1; CTLA-4; cyclin B1; DAGE; EBNA; EGFR; EGFRvIII, ephrinB2; ErbB2; ErbB3; ErbB4; EphA2; estrogen receptor; FAP; ferritin; α-fetoprotein (AFP); FLT1; FLT4; folate-binding protein; Frizzled; GAGE; G250; GD-2; GHRHR; GHR; GITR; GM2; GPRC5D; gp75; gp100 (Pmel 17); gp130; HLA; HER-2/neu; HPV E6; HPV E7; hTERT; HVEM; IGF1R; IL6R; KDR; Ki-67; Lewis A; Lewis Y; LIFRB; LRP; LRP5; LTBR; MAGE; MART; mesothelin; MUC; MUC1; MUM⁻1-B; myc; NYESO-1; O-acetyl GD-2; O-acetyl GD3; OSMRB; p53; PD1; PD-L1; PD-L2; PRAME; progesterone receptor; PSA; PSMA; PTCH1; RANK; ras; Robo1; RORI; survivin; TCRα; TCRβ; tenascin; TGFBR1; TGFBR2; TLR7; TLR9; TNFR1; TNFR2; TNFRSF4; TWEAK-R; TSTA tyrosinase; VEGF; WT1; glycoprotein B; CMV pp65; EBV EBNAI; EBV P18; the HBV S protein; the HBV M protein; the HBV L protein; the pre-S antigen of HBV; HBCAG DELTA; HBV HBE; hepatitis C viral RNA; HCV NS3; HCV NS4; herpes simplex virus immediate early proteins; herpes simplex virus glycoprotein D; HIV gp32; HIV gp41; HIV gp120; HIV gp160; HIV P17/24; HIV P24; HIV P55 GAG; HIV P66 POL; HIV TAT; HIV GP36; Hemagglutinin; neuraminidase; Japanese encephalitis protein E; Japanese encephalitis protein M-E; Japanese encephalitis protein M-E-NS1; Japanese encephalitis protein NS1; Japanese encephalitis protein NS1-NS2A; the measles virus fusion protein; rabies glycoprotein; rabies nucleoprotein; the respiratory syncytial virus fusion protein; the respiratory syncytial virus M2 protein; VP7sc; rubella protein E1; rubella protein E2; varicella zoster virus gpl; varicella zoster virus gpll; Nef (66-97); Nef (116-145); Gag p17 (17-35); Gag p17-p24 (253-284); or Pol 325-355 (RT 158-188).

48. A formulation including a T cell population of embodiment 41 or 42 and a pharmaceutically acceptable carrier.

49. A formulation including a T cell of any of embodiments 43-47, and a pharmaceutically acceptable carrier.

50. An ex vivo method of manufacturing a T cell population, the method including contacting the T cell population with the single chain protein of any of embodiments 1-40.

51. An ex vivo method of manufacturing a T cell population, the method including contacting the T cell population with the single chain protein of any of embodiments 1-40 and a culture media. 52. An ex vivo method of manufacturing a T cell population, the method including obtaining a population of T cells; and culturing the T cells within a culture media including a single chain protein of any of embodiments 1-40.

53. The method of any of embodiments 50-52, wherein the population of T cells is enriched for T cells.

54. The method of embodiment 53, wherein the population of T cell is enriched for CD8$^+$ T cells. 55. The method of any of embodiments 47-50, wherein the culture media further includes a CD3 stimulating molecule.

56. The method of any of embodiments 50-55, further including contacting the T with a CD3 stimulating molecule.

57. The method of embodiment 56, wherein the CD3 stimulating molecule includes a CD3 antibody, optionally wherein the CD3 antibody is an OKT3 or a binding domain fragment thereof.

58. The method of embodiment 57, wherein the OKT3 or binding domain fragment thereof includes the single chain variable fragment having the sequence set forth in SEQ ID NO: 84; a variable light chain having the sequence set forth in SEQ ID NO: 73 and a variable heavy chain having the sequence set forth in SEQ ID NO: 74; or a set of complementarity determining regions (CDRs) having the sequences as set forth in SEQ ID NO: 75, SEQ ID NO: 76, SEQ ID NO: 77, SEQ ID NO: 78, SEQ ID NO: 79, and SEQ ID NO: 80; and/or MarSEQ ID NO: 81, SEQ ID NO: 76, SEQ ID NO: 82, SEQ ID NO: 78, SEQ ID NO: 83, and SEQ ID NO: 80.

59. The method of embodiment 55, wherein the CD3 stimulating molecule includes a CD3 binding domain having the CDRs of 20G6-F3, 4B4-D7, 4E7-C9, or 18F5-H10.

60. The method of any of embodiments 50-59, further including contacting the T cells with interleukin-2 (IL-2).

61. The method of any of embodiments 50-60, wherein the single chain protein is immobilized on a surface, optionally within a culture media.

62. The method of any of embodiments 50-60, wherein the single chain protein is soluble within a culture media.

63. The method of any of embodiments 50-60, wherein the single chain protein is immobilized on a surface and is also soluble within a culture media.

64. The method of any of embodiments 50-63, wherein the single chain protein is at a concentration of 0.1-10 μg/ml within a culture media.

65. The method of any of embodiments 50-63, wherein the single chain protein is at a concentration of 0.2 μg/ml, 1 μg/ml, or 5 μg/ml within a culture media.

66. The method of any of embodiments 50-65, wherein the CD3 stimulating molecule is at a concentration of 2.5-10 µg/ml within a culture media.

67. The method of any of embodiments 50-65, wherein the CD3 stimulating molecule is at a concentration of 5 µg/ml within the culture media.

68. The method of any of embodiments 50-67, wherein the single chain protein and the CD3 stimulating molecule are utilized within the method at a 1:1 ratio.

69. The method of any of embodiments 50-68, wherein the single chain protein and the CD3 stimulating molecule are within a culture media at a 1:1 ratio at a concentration of 5 µg/ml: 5 µg/ml.

70. The method of any of embodiments 60-69, wherein the IL-2 is at a concentration of 25-75 U/ml within the culture media.

71. The method of any of embodiments 50-69, wherein the IL-2 is at a concentration of 50 U/ml within the culture media.

72. The method of any of embodiments 50-71, wherein the T cell population is in contact with the single chain protein for 1, 2, 3, 4, or 5 days, optionally within a culture media.

73. The method of any of embodiments 47-66, wherein the T cell population in contact with the single chain protein for 3 days, optionally within a culture media.

74. The method of any of embodiments 50-73, wherein following the contacting of the T cells with a single chain protein of any of embodiments 1-40, the T cells are cultured in a culture media lacking the single chain protein for 3, 4, 5, 6, 7, 8, 9, or 10 days.

75. The method of any of embodiments 50-73, wherein following the contacting of the T cells with a single chain protein of any of embodiments 1-40, the T cells are cultured in a culture media lacking the single chain protein for 7 days.

76. The method of any of embodiments 50-75, further including genetically modifying T cells within the T cell population to express a recombinant molecule.

77. The method of embodiment 76, wherein the recombinant molecule is a chimeric antigen receptor (CAR).

78. The method of embodiment 76, wherein the recombinant molecule includes a T cell receptor. 79. The methods of any of embodiments 76-78, wherein the recombinant molecule specifically binds a marker on a cancer cell or a virally infected cell.

80. The method of embodiment 79, wherein the marker includes A33; BAGE; Bcl-2; β-catenin; BCMA; B7H4; BTLA; CA125; CA19-9; CD3, CD5; CD19; CD20; CD21; CD22; CD25; CD28; CD30; CD33; CD37; CD38; CD40; CD52; CD44v6; CD45; CD56; CD79b; CD80; CD81; CD86; CD123; CD134; CD137; CD151; CD171; CD276; CEA; CEACAM6; c-Met; CS-1; CTLA-4; cyclin B1; DAGE; EBNA; EGFR; EGFRvIII; ephrinB2; ErbB2; ErbB3; ErbB4; EphA2; estrogen receptor; FAP; ferritin; α-fetoprotein (AFP); FLT1; FLT4; folate-binding protein; Frizzled; GAGE; G250; GD-2; GHRHR; GHR; GITR; GM2; GPRC5D; gp75; gp100 (Pmel 17); gp130; HLA; HER-2/neu; HPV E6; HPV E7; hTERT; HVEM; IGF1R; IL6R; KDR; Ki-67; Lewis A; Lewis Y; LIFRβ; LRP; LRP5; LTβR; MAGE; MART; mesothelin; MUC; MUC1; MUM⁻1-B; myc; NYESO-1; O-acetyl GD-2; O-acetyl GD3; OSMRB; p53; PD1; PD-L1; PD-L2; PRAME; progesterone receptor; PSA; PSMA; PTCH1; RANK; ras; Robo1; RORI; survivin; TCRα; TCRβ; tenascin; TGFBR1; TGFBR2; TLR7; TLR9; TNFR1; TNFR2; TNFRSF4; TWEAK-R; TSTA tyrosinase; VEGF; WT1; glycoprotein B; CMV pp65; EBV EBNAI; EBV P18; the HBV S protein; the HBV M protein; the HBV L protein; the pre-S antigen of HBV; HBCAG DELTA; HBV HBE; hepatitis C viral RNA; HCV NS3; HCV NS4; herpes simplex virus immediate early proteins; herpes simplex virus glycoprotein D; HIV gp32; HIV gp41; HIV gp120; HIV gp160; HIV P17/24; HIV P24; HIV P55 GAG; HIV P66 POL; HIV TAT; HIV GP36; Hemagglutinin; neuraminidase; Japanese encephalitis protein E; Japanese encephalitis protein M-E; Japanese encephalitis protein M-E-NS1; Japanese encephalitis protein NS1; Japanese encephalitis protein NS1-NS2A; the measles virus fusion protein; rabies glycoprotein; rabies nucleoprotein; the respiratory syncytial virus fusion protein; the respiratory syncytial virus M2 protein; VP7sc; rubella protein E1; rubella protein E2; varicella zoster virus gpl; varicella zoster virus gpll; Nef (66-97); Nef (116-145); Gag p17 (17-35); Gag p17-p24 (253-284); or Pol 325-355 (RT 158-188).

81. A method including a 10-day ex vivo T cell manufacturing process according to the methods of embodiments 73-75 (see also, FIGS. 9A, 10A, and 14A).

82. The method of any of embodiments 50-81, including or further including formulating the manufactured T cells for administration to a subject.

83. The method of embodiment 82, wherein the formulating includes harvesting the manufactured T cells from the culture media and adding them to a pharmaceutically acceptable carrier.

84. The method of embodiment 83, wherein the adding includes adding the manufactured T cells to the carrier in a therapeutically-effective amount.

85. The method of embodiment 84, wherein the therapeutically-effective amount includes greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

86. The method of embodiment 84, wherein the therapeutically-effective amount includes a cell density of greater than $10^4$ cells/ml, greater than $10^7$ cells/ml, or greater than $10^8$ cells/ml.

87. A T cell population expanded according to the method of any of embodiments 50-86.

88. A T cell population expanded according to the method of any of embodiments 50-87 wherein the T cell population is a bulk T cell population or enriched for a T cell type (e.g., CD4 and/or CD8).

89. The T cell population of embodiment 87 or 88, wherein the T cell population is administered to a subject.

90. The T cell population of embodiment 89, wherein the T cell population is autologous or allogeneic to the subject.

91. The method of any of the embodiments of 50-86, wherein the ex vivo method of manufacturing the T cell population results in a T cell population with enhanced properties.

92. The method of embodiment 91, wherein the enhanced properties include an improvement selected from the group consisting of an increase in T cell expansion, an increase in T cell proliferation, a decrease in T cell exhaustion, an increase in the expansion of a less differentiated T cell population, an increase in the expansion of memory T cells, a decrease in glucose metabolism, a decrease in glycolytic switch capacity, a decrease in the induction of mTORC1/S6K signaling, a decrease in mTORC1-dependent protein translation, an increase in T cell survival ex vivo, an increase in T cell survival following administration, an increase in expansion ex vivo, an increase in expansion following administration, an increase in engraftment following administration, an increase in killing capacity, an increase in serial killing capacity, and an increase in the targeting of tumor cells.

93. The method of embodiment 91, wherein the enhanced properties include an improvement selected from the group consisting of an increase in T cell expansion, an increase in T cell proliferation, an increase in the expansion of a less differentiated T cell population, an increase in the expansion of memory T cells, an increase in T cell survival ex vivo, an increase in T cell survival following administration, an increase in expansion ex vivo, an increase in expansion following administration, an increase in engraftment following administration, an increase in killing capacity, an increase in serial killing capacity, and an increase in the targeting of tumor cells.

94. The method of embodiment 91, wherein the enhanced properties include an increase in T cell expansion, an increase in T cell proliferation, a decrease in T cell exhaustion, selective expansion of less differentiated T cell populations, selective expansion of naïve and memory T cells, a decrease in glucose metabolism, a decrease in glycolytic switch capacity, a weaker induction of mTORC1/S6K signaling, a decrease in mTORC1-dependent protein translation during late expansion phase, an increase in T cell survival ex vivo and following administration, an increase in expansion ex vivo and following administration, an increase in engraftment following administration, an increase in killing capacity, an increase in serial killing capacity, and/or an increase in the targeting of tumor cells when compared to T cell activation under comparable control conditions using αCD28/CD3 stimulating molecule (e.g., DynaBeads).

95. The method of embodiment 91, wherein the enhanced properties include enhanced acquisition of a memory gene signature (see, e.g., FIG. 10D), superior acquisition of a $T_{SCM}$-like T cell phenotype (see, e.g., FIGS. 13A-13D), reduced expression of Tigit and LAG 3 inhibitory receptors (see, e.g., FIG. 11A-11G), reduced acquisition of an effector metabolic phenotype (see, e.g., 14A, 14B), increased frequency of gene-modified blood mononuclear cells (see, e.g., FIG. 11F), reduced granzyme b expression, glucose uptake, and fatty acid oxidation (see, e.g., 14A, 14B), higher abundance of CD27$^+$ TCF1$^+$ T cells within 4-6 days of activation, indicative of a stem cell memory phenotype (see, e.g., FIGS. 15A-15D), faster transition into a stem cell memory T cell state (see, e.g., 17A-17C), a less pronounced switch to an effector metabolic phenotype as evidenced by decreased MYC gene expression and MYC-dependent glucose metabolism (see, e.g., FIGS. 19A-19C), reduced GLUT1 expression (see, e.g., FIG. 19B), reduced glycolysis as measured by oxygen consumption rate (OCR) and extracellular acidification rate (ECAR) (see, e.g., FIGS. 20A, 20B), less mTORC1 signaling (see, e.g., FIG. 21) and/or less mTORC1-dependent protein translation (see, e.g., FIG. 22) when compared to T cell activation under comparable control conditions using αCD28/CD3 stimulating molecule (e.g., DynaBeads).

96. The method of any of embodiments 91-95 wherein an enhanced property increase is at least a 10%, at least a 20%, at least a 30%, at least a 40%, or at least a 50% increase.

97. The method of any of embodiments 91-95 wherein an enhanced property increase is a 2-1000 fold increase, a $10^{-100}$ fold increase, a $10^{-90}$ fold increase, a $10^{-80}$ fold increase, a $10^{-75}$ fold increase, a $10^{-70}$ fold increase, a $10^{-60}$ fold increase, a $10^{-50}$ fold increase, a 3, 4, 5, 6, 7, 8, 9, 10, 15, 20, 25, 30, 35, 40, 45, 50, or higher fold increase.

98. The method of any of embodiments 91-95 wherein an enhanced property decrease is at least a 10%, at least a 20%, at least a 30%, at least a 40%, or at least a 50% decrease.

99. The method of any of embodiments 91-95 wherein a decrease in one or more particular properties is a 2-1000 fold decrease, a $10^{-100}$ fold decrease, a $10^{-90}$ fold decrease, a $10^{-80}$ fold decrease, a $10^{-75}$ fold decrease, a $10^{-70}$ fold decrease, a $10^{-60}$ fold decrease, a $10^{-50}$ fold decrease, a 3, 4, 5, 6, 7, 8, 9, 10, 15, 20, 25, 30, 35, 40, 45, 50, or higher fold decrease.

100. The method of embodiment 98 or 99, wherein the decrease is a decrease in T cell exhaustion, a decrease in glucose metabolism, a decrease in glycolytic switch capacity, a decrease in the induction of mTORC1/S6K signaling, and a decrease in mTORC1-dependent protein translation.

101. The method of any of embodiments 91-100, wherein the method includes culturing the T cells within a culture media further including a CD3 stimulating molecule.

102. The method of any of embodiments 91-101, wherein the enhanced property is as when compared to T cell activation using a combination CD28/CD3 stimulating molecule.

103. The method of any of embodiments 91-102, wherein the enhanced properties are exhibited when the engineered CD70 proteins of the disclosure are used in conjunction with a CD3 stimulating molecule.

104. A method of treating a subject in need thereof including administering to the subject a therapeutically effective amount of a T cell, T cell population or formulation of any of embodiments 41-49 or 87-90 thereby treating the subject in need thereof.

105. The method of embodiment 104, wherein the therapeutically effective amount provides an anti-cancer effect.

106. The method of embodiment 105, wherein the anti-cancer effect is against prostate cancer, breast cancer, stem cell cancer, ovarian cancer, mesothelioma, renal cell carcinoma melanoma, pancreatic cancer, lung cancer, HBV-induced hepatocellular carcinoma, multiple myeloma, leukemia, and/or lymphoma.

107. The method of embodiment 104, wherein the therapeutically effective amount provides an anti-pathogen effect.

108. The method of embodiment 107, wherein the anti-pathogen effect is against adenovirus, arenavirus, bunyavirus, coronavirus, flavivirus, hantavirus, hepadnavirus, herpesvirus, human immunodeficiency virus, papillomavirus, paramyxovirus, parvovirus, picornavirus, poxvirus, orthomyxovirus, retroviruses, reovirus, rhabdovirus, rotavirus, spongiform virus or togavirus.

| (xi) Sequence Listing Summary. | | |
|---|---|---|
| SEQ ID NO: | Identity | Location in Application |
| 1 | CD70 | FIG. 1C |
| 2 | Cytoplasmic Domain of CD70 | FIG. 1C |
| 3 | Transmembrane Domain of CD70 | FIG. 1C |
| 4 | Extracellular Domain of CD70 | FIG. 1C, 5B, 6B, 7B, 8B, 27 |

-continued

Figure 5D:
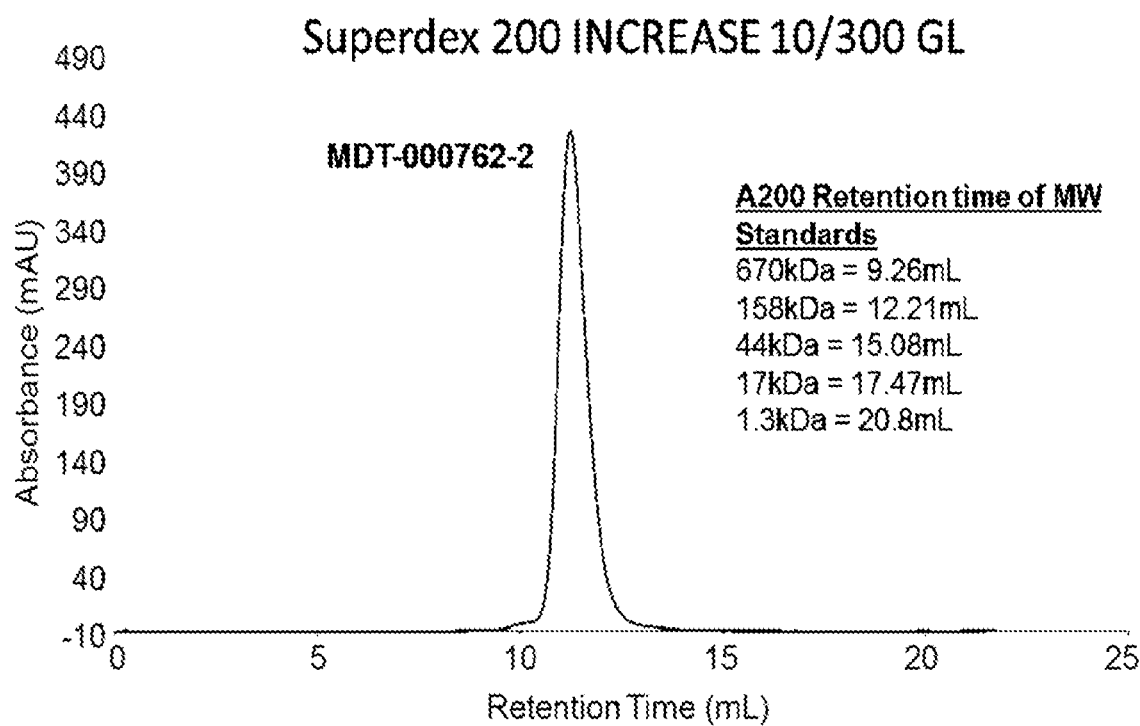
Figure 5E:
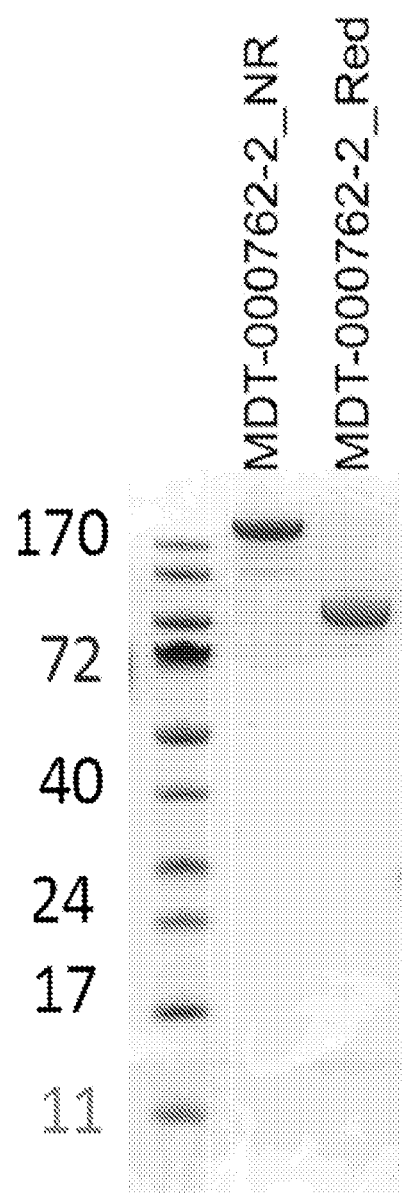
Figure 6C:
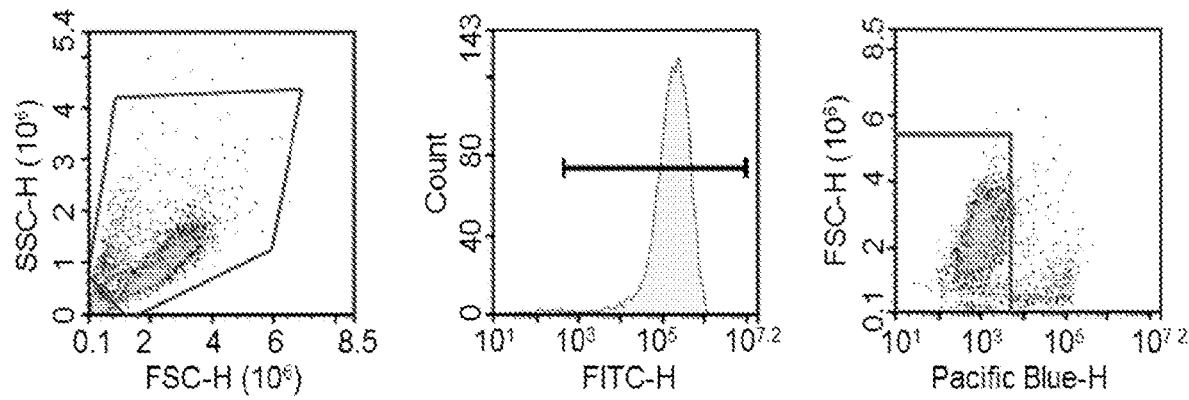
Figure 6D:
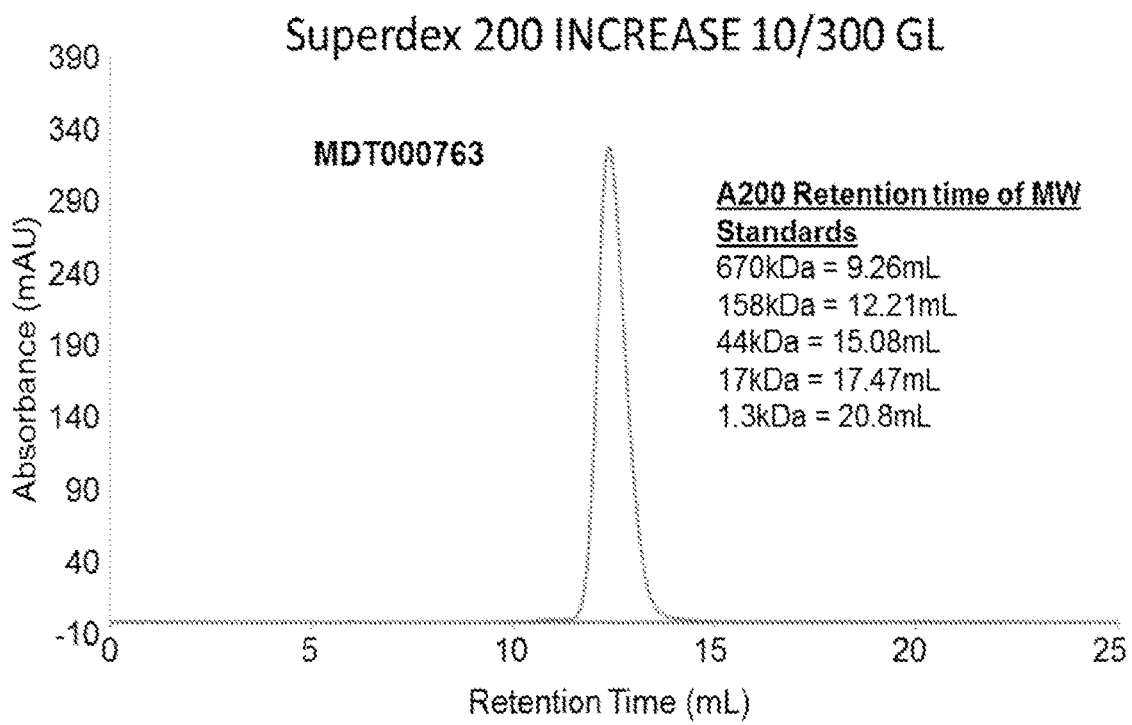
Figure 6E:
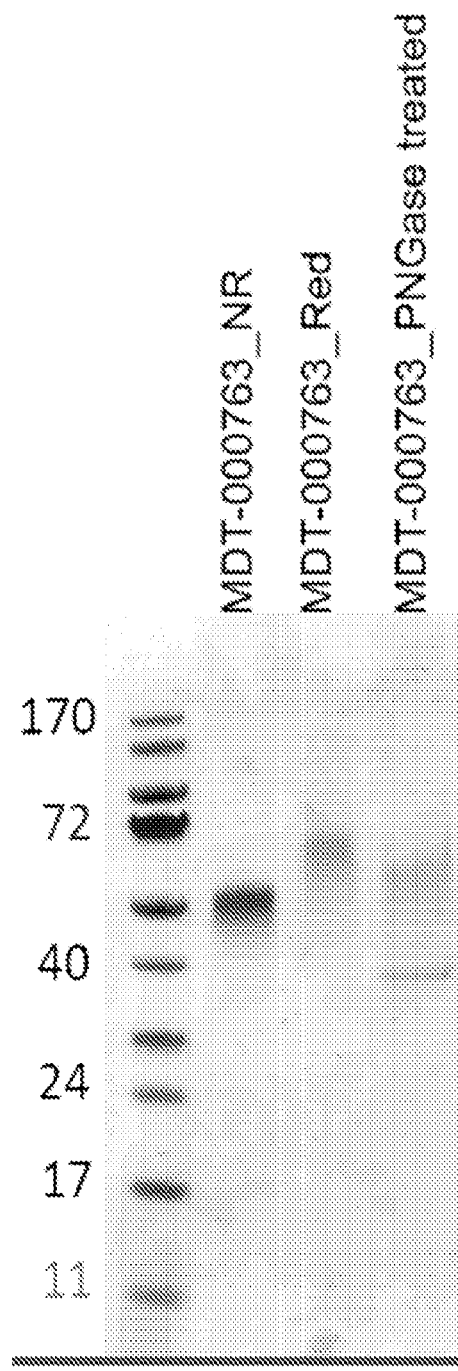
Figure 7C:
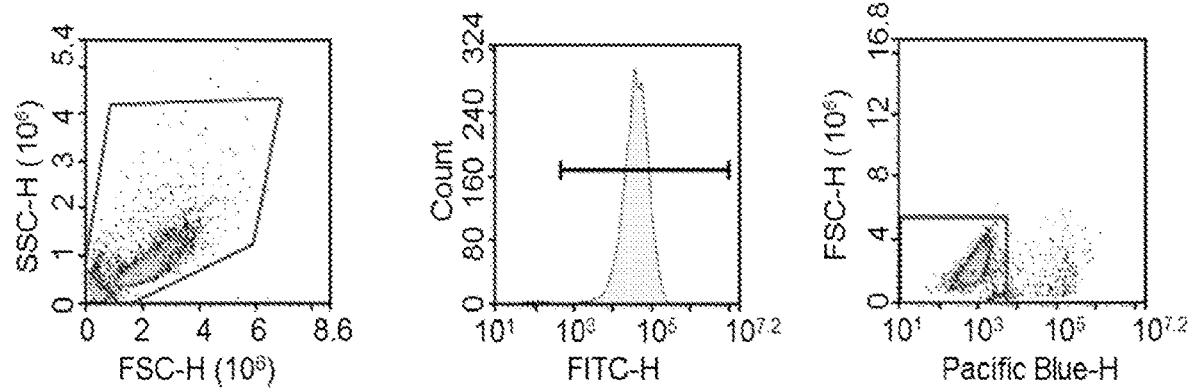
Figure 7D:
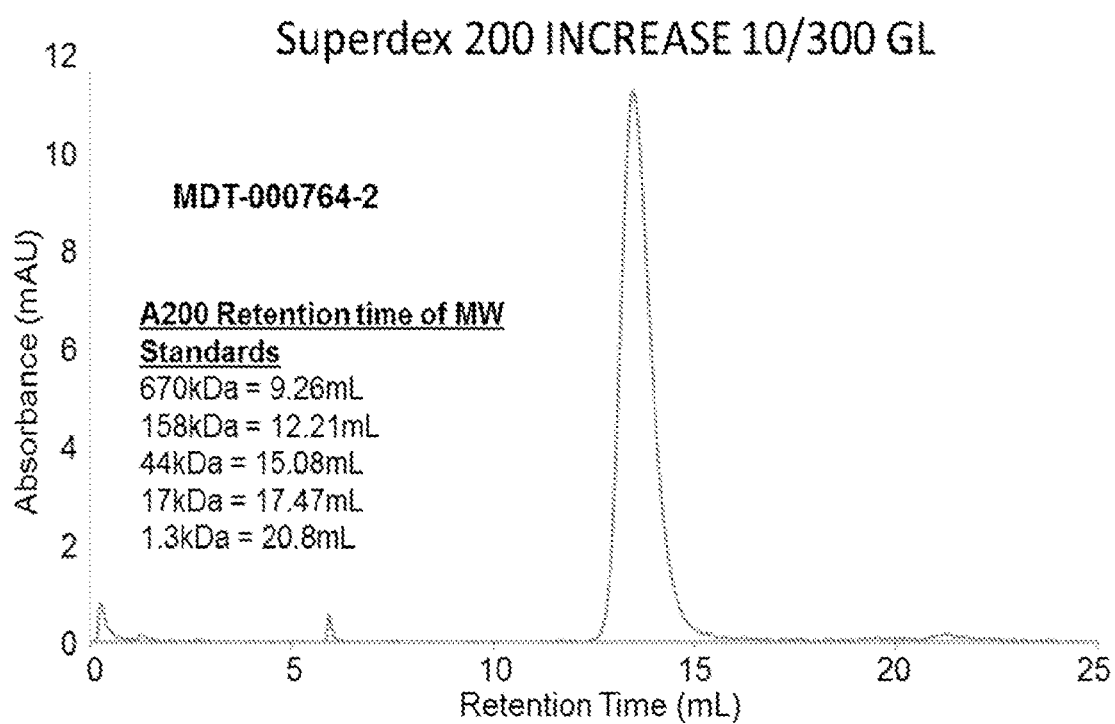
Figure 7E:
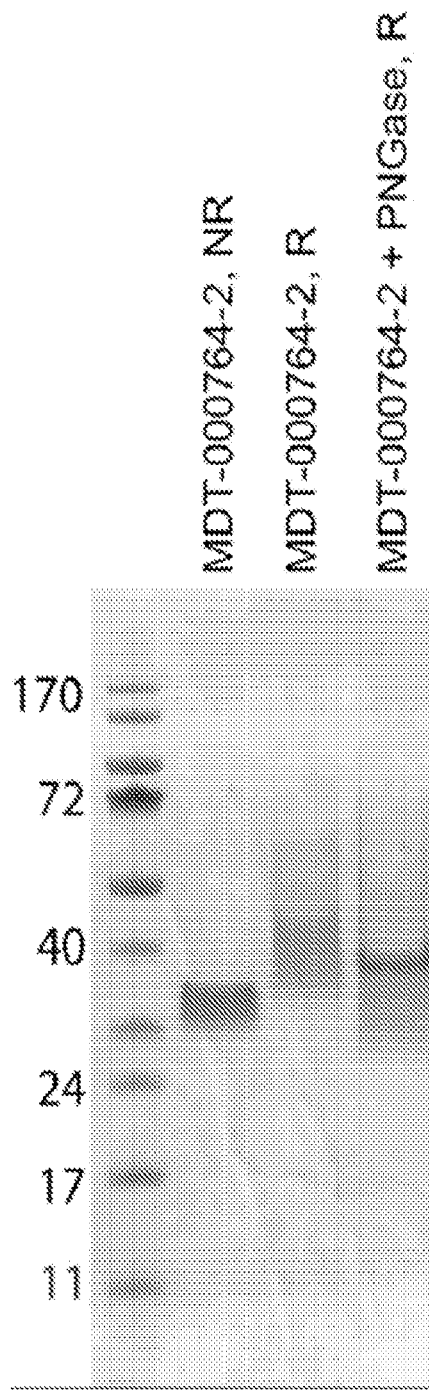

| | (xi) Sequence Listing Summary. | |
|---|---|---|
| SEQ ID NO: | Identity | Location in Application |
| 5 | MDT-000762-2: hsCD70_SC-His-Avi-Tev-Fc_hsIgG1 | FIG. 5B |
| 6 | Signal Peptide | FIG. 5B, 6B, 7B, 8B, 27 |
| 7 | MDT-001100: hsCD70_SC-Toroidx6_SS_tetramer-His | FIG. 8B |
| 8 | Linker | FIG. 5B, 6B, 27 |
| 9 | His | FIG. 5B, 6B, 7B, 8B, 27 |
| 10 | Avi | FIG. 5B, 6B, 7B, 27 |
| 11 | Tev within MDT-000762-2 | FIG. 5B, 27 |
| 12 | hsIgG1 | FIG. 5B, 27 |
| 13 | MDT-000763: hsTetranectin_TD-hsCD70-His-Avi | FIG. 6B |
| 14 | hsTetranectin_TD | FIG. 6B |
| 15 | MDT-000764-2: hsCD70-Collagen_TD-His-Avi | FIG. 7B |
| 16 | Trimer_Collagen-hsCD70 | FIG. 7B |
| 17 | hsCD70-hsCollagen_TD-Avi | FIG. 7B |
| 18 | Signal Peptide | FIG. 7B, 27 |
| 19 | hsTetranectin trimer | FIG. 7B, 27 |
| 20 | Collagen_TD | FIG. 7B, 27 |
| 21 | Linker | FIG. 7B, 27 |
| 22 | sFLAG | FIG. 7B, 27 |
| 23 | Tev | FIG. 7B |
| 24 | Linker | FIG. 8B |
| 25 | cTRP Scaffold | FIG. 8B, 27 |
| 26 | cTRP cysteine-modified N-terminal α-helix forming b segment | FIG. 8B |
| 27 | cTRP internal α-helix forming b and y segments | FIG. 8B |
| 28 | cTRP cysteine-modified C-terminal α-helix forming b segment | FIG. 8B |
| 29 | hsCD70_SC-Toroidx6_SS_tetramer-His | FIG. 8B |
| 30 | hsTetranectin_TD | FIG. 27 |
| 31 | Mature Human Tetranectin Polypeptide Chain | FIG. 27 |
| 32 | Collagen XV trimerization domain | FIG. 27 |
| 33 | Collagen XVIII trimerization domain | FIG. 27 |
| 34 | Clathrin (PDB ID 3QIL) | FIG. 27 |
| 35 | SadB or *Salmonella enterica* trimeric lipoprotein (PDB ID 4C47) | FIG. 27 |
| 36 | EML4 (PDB ID 4CGC) | FIG. 27 |
| 37 | Wildtype Matrilin-1 (CMP trimerization domain) | FIG. 27 |
| 38 | Matrilin1 variant | FIG. 27 |
| 39 | Wildtype DMPK | FIG. 27 |
| 40 | DMPK variant | FIG. 27 |
| 41 | Wildtype Langerin | FIG. 27 |
| 42 | Variant of Langerin | FIG. 27 |
| 43 | Coronin 1a wildtype | FIG. 27 |
| 44 | Coronin 1a variant | FIG. 27 |
| 45 | Coronin 1a variant | FIG. 27 |
| 46 | Coronin 1a variant | FIG. 27 |
| 47 | Coronin 1a variant | FIG. 27 |
| 48 | Coronin 1a variant | FIG. 27 |
| 49 | Coronin 1a variant | FIG. 27 |
| 50 | Coronin 1a variant | FIG. 27 |
| 51 | Full length human CMP | FIG. 27 |
| 52 | Cartilage matrix protein precursor [*Homo sapiens*] | FIG. 27 |
| 53 | T4 fibritin | FIG. 27 |
| 54 | Trimerization domain of T4 fibritin | FIG. 27 |
| 55 | RB69 fibritin | FIG. 27 |
| 56 | Trimerization domain of RB69 fibritin | FIG. 27 |
| 57 | TNF receptor-associated factor-2 (TRAF2) (GENBANK ® Accession No. Q12933.2) | FIG. 27 |
| 58 | Thrombospondin 1 (Accession No. P07996 [gi: 135717] | FIG. 27 |
| 59 | Matrilin-4 (Accession No. 095460 [gi: 14548117] | FIG. 27 |
| 60 | Heat shock transcription factor (HSF) (Accession No. AAX42211 [gi: 61362386] | FIG. 27 |
| 61 | Cubilin (Accession No. NP001072 [gi: 4557503] | FIG. 27 |
| 62 | Lipocalin | FIG. 27 |
| 63-72 | Linkers | Text of Specification |
| 73 | variable light chain of huOKT3 | Text of Specification |
| 74 | variable heavy chain of huOKT3 | Text of Specification |
| 75-80 | CDR regions of huOKT3 | Text of Specification |

(xi) Sequence Listing Summary.

| SEQ ID NO: | Identity | Location in Application |
|---|---|---|
| 81-83 | CDR regions of OKT3 (also including SEQ ID NO: 76, 78, and 80) | Text of Specification |
| 84 | scFv derived from OKT3 | Text of Specification |
| 85-89 | CDR regions of 20G6-F3 (due to length, CDRL2 lacks a SEQ ID NO) | Text of Specification |
| 90-93 | CDR regions of 4B4-D7 (also including SEQ ID NO: 86; due to length, CDRL2 lacks a SEQ ID NO) | Text of Specification |
| 94-96 | CDR regions of 4E7-C9 (also including SEQ ID NO: 86 and 91; due to length, CDRL2 lacks a SEQ ID NO) | Text of Specification |
| 97-101 | CDR regions of 18F5-H10 (due to length, CDRL2 lacks a SEQ ID NO) | Text of Specification |
| 102 | variable heavy chain of TGN1412 | Text of Specification |
| 103 | variable light chain of TGN1412 | Text of Specification |
| 104-110 | CDR regions of TGN1412 | Text of Specification |
| 111-116 | CDR regions of CD80/CD86 binding domain | Text of Specification |
| 117-121 | CDR regions of 4-1BB binding domain (due to length, CDRH2 lacks a SEQ ID NO) | Text of Specification |
| 122-127 | CDR regions of 4-1BB binding domain | Text of Specification |
| 128-133 | Linkers | Text of Specification |
| 134 | Nef (66-97) | Text of Specification |
| 135 | Nef (116-145) | Text of Specification |
| 136 | Gag p17 (17-35) | Text of Specification |
| 137 | Gag p17-p24 (253-284) | Text of Specification |
| 138 | Pol 325-355 (RT 158-188) | Text of Specification |
| 139 | scFV that binds human CD19 | Text of Specification |
| 140 | scFV that binds human ROR1 | Text of Specification |
| 141-146 | CDR regions of ROR1 binding domain | Text of Specification |
| 147-152 | CDR regions of R11 | Text of Specification |
| 153-158 | CDR regions of R12 | Text of Specification |
| 159 | Variable light chain of scFV that binds human CD33 | Text of Specification |
| 160 | Variable heavy chain of scFV that binds human CD33 | Text of Specification |
| 161 | Variable heavy chain of Avelumab | Text of Specification |
| 162 | Variable light chain of Avelumab | Text of Specification |
| 163-168 | CDR regions of Avelumab | Text of Specification |
| 169 | Variable heavy chain of Atezolizumab | Text of Specification |
| 170 | Variable light chain of Atezolizumab | Text of Specification |
| 171-176 | CDR regions of Atezolizumab | Text of Specification |
| 177-181 | CDR regions of MUC16 binding domain | Text of Specification |
| 182-187 | CDR regions of FOLR binding domain | Text of Specification |
| 188 | Variable heavy chain of Amatuximab | Text of Specification |
| 189 | Variable light chain of Amatuximab | Text of Specification |
| 190-194 | CDR regions of Amatuximab (also including SEQ ID NO: 79) | Text of Specification |
| 195 | Flag tag | Text of Specification |
| 196 | Xpress tag | Text of Specification |
| 197 | Calmodulin tag | Text of Specification |
| 198 | HA tag | Text of Specification |
| 199 | Myc tag | Text of Specification |
| 200 | Softag 1 | Text of Specification |
| 201 | Softag 3 | Text of Specification |
| 202 | STREP ® tag | Text of Specification |
| 203 | STREP ® tag II | Text of Specification |
| 204 | V5 tag | Text of Specification |
| 205 | CD3z | FIG. 27 |
| 206 | CD3z | FIG. 27 |
| 207 | 4-1BB cytoplasmic domain | FIG. 27 |
| 208 | 4-1BB cytoplasmic domain | FIG. 27 |
| 209 | CD28_Transmembrane domain | FIG. 27 |
| 210 | CD28_Transmembrane domain | FIG. 27 |
| 211 | P2A | FIG. 27 |
| 212 | T2A | FIG. 27 |
| 213 | E2A | FIG. 27 |
| 214 | F2A | FIG. 27 |
| 215 | IgG4 linker | Text of Specification |

CLOSING PARAGRAPHS

In some embodiments, the cultured T cells exhibit one or more specified phenotypic and/or functional features based on or related to their proliferation capacity, surface marker expression, differentiation state, activation state, and/or metabolic profile. In some embodiments, the culturing of the T cells with a trimeric CD70 protein disclosed herein results in a change in a parameter associated with the function (e.g., increase or decrease of a functional activity) or phenotype (e.g., higher or lower expression of a marker or markers) of cells compared to the corresponding or respective function or phenotype of cells in the composition prior to incubation in accord with trimeric CD70 proteins provided herein.

In some embodiments, the change in the parameter as measured in the cultured T cells is compared or with reference to the same or similar parameter as measured in a reference T cell composition or preparation not cultured in the presence of a trimeric CD70 protein disclosed herein. Typically, T cells in the reference T cell composition or preparation include or are derived from the same or substantially the same composition of T cells prior to incubation with the trimeric CD70 protein, except such cells were proceeded through the same incubations but for the presence of the trimeric CD70 protein.

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157 (1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within +2 is preferred, those within +1 are particularly preferred, and those within +0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within +2 is preferred, those within +1 are particularly preferred, and those within +0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignments of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N. Y . . . . Within the context of this disclosure, it will be understood that where sequence analysis software is used for analysis, the results of the analysis are based on the "default values" of the program referenced. As used herein, "default values" will mean any set of values or parameters, which originally load with the software when first initialized.

Variants also include nucleic acid molecules that hybridize under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH2PO4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g., 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Throughout this disclosure, Kabat numbering for CDR residues are used unless otherwise noted.

In particular embodiments, the disclosure provides proteins that bind with a cognate binding molecule with an association rate constant or $k_{on}$ rate of not more than 107 $M^{-1}s^{-1}$, less than $5\times10^6$ $M^{-1}s^{-1}$, less than $2.5\times10^6$ $M^{-1}s^{-1}$, less than $2\times10^6$ $M^{-1}s^{-1}$, less than $1.5\times10^6$ $M^{-1}s^{-1}$, less than $10^6$ $M^{-1}s^{-1}$, less than $5\times10^5$ $M^{-1}s^{-1}$, less than $2.5\times10^5$ $M^{-1}s^{-1}$, less than $2\times10^5$ $M^{-1}s^{-1}$, less than $1.5\times10^5$ $M^{-1}s^{-1}$, less than $10^5$ $M^{-1}s^{-1}$, less than $5\times10^4$ $M^{-1}s^{-1}$, less than $2.5\times10^4$ $M^{-1}s^{-1}$, less than $2\times10^4$ $M^{-1}s^{-1}$, less than $1.5\times10^4$ $M^{-1}s^{-1}$, less than $10^4$ $M^{-1}s^{-1}$, less than $10^3$ $M^{-1}s^{-1}$, less than 102 $M^{-1}s^{-1}$, or in a range of 102 $M^{-1}s^{-1}$ to 107 $M^{-1}s^{-1}$, in a range of $10^3$ $M^{-1}s^{-1}$ to $10^6$ $M^{-1}s^{-1}$, in a range of 104 $M^{-1}s^{-1}$ to $10^5$ $M^{-1}s^{-1}$, or in a range of $10^3$ $M^{-1}s^{-1}$ to 107 $M^{-1}s^{-1}$.

In particular embodiments, the disclosure provides proteins that bind with a cognate binding molecule a $k_{off}$ rate of not less than 0.5 $s^{-1}$, not less than 0.25 $s^{-1}$, not less than 0.2 $s^{-1}$, not less than 0.1 $s^{-1}$, not less than $5\times10^{-2}$ $s^{-1}$, not less than $2.5\times10^{-2}$ $s^{-1}$, not less than $2\times10^{-2}$ $s^{-1}$, not less than $1.5\times10^{-2}$ $s^{-1}$, not less than $10^{-2}$ $s^{-1}$, not less than $5\times10^{-3}$ $s^{-1}$, not less than 2.5×10-3 $s^{-1}$, not less than $2\times10^{-3}$ $s^{-1}$, not less than $1.5\times10^{-3}$ $s^{-1}$, not less than $10^{-3}$ $s^{-1}$, not less than $5\times10^{-4}$ $s^{-1}$, not less than $2.5\times10^{-4}$ $s^{-1}$, not less than $2\times10^{-4}$ $s^{-1}$, not less than $1.5\times10^{-4}$ $s^{-1}$, not less than $10^{-4}$ $s^{-1}$, not less than $5\times10^{-5}$ $s^{-1}$, not less than $2.5\times10^{-5}$ $s^{-1}$, not less than $2\times10^{-5}$ $s^{-1}$, not less than $1.5\times10^{-5}$ $s^{-1}$, not less than $10^{-5}$ $s^{-1}$, not less than $5\times10^{-6}$ $s^{-1}$, not less than $2.5\times10^{-6}$ s-1, not less than $2\times10^{-6}$ $s^{-1}$, not less than $1.5\times10^{-6}$ $s^{-1}$, not less than $10^{-6}$ $s^{-1}$, or in a range of 0.5 to $10^{-6}$ $s^{-1}$, in a range of $10^{-2}$ $s^{-1}$ to $10^{-5}$ $s^{-1}$, or in a range of $10^{-3}$ $s^{-1}$ to $10^{-4}$ $s^{-1}$.

In particular embodiments, the disclosure provides proteins that bind with a cognate binding molecule with an affinity constant or $K_a$ ($k_{on}/k_{off}$) of, either before and/or after modification, less than $10^6$ $M^{-1}$, less than $5\times10^5$ $M^{-1}$, less than $2.5\times10^5$ $M^{-1}$, less than $2\times10^5$ $M^{-1}$, less than $1.5\times10^5$ $M^{-1}$, less than $10^5$ $M^{-1}$, less than $5\times10^4$ $M^{-1}$, less than $2.5\times10^4$ $M^{-1}$, less than $2\times10^4$ $M^{-1}$, less than $1.5\times10^4$ $M^{-1}$, less than $10^4$ $M^{-1}$, less than $5\times10^3$ $M^{-1}$, less than $2.5\times10^3$ $M^{-1}$, less than $2\times10^3$ $M^{-1}$, less than $1.5\times10^3$ $M^{-1}$, less than $10^3$ $M^{-1}$, less than 500 $M^{-1}$, less than 250 $M^{-1}$, less than 200 $M^{-1}$, less than 150 $M^{-1}$, less than 100 $M^{-1}$, less than 50 $M^{-1}$, less than 25 $M^{-1}$, less than 20 $M^{-1}$, less than 15 $M^{-1}$, or less than 10 $M^{-1}$, or in a range of 10 $M^{-1}$ to $10^6$ $M^{-1}$, in a range of 102 $M^{-1}$ to $10^5$ $M^{-1}$, or in a range of $10^3$ $M^{-1}$ to $1\times10^4$ $M^{-1}$.

In particular embodiments, the disclosure provides proteins that bind with a cognate binding molecule with a dissociation constant or $K_d$ ($K_{off}/k_{on}$) of, either before and/or after modification, not less than .05 M, not less than .025 M, not less than .02 M, not less than .01 M, not less than $5\times10^{-3}$ M, not less than $2.5\times10^{-3}$ M, not less than $2\times10^{-3}$ M, not less than $1.5\times10^{-3}$ M, not less than $10^{-3}$ M, not less than $5\times10^{-4}$ M, not less than $2.5\times10^{-4}$ M, not less than $2\times10^{-4}$ M, not less than $1.5\times10^{-4}$ M, not less than $10^{-4}$ M, not less than $5\times10^{-5}$ M, not less than $2.5\times10^{-5}$ M, not less than $2\times10^{-5}$ M, not less than $1.5\times10^{-5}$ M, not less than $10^{-5}$ M, not less than $5\times10^{-6}$ M, not less than $2.5\times10^{-6}$ M, not less than $2\times10^{-6}$ M, not less than $1.5\times10^{-6}$ M, not less than $10^{-6}$ M, or not less than $10^{-7}$ M, or in a range of 0.05 M to $10^{-7}$ M, in a range of 5×10⁻3 M to $10^{-6}$ M, or in a range of $10^{-4}$ M to $10^{-7}$ M.

Unless otherwise indicated, aspects of the present disclosure can employ conventional techniques of immunology, molecular biology, microbiology, cell biology, and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components and to those that do not materially affect the embodiment. A material effect would result in an expanded T cell population that does not have an increased percentage of cells with a memory signature.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or +1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles, and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition, or a dictionary known to those of ordinary skill in the art, such as the Oxford Dictionary of Biochemistry and Molecular Biology (Ed. Anthony Smith, Oxford University Press, Oxford, 2004).

What is claimed is:

1. An ex vivo method of manufacturing a T cell population for administration to a subject, the method comprising:
   obtaining a population of T cells;
   culturing the population of T cells within a culture media comprising:
      a CD3 stimulating molecule and an Fc-dimerized protein at a concentration sufficient to increase T cell activation, wherein the Fc-dimerized protein has two copies of the single chain protein sequence as set forth in SEQ ID NO: 5 or a sequence having at least 95% sequence identity to the sequence as set forth in SEQ ID NO: 5 to create an activated T cell population;
   culturing the activated T cell population within a culture media lacking the CD3 stimulating molecule; and
   formulating the expanded T cell population into a pharmaceutically acceptable carrier in a therapeutically effective amount,
   thereby ex vivo manufacturing the T cell population for administration to the subject.

2. The method of claim 1, further comprising genetically modifying T cells within the population to express a recombinant molecule.

3. The method of claim 1, further comprising administering the manufactured T cell population to a subject in need.

4. The method of claim 1, wherein the therapeutically-effective amount comprises greater than $10^2$ T cells, greater than $10^3$ T cells, greater than $10^4$ T cells, greater than $10^5$ T cells, greater than $10^6$ T cells, greater than $10^7$ T cells, greater than $10^8$ T cells, greater than $10^9$ T cells, greater than $10^{10}$ T cells, or greater than $10^{11}$ T cells.

5. The method of claim 1, wherein the CD3 stimulating molecule comprises OKT3, 20G6-F3, 4B4-D7, 4E7-C9, or 18F5-H10 or a binding domain fragment of OKT3, 20G6-F3, 4B4-D7, 4E7-C9, or 18F5-H10.

6. The method of claim 1, wherein the CD3 stimulating molecule comprises an OKT3 binding domain.

7. The method of claim 1, wherein the i) CD3 stimulating molecule and the ii) Fc-dimerized protein or single chain protein sequence are within the culture media at a 1:1 ratio.

8. The method of claim 2, wherein the recombinant molecule is a chimeric antigen receptor (CAR), a T cell receptor (TCR), or a TCR/CAR hybrid.

9. The method of claim 2, wherein the recombinant molecule binds a marker on a cancer cell or a virally infected cell.

10. The method of claim 3, wherein the administering provides an anti-cancer effect or an anti-pathogen effect.

11. The method of claim 10, wherein the anti-cancer effect is against prostate cancer, breast cancer, stem cell cancer, ovarian cancer, mesothelioma, renal cell carcinoma melanoma, pancreatic cancer, lung cancer, HBV-induced hepatocellular carcinoma, multiple myeloma, leukemia, and/or lymphoma.

12. The method of claim 10, wherein the anti-pathogen effect is against adenovirus, arenavirus, bunyavirus, coronavirus, flavirvirus, hantavirus, hepadnavirus, herpesvirus, human immunodeficiency virus, papilomavirus, paramyxovirus, parvovirus, picornavirus, poxvirus, orthomyxovirus, retroviruses, reovirus, rhabdovirus, rotavirus, spongiform virus or togavirus.

13. The method of claim 1, further comprising contacting the activated T cell population with interleukin-2.

14. The method of claim 1, wherein the culturing the population of T cells within a culture media comprising the Fc-dimerized protein is for 1, 2, 3, 4, or 5 days.

15. The method of claim 1, wherein the culturing the population of T cells within a culture media comprising the Fc-dimerized protein is for 3 days.

16. The method of claim 1, wherein following the culturing the population of T cells within a culture media comprising the Fc-dimerized protein, the activated T cell population are cultured in a culture media lacking the Fc-dimerized protein for 3, 4, 5, 6, 7, 8, 9, or 10 days.

17. The method of claim 1, wherein following the culturing the population of T cells within a culture media comprising the Fc-dimerized protein, the activated T cell population are cultured in a culture media lacking the Fc-dimerized protein for 7 days.

18. The method of claim 1, further comprising enriching the expanded T cell population for CD8 T cells.

* * * * *

SEQUENCE LISTING

<160> NUMBER OF SEQ ID NOS: 215

<210> SEQ ID NO 1
<211> LENGTH: 193
<212> TYPE: PRT
<213> ORGANISM: Homo sapiens

<400> SEQUENCE: 1

Met Pro Glu Glu Gly Ser Gly Cys Ser Val Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
                35                  40                  45

Pro Leu Glu Ser Leu Gly Trp Asp Val Ala Glu Leu Gln Leu Asn His
50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
                100                 105                 110

Ala Ile Cys Ser Ser Thr Thr Ala Ser Arg His His Pro Thr Thr Leu
                115                 120                 125

Ala Val Gly Ile Cys Ser Pro Ala Ser Arg Ser Ile Ser Leu Leu Arg
                130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
                180                 185                 190

Pro

<210> SEQ ID NO 2
<211> LENGTH: 17
<212> TYPE: PRT
<213> ORGANISM: Homo sapiens

<400> SEQUENCE: 2

Met Pro Glu Glu Gly Ser Gly Cys Ser Val Arg Arg Pro Tyr Gly
1               5                   10                  15

Cys

<210> SEQ ID NO 3
<211> LENGTH: 21
<212> TYPE: PRT
<213> ORGANISM: Homo sapiens

<400> SEQUENCE: 3

Val Leu Arg Ala Ala Leu Val Pro Leu Val Ala Gly Leu Val Ile Cys
1               5                   10                  15

Leu Val Val Cys Ile
                20

<210> SEQ ID NO 4
<211> LENGTH: 155
<212> TYPE: PRT

<213> ORGANISM: Homo sapiens

<400> SEQUENCE: 4

```
Gln Arg Phe Ala Gln Ala Gln Gln Gln Leu Pro Leu Glu Ser Leu Gly
1               5                   10                  15

Trp Asp Val Ala Glu Leu Gln Leu Asn His Thr Gly Pro Gln Gln Asp
            20                  25                  30

Pro Arg Leu Tyr Trp Gln Gly Gly Pro Ala Leu Gly Arg Ser Phe Leu
        35                  40                  45

His Gly Pro Glu Leu Asp Lys Gly Gln Leu Arg Ile His Arg Asp Gly
    50                  55                  60

Ile Tyr Met Val His Ile Gln Val Thr Leu Ala Ile Cys Ser Ser Thr
65                  70                  75                  80

Thr Ala Ser Arg His His Pro Thr Thr Leu Ala Val Gly Ile Cys Ser
                85                  90                  95

Pro Ala Ser Arg Ser Ile Ser Leu Leu Arg Leu Ser Phe His Gln Gly
            100                 105                 110

Cys Thr Ile Ala Ser Gln Arg Leu Thr Pro Leu Ala Arg Gly Asp Thr
        115                 120                 125

Leu Cys Thr Asn Leu Thr Gly Thr Leu Leu Pro Ser Arg Asn Thr Asp
    130                 135                 140

Glu Thr Phe Phe Gly Val Gln Trp Val Arg Pro
145                 150                 155
```

<210> SEQ ID NO 5
<211> LENGTH: 762
<212> TYPE: PRT
<213> ORGANISM: Artificial Sequence
<220> FEATURE:
<223> OTHER INFORMATION: MDT-000762-2: hsCD70_SC-His-Avi-Tev-Fc_hsIgG1

<400> SEQUENCE: 5

```
Met Glu Thr Asp Thr Leu Leu Leu Trp Val Leu Leu Leu Trp Val Pro
1               5                   10                  15

Gly Ser Thr Gly Gln Arg Phe Ala Gln Ala Gln Gln Gln Leu Pro Leu
            20                  25                  30

Glu Ser Leu Gly Trp Asp Val Ala Glu Leu Gln Leu Asn His Thr Gly
        35                  40                  45

Pro Gln Gln Asp Pro Arg Leu Tyr Trp Gln Gly Gly Pro Ala Leu Gly
    50                  55                  60

Arg Ser Phe Leu His Gly Pro Glu Leu Asp Lys Gly Gln Leu Arg Ile
65                  70                  75                  80

His Arg Asp Gly Ile Tyr Met Val His Ile Gln Val Thr Leu Ala Ile
                85                  90                  95

Cys Ser Ser Thr Thr Ala Ser Arg His His Pro Thr Thr Leu Ala Val
            100                 105                 110

Gly Ile Cys Ser Pro Ala Ser Arg Ser Ile Ser Leu Leu Arg Leu Ser
        115                 120                 125

Phe His Gln Gly Cys Thr Ile Ala Ser Gln Arg Leu Thr Pro Leu Ala
    130                 135                 140

Arg Gly Asp Thr Leu Cys Thr Asn Leu Thr Gly Thr Leu Leu Pro Ser
145                 150                 155                 160

Arg Asn Thr Asp Glu Thr Phe Phe Gly Val Gln Trp Val Arg Pro Gly
                165                 170                 175

Ser Gln Arg Phe Ala Gln Ala Gln Gln Gln Leu Pro Leu Glu Ser Leu
            180                 185                 190
```

```
Gly Trp Asp Val Ala Glu Leu Gln Leu Asn His Thr Gly Pro Gln Gln
            195                 200                 205

Asp Pro Arg Leu Tyr Trp Gln Gly Pro Ala Leu Gly Arg Ser Phe
210                 215                 220

Leu His Gly Pro Glu Leu Asp Lys Gly Gln Leu Arg Ile His Arg Asp
225                 230                 235                 240

Gly Ile Tyr Met Val His Ile Gln Val Thr Leu Ala Ile Cys Ser Ser
                245                 250                 255

Thr Thr Ala Ser Arg His His Pro Thr Thr Leu Ala Val Gly Ile Cys
                260                 265                 270

Ser Pro Ala Ser Arg Ser Ile Ser Leu Leu Arg Leu Ser Phe His Gln
                275                 280                 285

Gly Cys Thr Ile Ala Ser Gln Arg Leu Thr Pro Leu Ala Arg Gly Asp
                290                 295                 300

Thr Leu Cys Thr Asn Leu Thr Gly Thr Leu Leu Pro Ser Arg Asn Thr
305                 310                 315                 320

Asp Glu Thr Phe Phe Gly Val Gln Trp Val Arg Pro Gly Ser Gln Arg
                325                 330                 335

Phe Ala Gln Ala Gln Gln Gln Leu Pro Leu Glu Ser Leu Gly Trp Asp
                340                 345                 350

Val Ala Glu Leu Gln Leu Asn His Thr Gly Pro Gln Gln Asp Pro Arg
                355                 360                 365

Leu Tyr Trp Gln Gly Gly Pro Ala Leu Gly Arg Ser Phe Leu His Gly
                370                 375                 380

Pro Glu Leu Asp Lys Gly Gln Leu Arg Ile His Arg Asp Gly Ile Tyr
385                 390                 395                 400

Met Val His Ile Gln Val Thr Leu Ala Ile Cys Ser Ser Thr Thr Ala
                405                 410                 415

Ser Arg His His Pro Thr Thr Leu Ala Val Gly Ile Cys Ser Pro Ala
                420                 425                 430

Ser Arg Ser Ile Ser Leu Leu Arg Leu Ser Phe His Gln Gly Cys Thr
                435                 440                 445

Ile Ala Ser Gln Arg Leu Thr Pro Leu Ala Arg Gly Asp Thr Leu Cys
                450                 455                 460

Thr Asn Leu Thr Gly Thr Leu Leu Pro Ser Arg Asn Thr Asp Glu Thr
465                 470                 475                 480

Phe Phe Gly Val Gln Trp Val Arg Pro Gly Gly Gly Ser His His
                485                 490                 495

His His His His Gly Gly Ser Gly Leu Asn Asp Ile Phe Glu Ala Gln
                500                 505                 510

Lys Ile Glu Trp His Glu Gly Glu Asn Leu Tyr Phe Gln Gly Gly
                515                 520                 525

Gly Ser Glu Pro Lys Ser Ser Asp Lys Thr His Thr Cys Pro Pro Cys
                530                 535                 540

Pro Ala Pro Glu Leu Leu Gly Gly Pro Ser Val Phe Leu Phe Pro Pro
545                 550                 555                 560

Lys Pro Lys Asp Thr Leu Met Ile Ser Arg Thr Pro Glu Val Thr Cys
                565                 570                 575

Val Val Val Asp Val Ser His Glu Asp Pro Glu Val Lys Phe Asn Trp
                580                 585                 590

Tyr Val Asp Gly Val Glu Val His Asn Ala Lys Thr Lys Pro Arg Glu
                595                 600                 605
```

```
Glu Gln Tyr Asn Ser Thr Tyr Arg Val Val Ser Val Leu Thr Val Leu
    610             615             620

His Gln Asp Trp Leu Asn Gly Lys Glu Tyr Lys Cys Lys Val Ser Asn
625             630             635             640

Lys Ala Leu Pro Ala Pro Ile Glu Lys Thr Ile Ser Lys Ala Lys Gly
                645             650             655

Gln Pro Arg Glu Pro Gln Val Tyr Thr Leu Pro Pro Ser Arg Asp Glu
            660             665             670

Leu Thr Lys Asn Gln Val Ser Leu Thr Cys Leu Val Lys Gly Phe Tyr
        675             680             685

Pro Ser Asp Ile Ala Val Glu Trp Glu Ser Asn Gly Gln Pro Glu Asn
690             695             700

Asn Tyr Lys Thr Thr Pro Pro Val Leu Asp Ser Asp Gly Ser Phe Phe
705             710             715             720

Leu Tyr Ser Lys Leu Thr Val Asp Lys Ser Arg Trp Gln Gln Gly Asn
            725             730             735

Val Phe Ser Cys Ser Val Met His Glu Ala Leu His Asn His Tyr Thr
        740             745             750

Gln Lys Ser Leu Ser Leu Ser Pro Gly Lys
        755             760

<210> SEQ ID NO 6
<211> LENGTH: 20
<212> TYPE: PRT
<213> ORGANISM: Homo sapiens

<400> SEQUENCE: 6

Met Glu Thr Asp Thr Leu Leu Leu Trp Val Leu Leu Leu Trp Val Pro
1               5                   10                  15

Gly Ser Thr Gly
            20

<210> SEQ ID NO 7
<211> LENGTH: 707
<212> TYPE: PRT
<213> ORGANISM: Artificial Sequence
<220> FEATURE:
<223> OTHER INFORMATION: MDT-001100: hsCD70_SC-Toroidx6_SS_tetramer-His

<400> SEQUENCE: 7

Met Glu Thr Asp Thr Leu Leu Leu Trp Val Leu Leu Leu Trp Val Pro
1               5                   10                  15

Gly Ser Thr Gly Gln Arg Phe Ala Gln Ala Gln Gln Leu Pro Leu
            20                  25                  30

Glu Ser Leu Gly Trp Asp Val Ala Glu Leu Gln Leu Asn His Thr Gly
        35                  40                  45

Pro Gln Gln Asp Pro Arg Leu Tyr Trp Gln Gly Gly Pro Ala Leu Gly
50                  55                  60

Arg Ser Phe Leu His Gly Pro Glu Leu Asp Lys Gly Gln Leu Arg Ile
65              70                  75                  80

His Arg Asp Gly Ile Tyr Met Val His Ile Gln Val Thr Leu Ala Ile
                85                  90                  95

Cys Ser Ser Thr Thr Ala Ser Arg His His Pro Thr Thr Leu Ala Val
            100                 105                 110

Gly Ile Cys Ser Pro Ala Ser Arg Ser Ile Ser Leu Leu Arg Leu Ser
        115                 120                 125

Phe His Gln Gly Cys Thr Ile Ala Ser Gln Arg Leu Thr Pro Leu Ala
```

-continued

```
            130                 135                 140
Arg Gly Asp Thr Leu Cys Thr Asn Leu Thr Gly Thr Leu Leu Pro Ser
145                 150                 155                 160

Arg Asn Thr Asp Glu Thr Phe Phe Gly Val Gln Trp Val Arg Pro Gly
                165                 170                 175

Gly Ser Gln Arg Phe Ala Gln Ala Gln Gln Leu Pro Leu Glu Ser
                180                 185                 190

Leu Gly Trp Asp Val Ala Glu Leu Gln Leu Asn His Thr Gly Pro Gln
                195                 200                 205

Gln Asp Pro Arg Leu Tyr Trp Gln Gly Gly Pro Ala Leu Gly Arg Ser
    210                 215                 220

Phe Leu His Gly Pro Glu Leu Asp Lys Gly Gln Leu Arg Ile His Arg
225                 230                 235                 240

Asp Gly Ile Tyr Met Val His Ile Gln Val Thr Leu Ala Ile Cys Ser
                245                 250                 255

Ser Thr Thr Ala Ser Arg His His Pro Thr Thr Leu Ala Val Gly Ile
                260                 265                 270

Cys Ser Pro Ala Ser Arg Ser Ile Ser Leu Leu Arg Leu Ser Phe His
            275                 280                 285

Gln Gly Cys Thr Ile Ala Ser Gln Arg Leu Thr Pro Leu Ala Arg Gly
            290                 295                 300

Asp Thr Leu Cys Thr Asn Leu Thr Gly Thr Leu Leu Pro Ser Arg Asn
305                 310                 315                 320

Thr Asp Glu Thr Phe Phe Gly Val Gln Trp Val Arg Pro Gly Gly Ser
                325                 330                 335

Gln Arg Phe Ala Gln Ala Gln Gln Leu Pro Leu Glu Ser Leu Gly
                340                 345                 350

Trp Asp Val Ala Glu Leu Gln Leu Asn His Thr Gly Pro Gln Gln Asp
            355                 360                 365

Pro Arg Leu Tyr Trp Gln Gly Gly Pro Ala Leu Gly Arg Ser Phe Leu
            370                 375                 380

His Gly Pro Glu Leu Asp Lys Gly Gln Leu Arg Ile His Arg Asp Gly
385                 390                 395                 400

Ile Tyr Met Val His Ile Gln Val Thr Leu Ala Ile Cys Ser Ser Thr
                405                 410                 415

Thr Ala Ser Arg His His Pro Thr Thr Leu Ala Val Gly Ile Cys Ser
                420                 425                 430

Pro Ala Ser Arg Ser Ile Ser Leu Leu Arg Leu Ser Phe His Gln Gly
            435                 440                 445

Cys Thr Ile Ala Ser Gln Arg Leu Thr Pro Leu Ala Arg Gly Asp Thr
    450                 455                 460

Leu Cys Thr Asn Leu Thr Gly Thr Leu Leu Pro Ser Arg Asn Thr Asp
465                 470                 475                 480

Glu Thr Phe Phe Gly Val Gln Trp Val Arg Pro Gly Gly Gly Ser
                485                 490                 495

Gly Gly Gly Gly Ser Cys Glu Ala Ile Lys Ala Ala Ala Glu Leu Gly
            500                 505                 510

Lys Ala Gly Ile Ser Ser Glu Glu Ile Leu Glu Leu Leu Arg Ala Ala
            515                 520                 525

His Glu Leu Gly Leu Asp Pro Glu Ala Ile Lys Ala Ala Ala Glu Leu
            530                 535                 540

Gly Lys Ala Gly Ile Ser Ser Glu Glu Ile Leu Glu Leu Leu Arg Ala
545                 550                 555                 560
```

```
Ala His Glu Leu Gly Leu Asp Pro Glu Ala Ile Lys Ala Ala Glu
            565                 570                 575

Leu Gly Lys Ala Gly Ile Ser Ser Glu Ile Leu Glu Leu Leu Arg
            580                 585                 590

Ala Ala His Glu Leu Gly Leu Asp Pro Glu Ala Ile Lys Ala Ala
            595                 600                 605

Glu Leu Gly Lys Ala Gly Ile Ser Ser Glu Ile Leu Glu Leu Leu
            610                 615                 620

Arg Ala Ala His Glu Leu Gly Leu Asp Pro Glu Ala Ile Lys Ala Ala
625                 630                 635                 640

Ala Glu Leu Gly Lys Ala Gly Ile Ser Ser Glu Ile Leu Glu Leu
            645                 650                 655

Leu Arg Ala Ala His Glu Leu Gly Leu Asp Pro Glu Cys Ile Lys Ala
            660                 665                 670

Ala Ala Glu Leu Gly Lys Ala Gly Ile Ser Ser Glu Ile Leu Glu
            675                 680                 685

Leu Leu Arg Ala Ala His Glu Leu Gly Leu Gly Ser His His His
            690                 695                 700

His His His
705

<210> SEQ ID NO 8
<211> LENGTH: 4
<212> TYPE: PRT
<213> ORGANISM: Artificial Sequence
<220> FEATURE:
<223> OTHER INFORMATION: Linker

<400> SEQUENCE: 8

Gly Gly Gly Ser
1

<210> SEQ ID NO 9
<211> LENGTH: 6
<212> TYPE: PRT
<213> ORGANISM: Artificial Sequence
<220> FEATURE:
<223> OTHER INFORMATION: His tag

<400> SEQUENCE: 9

His His His His His His
1               5

<210> SEQ ID NO 10
<211> LENGTH: 15
<212> TYPE: PRT
<213> ORGANISM: Artificial Sequence
<220> FEATURE:
<223> OTHER INFORMATION: Avi tag

<400> SEQUENCE: 10

Gly Leu Asn Asp Ile Phe Glu Ala Gln Lys Ile Glu Trp His Glu
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Tev within MDT-000762-2

<400> SEQUENCE: 11
```

Glu Asn Leu Tyr Phe Gln Gly
1               5

<210> SEQ ID NO 12
<211> LENGTH: 232
<212> TYPE: PRT
<213> ORGANISM: Homo sapiens

<400> SEQUENCE: 12

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 13
<211> LENGTH: 254
<212> TYPE: PRT
<213> ORGANISM: Artificial Sequence
<220> FEATURE:
<223> OTHER INFORMATION: MDT-000763: hsTetranectin_TD-hsCD70-His-Avi

<400> SEQUENCE: 13

Met Glu Thr Asp Thr Leu Leu Leu Trp Val Leu Leu Leu Trp Val Pro
1               5                   10                  15

Gly Ser Thr Gly Glu Pro Pro Thr Gln Lys Pro Lys Lys Ile Val Asn
            20                  25                  30

Ala Lys Lys Asp Val Val Asn Thr Lys Met Phe Glu Glu Leu Lys Ser
        35                  40                  45

Arg Leu Asp Thr Leu Ala Gln Glu Val Ala Leu Leu Lys Glu Gln Gln
    50                  55                  60

```
Ala Leu Gln Thr Val Gly Gly Gly Ser Gln Arg Phe Ala Gln Ala
 65                  70                  75                  80

Gln Gln Gln Leu Pro Leu Glu Ser Leu Gly Trp Asp Val Ala Glu Leu
             85                  90                  95

Gln Leu Asn His Thr Gly Pro Gln Gln Asp Pro Arg Leu Tyr Trp Gln
            100                 105                 110

Gly Gly Pro Ala Leu Gly Arg Ser Phe Leu His Gly Pro Glu Leu Asp
        115                 120                 125

Lys Gly Gln Leu Arg Ile His Arg Asp Gly Ile Tyr Met Val His Ile
    130                 135                 140

Gln Val Thr Leu Ala Ile Cys Ser Ser Thr Thr Ala Ser Arg His His
145                 150                 155                 160

Pro Thr Thr Leu Ala Val Gly Ile Cys Ser Pro Ala Ser Arg Ser Ile
                165                 170                 175

Ser Leu Leu Arg Leu Ser Phe His Gln Gly Cys Thr Ile Ala Ser Gln
                180                 185                 190

Arg Leu Thr Pro Leu Ala Arg Gly Asp Thr Leu Cys Thr Asn Leu Thr
            195                 200                 205

Gly Thr Leu Leu Pro Ser Arg Asn Thr Asp Glu Thr Phe Phe Gly Val
        210                 215                 220

Gln Trp Val Arg Pro Gly Gly Gly Ser His His His His His His Gly
225                 230                 235                 240

Leu Asn Asp Ile Phe Glu Ala Gln Lys Ile Glu Trp His Glu
                245                 250

<210> SEQ ID NO 14
<211> LENGTH: 54
<212> TYPE: PRT
<213> ORGANISM: Homo sapiens

<400> SEQUENCE: 14

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
                20                  25                  30

Leu Ala Gln Glu Val Ala Leu Leu Lys Glu Gln Gln Ala Leu Gln Thr
            35                  40                  45

Val Gly Gly Gly Gly Ser
        50

<210> SEQ ID NO 15
<211> LENGTH: 257
<212> TYPE: PRT
<213> ORGANISM: Artificial Sequence
<220> FEATURE:
<223> OTHER INFORMATION: MDT-000764-2: hsCD70-Collagen_TD-His-Avi

<400> SEQUENCE: 15

Met Glu Thr Asp Thr Leu Leu Leu Trp Val Leu Leu Leu Trp Val Pro
1               5                   10                  15

Gly Ser Thr Gly Gln Arg Phe Ala Gln Ala Gln Gln Gln Leu Pro Leu
                20                  25                  30

Glu Ser Leu Gly Trp Asp Val Ala Glu Leu Gln Leu Asn His Thr Gly
            35                  40                  45

Pro Gln Gln Asp Pro Arg Leu Tyr Trp Gln Gly Gly Pro Ala Leu Gly
        50                  55                  60

Arg Ser Phe Leu His Gly Pro Glu Leu Asp Lys Gly Gln Leu Arg Ile
```

```
            65                  70                  75                  80
His Arg Asp Gly Ile Tyr Met Val His Ile Gln Val Thr Leu Ala Ile
                85                  90                  95

Cys Ser Ser Thr Thr Ala Ser Arg His His Pro Thr Thr Leu Ala Val
            100                 105                 110

Gly Ile Cys Ser Pro Ala Ser Arg Ser Ile Ser Leu Leu Arg Leu Ser
        115                 120                 125

Phe His Gln Gly Cys Thr Ile Ala Ser Gln Arg Leu Thr Pro Leu Ala
    130                 135                 140

Arg Gly Asp Thr Leu Cys Thr Asn Leu Thr Gly Thr Leu Leu Pro Ser
145                 150                 155                 160

Arg Asn Thr Asp Glu Thr Phe Phe Gly Val Gln Trp Val Arg Pro Gly
                165                 170                 175

Ser Asn Leu Val Thr Ala Phe Ser Asn Met Asp Asp Met Leu Gln Lys
            180                 185                 190

Ala His Leu Val Ile Glu Gly Thr Phe Ile Tyr Leu Arg Asp Ser Thr
        195                 200                 205

Glu Phe Phe Ile Arg Val Arg Asp Gly Trp Lys Lys Leu Gln Leu Gly
    210                 215                 220

Glu Leu Ile Pro Ile Pro Ala Gly Ser His His His His His His Gly
225                 230                 235                 240

Gly Ser Gly Leu Asn Asp Ile Phe Glu Ala Gln Lys Ile Glu Trp His
                245                 250                 255

Glu

<210> SEQ ID NO 16
<211> LENGTH: 258
<212> TYPE: PRT
<213> ORGANISM: Artificial Sequence
<220> FEATURE:
<223> OTHER INFORMATION: Trimer_Collagen-hsCD70

<400> SEQUENCE: 16

Met Glu Leu Trp Gly Ala Tyr Leu Leu Leu Cys Leu Phe Ser Leu Leu
1               5                   10                  15

Thr Gln Val Thr Thr Glu Pro Pro Thr Gln Lys Pro Lys Lys Ile Val
            20                  25                  30

Asn Ala Lys Lys Asp Val Val Asn Thr Lys Met Phe Glu Glu Leu Lys
        35                  40                  45

Ser Arg Leu Asp Thr Leu Ala Gln Glu Val Ala Leu Leu Lys Glu Gln
    50                  55                  60

Gln Ala Leu Gln Thr Val Cys Leu Lys Gly Gly Gly Ser Gln Arg
65                  70                  75                  80

Phe Ala Gln Ala Gln Gln Leu Pro Leu Glu Ser Leu Gly Trp Asp
                85                  90                  95

Val Ala Glu Leu Gln Leu Asn His Thr Gly Pro Gln Gln Asp Pro Arg
            100                 105                 110

Leu Tyr Trp Gln Gly Gly Pro Ala Leu Gly Arg Ser Phe Leu His Gly
        115                 120                 125

Pro Glu Leu Asp Lys Gly Gln Leu Arg Ile His Arg Asp Gly Ile Tyr
    130                 135                 140

Met Val His Ile Gln Val Thr Leu Ala Ile Cys Ser Ser Thr Thr Ala
145                 150                 155                 160

Ser Arg His His Pro Thr Thr Leu Ala Val Gly Ile Cys Ser Pro Ala
                165                 170                 175
```

```
Ser Arg Ser Ile Ser Leu Leu Arg Leu Ser Phe His Gln Gly Cys Thr
                180                 185                 190

Ile Ala Ser Gln Arg Leu Thr Pro Leu Ala Arg Gly Asp Thr Leu Cys
            195                 200                 205

Thr Asn Leu Thr Gly Thr Leu Leu Pro Ser Arg Asn Thr Asp Glu Thr
210                 215                 220

Phe Phe Gly Val Gln Trp Val Arg Pro Gly Gly Ser His His His
225                 230                 235                 240

His His His Gly Leu Asn Asp Ile Phe Glu Ala Gln Lys Ile Glu Trp
                245                 250                 255

His Glu

<210> SEQ ID NO 17
<211> LENGTH: 461
<212> TYPE: PRT
<213> ORGANISM: Artificial Sequence
<220> FEATURE:
<223> OTHER INFORMATION: hsCD70-hsCollagen_TD-Avi

<400> SEQUENCE: 17

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Cys Gln Pro Gly Glu Phe Thr Leu
        115                 120                 125

Gly Asn Ile Lys Ser Tyr Pro Gly Leu Thr Ser Tyr Leu Val Arg Val
130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
            180                 185                 190

Leu Gly Leu Pro Glu Asn His Ile Val Phe Pro Val Pro Ile Asp Gln
        195                 200                 205

Cys Ile Asp Gly Gly Gly Ser Glu Asn Leu Tyr Phe Gln Gly Gly Ser
210                 215                 220

Gln Arg Phe Ala Gln Ala Gln Gln Leu Pro Leu Glu Ser Leu Gly
225                 230                 235                 240

Trp Asp Val Ala Glu Leu Gln Leu Asn His Thr Gly Pro Gln Gln Asp
                245                 250                 255

Pro Arg Leu Tyr Trp Gln Gly Gly Pro Ala Leu Gly Arg Ser Phe Leu
            260                 265                 270
```

-continued

His Gly Pro Glu Leu Asp Lys Gly Gln Leu Arg Ile His Arg Asp Gly
             275                 280                 285

Ile Tyr Met Val His Ile Gln Val Thr Leu Ala Ile Cys Ser Ser Thr
    290                 295                 300

Thr Ala Ser Arg His His Pro Thr Thr Leu Ala Val Gly Ile Cys Ser
305                 310                 315                 320

Pro Ala Ser Arg Ser Ile Ser Leu Leu Arg Leu Ser Phe His Gln Gly
                325                 330                 335

Cys Thr Ile Ala Ser Gln Arg Leu Thr Pro Leu Ala Arg Gly Asp Thr
            340                 345                 350

Leu Cys Thr Asn Leu Thr Gly Thr Leu Leu Pro Ser Arg Asn Thr Asp
        355                 360                 365

Glu Thr Phe Phe Gly Val Gln Trp Val Arg Pro Gly Ser Asn Leu Val
    370                 375                 380

Thr Ala Phe Ser Asn Met Asp Asp Met Leu Gln Lys Ala His Leu Val
385                 390                 395                 400

Ile Glu Gly Thr Phe Ile Tyr Leu Arg Asp Ser Thr Glu Phe Phe Ile
                405                 410                 415

Arg Val Arg Asp Gly Trp Lys Lys Leu Gln Leu Gly Glu Leu Ile Pro
            420                 425                 430

Ile Pro Ala Gly Ser His His His His His Gly Gly Ser Gly Leu
        435                 440                 445

Asn Asp Ile Phe Glu Ala Gln Lys Ile Glu Trp His Glu
    450                 455                 460

<210> SEQ ID NO 18
<211> LENGTH: 21
<212> TYPE: PRT
<213> ORGANISM: Homo sapiens

<400> SEQUENCE: 18

Met Glu Leu Trp Gly Ala Tyr Leu Leu Leu Cys Leu Phe Ser Leu Leu
1               5                   10                  15

Thr Gln Val Thr Thr
            20

<210> SEQ ID NO 19
<211> LENGTH: 52
<212> TYPE: PRT
<213> ORGANISM: Homo sapiens

<400> SEQUENCE: 19

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys
    50

<210> SEQ ID NO 20
<211> LENGTH: 54
<212> TYPE: PRT
<213> ORGANISM: Homo sapiens

<400> SEQUENCE: 20

Asn Leu Val Thr Ala Phe Ser Asn Met Asp Asp Met Leu Gln Lys Ala

```
                1               5                   10                  15
            His Leu Val Ile Glu Gly Thr Phe Ile Tyr Leu Arg Asp Ser Thr Glu
                            20                  25                  30

Phe Phe Ile Arg Val Arg Asp Gly Trp Lys Lys Leu Gln Leu Gly Glu
                        35                  40                  45

Leu Ile Pro Ile Pro Ala
                    50

<210> SEQ ID NO 21
<211> LENGTH: 5
<212> TYPE: PRT
<213> ORGANISM: Artificial Sequence
<220> FEATURE:
<223> OTHER INFORMATION: Linker

<400> SEQUENCE: 21

Gly Gly Gly Gly Ser
1               5

<210> SEQ ID NO 22
<211> LENGTH: 5
<212> TYPE: PRT
<213> ORGANISM: Artificial Sequence
<220> FEATURE:
<223> OTHER INFORMATION: sFLAG

<400> SEQUENCE: 22

Asp Tyr Lys Asp Glu
1               5

<210> SEQ ID NO 23
<211> LENGTH: 9
<212> TYPE: PRT
<213> ORGANISM: Artificial Sequence
<220> FEATURE:
<223> OTHER INFORMATION: Tev

<400> SEQUENCE: 23

Glu Asn Leu Tyr Phe Gln Gly Gly Ser
1               5

<210> SEQ ID NO 24
<211> LENGTH: 10
<212> TYPE: PRT
<213> ORGANISM: Artificial Sequence
<220> FEATURE:
<223> OTHER INFORMATION: Linker

<400> SEQUENCE: 24

Gly Gly Gly Gly Ser Gly Gly Gly Gly Ser
1               5                   10

<210> SEQ ID NO 25
<211> LENGTH: 197
<212> TYPE: PRT
<213> ORGANISM: Artificial Sequence
<220> FEATURE:
<223> OTHER INFORMATION: cTRP Scaffold

<400> SEQUENCE: 25

Cys Glu Ala Ile Lys Ala Ala Ala Glu Leu Gly Lys Ala Gly Ile Ser
1               5                   10                  15

Ser Glu Glu Ile Leu Glu Leu Leu Arg Ala Ala His Glu Leu Gly Leu
                20                  25                  30
```

```
Asp Pro Glu Ala Ile Lys Ala Ala Ala Glu Leu Gly Lys Ala Gly Ile
        35                  40                  45

Ser Ser Glu Glu Ile Leu Glu Leu Leu Arg Ala Ala His Glu Leu Gly
 50                  55                  60

Leu Asp Pro Glu Ala Ile Lys Ala Ala Ala Glu Leu Gly Lys Ala Gly
 65                  70                  75                  80

Ile Ser Ser Glu Glu Ile Leu Glu Leu Leu Arg Ala Ala His Glu Leu
                 85                  90                  95

Gly Leu Asp Pro Glu Ala Ile Lys Ala Ala Ala Glu Leu Gly Lys Ala
            100                 105                 110

Gly Ile Ser Ser Glu Glu Ile Leu Glu Leu Leu Arg Ala Ala His Glu
        115                 120                 125

Leu Gly Leu Asp Pro Glu Ala Ile Lys Ala Ala Ala Glu Leu Gly Lys
130                 135                 140

Ala Gly Ile Ser Ser Glu Glu Ile Leu Glu Leu Leu Arg Ala Ala His
145                 150                 155                 160

Glu Leu Gly Leu Asp Pro Glu Cys Ile Lys Ala Ala Ala Glu Leu Gly
                165                 170                 175

Lys Ala Gly Ile Ser Ser Glu Glu Ile Leu Glu Leu Leu Arg Ala Ala
            180                 185                 190

His Glu Leu Gly Leu
            195

<210> SEQ ID NO 26
<211> LENGTH: 13
<212> TYPE: PRT
<213> ORGANISM: Artificial Sequence
<220> FEATURE:
<223> OTHER INFORMATION: cTRP cysteine-modified N-terminal alpha-helix
      forming b segment

<400> SEQUENCE: 26

Cys Glu Ala Ile Lys Ala Ala Ala Glu Leu Gly Lys Ala
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: cTRP internal alpha-helix forming b and y
      segments

<400> SEQUENCE: 27

Ser Glu Glu Ile Leu Glu Leu Leu Arg Ala Ala His Glu Leu
 1               5                  10

<210> SEQ ID NO 28
<211> LENGTH: 13
<212> TYPE: PRT
<213> ORGANISM: Artificial Sequence
<220> FEATURE:
<223> OTHER INFORMATION: cTRP cysteine-modified C-terminal alpha-helix
      forming b segment

<400> SEQUENCE: 28

Pro Glu Cys Ile Lys Ala Ala Ala Glu Leu Gly Lys Ala
 1               5                  10

<210> SEQ ID NO 29
<211> LENGTH: 2121
<212> TYPE: DNA
```

<213> ORGANISM: Artificial Sequence
<220> FEATURE:
<223> OTHER INFORMATION: hsCD70_SC-Toroidx6_SS_tetramer-His

<400> SEQUENCE: 29

| | |
|---|---|
| atggagaccg atacactgct gctgtgggtg ctgctgctgt gggtgcctgg cagcaccgga | 60 |
| cagcggttcg cacaggcaca gcagcagctg ccactggagt ccctgggatg ggacgtggca | 120 |
| gagctgcagc tgaaccacac aggcccccag caggacccca ggctgtactg cagggcggc | 180 |
| cccgccctgg gccgctcctt tctgcacggc cctgagctgg acaagggcca gctgagaatc | 240 |
| cacagagatg gcatctatat ggtgcacatc caggtgaccc tggccatctg cagctccacc | 300 |
| acagcctctc ggcaccaccc aaccacactg gccgtgggca tctgtagccc agccagcagg | 360 |
| tccatctctc tgctgcgcct gtctttccac cagggatgca ccatcgccag ccagcggctg | 420 |
| acaccactgg ccagaggcga caccctgtgc acaaacctga ccggcacact gctgcccagc | 480 |
| cggaataccg atgagacatt ctttggcgtg cagtgggtga ggccaggagg ctctcagcgg | 540 |
| ttcgcccagg cccagcagca gctgcctctg gagagcctgg gctgggacgt ggccgagctg | 600 |
| cagctgaatc acaccggccc acagcaggac cccagactgt attggcaggg cggccctgcc | 660 |
| ctgggccgga gcttcctgca cggccccgag ctggacaagg acagctgag aatccaccgc | 720 |
| gacggaatct atatggtcca tattcaagtg accctggcca tctgctctag caccacagcc | 780 |
| tccaggcatc atcctaccac actggccgtc ggcatctgtt cctgccag ccggtccatc | 840 |
| tctctgctga actgtccctt tcaccagggc tgcaccatcg cctctcagag gctgacacct | 900 |
| ctggcccgcg gcgacactct gtgcaccaac ctgactggca cactgctgcc atcccgcaac | 960 |
| actgatgaga cattctttgg agtgcagtgg gtgcggccag aggctcccca gagattcgcc | 1020 |
| caggctcagc agcagctgcc cctggagtct ctggctggg acgtggctga actgcagctg | 1080 |
| aaccataccg gccctcagca ggaccccgc ttatactggc agggcggccc agccctgggc | 1140 |
| cgcagctttc tgcacggccc cgaactggat aaagggcagc tgagaatcca cagggacgga | 1200 |
| atctatatgg tgcatattca ggtgaccctg gccatctgct cctctaccac agccagcagg | 1260 |
| caccacccta ccacactggc cgttggcatc tgttctcccg ccagcaggtc catctctctg | 1320 |
| ttacgcctga gcttccatca gggctgtact atcgcctccc agcggctgac acccctggcc | 1380 |
| agaggcgaca ctctgtgcac taacctgact ggcacactgt taccctcccg gaacactgac | 1440 |
| gagacattct ttgggtcca gtgggtgaga cctggaggag gaggatccgg cggaggaggc | 1500 |
| tcctgcgagg ccatcaaggc tgccgccgag ctgggcaagg caggcatcag ctccgaggag | 1560 |
| atcctggagc tgctgagggc agcacacgag ctgggcctgg accccgaagc catcaaggct | 1620 |
| gccgccgaac tgggcaaggc cggcatctct agcgaagaaa tcctggagct gctgagagcc | 1680 |
| gcccatgaac tgggcctgga ccccgaggcc atcaaggctg ccgccgagtt aggcaaggca | 1740 |
| ggcatctcct ctgaagagat cctggagtta ttaagagccg cccatgagct gggcctggac | 1800 |
| ccagaggcca tcaaggctgc cgccgagcta ggcaaggccg catcagctc gaagaaatc | 1860 |
| ctggagttac tgagagccgc ccacgaatta ggcctggacc ccgaggccat caaggctgcc | 1920 |
| gccgagcttg gcaaggcagg catctctagc gaagagatcc tggagctttt aagagccgcc | 1980 |
| cacgaactgg gcctggaccc tgagtgtatc aaggctgccg ccgagctcgg caaggccggc | 2040 |
| atctcctctg aggaaatcct ggagttgtta cgcgccgccc acgagctggg cctgggcggc | 2100 |
| agccaccacc accaccacca c | 2121 |

```
<210> SEQ ID NO 30
<211> LENGTH: 49
<212> TYPE: PRT
<213> ORGANISM: Homo sapiens

<400> SEQUENCE: 30

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val

<210> SEQ ID NO 31
<211> LENGTH: 181
<212> TYPE: PRT
<213> ORGANISM: Homo sapiens

<400> SEQUENCE: 31

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu Lys Gly Thr Lys Val His Met Lys Cys Phe Leu Ala Phe
    50                  55                  60

Thr Gln Thr Lys Thr Phe His Glu Ala Ser Glu Asp Cys Ile Ser Arg
65                  70                  75                  80

Gly Gly Thr Leu Ser Thr Pro Gln Thr Gly Ser Glu Asn Asp Ala Leu
                85                  90                  95

Tyr Glu Tyr Leu Arg Gln Ser Val Gly Asn Glu Ala Glu Ile Trp Leu
            100                 105                 110

Gly Leu Asn Asp Met Ala Ala Glu Gly Thr Trp Val Asp Met Thr Gly
        115                 120                 125

Ala Arg Ile Ala Tyr Lys Asn Trp Glu Thr Glu Ile Thr Ala Gln Pro
130                 135                 140

Asp Gly Gly Lys Thr Glu Asn Cys Ala Val Leu Ser Gly Ala Ala Asn
145                 150                 155                 160

Gly Lys Trp Phe Asp Lys Arg Cys Arg Asp Gln Leu Pro Tyr Ile Cys
                165                 170                 175

Gln Phe Gly Ile Val
            180

<210> SEQ ID NO 32
<211> LENGTH: 64
<212> TYPE: PRT
<213> ORGANISM: Homo sapiens

<400> SEQUENCE: 32

Val Thr Ala Phe Ser Asn Met Asp Asp Met Leu Gln Lys Ala His Leu
1               5                   10                  15

Val Ile Glu Gly Thr Phe Ile Tyr Leu Arg Asp Ser Thr Glu Phe Phe
            20                  25                  30

Ile Arg Val Arg Asp Gly Trp Lys Lys Leu Gln Leu Gly Glu Leu Ile
        35                  40                  45
```

```
Pro Ile Pro Ala Asp Ser Pro Pro Pro Ala Leu Ser Ser Asn Pro
    50                  55                  60

<210> SEQ ID NO 33
<211> LENGTH: 59
<212> TYPE: PRT
<213> ORGANISM: Homo sapiens

<400> SEQUENCE: 33

Ser Gly Val Arg Leu Trp Ala Thr Arg Gln Ala Met Leu Gly Gln Val
1               5                   10                  15

His Glu Val Pro Glu Gly Trp Leu Ile Phe Val Ala Glu Gln Glu Glu
                20                  25                  30

Leu Tyr Val Arg Val Gln Asn Gly Phe Arg Lys Val Gln Leu Glu Ala
            35                  40                  45

Arg Thr Pro Leu Pro Arg Gly Thr Asp Asn Glu
        50                  55

<210> SEQ ID NO 34
<211> LENGTH: 125
<212> TYPE: PRT
<213> ORGANISM: Bos taurus

<400> SEQUENCE: 34

Met Gly Ser Ser His His His His His Ser Ser Gly Leu Val Pro
1               5                   10                  15

Arg Gly Ser His Met Trp Lys Gln Ser Val Glu Leu Ala Lys Lys Asp
                20                  25                  30

Ser Leu Tyr Lys Asp Ala Met Gln Tyr Ala Ser Glu Ser Lys Asp Thr
            35                  40                  45

Glu Leu Ala Glu Glu Leu Leu Gln Trp Phe Leu Gln Glu Glu Lys Arg
        50                  55                  60

Glu Cys Phe Gly Ala Cys Leu Phe Thr Cys Tyr Asp Leu Leu Arg Pro
65                  70                  75                  80

Asp Val Val Leu Glu Leu Ala Trp Arg His Asn Ile Met Asp Phe Ala
                85                  90                  95

Met Pro Tyr Phe Ile Gln Val Met Lys Glu Tyr Leu Thr Lys Val Asp
                100                 105                 110

Lys Leu Asp Ala Ser Glu Ser Leu Arg Lys Glu Glu Glu
            115                 120                 125

<210> SEQ ID NO 35
<211> LENGTH: 207
<212> TYPE: PRT
<213> ORGANISM: Salmonella enterica

<400> SEQUENCE: 35

Met Ser Asp Tyr Phe Ala Asp Lys His Leu Val Glu Met Lys Glu
1               5                   10                  15

Gln Gln Lys Glu Gln Glu Thr Lys Ile Asn Leu Leu Lys Gln Gln
                20                  25                  30

Lys Glu Gln Glu Ala Lys Ile Asn Leu Leu Lys Gln Gln Ala Thr
            35                  40                  45

Ile Ile Asn Thr Thr Lys Lys Val Thr Glu Val Val Gly Arg Val Glu
            50                  55                  60

Arg Lys Gln Arg Leu Phe Asp Tyr Thr Glu Leu Asp Pro Ser Gln Thr
65                  70                  75                  80

His Tyr Phe Ile Ile Asn Asn Gly Asn Ile Gly Leu Ala Gly Arg Ile
```

```
                    85                  90                  95
Leu Ser Ile Glu Pro Ile Asp Asn Gly Ser Val Ile His Leu Asp Leu
                100                 105                 110

Val Asn Leu Leu Ser Ile Pro Val Ser Asn Leu Ala Phe Asn Met Thr
            115                 120                 125

Trp Gly Thr Lys Lys Pro Ser Glu Ala Lys Asp Leu Pro Arg Trp Lys
        130                 135                 140

Gln Leu Leu Asn Thr Lys Met Asp Ser Thr Ile Glu Leu Leu Pro
145                 150                 155                 160

Gly Ala Trp Thr Asn Val Thr Leu Thr Leu Lys Gly Val Ser Pro Asn
                165                 170                 175

Asn Leu Lys Tyr Leu Lys Ile Gly Ile Asp Met Glu Asn Val Ile Phe
                180                 185                 190

Asp Ser Ile Gln Pro Ile Asn Asp Thr Lys Lys Pro Lys Lys
                195                 200                 205
```

<210> SEQ ID NO 36
<211> LENGTH: 59
<212> TYPE: PRT
<213> ORGANISM: Homo sapiens

<400> SEQUENCE: 36

```
Gly Ser Leu Asp Asp Ser Ile Ser Ala Ala Ser Thr Ser Asp Val Gln
1               5                   10                  15

Asp Arg Leu Ser Ala Leu Glu Ser Arg Val Gln Gln Gln Glu Asp Glu
            20                  25                  30

Met Thr Val Leu Lys Ala Ala Leu Ala Asp Val Leu Arg Arg Leu Ala
        35                  40                  45

Ile Ser Glu Asp His Val Ala Ser Val Lys Lys
    50                  55
```

<210> SEQ ID NO 37
<211> LENGTH: 39
<212> TYPE: PRT
<213> ORGANISM: Homo sapiens

<400> SEQUENCE: 37

```
Cys Ala Cys Glu Ser Leu Val Lys Phe Gln Ala Lys Val Glu Gly Leu
1               5                   10                  15

Leu Gln Ala Leu Thr Arg Lys Leu Glu Ala Val Ser Lys Arg Leu Ala
            20                  25                  30

Ile Leu Glu Asn Thr Val Val
        35
```

<210> SEQ ID NO 38
<211> LENGTH: 39
<212> TYPE: PRT
<213> ORGANISM: Artificial Sequence
<220> FEATURE:
<223> OTHER INFORMATION: Matrilin-1 variant

<400> SEQUENCE: 38

```
Cys Ala Cys Glu Ser Leu Val Lys Phe Gln Ala Lys Val Glu Gly Leu
1               5                   10                  15

Ile Gln Ala Leu Thr Arg Lys Leu Glu Ala Val Ser Lys Arg Ile Ala
            20                  25                  30

Ile Leu Glu Asn Thr Val Val
        35
```

<210> SEQ ID NO 39
<211> LENGTH: 70
<212> TYPE: PRT
<213> ORGANISM: Homo sapiens

<400> SEQUENCE: 39

```
Glu Ala Glu Ala Glu Val Thr Leu Arg Glu Leu Gln Glu Ala Leu Glu
1               5                   10                  15

Glu Glu Val Leu Thr Arg Gln Ser Leu Ser Arg Glu Met Glu Ala Ile
            20                  25                  30

Arg Thr Asp Asn Gln Asn Phe Ala Ser Gln Leu Arg Glu Ala Glu Ala
        35                  40                  45

Arg Asn Arg Asp Leu Glu Ala His Val Arg Gln Leu Gln Glu Arg Met
    50                  55                  60

Glu Leu Leu Gln Ala Glu
65                  70
```

<210> SEQ ID NO 40
<211> LENGTH: 70
<212> TYPE: PRT
<213> ORGANISM: Artificial Sequence
<220> FEATURE:
<223> OTHER INFORMATION: DMPK variant

<400> SEQUENCE: 40

```
Ile Ala Glu Ile Glu Val Thr Ile Arg Glu Leu Gln Glu Ala Ile Glu
1               5                   10                  15

Glu Glu Val Leu Thr Arg Gln Ser Leu Ser Arg Glu Ile Glu Ala Ile
            20                  25                  30

Arg Thr Asp Ile Gln Asn Ile Ala Ser Gln Leu Arg Glu Ile Glu Ala
        35                  40                  45

Arg Ile Arg Asp Leu Glu Ala His Val Arg Gln Leu Gln Glu Arg Met
    50                  55                  60

Glu Leu Leu Gln Ala Glu
65                  70
```

<210> SEQ ID NO 41
<211> LENGTH: 33
<212> TYPE: PRT
<213> ORGANISM: Homo sapiens

<400> SEQUENCE: 41

```
Ala Ser Ala Leu Asn Thr Lys Ile Arg Ala Leu Gln Gly Ser Leu Glu
1               5                   10                  15

Asn Met Ser Lys Leu Leu Lys Arg Gln Asn Asp Ile Leu Gln Val Val
            20                  25                  30

Ser
```

<210> SEQ ID NO 42
<211> LENGTH: 33
<212> TYPE: PRT
<213> ORGANISM: Artificial Sequence
<220> FEATURE:
<223> OTHER INFORMATION: Variant of Langerin

<400> SEQUENCE: 42

```
Ile Ser Ala Leu Asn Thr Lys Ile Arg Ala Ile Gln Gly Ser Ile Glu
1               5                   10                  15

Asn Met Ser Lys Leu Ile Lys Arg Gln Asn Asp Ile Ile Gln Val Val
            20                  25                  30
```

Ser

<210> SEQ ID NO 43
<211> LENGTH: 32
<212> TYPE: PRT
<213> ORGANISM: Homo sapiens

<400> SEQUENCE: 43

Val Ser Arg Leu Glu Glu Glu Met Arg Lys Leu Gln Ala Thr Val Gln
1               5                   10                  15

Glu Leu Gln Lys Arg Leu Asp Arg Leu Glu Glu Thr Val Gln Ala Lys
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Coronin 1a variant

<400> SEQUENCE: 44

Val Ser Arg Leu Glu Glu Glu Ile Arg Lys Leu Gln Ala Thr Val Gln
1               5                   10                  15

Glu Leu Gln Lys Arg Leu Asp Arg Leu Glu Glu Thr Val Gln Ala Lys
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Coronin 1a variant

<400> SEQUENCE: 45

Val Ser Arg Ile Glu Glu Glu Ile Arg Lys Leu Gln Ala Thr Val Gln
1               5                   10                  15

Glu Leu Gln Lys Arg Leu Asp Arg Leu Glu Glu Thr Val Gln Ala Lys
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Coronin 1a variant

<400> SEQUENCE: 46

Ile Ser Arg Ile Glu Glu Glu Ile Arg Lys Leu Gln Ala Thr Val Gln
1               5                   10                  15

Glu Leu Gln Lys Arg Leu Asp Arg Leu Glu Glu Thr Val Gln Ala Lys
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: Coronin 1a variant

<400> SEQUENCE: 47

Ile Ser Arg Ile Glu Glu Glu Ile Arg Lys Ile Gln Ala Thr Val Gln
1               5                   10                  15

Glu Leu Gln Lys Arg Leu Asp Arg Leu Glu Glu Thr Val Gln Ala Lys

<210> SEQ ID NO 48
<211> LENGTH: 32
<212> TYPE: PRT
<213> ORGANISM: Artificial Sequence
<220> FEATURE:
<223> OTHER INFORMATION: Coronin 1a variant

<400> SEQUENCE: 48

Ile Ser Arg Ile Glu Glu Glu Ile Arg Lys Ile Gln Ala Thr Val Gln
1               5                   10                  15

Glu Leu Gln Lys Arg Ile Asp Arg Leu Glu Glu Thr Val Gln Ala Lys
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Coronin 1a variant

<400> SEQUENCE: 49

Ile Ser Arg Ile Glu Glu Glu Ile Arg Lys Ile Asn Ala Thr Val Gln
1               5                   10                  15

Glu Leu Gln Lys Arg Ile Asp Arg Leu Glu Glu Thr Val Gln Ala Lys
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Coronin 1a variant

<400> SEQUENCE: 50

Ile Ser Arg Ile Glu Glu Glu Ile Arg Lys Ile Asn Ala Thr Ile Gln
1               5                   10                  15

Glu Leu Gln Lys Arg Ile Asp Arg Leu Glu Glu Thr Val Gln Ala Lys
            20                  25                  30

<210> SEQ ID NO 51

<400> SEQUENCE: 51

000

<210> SEQ ID NO 52
<211> LENGTH: 496
<212> TYPE: PRT
<213> ORGANISM: Homo sapiens

<400> SEQUENCE: 52

Met Arg Val Leu Ser Gly Thr Ser Leu Met Leu Cys Ser Leu Leu Leu
1               5                   10                  15

Leu Leu Gln Ala Leu Cys Ser Pro Gly Leu Ala Pro Gln Ser Arg Gly
            20                  25                  30

His Leu Cys Arg Thr Arg Pro Thr Asp Leu Val Phe Val Val Asp Ser
                35                  40                  45

Ser Arg Ser Val Arg Pro Val Glu Phe Glu Lys Val Lys Val Phe Leu
        50                  55                  60

Ser Gln Val Ile Glu Ser Leu Asp Val Gly Pro Asn Ala Thr Arg Val
65                  70                  75                  80

-continued

```
Gly Met Val Asn Tyr Ala Ser Thr Val Lys Gln Glu Phe Ser Leu Arg
                 85                  90                  95

Ala His Val Ser Lys Ala Ala Leu Leu Gln Ala Val Arg Arg Ile Gln
                100                 105                 110

Pro Leu Ser Thr Gly Thr Met Thr Gly Leu Ala Ile Gln Phe Ala Ile
            115                 120                 125

Thr Lys Ala Phe Gly Asp Ala Glu Gly Gly Arg Ser Arg Ser Pro Asp
130                 135                 140

Ile Ser Lys Val Val Ile Val Val Thr Asp Gly Arg Pro Gln Asp Ser
145                 150                 155                 160

Val Gln Asp Val Ser Ala Arg Ala Arg Ala Ser Gly Val Glu Leu Phe
                165                 170                 175

Ala Ile Gly Val Gly Ser Val Asp Lys Ala Thr Leu Arg Gln Ile Ala
                180                 185                 190

Ser Glu Pro Gln Asp Glu His Val Asp Tyr Val Glu Ser Tyr Ser Val
                195                 200                 205

Ile Glu Lys Leu Ser Arg Lys Phe Gln Glu Ala Phe Cys Val Val Ser
            210                 215                 220

Asp Leu Cys Ala Thr Gly Asp His Asp Cys Glu Gln Val Cys Ile Ser
225                 230                 235                 240

Ser Pro Gly Ser Tyr Thr Cys Ala Cys His Glu Gly Phe Thr Leu Asn
                245                 250                 255

Ser Asp Gly Lys Thr Cys Asn Val Cys Ser Gly Gly Gly Ser Ser
                260                 265                 270

Ala Thr Asp Leu Val Phe Leu Ile Asp Gly Ser Lys Ser Val Arg Pro
            275                 280                 285

Glu Asn Phe Glu Leu Val Lys Lys Phe Ile Ser Gln Ile Val Asp Thr
290                 295                 300

Leu Asp Val Ser Asp Lys Leu Ala Gln Val Gly Leu Val Gln Tyr Ser
305                 310                 315                 320

Ser Ser Val Arg Gln Glu Phe Pro Leu Gly Arg Phe His Thr Lys Lys
                325                 330                 335

Asp Ile Lys Ala Ala Val Arg Asn Met Ser Tyr Met Glu Lys Gly Thr
            340                 345                 350

Met Thr Gly Ala Ala Leu Lys Tyr Leu Ile Asp Asn Ser Phe Thr Val
            355                 360                 365

Ser Ser Gly Ala Arg Pro Gly Ala Gln Lys Val Gly Ile Val Phe Thr
            370                 375                 380

Asp Gly Arg Ser Gln Asp Tyr Ile Asn Asp Ala Ala Lys Lys Ala Lys
385                 390                 395                 400

Asp Leu Gly Phe Lys Met Phe Ala Val Gly Val Gly Asn Ala Val Glu
                405                 410                 415

Asp Glu Leu Arg Glu Ile Ala Ser Glu Pro Val Ala Glu His Tyr Phe
            420                 425                 430

Tyr Thr Ala Asp Phe Lys Thr Ile Asn Gln Ile Gly Lys Lys Leu Gln
                435                 440                 445

Lys Lys Ile Cys Val Glu Glu Asp Pro Cys Ala Cys Glu Ser Leu Val
            450                 455                 460

Lys Phe Gln Ala Lys Val Glu Gly Leu Leu Gln Ala Leu Thr Arg Lys
465                 470                 475                 480

Leu Glu Ala Val Ser Lys Arg Leu Ala Ile Leu Glu Asn Thr Val Val
                485                 490                 495
```

```
<210> SEQ ID NO 53
<211> LENGTH: 487
<212> TYPE: PRT
<213> ORGANISM: Artificial Sequence
<220> FEATURE:
<223> OTHER INFORMATION: T4 fibritin

<400> SEQUENCE: 53

Met Thr Asp Ile Val Leu Asn Asp Leu Pro Phe Val Asp Gly Pro Pro
1               5                   10                  15

Ala Glu Gly Gln Ser Arg Ile Ser Trp Ile Lys Asn Gly Glu Glu Ile
            20                  25                  30

Leu Gly Ala Asp Thr Gln Tyr Gly Ser Glu Gly Ser Met Asn Arg Pro
        35                  40                  45

Thr Val Ser Val Leu Arg Asn Val Glu Val Leu Asp Lys Asn Ile Gly
    50                  55                  60

Ile Leu Lys Thr Ser Leu Glu Thr Ala Asn Ser Asp Ile Lys Thr Ile
65                  70                  75                  80

Gln Gly Ile Leu Asp Val Ser Gly Asp Ile Glu Ala Leu Ala Gln Ile
                85                  90                  95

Gly Ile Asn Lys Lys Asp Ile Ser Asp Leu Lys Thr Leu Thr Ser Glu
            100                 105                 110

His Thr Glu Ile Leu Asn Gly Thr Asn Asn Thr Val Asp Ser Ile Leu
        115                 120                 125

Ala Asp Ile Gly Pro Phe Asn Ala Glu Ala Asn Ser Val Tyr Arg Thr
    130                 135                 140

Ile Arg Asn Asp Leu Leu Trp Ile Lys Arg Glu Leu Gly Gln Tyr Thr
145                 150                 155                 160

Gly Gln Asp Ile Asn Gly Leu Pro Val Val Gly Asn Pro Ser Ser Gly
                165                 170                 175

Met Lys His Arg Ile Ile Asn Asn Thr Asp Val Ile Thr Ser Gln Gly
            180                 185                 190

Ile Arg Leu Ser Glu Leu Glu Thr Lys Phe Ile Glu Ser Asp Val Gly
        195                 200                 205

Ser Leu Thr Ile Glu Val Gly Asn Leu Arg Glu Glu Leu Gly Pro Lys
    210                 215                 220

Pro Pro Ser Phe Ser Gln Asn Val Tyr Ser Arg Leu Asn Glu Ile Asp
225                 230                 235                 240

Thr Lys Gln Thr Thr Val Glu Ser Asp Ile Ser Ala Ile Lys Thr Ser
                245                 250                 255

Ile Gly Tyr Pro Gly Asn Asn Ser Ile Ile Thr Ser Val Asn Thr Asn
            260                 265                 270

Thr Asp Asn Ile Ala Ser Ile Asn Leu Glu Leu Asn Gln Ser Gly Gly
        275                 280                 285

Ile Lys Gln Arg Leu Thr Val Ile Glu Thr Ser Ile Gly Ser Asp Asp
    290                 295                 300

Ile Pro Ser Ser Ile Lys Gly Gln Ile Lys Asp Asn Thr Thr Ser Ile
305                 310                 315                 320

Glu Ser Leu Asn Gly Ile Val Gly Glu Asn Thr Ser Ser Gly Leu Arg
                325                 330                 335

Ala Asn Val Ser Trp Leu Asn Gln Ile Val Gly Thr Asp Ser Ser Gly
            340                 345                 350

Gly Gln Pro Ser Pro His Gly Ser Leu Leu Asn Arg Val Ser Thr Ile
        355                 360                 365
```

```
Glu Thr Ser Val Ser Gly Leu Asn Asn Ala Val Gln Asn Leu Gln Val
370                 375                 380

Glu Ile Gly Asn Asn Ser Ala Gly Ile Lys Gly Gln Val Val Ala Leu
385                 390                 395                 400

Asn Thr Leu Val Asn Gly Thr Asn Pro Asn Gly Ser Thr Val Glu Glu
                405                 410                 415

Arg Gly Leu Thr Asn Ser Ile Lys Ala Asn Glu Thr Asn Ile Ala Ser
                420                 425                 430

Val Thr Gln Glu Val Asn Thr Ala Lys Gly Asn Ile Ser Ser Leu Gln
                435                 440                 445

Gly Asp Val Gln Ala Leu Gln Glu Ala Gly Tyr Ile Pro Glu Ala Pro
450                 455                 460

Arg Asp Gly Gln Ala Tyr Val Arg Lys Asp Gly Glu Trp Val Leu Leu
465                 470                 475                 480

Ser Thr Phe Leu Ser Pro Ala
                485

<210> SEQ ID NO 54
<211> LENGTH: 27
<212> TYPE: PRT
<213> ORGANISM: Artificial Sequence
<220> FEATURE:
<223> OTHER INFORMATION: Trimerization domain of T4 fibritin

<400> SEQUENCE: 54

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
                20                  25

<210> SEQ ID NO 55
<211> LENGTH: 480
<212> TYPE: PRT
<213> ORGANISM: Artificial Sequence
<220> FEATURE:
<223> OTHER INFORMATION: RB69 fibritin

<400> SEQUENCE: 55

Met Ile Glu Leu Lys Ser Leu Pro Tyr Val Asp Gly Pro Pro Asp Glu
1               5                   10                  15

Gly Gln Lys Arg Leu Asn Trp Ile Lys Asn Ser Glu Glu Ile Thr Gly
                20                  25                  30

Ala Asp Thr Leu Tyr Gly Ser Glu Gly Val Met Asn Arg Pro Ile Thr
                35                  40                  45

Glu Val Gln Arg Asn Val Glu Thr Ile Asn Asp Asn Val Lys Thr Ile
50                  55                  60

Ala Glu Ser Leu Asp Thr Ala Asn Ala Asp Ile Val Thr Ile Lys Ser
65                  70                  75                  80

Ile Leu Asp Val Ser Gly Asp Val Asp Ala Leu Ala Gln Ile Gly His
                85                  90                  95

Asn Thr Asp Asp Ile Glu Val Leu Lys His Thr Val Asn Ser His Gly
                100                 105                 110

Val Asp Ile Leu Asn Thr Glu Glu Lys Leu Asp Asp Thr Ile Ala Asn
                115                 120                 125

Ile Gly Val Val Asn Pro Glu Thr Asp Ser Val Tyr Arg Thr Val Arg
                130                 135                 140

Asn Asp Leu Leu Trp Ile Lys Thr Glu Leu Gly Gln Tyr Thr Gly Gln
145                 150                 155                 160
```

```
Asp Ile Asn Gly Val Pro Thr Glu Gly Asn Glu Ser Thr Gly Met Lys
                165                 170                 175

Arg Arg Ile Ile Thr Asn Ser Ser Val Leu Val Asp Gln Gly Val Arg
            180                 185                 190

Leu Thr Glu Leu Glu Asn Lys Phe Ala Asp Ser Asp Val Gly Ala Leu
        195                 200                 205

Thr Thr Glu Val Glu Asn Leu Arg Gln Glu Ile Gly Pro Arg Pro Ser
    210                 215                 220

Leu Thr Val Pro Val Tyr Thr Arg Leu Ser Gly Ile Asp Ser Ser Ile
225                 230                 235                 240

Ser Ile Gln Thr Arg Asp Ile Ala Ala Leu Lys Asp Phe Val Gly Tyr
                245                 250                 255

Pro Asn Ser Thr Ala Ile Lys Thr Gln Val Glu Ala Asn Arg Leu Ser
            260                 265                 270

Ile Ser Thr Ile Asn Ser Asp Ile Asn Ser Pro Gly Gly Ile Lys Pro
        275                 280                 285

Arg Leu Thr Thr Leu Glu Thr Thr Ile Gly Ser Pro Asp Leu Pro Thr
    290                 295                 300

Thr Leu Gln Gly Lys Ile Lys Leu Asn Thr Asp Ser Ile Ser Gly Ile
305                 310                 315                 320

Asn Thr Val Leu Gly Val Asp Ser Ser Ser Gly Leu Arg Phe Asn Val
                325                 330                 335

Ala Trp Leu Asn Gln Val Val Gly Val Asp Ser Asn Gly Gly Gln Pro
            340                 345                 350

Glu Pro Ala Gly Ser Leu Leu Tyr Arg Thr Arg Ile Leu Glu Thr Gly
        355                 360                 365

Val Thr Asp Leu Gly Asn Asn Ile Gln Asn Val Gln Thr Glu Leu Gly
    370                 375                 380

Thr Asn Ser Ser Gly Ile Lys Gly Gln Val Thr Ser Leu Asn Lys Leu
385                 390                 395                 400

Ile Ser Gly Thr Asn Pro Asn Gly Gln Thr Ile Glu Glu Arg Gly Ile
                405                 410                 415

Leu Pro Thr Val Lys Asn His Asp Thr Ser Ile Met Ala Leu Thr Thr
            420                 425                 430

Arg Val Thr Thr Leu Glu Thr Asp Leu Ala Ala Ala Glu Ala Glu Ile
        435                 440                 445

Gln Ala Leu Lys Glu Ala Gly Tyr Ile Glu Asp Ala Pro Ser Asp Gly
    450                 455                 460

Lys Phe Tyr Val Arg Lys Asp Gly Ala Trp Val Glu Leu Pro Thr Ala
465                 470                 475                 480

<210> SEQ ID NO 56
<211> LENGTH: 26
<212> TYPE: PRT
<213> ORGANISM: Artificial Sequence
<220> FEATURE:
<223> OTHER INFORMATION: Trimerization domain of RB69 fibritin

<400> SEQUENCE: 56

Gly Tyr Ile Glu Asp Ala Pro Ser Asp Gly Lys Phe Tyr Val Arg Lys
1               5                   10                  15

Asp Gly Ala Trp Val Glu Leu Pro Thr Ala
            20                  25

<210> SEQ ID NO 57
```

<211> LENGTH: 501
<212> TYPE: PRT
<213> ORGANISM: Homo sapiens

<400> SEQUENCE: 57

Met Ala Ala Ser Val Thr Pro Pro Gly Ser Leu Glu Leu Leu Gln
1               5                   10                  15

Pro Gly Phe Ser Lys Thr Leu Leu Gly Thr Lys Leu Glu Ala Lys Tyr
            20                  25                  30

Leu Cys Ser Ala Cys Arg Asn Val Leu Arg Arg Pro Phe Gln Ala Gln
                35                  40                  45

Cys Gly His Arg Tyr Cys Ser Phe Cys Leu Ala Ser Ile Leu Ser Ser
50                  55                  60

Gly Pro Gln Asn Cys Ala Ala Cys Val His Glu Gly Ile Tyr Glu Glu
65                  70                  75                  80

Gly Ile Ser Ile Leu Glu Ser Ser Ala Phe Pro Asp Asn Ala Ala
                85                  90                  95

Arg Arg Glu Val Glu Ser Leu Pro Ala Val Cys Pro Ser Asp Gly Cys
                100                 105                 110

Thr Trp Lys Gly Thr Leu Lys Glu Tyr Glu Ser Cys His Glu Gly Arg
            115                 120                 125

Cys Pro Leu Met Leu Thr Glu Cys Pro Ala Cys Lys Gly Leu Val Arg
            130                 135                 140

Leu Gly Glu Lys Glu Arg His Leu Glu His Glu Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
                180                 185                 190

Gly Lys Lys Lys Ile Pro Arg Glu Lys Phe Gln Asp His Val Lys Thr
            195                 200                 205

Cys Gly Lys Cys Arg Val Pro Cys Arg Phe His Ala Ile Gly Cys Leu
210                 215                 220

Glu Thr Val Glu Gly Glu Lys Gln Gln Glu His Glu Val Gln Trp Leu
225                 230                 235                 240

Arg Glu His Leu Ala Met Leu Leu Ser Ser Val Leu Glu Ala Lys Pro
                245                 250                 255

Leu Leu Gly Asp Gln Ser His Ala Gly Ser Glu Leu Leu Gln Arg Cys
            260                 265                 270

Glu Ser Leu Glu Lys Lys Thr Ala Thr Phe Glu Asn Ile Val Cys Val
            275                 280                 285

Leu Asn Arg Glu Val Glu Arg Val Ala Met Thr Ala Glu Ala Cys Ser
290                 295                 300

Arg Gln His Arg Leu Asp Gln Asp Lys Ile Glu Ala Leu Ser Ser Lys
305                 310                 315                 320

Val Gln Gln Leu Glu Arg Ser Ile Gly Leu Lys Asp Leu Ala Met Ala
                325                 330                 335

Asp Leu Glu Gln Lys Val Leu Glu Met Glu Ala Ser Thr Tyr Asp Gly
            340                 345                 350

Val Phe Ile Trp Lys Ile Ser Asp Phe Ala Arg Lys Arg Gln Glu Ala
            355                 360                 365

Val Ala Gly Arg Ile Pro Ala Ile Phe Ser Pro Ala Phe Tyr Thr Ser
370                 375                 380

Arg Tyr Gly Tyr Lys Met Cys Leu Arg Ile Tyr Leu Asn Gly Asp Gly

```
                385                 390                 395                 400
            Thr Gly Arg Gly Thr His Leu Ser Leu Phe Phe Val Val Met Lys Gly
                            405                 410                 415

Pro Asn Asp Ala Leu Leu Arg Trp Pro Phe Asn Gln Lys Val Thr Leu
                            420                 425                 430

Met Leu Leu Asp Gln Asn Asn Arg Glu His Val Ile Asp Ala Phe Arg
                            435                 440                 445

Pro Asp Val Thr Ser Ser Phe Gln Arg Pro Val Asn Asp Met Asn
                450                 455                 460

Ile Ala Ser Gly Cys Pro Leu Phe Cys Pro Val Ser Lys Met Glu Ala
            465                 470                 475                 480

Lys Asn Ser Tyr Val Arg Asp Asp Ala Ile Phe Ile Lys Ala Ile Val
                            485                 490                 495

Asp Leu Thr Gly Leu
                            500

<210> SEQ ID NO 58
<211> LENGTH: 1170
<212> TYPE: PRT
<213> ORGANISM: Homo sapiens

<400> SEQUENCE: 58

Met Gly Leu Ala Trp Gly Leu Gly Val Leu Phe Leu Met His Val Cys
            1               5                   10                  15

Gly Thr Asn Arg Ile Pro Glu Ser Gly Gly Asp Asn Ser Val Phe Asp
                            20                  25                  30

Ile Phe Glu Leu Thr Gly Ala Ala Arg Lys Gly Ser Gly Arg Arg Leu
                        35                  40                  45

Val Lys Gly Pro Asp Pro Ser Ser Pro Ala Phe Arg Ile Glu Asp Ala
                50                  55                  60

Asn Leu Ile Pro Pro Val Pro Asp Asp Lys Phe Gln Asp Leu Val Asp
            65                  70                  75                  80

Ala Val Arg Ala Glu Lys Gly Phe Leu Leu Leu Ala Ser Leu Arg Gln
                            85                  90                  95

Met Lys Lys Thr Arg Gly Thr Leu Leu Ala Leu Glu Arg Lys Asp His
                            100                 105                 110

Ser Gly Gln Val Phe Ser Val Val Ser Asn Gly Lys Ala Gly Thr Leu
                        115                 120                 125

Asp Leu Ser Leu Thr Val Gln Gly Lys Gln His Val Val Ser Val Glu
                130                 135                 140

Glu Ala Leu Leu Ala Thr Gly Gln Trp Lys Ser Ile Thr Leu Phe Val
            145                 150                 155                 160

Gln Glu Asp Arg Ala Gln Leu Tyr Ile Asp Cys Glu Lys Met Glu Asn
                            165                 170                 175

Ala Glu Leu Asp Val Pro Ile Gln Ser Val Phe Thr Arg Asp Leu Ala
                            180                 185                 190

Ser Ile Ala Arg Leu Arg Ile Ala Lys Gly Gly Val Asn Asp Asn Phe
                        195                 200                 205

Gln Gly Val Leu Gln Asn Val Arg Phe Val Phe Gly Thr Thr Pro Glu
                210                 215                 220

Asp Ile Leu Arg Asn Lys Gly Cys Ser Ser Ser Thr Ser Val Leu Leu
            225                 230                 235                 240

Thr Leu Asp Asn Asn Val Val Asn Gly Ser Ser Pro Ala Ile Arg Thr
                            245                 250                 255
```

```
Asn Tyr Ile Gly His Lys Thr Lys Asp Leu Gln Ala Ile Cys Gly Ile
                260                 265                 270
Ser Cys Asp Glu Leu Ser Ser Met Val Leu Glu Leu Arg Gly Leu Arg
            275                 280                 285
Thr Ile Val Thr Thr Leu Gln Asp Ser Ile Arg Lys Val Thr Glu Glu
        290                 295                 300
Asn Lys Glu Leu Ala Asn Glu Leu Arg Arg Pro Pro Leu Cys Tyr His
305                 310                 315                 320
Asn Gly Val Gln Tyr Arg Asn Asn Glu Glu Trp Thr Val Asp Ser Cys
                325                 330                 335
Thr Glu Cys His Cys Gln Asn Ser Val Thr Ile Cys Lys Lys Val Ser
            340                 345                 350
Cys Pro Ile Met Pro Cys Ser Asn Ala Thr Val Pro Asp Gly Glu Cys
        355                 360                 365
Cys Pro Arg Cys Trp Pro Ser Asp Ser Ala Asp Asp Gly Trp Ser Pro
        370                 375                 380
Trp Ser Glu Trp Thr Ser Cys Ser Thr Ser Cys Gly Asn Gly Ile Gln
385                 390                 395                 400
Gln Arg Gly Arg Ser Cys Asp Ser Leu Asn Asn Arg Cys Glu Gly Ser
                405                 410                 415
Ser Val Gln Thr Arg Thr Cys His Ile Gln Glu Cys Asp Lys Arg Phe
            420                 425                 430
Lys Gln Asp Gly Gly Trp Ser His Trp Ser Pro Trp Ser Ser Cys Ser
        435                 440                 445
Val Thr Cys Gly Asp Gly Val Ile Thr Arg Ile Arg Leu Cys Asn Ser
450                 455                 460
Pro Ser Pro Gln Met Asn Gly Lys Pro Cys Glu Gly Glu Ala Arg Glu
465                 470                 475                 480
Thr Lys Ala Cys Lys Lys Asp Ala Cys Pro Ile Asn Gly Gly Trp Gly
                485                 490                 495
Pro Trp Ser Pro Trp Asp Ile Cys Ser Val Thr Cys Gly Gly Gly Val
            500                 505                 510
Gln Lys Arg Ser Arg Leu Cys Asn Asn Pro Thr Pro Gln Phe Gly Gly
        515                 520                 525
Lys Asp Cys Val Gly Asp Val Thr Glu Asn Gln Ile Cys Asn Lys Gln
        530                 535                 540
Asp Cys Pro Ile Asp Gly Cys Leu Ser Asn Pro Cys Phe Ala Gly Val
545                 550                 555                 560
Lys Cys Thr Ser Tyr Pro Asp Gly Ser Trp Lys Cys Gly Ala Cys Pro
                565                 570                 575
Pro Gly Tyr Ser Gly Asn Gly Ile Gln Cys Thr Asp Val Asp Glu Cys
            580                 585                 590
Lys Glu Val Pro Asp Ala Cys Phe Asn His Asn Gly Glu His Arg Cys
        595                 600                 605
Glu Asn Thr Asp Pro Gly Tyr Asn Cys Leu Pro Cys Pro Pro Arg Phe
610                 615                 620
Thr Gly Ser Gln Pro Phe Gly Gln Gly Val Glu His Ala Thr Ala Asn
625                 630                 635                 640
Lys Gln Val Cys Lys Pro Arg Asn Pro Cys Thr Asp Gly Thr His Asp
                645                 650                 655
Cys Asn Lys Asn Ala Lys Cys Ser Asn Tyr Leu Gly His Tyr Ser Asp Pro
            660                 665                 670
Met Tyr Arg Cys Glu Cys Lys Pro Gly Tyr Ala Gly Asn Gly Ile Ile
```

```
            675                 680                 685
Cys Gly Glu Asp Thr Asp Leu Asp Gly Trp Pro Asn Glu Asn Leu Val
    690                 695                 700
Cys Val Ala Asn Ala Thr Tyr His Cys Lys Lys Asp Asn Cys Pro Asn
705                 710                 715                 720
Leu Pro Asn Ser Gly Gln Glu Asp Tyr Asp Lys Asp Gly Ile Gly Asp
                725                 730                 735
Ala Cys Asp Asp Asp Asp Asn Asp Lys Ile Pro Asp Asp Arg Asp
    740                 745                 750
Asn Cys Pro Phe His Tyr Asn Pro Ala Gln Tyr Asp Tyr Asp Arg Asp
        755                 760                 765
Asp Val Gly Asp Arg Cys Asp Asn Cys Pro Tyr Asn His Asn Pro Asp
    770                 775                 780
Gln Ala Asp Thr Asp Asn Asn Gly Glu Gly Asp Ala Cys Ala Ala Asp
785                 790                 795                 800
Ile Asp Gly Asp Gly Ile Leu Asn Glu Arg Asp Asn Cys Gln Tyr Val
                805                 810                 815
Tyr Asn Val Asp Gln Arg Asp Thr Asp Met Asp Gly Val Gly Asp Gln
                820                 825                 830
Cys Asp Asn Cys Pro Leu Glu His Asn Pro Asp Gln Leu Asp Ser Asp
            835                 840                 845
Ser Asp Arg Ile Gly Asp Thr Cys Asp Asn Asn Gln Asp Ile Asp Glu
    850                 855                 860
Asp Gly His Gln Asn Asn Leu Asp Asn Cys Pro Tyr Val Pro Asn Ala
865                 870                 875                 880
Asn Gln Ala Asp His Asp Lys Asp Gly Lys Gly Asp Ala Cys Asp His
                885                 890                 895
Asp Asp Asp Asn Asp Gly Ile Pro Asp Asp Lys Asp Asn Cys Arg Leu
                900                 905                 910
Val Pro Asn Pro Asp Gln Lys Asp Ser Asp Gly Asp Gly Arg Gly Asp
            915                 920                 925
Ala Cys Lys Asp Asp Phe Asp His Asp Ser Val Pro Asp Ile Asp Asp
    930                 935                 940
Ile Cys Pro Glu Asn Val Asp Ile Ser Glu Thr Asp Phe Arg Arg Phe
945                 950                 955                 960
Gln Met Ile Pro Leu Asp Pro Lys Gly Thr Ser Gln Asn Asp Pro Asn
            965                 970                 975
Trp Val Val Arg His Gln Gly Lys Glu Leu Val Gln Thr Val Asn Cys
            980                 985                 990
Asp Pro Gly Leu Ala Val Gly Tyr Asp Glu Phe Asn Ala Val Asp Phe
        995                 1000                1005
Ser Gly Thr Phe Phe Ile Asn Thr Glu Arg Asp Asp Asp Tyr Ala
    1010                1015                1020
Gly Phe Val Phe Gly Tyr Gln Ser Ser Ser Arg Phe Tyr Val Val
    1025                1030                1035
Met Trp Lys Gln Val Thr Gln Ser Tyr Trp Asp Thr Asn Pro Thr
    1040                1045                1050
Arg Ala Gln Gly Tyr Ser Gly Leu Ser Val Lys Val Val Asn Ser
    1055                1060                1065
Thr Thr Gly Pro Gly Glu His Leu Arg Asn Ala Leu Trp His Thr
    1070                1075                1080
Gly Asn Thr Pro Gly Gln Val Arg Thr Leu Trp His Asp Pro Arg
    1085                1090                1095
```

```
His Ile Gly Trp Lys Asp Phe Thr Ala Tyr Arg Trp Arg Leu Ser
    1100                1105                1110

His Arg Pro Lys Thr Gly Phe Ile Arg Val Val Met Tyr Glu Gly
    1115                1120                1125

Lys Lys Ile Met Ala Asp Ser Gly Pro Ile Tyr Asp Lys Thr Tyr
    1130                1135                1140

Ala Gly Gly Arg Leu Gly Leu Phe Val Phe Ser Gln Glu Met Val
    1145                1150                1155

Phe Phe Ser Asp Leu Lys Tyr Glu Cys Arg Asp Pro
    1160                1165                1170

<210> SEQ ID NO 59
<211> LENGTH: 622
<212> TYPE: PRT
<213> ORGANISM: Homo sapiens

<400> SEQUENCE: 59

Met Arg Gly Leu Leu Cys Trp Pro Val Leu Leu Leu Leu Gln Pro
1               5                   10                  15

Trp Glu Thr Gln Leu Gln Leu Thr Gly Pro Arg Cys His Thr Gly Pro
                20                  25                  30

Leu Asp Leu Val Phe Val Ile Asp Ser Ser Arg Ser Val Arg Pro Phe
            35                  40                  45

Glu Phe Glu Thr Met Arg Gln Phe Leu Met Gly Leu Leu Arg Gly Leu
    50                  55                  60

Asn Val Gly Pro Asn Ala Thr Arg Val Gly Val Ile Gln Tyr Ser Ser
65                  70                  75                  80

Gln Val Gln Ser Val Phe Pro Leu Arg Ala Phe Ser Arg Arg Glu Asp
                85                  90                  95

Met Glu Arg Ala Ile Arg Asp Leu Val Pro Leu Ala Gln Gly Thr Met
                100                 105                 110

Thr Gly Leu Ala Ile Gln Tyr Ala Met Asn Val Ala Phe Ser Val Ala
            115                 120                 125

Glu Gly Ala Arg Pro Pro Glu Glu Arg Val Pro Arg Val Ala Val Ile
    130                 135                 140

Val Thr Asp Gly Arg Pro Gln Asp Arg Val Ala Glu Val Ala Ala Gln
145                 150                 155                 160

Ala Arg Ala Arg Gly Ile Glu Ile Tyr Ala Val Gly Val Gln Arg Ala
                165                 170                 175

Asp Val Gly Ser Leu Arg Ala Met Ala Ser Pro Pro Leu Asp Glu His
                180                 185                 190

Val Phe Leu Val Glu Ser Phe Asp Leu Ile Gln Glu Phe Gly Leu Gln
            195                 200                 205

Phe Gln Ser Arg Leu Cys Gly Lys Asp Gln Cys Ala Glu Gly Gly His
    210                 215                 220

Gly Cys Gln His Gln Cys Val Asn Ala Trp Ala Met Phe His Cys Thr
225                 230                 235                 240

Cys Asn Pro Gly Tyr Lys Leu Ala Ala Asp Asn Lys Ser Cys Leu Ala
                245                 250                 255

Ile Asp Leu Cys Ala Glu Gly Thr His Gly Cys Glu His His Cys Val
                260                 265                 270

Asn Ser Pro Gly Ser Tyr Phe Cys His Cys Gln Val Gly Phe Val Leu
            275                 280                 285

Gln Gln Asp Gln Arg Ser Cys Arg Ala Ile Asp Tyr Cys Ser Phe Gly
```

```
                290                 295                 300
Asn His Ser Cys Gln His Glu Cys Val Ser Thr Pro Gly Gly Pro Arg
305                 310                 315                 320

Cys His Cys Arg Glu Gly His Asp Leu Gln Pro Asp Gly Arg Ser Cys
                325                 330                 335

Gln Val Arg Asp Leu Cys Asn Gly Val Asp His Gly Cys Glu Phe Gln
                340                 345                 350

Cys Val Ser Glu Gly Leu Ser Tyr Arg Cys Leu Cys Pro Gly Arg
                355                 360                 365

Gln Leu Gln Ala Asp Gly Lys Ser Cys Asn Arg Cys Arg Glu Gly His
                370                 375                 380

Val Asp Leu Val Leu Leu Val Asp Gly Ser Lys Ser Val Arg Pro Gln
385                 390                 395                 400

Asn Phe Glu Leu Val Lys Arg Phe Val Asn Gln Ile Val Asp Phe Leu
                405                 410                 415

Asp Val Ser Pro Glu Gly Thr Arg Val Gly Leu Val Gln Phe Ser Ser
                420                 425                 430

Arg Val Arg Thr Glu Phe Pro Leu Gly Arg Tyr Gly Thr Ala Ala Glu
                435                 440                 445

Val Lys Gln Ala Val Leu Ala Val Glu Tyr Met Glu Arg Gly Thr Met
                450                 455                 460

Thr Gly Leu Ala Leu Arg His Met Val Glu His Ser Phe Ser Glu Ala
465                 470                 475                 480

Gln Gly Ala Arg Pro Arg Ala Leu Asn Val Pro Arg Val Gly Leu Val
                485                 490                 495

Phe Thr Asp Gly Arg Ser Gln Asp Asp Ile Ser Val Trp Ala Ala Arg
                500                 505                 510

Ala Lys Glu Glu Gly Ile Val Met Tyr Ala Val Gly Val Gly Lys Ala
                515                 520                 525

Val Glu Ala Glu Leu Arg Glu Ile Ala Ser Glu Pro Ala Glu Leu His
                530                 535                 540

Val Ser Tyr Ala Pro Asp Phe Gly Thr Met Thr His Leu Leu Glu Asn
545                 550                 555                 560

Leu Arg Gly Ser Ile Cys Pro Glu Glu Gly Ile Ser Ala Gly Thr Glu
                565                 570                 575

Leu Arg Ser Pro Cys Glu Cys Glu Ser Leu Val Glu Phe Gln Gly Arg
                580                 585                 590

Thr Leu Gly Ala Leu Glu Ser Leu Thr Leu Asn Leu Ala Gln Leu Thr
                595                 600                 605

Ala Arg Leu Glu Asp Leu Glu Asn Gln Leu Ala Asn Gln Lys
610                 615                 620

<210> SEQ ID NO 60
<211> LENGTH: 529
<212> TYPE: PRT
<213> ORGANISM: Artificial Sequence
<220> FEATURE:
<223> OTHER INFORMATION: Heat shock transcription factor (HSF)
      (Accession No. AAX42211 [gi:61362386]

<400> SEQUENCE: 60

Met Asp Leu Pro Val Gly Pro Gly Ala Ala Gly Pro Ser Asn Val Pro
1               5                   10                  15

Ala Phe Leu Thr Lys Leu Trp Thr Leu Val Ser Asp Pro Asp Thr Asp
                20                  25                  30
```

```
Ala Leu Ile Cys Trp Ser Pro Ser Gly Asn Ser Phe His Val Phe Asp
         35                  40                  45

Gln Gly Gln Phe Ala Lys Glu Val Leu Pro Lys Tyr Phe Lys His Asn
 50                  55                  60

Asn Met Ala Ser Phe Val Arg Gln Leu Asn Met Tyr Gly Phe Arg Lys
 65                  70                  75                  80

Val Val His Ile Glu Gln Gly Leu Val Lys Pro Glu Arg Asp Asp
                 85                  90                  95

Thr Glu Phe Gln His Pro Cys Phe Leu Arg Gly Gln Glu Gln Leu Leu
             100                 105                 110

Glu Asn Ile Lys Arg Lys Val Thr Ser Val Ser Thr Leu Lys Ser Glu
             115                 120                 125

Asp Ile Lys Ile Arg Gln Asp Ser Val Thr Lys Leu Leu Thr Asp Val
         130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
                 165                 170                 175

Gln Lys His Ala Gln Gln Lys Val Val Asn Lys Leu Ile Gln Phe
             180                 185                 190

Leu Ile Ser Leu Val Gln Ser Asn Arg Ile Leu Gly Val Lys Arg Lys
         195                 200                 205

Ile Pro Leu Met Leu Asn Asp Ser Gly Ser Ala His Ser Met Pro Lys
     210                 215                 220

Tyr Ser Arg Gln Phe Ser Leu Glu His Val His Gly Ser Gly Pro Tyr
225                 230                 235                 240

Ser Ala Pro Ser Pro Ala Tyr Ser Ser Ser Leu Tyr Ala Pro Asp
             245                 250                 255

Ala Val Ala Ser Ser Gly Pro Ile Ile Ser Asp Ile Thr Glu Leu Ala
             260                 265                 270

Pro Ala Ser Pro Met Ala Ser Pro Gly Gly Ser Ile Asp Glu Arg Pro
             275                 280                 285

Leu Ser Ser Ser Pro Leu Val Arg Val Lys Glu Glu Pro Pro Ser Pro
290                 295                 300

Pro Gln Ser Pro Arg Val Glu Glu Ala Ser Pro Gly Arg Pro Ser Ser
305                 310                 315                 320

Val Asp Thr Leu Leu Ser Pro Thr Ala Leu Ile Asp Ser Ile Leu Arg
                 325                 330                 335

Glu Ser Glu Pro Ala Pro Ala Ser Val Thr Ala Leu Thr Asp Ala Arg
             340                 345                 350

Gly His Thr Asp Thr Glu Gly Arg Pro Pro Ser Pro Pro Thr Ser
             355                 360                 365

Thr Pro Glu Lys Cys Leu Ser Val Ala Cys Leu Asp Lys Asn Glu Leu
370                 375                 380

Ser Asp His Leu Asp Ala Met Asp Ser Asn Leu Asp Asn Leu Gln Thr
385                 390                 395                 400

Met Leu Ser Ser His Gly Phe Ser Val Asp Thr Ser Ala Leu Leu Asp
                 405                 410                 415

Leu Phe Ser Pro Ser Val Thr Val Pro Asp Met Ser Leu Pro Asp Leu
             420                 425                 430

Asp Ser Ser Leu Ala Ser Ile Gln Glu Leu Leu Ser Pro Gln Glu Pro
         435                 440                 445

Pro Arg Pro Pro Glu Ala Glu Asn Ser Ser Pro Asp Ser Gly Lys Gln
```

```
               450                 455                 460
Leu Val His Tyr Thr Ala Gln Pro Leu Phe Leu Asp Pro Gly Ser
465                 470                 475                 480

Val Asp Thr Gly Ser Asn Asp Leu Pro Val Leu Phe Glu Leu Gly Glu
                    485                 490                 495

Gly Ser Tyr Phe Ser Glu Gly Asp Gly Phe Ala Glu Asp Pro Thr Ile
                    500                 505                 510

Ser Leu Leu Thr Gly Ser Glu Pro Pro Lys Ala Lys Asp Pro Thr Val
            515                 520                 525

Ser
```

<210> SEQ ID NO 61
<211> LENGTH: 3623
<212> TYPE: PRT
<213> ORGANISM: Homo sapiens

<400> SEQUENCE: 61

```
Met Met Asn Met Ser Leu Pro Phe Leu Trp Ser Leu Leu Thr Leu Leu
1               5                   10                  15

Ile Phe Ala Glu Val Asn Gly Glu Ala Gly Glu Leu Glu Leu Gln Arg
                20                  25                  30

Gln Lys Arg Ser Ile Asn Leu Gln Gln Pro Arg Met Ala Thr Glu Arg
            35                  40                  45

Gly Asn Leu Val Phe Leu Thr Gly Ser Ala Gln Asn Ile Glu Phe Arg
        50                  55                  60

Thr Gly Ser Leu Gly Lys Ile Lys Leu Asn Asp Glu Asp Leu Ser Glu
65                  70                  75                  80

Cys Leu His Gln Ile Gln Lys Asn Lys Glu Asp Ile Ile Glu Leu Lys
                85                  90                  95

Gly Ser Ala Ile Gly Leu Pro Gln Asn Ile Ser Ser Gln Ile Tyr Gln
                100                 105                 110

Leu Asn Ser Lys Leu Val Asp Leu Glu Arg Lys Phe Gln Gly Leu Gln
            115                 120                 125

Gln Thr Val Asp Lys Lys Val Cys Ser Ser Asn Pro Cys Gln Asn Gly
        130                 135                 140

Gly Thr Cys Leu Asn Leu His Asp Ser Phe Phe Cys Ile Cys Pro Pro
145                 150                 155                 160

Gln Trp Lys Gly Pro Leu Cys Ser Ala Asp Val Asn Glu Cys Glu Ile
                165                 170                 175

Tyr Ser Gly Thr Pro Leu Ser Cys Gln Asn Gly Gly Thr Cys Val Asn
                180                 185                 190

Thr Met Gly Ser Tyr Ser Cys His Cys Pro Pro Glu Thr Tyr Gly Pro
            195                 200                 205

Gln Cys Ala Ser Lys Tyr Asp Asp Cys Glu Gly Ser Val Ala Arg
        210                 215                 220

Cys Val His Gly Ile Cys Glu Asp Leu Met Arg Glu Gln Ala Gly Glu
225                 230                 235                 240

Pro Lys Tyr Ser Cys Val Cys Asp Ala Gly Trp Met Phe Ser Pro Asn
                245                 250                 255

Ser Pro Ala Cys Thr Leu Asp Arg Asp Glu Cys Ser Phe Gln Pro Gly
                260                 265                 270

Pro Cys Ser Thr Leu Val Gln Cys Phe Asn Thr Gln Gly Ser Phe Tyr
            275                 280                 285

Cys Gly Ala Cys Pro Thr Gly Trp Gln Gly Asn Gly Tyr Ile Cys Glu
```

```
                290             295             300
Asp Ile Asn Glu Cys Glu Ile Asn Asn Gly Gly Cys Ser Val Ala Pro
305             310             315             320
Pro Val Glu Cys Val Asn Thr Pro Gly Ser Ser His Cys Gln Ala Cys
                325             330             335
Pro Pro Gly Tyr Gln Gly Asp Gly Arg Val Cys Thr Leu Thr Asp Ile
            340             345             350
Cys Ser Val Ser Asn Gly Gly Cys His Pro Asp Ala Ser Cys Ser Ser
            355             360             365
Thr Leu Gly Ser Leu Pro Leu Cys Thr Cys Leu Pro Gly Tyr Thr Gly
        370             375             380
Asn Gly Tyr Gly Pro Asn Gly Cys Val Gln Leu Ser Asn Ile Cys Leu
385             390             395             400
Ser His Pro Cys Leu Asn Gly Gln Cys Ile Asp Thr Val Ser Gly Tyr
            405             410             415
Phe Cys Lys Cys Asp Ser Gly Trp Thr Gly Val Asn Cys Thr Glu Asn
            420             425             430
Ile Asn Glu Cys Leu Ser Asn Pro Cys Leu Asn Gly Gly Thr Cys Val
            435             440             445
Asp Gly Val Asp Ser Phe Ser Cys Glu Cys Thr Arg Leu Trp Thr Gly
        450             455             460
Ala Leu Cys Gln Val Pro Gln Gln Val Cys Gly Glu Ser Leu Ser Gly
465             470             475             480
Ile Asn Gly Ser Phe Ser Tyr Arg Ser Pro Asp Val Gly Tyr Val His
            485             490             495
Asp Val Asn Cys Phe Trp Val Ile Lys Thr Glu Met Gly Lys Val Leu
            500             505             510
Arg Ile Thr Phe Thr Phe Arg Leu Glu Ser Met Asp Asn Cys Pro
            515             520             525
His Glu Phe Leu Gln Val Tyr Asp Gly Asp Ser Ser Ala Phe Gln
        530             535             540
Leu Gly Arg Phe Cys Gly Ser Ser Leu Pro His Glu Leu Leu Ser Ser
545             550             555             560
Asp Asn Ala Leu Tyr Phe His Leu Tyr Ser Glu His Leu Arg Asn Gly
            565             570             575
Arg Gly Phe Thr Val Arg Trp Glu Thr Gln Gln Pro Glu Cys Gly Gly
            580             585             590
Ile Leu Thr Gly Pro Tyr Gly Ser Ile Lys Ser Pro Gly Tyr Pro Gly
            595             600             605
Asn Tyr Pro Pro Gly Arg Asp Cys Val Trp Ile Val Val Thr Ser Pro
            610             615             620
Asp Leu Leu Val Thr Phe Thr Phe Gly Thr Leu Ser Leu Glu His His
625             630             635             640
Asp Asp Cys Asn Lys Asp Tyr Leu Glu Ile Arg Asp Gly Pro Leu Tyr
            645             650             655
Gln Asp Pro Leu Leu Gly Lys Phe Cys Thr Thr Phe Ser Val Pro Pro
            660             665             670
Leu Gln Thr Thr Gly Pro Phe Ala Arg Ile His Phe His Ser Asp Ser
        675             680             685
Gln Ile Ser Asp Gln Gly Phe His Ile Thr Tyr Leu Thr Ser Pro Ser
        690             695             700
Asp Leu Arg Cys Gly Gly Asn Tyr Thr Asp Pro Glu Gly Glu Leu Phe
705             710             715             720
```

```
Leu Pro Glu Leu Ser Gly Pro Phe Thr His Thr Arg Gln Cys Val Tyr
            725                 730                 735

Met Met Lys Gln Pro Gln Gly Glu Gln Ile Gln Ile Asn Phe Thr His
            740                 745                 750

Val Glu Leu Gln Cys Gln Ser Asp Ser Ser Gln Asn Tyr Ile Glu Val
            755                 760                 765

Arg Asp Gly Glu Thr Leu Leu Gly Lys Val Cys Gly Asn Gly Thr Ile
            770                 775                 780

Ser His Ile Lys Ser Ile Thr Asn Ser Val Trp Ile Arg Phe Lys Ile
785                 790                 795                 800

Asp Ala Ser Val Glu Lys Ala Ser Phe Arg Ala Val Tyr Gln Val Ala
            805                 810                 815

Cys Gly Asp Glu Leu Thr Gly Glu Gly Val Ile Arg Ser Pro Phe Phe
            820                 825                 830

Pro Asn Val Tyr Pro Gly Glu Arg Thr Cys Arg Trp Thr Ile His Gln
            835                 840                 845

Pro Gln Ser Gln Val Ile Leu Leu Asn Phe Thr Val Phe Glu Ile Gly
            850                 855                 860

Ser Ser Ala His Cys Glu Thr Asp Tyr Val Glu Ile Gly Ser Ser Ser
865                 870                 875                 880

Ile Leu Gly Ser Pro Glu Asn Lys Lys Tyr Cys Gly Thr Asp Ile Pro
            885                 890                 895

Ser Phe Ile Thr Ser Val Tyr Asn Phe Leu Tyr Val Thr Phe Val Lys
            900                 905                 910

Ser Ser Ser Thr Glu Asn His Gly Phe Met Ala Lys Phe Ser Ala Glu
            915                 920                 925

Asp Leu Ala Cys Gly Glu Ile Leu Thr Glu Ser Thr Gly Thr Ile Gln
            930                 935                 940

Ser Pro Gly His Pro Asn Val Tyr Pro His Gly Ile Asn Cys Thr Trp
945                 950                 955                 960

His Ile Leu Val Gln Pro Asn His Leu Ile His Leu Met Phe Glu Thr
            965                 970                 975

Phe His Leu Glu Phe His Tyr Asn Cys Thr Asn Asp Tyr Leu Glu Val
            980                 985                 990

Tyr Asp Thr Asp Ser Glu Thr Ser Leu Gly Arg Tyr Cys Gly Lys Ser
            995                 1000                1005

Ile Pro Pro Ser Leu Thr Ser  Ser Gly Asn Ser Leu  Met Leu Val
    1010            1015                 1020

Phe Val Thr Asp Ser Asp Leu  Ala Tyr Glu Gly Phe  Leu Ile Asn
    1025            1030                 1035

Tyr Glu Ala Ile Ser Ala Ala  Thr Ala Cys Leu Gln  Asp Tyr Thr
    1040            1045                 1050

Asp Asp Leu Gly Thr Phe Thr  Ser Pro Asn Phe Pro  Asn Asn Tyr
    1055            1060                 1065

Pro Asn Asn Trp Glu Cys Ile  Tyr Arg Ile Thr Val  Arg Thr Gly
    1070            1075                 1080

Gln Leu Ile Ala Val His Phe  Thr Asn Phe Ser Leu  Glu Glu Ala
    1085            1090                 1095

Ile Gly Asn Tyr Tyr Thr Asp  Phe Leu Glu Ile Arg  Asp Gly Gly
    1100            1105                 1110

Tyr Glu Lys Ser Pro Leu Leu  Gly Ile Phe Tyr Gly  Ser Asn Leu
    1115            1120                 1125
```

```
Pro Pro Thr Ile Ile Ser His Ser Asn Lys Leu Trp Leu Lys Phe
    1130                1135                1140

Lys Ser Asp Gln Ile Asp Thr Arg Ser Gly Phe Ser Ala Tyr Trp
    1145                1150                1155

Asp Gly Ser Ser Thr Gly Cys Gly Gly Asn Leu Thr Thr Ser Ser
    1160                1165                1170

Gly Thr Phe Ile Ser Pro Asn Tyr Pro Met Pro Tyr Tyr His Ser
    1175                1180                1185

Ser Glu Cys Tyr Trp Trp Leu Lys Ser Ser His Gly Ser Ala Phe
    1190                1195                1200

Glu Leu Glu Phe Lys Asp Phe His Leu Glu His His Pro Asn Cys
    1205                1210                1215

Thr Leu Asp Tyr Leu Ala Val Tyr Asp Gly Pro Ser Ser Asn Ser
    1220                1225                1230

His Leu Leu Thr Gln Leu Cys Gly Asp Glu Lys Pro Pro Leu Ile
    1235                1240                1245

Arg Ser Ser Gly Asp Ser Met Phe Ile Lys Leu Arg Thr Asp Glu
    1250                1255                1260

Gly Gln Gln Gly Arg Gly Phe Lys Ala Glu Tyr Arg Gln Thr Cys
    1265                1270                1275

Glu Asn Val Val Ile Val Asn Gln Thr Tyr Gly Ile Leu Glu Ser
    1280                1285                1290

Ile Gly Tyr Pro Asn Pro Tyr Ser Glu Asn Gln His Cys Asn Trp
    1295                1300                1305

Thr Ile Arg Ala Thr Thr Gly Asn Thr Val Asn Tyr Thr Phe Leu
    1310                1315                1320

Ala Phe Asp Leu Glu His His Ile Asn Cys Ser Thr Asp Tyr Leu
    1325                1330                1335

Glu Leu Tyr Asp Gly Pro Arg Gln Met Gly Arg Tyr Cys Gly Val
    1340                1345                1350

Asp Leu Pro Pro Pro Gly Ser Thr Thr Ser Ser Lys Leu Gln Val
    1355                1360                1365

Leu Leu Leu Thr Asp Gly Val Gly Arg Arg Glu Lys Gly Phe Gln
    1370                1375                1380

Met Gln Trp Phe Val Tyr Gly Cys Gly Gly Glu Leu Ser Gly Ala
    1385                1390                1395

Thr Gly Ser Phe Ser Ser Pro Gly Phe Pro Asn Arg Tyr Pro Pro
    1400                1405                1410

Asn Lys Glu Cys Ile Trp Tyr Ile Arg Thr Asp Pro Gly Ser Ser
    1415                1420                1425

Ile Gln Leu Thr Ile His Asp Phe Asp Val Glu Tyr His Ser Arg
    1430                1435                1440

Cys Asn Phe Asp Val Leu Glu Ile Tyr Gly Gly Pro Asp Phe His
    1445                1450                1455

Ser Pro Arg Ile Ala Gln Leu Cys Thr Gln Arg Ser Pro Glu Asn
    1460                1465                1470

Pro Met Gln Val Ser Ser Thr Gly Asn Glu Leu Ala Ile Arg Phe
    1475                1480                1485

Lys Thr Asp Leu Ser Ile Asn Gly Arg Gly Phe Asn Ala Ser Trp
    1490                1495                1500

Gln Ala Val Thr Gly Gly Cys Gly Gly Ile Phe Gln Ala Pro Ser
    1505                1510                1515

Gly Glu Ile His Ser Pro Asn Tyr Pro Ser Pro Tyr Arg Ser Asn
```

-continued

```
            1520                1525                1530
Thr Asp Cys Ser Trp Val Ile Arg Val Asp Arg Asn His Arg Val
            1535                1540                1545
Leu Leu Asn Phe Thr Asp Phe Asp Leu Glu Pro Gln Asp Ser Cys
            1550                1555                1560
Ile Met Ala Tyr Asp Gly Leu Ser Ser Thr Met Ser Arg Leu Ala
            1565                1570                1575
Arg Thr Cys Gly Arg Glu Gln Leu Ala Asn Pro Ile Val Ser Ser
            1580                1585                1590
Gly Asn Ser Leu Phe Leu Arg Phe Gln Ser Gly Pro Ser Arg Gln
            1595                1600                1605
Asn Arg Gly Phe Arg Ala Gln Phe Arg Gln Ala Cys Gly Gly His
            1610                1615                1620
Ile Leu Thr Ser Ser Phe Asp Thr Val Ser Ser Pro Arg Phe Pro
            1625                1630                1635
Ala Asn Tyr Pro Asn Asn Gln Asn Cys Ser Trp Ile Ile Gln Ala
            1640                1645                1650
Gln Pro Pro Leu Asn His Ile Thr Leu Ser Phe Thr His Phe Glu
            1655                1660                1665
Leu Glu Arg Ser Thr Thr Cys Ala Arg Asp Phe Val Glu Ile Leu
            1670                1675                1680
Asp Gly Gly His Glu Asp Ala Pro Leu Arg Gly Arg Tyr Cys Gly
            1685                1690                1695
Thr Asp Met Pro His Pro Ile Thr Ser Phe Ser Ser Ala Leu Thr
            1700                1705                1710
Leu Arg Phe Val Ser Asp Ser Ser Ile Ser Ala Gly Gly Phe His
            1715                1720                1725
Thr Thr Val Thr Ala Ser Val Ser Ala Cys Gly Gly Thr Phe Tyr
            1730                1735                1740
Met Ala Glu Gly Ile Phe Asn Ser Pro Gly Tyr Pro Asp Ile Tyr
            1745                1750                1755
Pro Pro Asn Val Glu Cys Val Trp Asn Ile Val Ser Ser Pro Gly
            1760                1765                1770
Asn Arg Leu Gln Leu Ser Phe Ile Ser Phe Gln Leu Glu Asp Ser
            1775                1780                1785
Gln Asp Cys Ser Arg Asp Phe Val Glu Ile Arg Glu Gly Asn Ala
            1790                1795                1800
Thr Gly His Leu Val Gly Arg Tyr Cys Gly Asn Ser Phe Pro Leu
            1805                1810                1815
Asn Tyr Ser Ser Ile Val Gly His Thr Leu Trp Val Arg Phe Ile
            1820                1825                1830
Ser Asp Gly Ser Gly Ser Gly Thr Gly Phe Gln Ala Thr Phe Met
            1835                1840                1845
Lys Ile Phe Gly Asn Asp Asn Ile Val Gly Thr His Gly Lys Val
            1850                1855                1860
Ala Ser Pro Phe Trp Pro Glu Asn Tyr Pro His Asn Ser Asn Tyr
            1865                1870                1875
Gln Trp Thr Val Asn Val Asn Ala Ser His Val Val His Gly Arg
            1880                1885                1890
Ile Leu Glu Met Asp Ile Glu Glu Ile Gln Asn Cys Tyr Tyr Asp
            1895                1900                1905
Lys Leu Arg Ile Tyr Asp Gly Pro Ser Ile His Ala Arg Leu Ile
            1910                1915                1920
```

-continued

Gly Ala Tyr Cys Gly Thr Gln Thr Glu Ser Phe Ser Ser Thr Gly
1925                1930                1935

Asn Ser Leu Thr Phe His Phe Tyr Ser Asp Ser Ser Ile Ser Gly
1940                1945                1950

Lys Gly Phe Leu Leu Glu Trp Phe Ala Val Asp Ala Pro Asp Gly
1955                1960                1965

Val Leu Pro Thr Ile Ala Pro Gly Ala Cys Gly Gly Phe Leu Arg
1970                1975                1980

Thr Gly Asp Ala Pro Val Phe Leu Phe Ser Pro Gly Trp Pro Asp
1985                1990                1995

Ser Tyr Ser Asn Arg Val Asp Cys Thr Trp Leu Ile Gln Ala Pro
        2000                2005                2010

Asp Ser Thr Val Glu Leu Asn Ile Leu Ser Leu Asp Ile Glu Ser
        2015                2020                2025

His Arg Thr Cys Ala Tyr Asp Ser Leu Val Ile Arg Asp Gly Asp
        2030                2035                2040

Asn Asn Leu Ala Gln Gln Leu Ala Val Leu Cys Gly Arg Glu Ile
        2045                2050                2055

Pro Gly Pro Ile Arg Ser Thr Gly Glu Tyr Met Phe Ile Arg Phe
        2060                2065                2070

Thr Ser Asp Ser Ser Val Thr Arg Ala Gly Phe Asn Ala Ser Phe
        2075                2080                2085

His Lys Ser Cys Gly Gly Tyr Leu His Ala Asp Arg Gly Ile Ile
        2090                2095                2100

Thr Ser Pro Lys Tyr Pro Glu Thr Tyr Pro Ser Asn Leu Asn Cys
        2105                2110                2115

Ser Trp His Val Leu Val Gln Ser Gly Leu Thr Ile Ala Val His
        2120                2125                2130

Phe Glu Gln Pro Phe Gln Ile Pro Asn Gly Asp Ser Ser Cys Asn
        2135                2140                2145

Gln Gly Asp Tyr Leu Val Leu Arg Asn Gly Pro Asp Ile Cys Ser
        2150                2155                2160

Pro Pro Leu Gly Pro Pro Gly Gly Asn Gly His Phe Cys Gly Ser
        2165                2170                2175

His Ala Ser Ser Thr Leu Phe Thr Ser Asp Asn Gln Met Phe Val
        2180                2185                2190

Gln Phe Ile Ser Asp His Ser Asn Glu Gly Gln Gly Phe Lys Ile
        2195                2200                2205

Lys Tyr Glu Ala Lys Ser Leu Ala Cys Gly Gly Asn Val Tyr Ile
        2210                2215                2220

His Asp Ala Asp Ser Ala Gly Tyr Val Thr Ser Pro Asn His Pro
        2225                2230                2235

His Asn Tyr Pro Pro His Ala Asp Cys Ile Trp Ile Leu Ala Ala
        2240                2245                2250

Pro Pro Glu Thr Arg Ile Gln Leu Gln Phe Glu Asp Arg Phe Asp
        2255                2260                2265

Ile Glu Val Thr Pro Asn Cys Thr Ser Asn Tyr Leu Glu Leu Arg
        2270                2275                2280

Asp Gly Val Asp Ser Asp Ala Pro Ile Leu Ser Lys Phe Cys Gly
        2285                2290                2295

Thr Ser Leu Pro Ser Ser Gln Trp Ser Ser Gly Glu Val Met Tyr
        2300                2305                2310

```
Leu Arg Phe Arg Ser Asp Asn Ser Pro Thr His Val Gly Phe Lys
2315                2320                2325

Ala Lys Tyr Ser Ile Ala Gln Cys Gly Gly Arg Val Pro Gly Gln
2330                2335                2340

Ser Gly Val Val Glu Ser Ile Gly His Pro Thr Leu Pro Tyr Arg
2345                2350                2355

Asp Asn Leu Phe Cys Glu Trp His Leu Gln Gly Leu Ser Gly His
2360                2365                2370

Tyr Leu Thr Ile Ser Phe Glu Asp Phe Asn Leu Gln Asn Ser Ser
2375                2380                2385

Gly Cys Glu Lys Asp Phe Val Glu Ile Trp Asp Asn His Thr Ser
2390                2395                2400

Gly Asn Ile Leu Gly Arg Tyr Cys Gly Asn Thr Ile Pro Asp Ser
2405                2410                2415

Ile Asp Thr Ser Ser Asn Thr Ala Val Val Arg Phe Val Thr Asp
2420                2425                2430

Gly Ser Val Thr Ala Ser Gly Phe Arg Leu Arg Phe Glu Ser Ser
2435                2440                2445

Met Glu Glu Cys Gly Gly Asp Leu Gln Gly Ser Ile Gly Thr Phe
2450                2455                2460

Thr Ser Pro Asn Tyr Pro Asn Pro Asn Pro His Gly Arg Ile Cys
2465                2470                2475

Glu Trp Arg Ile Thr Ala Pro Glu Gly Arg Arg Ile Thr Leu Met
2480                2485                2490

Phe Asn Asn Leu Arg Leu Ala Thr His Pro Ser Cys Asn Asn Glu
2495                2500                2505

His Val Ile Val Phe Asn Gly Ile Arg Ser Asn Ser Pro Gln Leu
2510                2515                2520

Glu Lys Leu Cys Ser Ser Val Asn Val Ser Asn Glu Ile Lys Ser
2525                2530                2535

Ser Gly Asn Thr Met Lys Val Ile Phe Phe Thr Asp Gly Ser Arg
2540                2545                2550

Pro Tyr Gly Gly Phe Thr Ala Ser Tyr Thr Ser Ser Glu Asp Ala
2555                2560                2565

Val Cys Gly Gly Ser Leu Pro Asn Thr Pro Glu Gly Asn Phe Thr
2570                2575                2580

Ser Pro Gly Tyr Asp Gly Val Arg Asn Tyr Ser Arg Asn Leu Asn
2585                2590                2595

Cys Glu Trp Thr Leu Ser Asn Pro Asn Gln Gly Asn Ser Ser Ile
2600                2605                2610

Ser Ile His Phe Glu Asp Phe Tyr Leu Glu Ser His Gln Asp Cys
2615                2620                2625

Gln Phe Asp Val Leu Glu Phe Arg Val Gly Asp Ala Asp Gly Pro
2630                2635                2640

Leu Met Trp Arg Leu Cys Gly Pro Ser Lys Pro Thr Leu Pro Leu
2645                2650                2655

Val Ile Pro Tyr Ser Gln Val Trp Ile His Phe Val Thr Asn Glu
2660                2665                2670

Arg Val Glu His Ile Gly Phe His Ala Lys Tyr Ser Phe Thr Asp
2675                2680                2685

Cys Gly Gly Ile Gln Ile Gly Asp Ser Gly Val Ile Thr Ser Pro
2690                2695                2700

Asn Tyr Pro Asn Ala Tyr Asp Ser Leu Thr His Cys Ser Ser Leu
```

```
                    2705                2710                2715
Leu Glu Ala Pro Gln Gly His Thr Ile Thr Leu Thr Phe Ser Asp
        2720                2725                2730
Phe Asp Ile Glu Pro His Thr Thr Cys Ala Trp Asp Ser Val Thr
        2735                2740                2745
Val Arg Asn Gly Gly Ser Pro Glu Ser Pro Ile Ile Gly Gln Tyr
        2750                2755                2760
Cys Gly Asn Ser Asn Pro Arg Thr Ile Gln Ser Gly Ser Asn Gln
        2765                2770                2775
Leu Val Val Thr Phe Asn Ser Asp His Ser Leu Gln Gly Gly Gly
        2780                2785                2790
Phe Tyr Ala Thr Trp Asn Thr Gln Thr Leu Gly Cys Gly Gly Ile
        2795                2800                2805
Phe His Ser Asp Asn Gly Thr Ile Arg Ser Pro His Trp Pro Gln
        2810                2815                2820
Asn Phe Pro Glu Asn Ser Arg Cys Ser Trp Thr Ala Ile Thr His
        2825                2830                2835
Lys Ser Lys His Leu Glu Ile Ser Phe Asp Asn Asn Phe Leu Ile
        2840                2845                2850
Pro Ser Gly Asp Gly Gln Cys Gln Asn Ser Phe Val Lys Val Trp
        2855                2860                2865
Ala Gly Thr Glu Glu Val Asp Lys Ala Leu Leu Ala Thr Gly Cys
        2870                2875                2880
Gly Asn Val Ala Pro Gly Pro Val Ile Thr Pro Ser Asn Thr Phe
        2885                2890                2895
Thr Ala Val Phe Gln Ser Gln Glu Ala Pro Ala Gln Gly Phe Ser
        2900                2905                2910
Ala Ser Phe Val Ser Arg Cys Gly Ser Asn Phe Thr Gly Pro Ser
        2915                2920                2925
Gly Tyr Ile Ile Ser Pro Asn Tyr Pro Lys Gln Tyr Asp Asn Asn
        2930                2935                2940
Met Asn Cys Thr Tyr Val Ile Glu Ala Asn Pro Leu Ser Val Val
        2945                2950                2955
Leu Leu Thr Phe Val Ser Phe His Leu Glu Ala Arg Ser Ala Val
        2960                2965                2970
Thr Gly Ser Cys Val Asn Asp Gly Val His Ile Ile Arg Gly Tyr
        2975                2980                2985
Ser Val Met Ser Thr Pro Phe Ala Thr Val Cys Gly Asp Glu Met
        2990                2995                3000
Pro Ala Pro Leu Thr Ile Ala Gly Pro Val Leu Leu Asn Phe Tyr
        3005                3010                3015
Ser Asn Glu Gln Ile Thr Asp Phe Gly Phe Lys Phe Ser Tyr Arg
        3020                3025                3030
Ile Ile Ser Cys Gly Gly Val Phe Asn Phe Ser Ser Gly Ile Ile
        3035                3040                3045
Thr Ser Pro Ala Tyr Ser Tyr Ala Asp Tyr Pro Asn Asp Met His
        3050                3055                3060
Cys Leu Tyr Thr Ile Thr Val Ser Asp Asp Lys Val Ile Glu Leu
        3065                3070                3075
Lys Phe Ser Asp Phe Asp Val Pro Ser Thr Ser Cys Ser His
        3080                3085                3090
Asp Tyr Leu Ala Ile Tyr Asp Gly Ala Asn Thr Ser Asp Pro Leu
        3095                3100                3105
```

```
Leu Gly Lys Phe Cys Gly Ser Lys Arg Pro Pro Asn Val Lys Ser
    3110            3115            3120

Ser Asn Asn Ser Met Leu Leu Val Phe Lys Thr Asp Ser Phe Gln
    3125            3130            3135

Thr Ala Lys Gly Trp Lys Met Ser Phe Arg Gln Thr Leu Gly Pro
    3140            3145            3150

Gln Gln Gly Cys Gly Gly Tyr Leu Thr Gly Ser Asn Asn Thr Phe
    3155            3160            3165

Ala Ser Pro Asp Ser Asp Ser Asn Gly Met Tyr Asp Lys Asn Leu
    3170            3175            3180

Asn Cys Val Trp Ile Ile Ile Ala Pro Val Asn Lys Val Ile His
    3185            3190            3195

Leu Thr Phe Asn Thr Phe Ala Leu Glu Ala Ala Ser Thr Arg Gln
    3200            3205            3210

Arg Cys Leu Tyr Asp Tyr Val Lys Leu Tyr Asp Gly Asp Ser Glu
    3215            3220            3225

Asn Ala Asn Leu Ala Gly Thr Phe Cys Gly Ser Thr Val Pro Ala
    3230            3235            3240

Pro Phe Ile Ser Ser Gly Asn Phe Leu Thr Val Gln Phe Ile Ser
    3245            3250            3255

Asp Leu Thr Leu Glu Arg Glu Gly Phe Asn Ala Thr Tyr Thr Ile
    3260            3265            3270

Met Asp Met Pro Cys Gly Gly Thr Tyr Asn Ala Thr Trp Thr Pro
    3275            3280            3285

Gln Asn Ile Ser Ser Pro Asn Ser Ser Asp Pro Asp Val Pro Phe
    3290            3295            3300

Ser Ile Cys Thr Trp Val Ile Asp Ser Pro Pro His Gln Gln Val
    3305            3310            3315

Lys Ile Thr Val Trp Ala Leu Gln Leu Thr Ser Gln Asp Cys Thr
    3320            3325            3330

Gln Asn Tyr Leu Gln Leu Gln Asp Ser Pro Gln Gly His Gly Asn
    3335            3340            3345

Ser Arg Phe Gln Phe Cys Gly Arg Asn Ala Ser Ala Val Pro Val
    3350            3355            3360

Phe Tyr Ser Ser Met Ser Thr Ala Met Val Ile Phe Lys Ser Gly
    3365            3370            3375

Val Val Asn Arg Asn Ser Arg Met Ser Phe Thr Tyr Gln Ile Ala
    3380            3385            3390

Asp Cys Asn Arg Asp Tyr His Lys Ala Phe Gly Asn Leu Arg Ser
    3395            3400            3405

Pro Gly Trp Pro Asp Asn Tyr Asp Asn Asp Lys Asp Cys Thr Val
    3410            3415            3420

Thr Leu Thr Ala Pro Gln Asn His Thr Ile Ser Leu Phe Phe His
    3425            3430            3435

Ser Leu Gly Ile Glu Asn Ser Val Glu Cys Arg Asn Asp Phe Leu
    3440            3445            3450

Glu Val Arg Asn Gly Ser Asn Ser Asn Ser Pro Leu Leu Gly Lys
    3455            3460            3465

Tyr Cys Gly Thr Leu Leu Pro Asn Pro Val Phe Ser Gln Asn Asn
    3470            3475            3480

Glu Leu Tyr Leu Arg Phe Lys Ser Asp Ser Val Thr Ser Asp Arg
    3485            3490            3495
```

```
Gly Tyr Glu Ile Ile Trp Thr Ser Ser Pro Ser Gly Cys Gly Gly
    3500                3505                3510

Thr Leu Tyr Gly Asp Arg Gly Ser Phe Thr Ser Pro Gly Tyr Pro
    3515                3520                3525

Gly Thr Tyr Pro Asn Asn Thr Tyr Cys Glu Trp Val Leu Val Ala
    3530                3535                3540

Pro Ala Gly Arg Leu Val Thr Ile Asn Phe Tyr Phe Ile Ser Ile
    3545                3550                3555

Asp Asp Pro Gly Asp Cys Val Gln Asn Tyr Leu Thr Leu Tyr Asp
    3560                3565                3570

Gly Pro Asn Ala Ser Ser Pro Ser Ser Gly Pro Tyr Cys Gly Gly
    3575                3580                3585

Asp Thr Ser Ile Ala Pro Phe Val Ala Ser Ser Asn Gln Val Phe
    3590                3595                3600

Ile Lys Phe His Ala Asp Tyr Ala Arg Arg Pro Ser Ala Phe Arg
    3605                3610                3615

Leu Thr Trp Asp Ser
    3620

<210> SEQ ID NO 62
<211> LENGTH: 178
<212> TYPE: PRT
<213> ORGANISM: Homo sapiens

<400> SEQUENCE: 62

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 63
<211> LENGTH: 11
<212> TYPE: PRT
<213> ORGANISM: Artificial Sequence
<220> FEATURE:
<223> OTHER INFORMATION: Linker

<400> SEQUENCE: 63
```

```
Gly Gly Ser Gly Gly Gly Ser Gly Gly Ser Gly
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Linker

<400> SEQUENCE: 64

Gly Gly Ser Gly Gly Gly Ser Gly Ser Gly
1               5                   10

<210> SEQ ID NO 65
<211> LENGTH: 8
<212> TYPE: PRT
<213> ORGANISM: Artificial Sequence
<220> FEATURE:
<223> OTHER INFORMATION: Linker

<400> SEQUENCE: 65

Gly Gly Ser Gly Gly Gly Ser Gly
1               5

<210> SEQ ID NO 66
<211> LENGTH: 6
<212> TYPE: PRT
<213> ORGANISM: Artificial Sequence
<220> FEATURE:
<223> OTHER INFORMATION: Linker

<400> SEQUENCE: 66

Gly Gly Ser Gly Gly Ser
1               5

<210> SEQ ID NO 67
<211> LENGTH: 4
<212> TYPE: PRT
<213> ORGANISM: Artificial Sequence
<220> FEATURE:
<223> OTHER INFORMATION: Linker

<400> SEQUENCE: 67

Leu Pro His Asp
1

<210> SEQ ID NO 68
<211> LENGTH: 4
<212> TYPE: PRT
<213> ORGANISM: Artificial Sequence
<220> FEATURE:
<223> OTHER INFORMATION: Linker

<400> SEQUENCE: 68

Asn Pro Asn Asp
1

<210> SEQ ID NO 69
<211> LENGTH: 4
<212> TYPE: PRT
<213> ORGANISM: Artificial Sequence
<220> FEATURE:
<223> OTHER INFORMATION: Linker

<400> SEQUENCE: 69
```

Asp Pro Lys Asp
1

<210> SEQ ID NO 70
<211> LENGTH: 5
<212> TYPE: PRT
<213> ORGANISM: Artificial Sequence
<220> FEATURE:
<223> OTHER INFORMATION: Linker

<400> SEQUENCE: 70

Gly Leu Glu Pro Asp
1               5

<210> SEQ ID NO 71
<211> LENGTH: 5
<212> TYPE: PRT
<213> ORGANISM: Artificial Sequence
<220> FEATURE:
<223> OTHER INFORMATION: Linker

<400> SEQUENCE: 71

Gly Val Ser Leu Asp
1               5

<210> SEQ ID NO 72
<211> LENGTH: 5
<212> TYPE: PRT
<213> ORGANISM: Artificial Sequence
<220> FEATURE:
<223> OTHER INFORMATION: Linker

<400> SEQUENCE: 72

Gly Val Leu Pro Asp
1               5

<210> SEQ ID NO 73
<211> LENGTH: 107
<212> TYPE: PRT
<213> ORGANISM: Artificial Sequence
<220> FEATURE:
<223> OTHER INFORMATION: variable light chain of huOKT3

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105

<210> SEQ ID NO 74
<211> LENGTH: 119
<212> TYPE: PRT
<213> ORGANISM: Artificial Sequence
<220> FEATURE:

<223> OTHER INFORMATION: variable heavy chain of huOKT3

<400> SEQUENCE: 74

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser
        115

<210> SEQ ID NO 75
<211> LENGTH: 10
<212> TYPE: PRT
<213> ORGANISM: Artificial Sequence
<220> FEATURE:
<223> OTHER INFORMATION: CDRH1 of huOKT3

<400> SEQUENCE: 75

Gly Tyr Thr Phe Thr Arg Tyr Thr Met His
1               5                   10

<210> SEQ ID NO 76
<211> LENGTH: 16
<212> TYPE: PRT
<213> ORGANISM: Artificial Sequence
<220> FEATURE:
<223> OTHER INFORMATION: CDRH2 of huOKT3

<400> SEQUENCE: 76

Ile Asn Pro Ser Arg Gly Tyr Thr Asn Tyr Asn Gln Lys Phe Lys Asp
1               5                   10                  15

<210> SEQ ID NO 77
<211> LENGTH: 10
<212> TYPE: PRT
<213> ORGANISM: Artificial Sequence
<220> FEATURE:
<223> OTHER INFORMATION: CDRH3 of huOKT3

<400> SEQUENCE: 77

Tyr Tyr Asp Asp His Tyr Ser Leu Asp Tyr
1               5                   10

<210> SEQ ID NO 78
<211> LENGTH: 10
<212> TYPE: PRT
<213> ORGANISM: Artificial Sequence
<220> FEATURE:
<223> OTHER INFORMATION: CDRL1 of huOKT3

<400> SEQUENCE: 78

Ser Ala Ser Ser Ser Val Ser Tyr Met Asn
1               5                   10

<210> SEQ ID NO 79
<211> LENGTH: 7
<212> TYPE: PRT
<213> ORGANISM: Artificial Sequence
<220> FEATURE:
<223> OTHER INFORMATION: CDRL2 of huOKT3

<400> SEQUENCE: 79

Asp Thr Ser Lys Leu Ala Ser
1               5

<210> SEQ ID NO 80
<211> LENGTH: 9
<212> TYPE: PRT
<213> ORGANISM: Artificial Sequence
<220> FEATURE:
<223> OTHER INFORMATION: CDRL3 of huOKT3

<400> SEQUENCE: 80

Gln Gln Trp Ser Ser Asn Pro Phe Thr
1               5

<210> SEQ ID NO 81
<211> LENGTH: 13
<212> TYPE: PRT
<213> ORGANISM: Artificial Sequence
<220> FEATURE:
<223> OTHER INFORMATION: CDRH1 of OKT3

<400> SEQUENCE: 81

Lys Ala Ser Gly Tyr Thr Phe Thr Arg Tyr Thr Met His
1               5                   10

<210> SEQ ID NO 82
<211> LENGTH: 10
<212> TYPE: PRT
<213> ORGANISM: Artificial Sequence
<220> FEATURE:
<223> OTHER INFORMATION: CDRH3 of OKT3

<400> SEQUENCE: 82

Tyr Tyr Asp Asp His Tyr Cys Leu Asp Tyr
1               5                   10

<210> SEQ ID NO 83
<211> LENGTH: 11
<212> TYPE: PRT
<213> ORGANISM: Artificial Sequence
<220> FEATURE:
<223> OTHER INFORMATION: CDRL2 of OKT3

<400> SEQUENCE: 83

Arg Trp Ile Tyr Asp Thr Ser Lys Leu Ala Ser
1               5                   10

<210> SEQ ID NO 84
<211> LENGTH: 242
<212> TYPE: PRT
<213> ORGANISM: Artificial Sequence
<220> FEATURE:
<223> OTHER INFORMATION: scFv derived from OKT3

<400> SEQUENCE: 84

Gln Val Gln Leu Gln Gln Ser Gly Ala Glu Leu Ala Arg Pro Gly Ala
1               5                   10                  15

-continued

```
Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly
        115                 120                 125

Gly Ser Gly Gly Gly Gly Ser Gln Ile Val Leu Thr Gln Ser Pro Ala
130                 135                 140

Ile Met Ser Ala Ser Pro Gly Glu Lys Val Thr Met Thr Cys Ser Ala
145                 150                 155                 160

Ser Ser Ser Val Ser Tyr Met Asn Trp Tyr Gln Gln Lys Ser Gly Thr
                165                 170                 175

Ser Pro Lys Arg Trp Ile Tyr Asp Thr Ser Lys Leu Ala Ser Gly Val
            180                 185                 190

Pro Ala His Phe Arg Gly Ser Gly Ser Gly Thr Ser Tyr Ser Leu Thr
        195                 200                 205

Ile Ser Gly Met Glu Ala Glu Asp Ala Ala Thr Tyr Tyr Cys Gln Gln
210                 215                 220

Trp Ser Ser Asn Pro Phe Thr Phe Gly Ser Gly Thr Lys Leu Glu Ile
225                 230                 235                 240

Asn Arg

<210> SEQ ID NO 85
<211> LENGTH: 11
<212> TYPE: PRT
<213> ORGANISM: Artificial Sequence
<220> FEATURE:
<223> OTHER INFORMATION: CDRL1 of 20G6-F3

<400> SEQUENCE: 85

Gln Ser Leu Val His Asn Asn Gly Asn Thr Tyr
1               5                   10

<210> SEQ ID NO 86
<211> LENGTH: 9
<212> TYPE: PRT
<213> ORGANISM: Artificial Sequence
<220> FEATURE:
<223> OTHER INFORMATION: CDRL3 of 20G6-F3

<400> SEQUENCE: 86

Gly Gln Gly Thr Gln Tyr Pro Phe Thr
1               5

<210> SEQ ID NO 87
<211> LENGTH: 8
<212> TYPE: PRT
<213> ORGANISM: Artificial Sequence
<220> FEATURE:
<223> OTHER INFORMATION: CDRH1 of 20G6-F3

<400> SEQUENCE: 87
```

```
Gly Phe Thr Phe Thr Lys Ala Trp
1               5
```

<210> SEQ ID NO 88
<211> LENGTH: 10
<212> TYPE: PRT
<213> ORGANISM: Artificial Sequence
<220> FEATURE:
<223> OTHER INFORMATION: CDRH2 of 20G6-F3

<400> SEQUENCE: 88

```
Ile Lys Asp Lys Ser Asn Ser Tyr Ala Thr
1               5                   10
```

<210> SEQ ID NO 89
<211> LENGTH: 12
<212> TYPE: PRT
<213> ORGANISM: Artificial Sequence
<220> FEATURE:
<223> OTHER INFORMATION: CDRH3 of 20G6-F3

<400> SEQUENCE: 89

```
Arg Gly Val Tyr Tyr Ala Leu Ser Pro Phe Asp Tyr
1               5                   10
```

<210> SEQ ID NO 90
<211> LENGTH: 11
<212> TYPE: PRT
<213> ORGANISM: Artificial Sequence
<220> FEATURE:
<223> OTHER INFORMATION: CDRL1 of 4B4-D7

<400> SEQUENCE: 90

```
Gln Ser Leu Val His Asp Asn Gly Asn Thr Tyr
1               5                   10
```

<210> SEQ ID NO 91
<211> LENGTH: 8
<212> TYPE: PRT
<213> ORGANISM: Artificial Sequence
<220> FEATURE:
<223> OTHER INFORMATION: CDRH1 of 4B4-D7

<400> SEQUENCE: 91

```
Gly Phe Thr Phe Ser Asn Ala Trp
1               5
```

<210> SEQ ID NO 92
<211> LENGTH: 10
<212> TYPE: PRT
<213> ORGANISM: Artificial Sequence
<220> FEATURE:
<223> OTHER INFORMATION: CDRH2 of 4B4-D7

<400> SEQUENCE: 92

```
Ile Lys Ala Arg Ser Asn Asn Tyr Ala Thr
1               5                   10
```

<210> SEQ ID NO 93
<211> LENGTH: 12
<212> TYPE: PRT
<213> ORGANISM: Artificial Sequence
<220> FEATURE:
<223> OTHER INFORMATION: CDRH3 of 4B4-D7

<400> SEQUENCE: 93

```
Arg Gly Thr Tyr Tyr Ala Ser Lys Pro Phe Asp Tyr
1               5                   10

<210> SEQ ID NO 94
<211> LENGTH: 11
<212> TYPE: PRT
<213> ORGANISM: Artificial Sequence
<220> FEATURE:
<223> OTHER INFORMATION: CDRL1 of 4E7-C9

<400> SEQUENCE: 94

Gln Ser Leu Glu His Asn Asn Gly Asn Thr Tyr
1               5                   10

<210> SEQ ID NO 95
<211> LENGTH: 10
<212> TYPE: PRT
<213> ORGANISM: Artificial Sequence
<220> FEATURE:
<223> OTHER INFORMATION: CDRH2 of 4E7-C9

<400> SEQUENCE: 95

Ile Lys Asp Lys Ser Asn Asn Tyr Ala Thr
1               5                   10

<210> SEQ ID NO 96
<211> LENGTH: 13
<212> TYPE: PRT
<213> ORGANISM: Artificial Sequence
<220> FEATURE:
<223> OTHER INFORMATION: CDRH3 of 4E7-C9

<400> SEQUENCE: 96

Arg Tyr Val His Tyr Gly Ile Gly Tyr Ala Met Asp Ala
1               5                   10

<210> SEQ ID NO 97
<211> LENGTH: 11
<212> TYPE: PRT
<213> ORGANISM: Artificial Sequence
<220> FEATURE:
<223> OTHER INFORMATION: CDRL1 of 18F5-H10

<400> SEQUENCE: 97

Gln Ser Leu Val His Thr Asn Gly Asn Thr Tyr
1               5                   10

<210> SEQ ID NO 98
<211> LENGTH: 9
<212> TYPE: PRT
<213> ORGANISM: Artificial Sequence
<220> FEATURE:
<223> OTHER INFORMATION: CDRL3 of 18F5-H10

<400> SEQUENCE: 98

Gly Gln Gly Thr His Tyr Pro Phe Thr
1               5

<210> SEQ ID NO 99
<211> LENGTH: 8
<212> TYPE: PRT
<213> ORGANISM: Artificial Sequence
<220> FEATURE:
<223> OTHER INFORMATION: CDRH1 of 18F5-H10

<400> SEQUENCE: 99

Gly Phe Thr Phe Thr Asn Ala Trp
```

```
<210> SEQ ID NO 100
<211> LENGTH: 9
<212> TYPE: PRT
<213> ORGANISM: Artificial Sequence
<220> FEATURE:
<223> OTHER INFORMATION: CDRH2 of 18F5-H10

<400> SEQUENCE: 100

Lys Asp Lys Ser Asn Asn Tyr Ala Thr
1               5

<210> SEQ ID NO 101
<211> LENGTH: 13
<212> TYPE: PRT
<213> ORGANISM: Artificial Sequence
<220> FEATURE:
<223> OTHER INFORMATION: CDRH3 of 18F5-H10

<400> SEQUENCE: 101

Arg Tyr Val His Tyr Arg Phe Ala Tyr Ala Leu Asp Ala
1               5                   10

<210> SEQ ID NO 102
<211> LENGTH: 120
<212> TYPE: PRT
<213> ORGANISM: Artificial Sequence
<220> FEATURE:
<223> OTHER INFORMATION: variable heavy chain of TGN1412

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser
        115                 120

<210> SEQ ID NO 103
<211> LENGTH: 107
<212> TYPE: PRT
<213> ORGANISM: Artificial Sequence
<220> FEATURE:
<223> OTHER INFORMATION: variable light chain of TGN1412

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
```

```
                35                  40                  45
Tyr Lys Ala Ser Asn Leu His Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gln Thr Tyr Pro Tyr
                 85                  90                  95

Thr Phe Gly Gly Gly Thr Lys Val Glu Ile Lys
            100                 105

<210> SEQ ID NO 104
<211> LENGTH: 11
<212> TYPE: PRT
<213> ORGANISM: Artificial Sequence
<220> FEATURE:
<223> OTHER INFORMATION: CDRL1 of TGN1412

<400> SEQUENCE: 104

His Ala Ser Gln Asn Ile Tyr Val Trp Leu Asn
 1               5                   10

<210> SEQ ID NO 105
<211> LENGTH: 7
<212> TYPE: PRT
<213> ORGANISM: Artificial Sequence
<220> FEATURE:
<223> OTHER INFORMATION: CDRL2 of TGN1412

<400> SEQUENCE: 105

Lys Ala Ser Asn Leu His Thr
 1               5

<210> SEQ ID NO 106
<211> LENGTH: 9
<212> TYPE: PRT
<213> ORGANISM: Artificial Sequence
<220> FEATURE:
<223> OTHER INFORMATION: CDRL3 of TGN1412

<400> SEQUENCE: 106

Gln Gln Gly Gln Thr Tyr Pro Tyr Thr
 1               5

<210> SEQ ID NO 107
<211> LENGTH: 10
<212> TYPE: PRT
<213> ORGANISM: Artificial Sequence
<220> FEATURE:
<223> OTHER INFORMATION: CDRH1 of TGN1412

<400> SEQUENCE: 107

Gly Tyr Thr Phe Thr Ser Tyr Tyr Ile His
 1               5                   10

<210> SEQ ID NO 108
<211> LENGTH: 5
<212> TYPE: PRT
<213> ORGANISM: Artificial Sequence
<220> FEATURE:
<223> OTHER INFORMATION: CDRH1 of TGN1412

<400> SEQUENCE: 108

Ser Tyr Tyr Ile His
 1               5
```

<210> SEQ ID NO 109
<211> LENGTH: 14
<212> TYPE: PRT
<213> ORGANISM: Artificial Sequence
<220> FEATURE:
<223> OTHER INFORMATION: CDRH2 of TGN1412

<400> SEQUENCE: 109

Cys Ile Tyr Pro Gly Asn Val Asn Thr Asn Tyr Asn Glu Lys
1               5                   10

<210> SEQ ID NO 110
<211> LENGTH: 11
<212> TYPE: PRT
<213> ORGANISM: Artificial Sequence
<220> FEATURE:
<223> OTHER INFORMATION: CDRH3 of TGN1412

<400> SEQUENCE: 110

Ser His Tyr Gly Leu Asp Trp Asn Phe Asp Val
1               5                   10

<210> SEQ ID NO 111
<211> LENGTH: 12
<212> TYPE: PRT
<213> ORGANISM: Artificial Sequence
<220> FEATURE:
<223> OTHER INFORMATION: CDRL1 of CD80/CD86 binding domain

<400> SEQUENCE: 111

Ser Val Ser Ser Ser Ile Ser Ser Ser Asn Leu His
1               5                   10

<210> SEQ ID NO 112
<211> LENGTH: 7
<212> TYPE: PRT
<213> ORGANISM: Artificial Sequence
<220> FEATURE:
<223> OTHER INFORMATION: CDRL2 of CD80/CD86 binding domain

<400> SEQUENCE: 112

Gly Thr Ser Asn Leu Ala Ser
1 5

<210> SEQ ID NO 113
<211> LENGTH: 9
<212> TYPE: PRT
<213> ORGANISM: Artificial Sequence
<220> FEATURE:
<223> OTHER INFORMATION: CDRL3 of CD80/CD86 binding domain

<400> SEQUENCE: 113

Gln Gln Trp Ser Ser Tyr Pro Leu Thr
1 5

<210> SEQ ID NO 114
<211> LENGTH: 5
<212> TYPE: PRT
<213> ORGANISM: Artificial Sequence
<220> FEATURE:
<223> OTHER INFORMATION: CDRH1 of CD80/CD86 binding domain

<400> SEQUENCE: 114

Asp Tyr Tyr Met His
1 5

-continued

<210> SEQ ID NO 115
<211> LENGTH: 17
<212> TYPE: PRT
<213> ORGANISM: Artificial Sequence
<220> FEATURE:
<223> OTHER INFORMATION: CDRH2 of CD80/CD86 binding domain

<400> SEQUENCE: 115

Trp Ile Asp Pro Glu Asn Gly Asn Thr Leu Tyr Asp Pro Lys Phe Gln
1 5 10 15

Gly

<210> SEQ ID NO 116
<211> LENGTH: 7
<212> TYPE: PRT
<213> ORGANISM: Artificial Sequence
<220> FEATURE:
<223> OTHER INFORMATION: CDRH3 of CD80/CD86 binding domain

<400> SEQUENCE: 116

Glu Gly Leu Phe Phe Ala Tyr
1 5

<210> SEQ ID NO 117
<211> LENGTH: 7
<212> TYPE: PRT
<213> ORGANISM: Artificial Sequence
<220> FEATURE:
<223> OTHER INFORMATION: CDRL1 of 4-1BB binding domain

<400> SEQUENCE: 117

Arg Ala Ser Gln Ser Val Ser
1 5

<210> SEQ ID NO 118
<211> LENGTH: 6
<212> TYPE: PRT
<213> ORGANISM: Artificial Sequence
<220> FEATURE:
<223> OTHER INFORMATION: CDRL2 of 4-1BB binding domain

<400> SEQUENCE: 118

Ala Ser Asn Arg Ala Thr
1 5

<210> SEQ ID NO 119
<211> LENGTH: 10
<212> TYPE: PRT
<213> ORGANISM: Artificial Sequence
<220> FEATURE:
<223> OTHER INFORMATION: CDRL3 of 4-1BB binding domain

<400> SEQUENCE: 119

Gln Arg Ser Asn Trp Pro Pro Ala Leu Thr
1 5 10

<210> SEQ ID NO 120
<211> LENGTH: 4
<212> TYPE: PRT
<213> ORGANISM: Artificial Sequence
<220> FEATURE:
<223> OTHER INFORMATION: CDRH1 of 4-1BB binding domain

<400> SEQUENCE: 120

Tyr Tyr Trp Ser
1

```
<210> SEQ ID NO 121
<211> LENGTH: 12
<212> TYPE: PRT
<213> ORGANISM: Artificial Sequence
<220> FEATURE:
<223> OTHER INFORMATION: CDRH3 of 4-1BB binding domain

<400> SEQUENCE: 121

Tyr Gly Pro Gly Asn Tyr Asp Trp Tyr Phe Asp Leu
1               5                   10

<210> SEQ ID NO 122
<211> LENGTH: 11
<212> TYPE: PRT
<213> ORGANISM: Artificial Sequence
<220> FEATURE:
<223> OTHER INFORMATION: CDRL1 of 4-1BB binding domain

<400> SEQUENCE: 122

Ser Gly Asp Asn Ile Gly Asp Gln Tyr Ala His
1               5                   10

<210> SEQ ID NO 123
<211> LENGTH: 7
<212> TYPE: PRT
<213> ORGANISM: Artificial Sequence
<220> FEATURE:
<223> OTHER INFORMATION: CDRL2 of 4-1BB binding domain

<400> SEQUENCE: 123

Gln Asp Lys Asn Arg Pro Ser
1               5

<210> SEQ ID NO 124
<211> LENGTH: 11
<212> TYPE: PRT
<213> ORGANISM: Artificial Sequence
<220> FEATURE:
<223> OTHER INFORMATION: CDRL3 of 4-1BB binding domain

<400> SEQUENCE: 124

Ala Thr Tyr Thr Gly Phe Gly Ser Leu Ala Val
1               5                   10

<210> SEQ ID NO 125
<211> LENGTH: 10
<212> TYPE: PRT
<213> ORGANISM: Artificial Sequence
<220> FEATURE:
<223> OTHER INFORMATION: CDRH1 of 4-1BB binding domain

<400> SEQUENCE: 125

Gly Tyr Ser Phe Ser Thr Tyr Trp Ile Ser
1               5                   10

<210> SEQ ID NO 126
<211> LENGTH: 14
<212> TYPE: PRT
<213> ORGANISM: Artificial Sequence
<220> FEATURE:
<223> OTHER INFORMATION: CDRH2 of 4-1BB binding domain

<400> SEQUENCE: 126

Lys Ile Tyr Pro Gly Asp Ser Tyr Thr Asn Tyr Ser Pro Ser
1               5                   10
```

```
<210> SEQ ID NO 127
<211> LENGTH: 7
<212> TYPE: PRT
<213> ORGANISM: Artificial Sequence
<220> FEATURE:
<223> OTHER INFORMATION: CDRH3 of 4-1BB binding domain

<400> SEQUENCE: 127

Gly Tyr Gly Ile Phe Asp Tyr
1               5

<210> SEQ ID NO 128
<211> LENGTH: 50
<212> TYPE: PRT
<213> ORGANISM: Artificial Sequence
<220> FEATURE:
<223> OTHER INFORMATION: Linker

<400> SEQUENCE: 128

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser
    50

<210> SEQ ID NO 129
<211> LENGTH: 90
<212> TYPE: PRT
<213> ORGANISM: Artificial Sequence
<220> FEATURE:
<223> OTHER INFORMATION: Linker

<400> SEQUENCE: 129

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly Ser Gly Gly Gly Ser Gly Gly Gly Ser Gly Gly Gly Gly
            35                  40                  45

Gly Ser Gly Gly Gly Gly Ser Gly Gly Gly Gly Ser Gly Gly Gly Gly
        50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser
                85                  90

<210> SEQ ID NO 130
<211> LENGTH: 70
<212> TYPE: PRT
<213> ORGANISM: Artificial Sequence
<220> FEATURE:
<223> OTHER INFORMATION: Linker

<400> SEQUENCE: 130

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly Ser Gly Gly Gly Ser Gly Gly Ser Gly Gly Ser Gly Gly
```

```
                35                  40                  45
Ser Gly Gly Ser Gly Gly Ser Gly Gly Ser Gly Gly Ser
         50                  55                  60

Gly Gly Ser Gly Gly Ser
 65                  70
```

<210> SEQ ID NO 131
<211> LENGTH: 45
<212> TYPE: PRT
<213> ORGANISM: Artificial Sequence
<220> FEATURE:
<223> OTHER INFORMATION: Linker

<400> SEQUENCE: 131

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly Ser Gly Gly Gly Ser Gly Gly Gly Ser
         35                  40                  45
```

<210> SEQ ID NO 132
<211> LENGTH: 20
<212> TYPE: PRT
<213> ORGANISM: Artificial Sequence
<220> FEATURE:
<223> OTHER INFORMATION: Linker

<400> SEQUENCE: 132

```
Gly Gly Gly Gly Ser Gly Gly Gly Gly Ser Gly Gly Gly Gly Ser Gly
1               5                   10                  15

Gly Gly Gly Ser
         20
```

<210> SEQ ID NO 133
<211> LENGTH: 15
<212> TYPE: PRT
<213> ORGANISM: Artificial Sequence
<220> FEATURE:
<223> OTHER INFORMATION: Linker

<400> SEQUENCE: 133

```
Gly Gly Gly Gly Ser Gly Gly Gly Gly Ser Gly Gly Gly Gly Ser
1               5                   10                  15
```

<210> SEQ ID NO 134
<211> LENGTH: 32
<212> TYPE: PRT
<213> ORGANISM: Artificial Sequence
<220> FEATURE:
<223> OTHER INFORMATION: Nef (66-97)

<400> SEQUENCE: 134

```
Val Gly Phe Pro Val Thr Pro Gln Val Pro Leu Arg Pro Met Thr Tyr
1               5                   10                  15

Lys Ala Ala Val Asp Leu Ser His Phe Leu Lys Glu Lys Gly Gly Leu
                20                  25                  30
```

<210> SEQ ID NO 135
<211> LENGTH: 30
<212> TYPE: PRT
<213> ORGANISM: Artificial Sequence
<220> FEATURE:
<223> OTHER INFORMATION: Nef (116-145)

<400> SEQUENCE: 135

His Thr Gln Gly Tyr Phe Pro Asp Trp Gln Asn Tyr Thr Pro Gly Pro
1               5                   10                  15

Gly Val Arg Tyr Pro Leu Thr Phe Gly Trp Leu Tyr Lys Leu
            20                  25                  30

<210> SEQ ID NO 136
<211> LENGTH: 19
<212> TYPE: PRT
<213> ORGANISM: Artificial Sequence
<220> FEATURE:
<223> OTHER INFORMATION: Gag p17 (17-35)

<400> SEQUENCE: 136

Glu Lys Ile Arg Leu Arg Pro Gly Gly Lys Lys Tyr Lys Leu Lys
1               5                   10                  15

His Ile Val

<210> SEQ ID NO 137
<211> LENGTH: 32
<212> TYPE: PRT
<213> ORGANISM: Artificial Sequence
<220> FEATURE:
<223> OTHER INFORMATION: Gag p17-p24 (253-284)

<400> SEQUENCE: 137

Asn Pro Pro Ile Pro Val Gly Glu Ile Tyr Lys Arg Trp Ile Ile Leu
1               5                   10                  15

Gly Leu Asn Lys Ile Val Arg Met Tyr Ser Pro Thr Ser Ile Leu Asp
            20                  25                  30

<210> SEQ ID NO 138
<211> LENGTH: 31
<212> TYPE: PRT
<213> ORGANISM: Artificial Sequence
<220> FEATURE:
<223> OTHER INFORMATION: Pol 325-355 (RT 158-188)

<400> SEQUENCE: 138

Ala Ile Phe Gln Ser Ser Met Thr Lys Ile Leu Glu Pro Phe Arg Lys
1               5                   10                  15

Gln Asn Pro Asp Ile Val Ile Tyr Gln Tyr Met Asp Asp Leu Tyr
            20                  25                  30

<210> SEQ ID NO 139
<211> LENGTH: 307
<212> TYPE: PRT
<213> ORGANISM: Artificial Sequence
<220> FEATURE:
<223> OTHER INFORMATION: scFV that binds human CD19

<400> SEQUENCE: 139

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
                35                  40                  45

Ser Tyr Trp Met Asn Trp Val Lys Gln Arg Pro Gly Gln Gly Leu Glu
        50                  55                  60

Trp Ile Gly Gln Ile Tyr Pro Gly Asp Gly Asp Thr Asn Tyr Asn Gly

```
            65                  70                  75                  80
Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Val Val Asp Phe Tyr Phe Asp
            115                 120                 125

Tyr Trp Gly Gln Gly Thr Thr Val Thr Val Ser Ser Gly Gly Gly
130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
                180                 185                 190

Gln Lys Pro Gly Gln Ser Pro Lys Pro Leu Ile Tyr Ser Ala Thr Tyr
                195                 200                 205

Arg Asn Ser Gly Val Pro Asp Arg Phe Thr Gly Ser Gly Ser Gly Thr
                210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Ile Glu Val Met Tyr Pro
                260                 265                 270

Pro Pro Tyr Leu Asp Asn Glu Lys Ser Asn Gly Thr Ile Ile His Val
                275                 280                 285

Lys Gly Lys His Leu Cys Pro Ser Pro Leu Phe Pro Gly Pro Ser Lys
                290                 295                 300

Pro Phe Trp
305

<210> SEQ ID NO 140
<211> LENGTH: 301
<212> TYPE: PRT
<213> ORGANISM: Artificial Sequence
<220> FEATURE:
<223> OTHER INFORMATION: scFV that binds human ROR1

<400> SEQUENCE: 140

Met Leu Leu Leu Val Thr Ser Leu Leu Leu Cys Glu Leu Pro His Pro
1               5                   10                  15

Ala Phe Leu Leu Ile Pro Gln Glu Gln Leu Val Glu Ser Gly Gly Arg
                20                  25                  30

Leu Val Thr Pro Gly Gly Ser Leu Thr Leu Ser Cys Lys Ala Ser Gly
            35                  40                  45

Phe Asp Phe Ser Ala Tyr Tyr Met Ser Trp Val Arg Gln Ala Pro Gly
        50                  55                  60

Lys Gly Leu Glu Trp Ile Ala Thr Ile Tyr Pro Ser Ser Gly Lys Thr
65                  70                  75                  80

Tyr Tyr Ala Thr Trp Val Asn Gly Arg Phe Thr Ile Ser Ser Asp Asn
                85                  90                  95

Ala Gln Asn Thr Val Asp Leu Gln Met Asn Ser Leu Thr Ala Ala Asp
            100                 105                 110

Arg Ala Thr Tyr Phe Cys Ala Arg Asp Ser Tyr Ala Asp Asp Gly Ala
```

```
              115                 120                 125
Leu Phe Asn Ile Trp Gly Pro Gly Thr Leu Val Thr Ile Ser Ser Gly
            130                 135                 140

Gly Gly Gly Ser Gly Gly Gly Ser Gly Gly Gly Ser Glu Leu
145                 150                 155                 160

Val Leu Thr Gln Ser Pro Ser Val Ser Ala Leu Gly Ser Pro Ala
                165                 170                 175

Lys Ile Thr Cys Thr Leu Ser Ser Ala His Lys Thr Asp Thr Ile Asp
                180                 185                 190

Trp Tyr Gln Gln Leu Gln Gly Glu Ala Pro Arg Tyr Leu Met Gln Val
                195                 200                 205

Gln Ser Asp Gly Ser Tyr Thr Lys Arg Pro Gly Val Pro Asp Arg Phe
        210                 215                 220

Ser Gly Ser Ser Ser Gly Ala Asp Arg Tyr Leu Ile Ile Pro Ser Val
225                 230                 235                 240

Gln Ala Asp Asp Glu Ala Asp Tyr Tyr Cys Gly Ala Asp Tyr Ile Gly
                245                 250                 255

Gly Tyr Val Phe Gly Gly Gly Thr Gln Leu Thr Val Thr Gly Glu Ser
                260                 265                 270

Lys Tyr Gly Pro Pro Cys Pro Pro Cys Pro Met Phe Trp Val Leu Val
                275                 280                 285

Val Val Gly Gly Val Leu Ala Cys Tyr Ser Leu Leu Val
                290                 295                 300

<210> SEQ ID NO 141
<211> LENGTH: 11
<212> TYPE: PRT
<213> ORGANISM: Artificial Sequence
<220> FEATURE:
<223> OTHER INFORMATION: CDRL1 binding ROR1

<400> SEQUENCE: 141

Ala Ser Gly Phe Asp Phe Ser Ala Tyr Tyr Met
1               5                   10

<210> SEQ ID NO 142
<211> LENGTH: 7
<212> TYPE: PRT
<213> ORGANISM: Artificial Sequence
<220> FEATURE:
<223> OTHER INFORMATION: CDRL2 binding ROR1

<400> SEQUENCE: 142

Thr Ile Tyr Pro Ser Ser Gly
1               5

<210> SEQ ID NO 143
<211> LENGTH: 9
<212> TYPE: PRT
<213> ORGANISM: Artificial Sequence
<220> FEATURE:
<223> OTHER INFORMATION: CDRL3 binding ROR1

<400> SEQUENCE: 143

Ala Asp Arg Ala Thr Tyr Phe Cys Ala
1               5

<210> SEQ ID NO 144
<211> LENGTH: 6
<212> TYPE: PRT
<213> ORGANISM: Artificial Sequence
```

```
<220> FEATURE:
<223> OTHER INFORMATION: CDRH1 binding ROR1

<400> SEQUENCE: 144

Asp Thr Ile Asp Trp Tyr
1               5

<210> SEQ ID NO 145
<211> LENGTH: 16
<212> TYPE: PRT
<213> ORGANISM: Artificial Sequence
<220> FEATURE:
<223> OTHER INFORMATION: CDRH2 binding ROR1

<400> SEQUENCE: 145

Val Gln Ser Asp Gly Ser Tyr Thr Lys Arg Pro Gly Val Pro Asp Arg
1               5                   10                  15

<210> SEQ ID NO 146
<211> LENGTH: 8
<212> TYPE: PRT
<213> ORGANISM: Artificial Sequence
<220> FEATURE:
<223> OTHER INFORMATION: CDRH3 binding ROR1

<400> SEQUENCE: 146

Tyr Ile Gly Gly Tyr Val Phe Gly
1               5

<210> SEQ ID NO 147
<211> LENGTH: 11
<212> TYPE: PRT
<213> ORGANISM: Artificial Sequence
<220> FEATURE:
<223> OTHER INFORMATION: CDRL1 of R11

<400> SEQUENCE: 147

Gln Ala Ser Gln Ser Ile Asp Ser Asn Leu Ala
1               5                   10

<210> SEQ ID NO 148
<211> LENGTH: 7
<212> TYPE: PRT
<213> ORGANISM: Artificial Sequence
<220> FEATURE:
<223> OTHER INFORMATION: CDRL2 of R11

<400> SEQUENCE: 148

Arg Ala Ser Asn Leu Ala Ser
1               5

<210> SEQ ID NO 149
<211> LENGTH: 12
<212> TYPE: PRT
<213> ORGANISM: Artificial Sequence
<220> FEATURE:
<223> OTHER INFORMATION: CDRL3 of R11

<400> SEQUENCE: 149

Leu Gly Gly Val Gly Asn Val Ser Tyr Arg Thr Ser
1               5                   10

<210> SEQ ID NO 150
<211> LENGTH: 5
<212> TYPE: PRT
<213> ORGANISM: Artificial Sequence
<220> FEATURE:
```

```
<223> OTHER INFORMATION: CDRH1 of R11

<400> SEQUENCE: 150

Asp Tyr Pro Ile Ser
1               5

<210> SEQ ID NO 151
<211> LENGTH: 16
<212> TYPE: PRT
<213> ORGANISM: Artificial Sequence
<220> FEATURE:
<223> OTHER INFORMATION: CDRH2 of R11

<400> SEQUENCE: 151

Phe Ile Asn Ser Gly Gly Ser Thr Trp Tyr Ala Ser Trp Val Lys Gly
1               5                   10                  15

<210> SEQ ID NO 152
<211> LENGTH: 11
<212> TYPE: PRT
<213> ORGANISM: Artificial Sequence
<220> FEATURE:
<223> OTHER INFORMATION: CDRH3 of R11

<400> SEQUENCE: 152

Gly Tyr Ser Thr Tyr Tyr Cys Asp Phe Asn Ile
1               5                   10

<210> SEQ ID NO 153
<211> LENGTH: 12
<212> TYPE: PRT
<213> ORGANISM: Artificial Sequence
<220> FEATURE:
<223> OTHER INFORMATION: CDRL1 of R12

<400> SEQUENCE: 153

Thr Leu Ser Ser Ala His Lys Thr Asp Thr Ile Asp
1               5                   10

<210> SEQ ID NO 154
<211> LENGTH: 7
<212> TYPE: PRT
<213> ORGANISM: Artificial Sequence
<220> FEATURE:
<223> OTHER INFORMATION: CDRL2 of R12

<400> SEQUENCE: 154

Gly Ser Tyr Thr Lys Arg Pro
1               5

<210> SEQ ID NO 155
<211> LENGTH: 9
<212> TYPE: PRT
<213> ORGANISM: Artificial Sequence
<220> FEATURE:
<223> OTHER INFORMATION: CDRL3 of R12

<400> SEQUENCE: 155

Gly Ala Asp Tyr Ile Gly Gly Tyr Val
1               5

<210> SEQ ID NO 156
<211> LENGTH: 5
<212> TYPE: PRT
<213> ORGANISM: Artificial Sequence
<220> FEATURE:
<223> OTHER INFORMATION: CDRH1 of R12
```

<400> SEQUENCE: 156

Ala Tyr Tyr Met Ser
1               5

<210> SEQ ID NO 157
<211> LENGTH: 17
<212> TYPE: PRT
<213> ORGANISM: Artificial Sequence
<220> FEATURE:
<223> OTHER INFORMATION: CDRH2 of R12

<400> SEQUENCE: 157

Thr Ile Tyr Pro Ser Ser Gly Lys Thr Tyr Tyr Ala Thr Trp Val Asn
1               5                   10                  15

Gly

<210> SEQ ID NO 158
<211> LENGTH: 12
<212> TYPE: PRT
<213> ORGANISM: Artificial Sequence
<220> FEATURE:
<223> OTHER INFORMATION: CDRH3 of R12

<400> SEQUENCE: 158

Asp Ser Tyr Ala Asp Asp Gly Ala Leu Phe Asn Ile
1               5                   10

<210> SEQ ID NO 159
<211> LENGTH: 115
<212> TYPE: PRT
<213> ORGANISM: Artificial Sequence
<220> FEATURE:
<223> OTHER INFORMATION: Variable light chain of scFV that binds human
      CD33

<400> SEQUENCE: 159

Asp Ile Val Leu Thr Gln Ser Pro Thr Ile Met Ser Ala Ser Pro Gly
1               5                   10                  15

Glu Arg Val Thr Met Thr Cys Thr Ala Ser Ser Ser Val Asn Tyr Ile
            20                  25                  30

His Trp Tyr Gln Gln Lys Ser Gly Asp Ser Pro Lys Arg Trp Ile Phe
        35                  40                  45

Asp Thr Ser Lys Val Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Arg Ser Tyr Pro Leu Thr
                85                  90                  95

Phe Gly Asp Gly Thr Arg Leu Glu Leu Lys Arg Ala Asp Ala Ala Pro
            100                 105                 110

Thr Val Ser
        115

<210> SEQ ID NO 160
<211> LENGTH: 115
<212> TYPE: PRT
<213> ORGANISM: Artificial Sequence
<220> FEATURE:
<223> OTHER INFORMATION: Variable heavy chain of scFV that binds human
      CD33

<400> SEQUENCE: 160

```
Asp Ile Val Leu Thr Gln Ser Pro Ala Ile Met Ser Ala Ser Pro Gly
1               5                   10                  15

Glu Lys Val Thr Met Thr Cys Ser Ala Asn Ser Ser Val Ser Tyr Ile
            20                  25                  30

His Trp Tyr Gln Gln Lys Ser Gly Thr Ser Pro Lys Arg Trp Ile Phe
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ser His Pro Leu Thr
                85                  90                  95

Phe Gly Thr Gly Thr Lys Leu Gln Leu Lys Arg Ala Asp Ala Ala Pro
            100                 105                 110

Thr Val Ser
        115

<210> SEQ ID NO 161
<211> LENGTH: 120
<212> TYPE: PRT
<213> ORGANISM: Artificial Sequence
<220> FEATURE:
<223> OTHER INFORMATION: Variable heavy chain of Avelumab

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 162
<211> LENGTH: 110
<212> TYPE: PRT
<213> ORGANISM: Artificial Sequence
<220> FEATURE:
<223> OTHER INFORMATION: Variable light chain of Avelumab

<400> SEQUENCE: 162

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
```

```
                    50                  55                  60
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                     85                  90                  95

Ser Thr Arg Val Phe Gly Thr Gly Thr Lys Val Thr Val Leu
                100                 105                 110
```

<210> SEQ ID NO 163
<211> LENGTH: 11
<212> TYPE: PRT
<213> ORGANISM: Artificial Sequence
<220> FEATURE:
<223> OTHER INFORMATION: CDRH1 of Avelumab

<400> SEQUENCE: 163

```
Ser Gly Phe Thr Phe Ser Ser Tyr Ile Met Met
 1               5                  10
```

<210> SEQ ID NO 164
<211> LENGTH: 17
<212> TYPE: PRT
<213> ORGANISM: Artificial Sequence
<220> FEATURE:
<223> OTHER INFORMATION: CDRH2 of Avelumab

<400> SEQUENCE: 164

```
Ser Ile Tyr Pro Ser Gly Gly Ile Thr Phe Tyr Ala Asp Thr Val Lys
 1               5                  10                  15

Gly
```

<210> SEQ ID NO 165
<211> LENGTH: 11
<212> TYPE: PRT
<213> ORGANISM: Artificial Sequence
<220> FEATURE:
<223> OTHER INFORMATION: CDRH3 of Avelumab

<400> SEQUENCE: 165

```
Ile Lys Leu Gly Thr Val Thr Thr Val Asp Tyr
 1               5                  10
```

<210> SEQ ID NO 166
<211> LENGTH: 14
<212> TYPE: PRT
<213> ORGANISM: Artificial Sequence
<220> FEATURE:
<223> OTHER INFORMATION: CDRL1 of Avelumab

<400> SEQUENCE: 166

```
Thr Gly Thr Ser Ser Asp Val Gly Gly Tyr Asn Tyr Val Ser
 1               5                  10
```

<210> SEQ ID NO 167
<211> LENGTH: 7
<212> TYPE: PRT
<213> ORGANISM: Artificial Sequence
<220> FEATURE:
<223> OTHER INFORMATION: CDRL2 of Avelumab

<400> SEQUENCE: 167

```
Asp Val Ser Asn Arg Pro Ser
 1               5
```

-continued

```
<210> SEQ ID NO 168
<211> LENGTH: 10
<212> TYPE: PRT
<213> ORGANISM: Artificial Sequence
<220> FEATURE:
<223> OTHER INFORMATION: CDRL3 of Avelumab

<400> SEQUENCE: 168

Ser Ser Tyr Thr Ser Ser Ser Thr Arg Val
1               5                   10

<210> SEQ ID NO 169
<211> LENGTH: 118
<212> TYPE: PRT
<213> ORGANISM: Artificial Sequence
<220> FEATURE:
<223> OTHER INFORMATION: Variable heavy chain of Atezolizumab

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 170
<211> LENGTH: 107
<212> TYPE: PRT
<213> ORGANISM: Artificial Sequence
<220> FEATURE:
<223> OTHER INFORMATION: Variable light chain of Atezolizumab

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 171
```

```
<211> LENGTH: 11
<212> TYPE: PRT
<213> ORGANISM: Artificial Sequence
<220> FEATURE:
<223> OTHER INFORMATION: CDRH1 of Atezolizumab

<400> SEQUENCE: 171

Ser Gly Phe Thr Phe Ser Asp Ser Trp Ile His
1               5                   10

<210> SEQ ID NO 172
<211> LENGTH: 17
<212> TYPE: PRT
<213> ORGANISM: Artificial Sequence
<220> FEATURE:
<223> OTHER INFORMATION: CDRH2 of Atezolizumab

<400> SEQUENCE: 172

Trp Ile Ser Pro Tyr Gly Gly Ser Thr Tyr Tyr Ala Asp Ser Val Lys
1               5                   10                  15

Gly

<210> SEQ ID NO 173
<211> LENGTH: 9
<212> TYPE: PRT
<213> ORGANISM: Artificial Sequence
<220> FEATURE:
<223> OTHER INFORMATION: CDRH3 of Atezolizumab

<400> SEQUENCE: 173

Arg His Trp Pro Gly Gly Phe Asp Tyr
1               5

<210> SEQ ID NO 174
<211> LENGTH: 11
<212> TYPE: PRT
<213> ORGANISM: Artificial Sequence
<220> FEATURE:
<223> OTHER INFORMATION: CDRL1 of Atezolizumab

<400> SEQUENCE: 174

Arg Ala Ser Gln Asp Val Ser Thr Ala Val Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: CDRL2 of Atezolizumab

<400> SEQUENCE: 175

Ser Ala Ser Phe Leu Tyr Ser
1               5

<210> SEQ ID NO 176
<211> LENGTH: 9
<212> TYPE: PRT
<213> ORGANISM: Artificial Sequence
<220> FEATURE:
<223> OTHER INFORMATION: CDRL3 of Atezolizumab

<400> SEQUENCE: 176

Gln Gln Tyr Leu Tyr His Pro Ala Thr
1               5
```

```
<210> SEQ ID NO 177
<211> LENGTH: 7
<212> TYPE: PRT
<213> ORGANISM: Artificial Sequence
<220> FEATURE:
<223> OTHER INFORMATION: CDRL1 that binds MUC16

<400> SEQUENCE: 177

Ser Glu Asp Ile Tyr Ser Gly
1               5

<210> SEQ ID NO 178
<211> LENGTH: 8
<212> TYPE: PRT
<213> ORGANISM: Artificial Sequence
<220> FEATURE:
<223> OTHER INFORMATION: CDRL3 that binds MUC16

<400> SEQUENCE: 178

Gly Tyr Ser Tyr Ser Ser Thr Leu
1               5

<210> SEQ ID NO 179
<211> LENGTH: 7
<212> TYPE: PRT
<213> ORGANISM: Artificial Sequence
<220> FEATURE:
<223> OTHER INFORMATION: CDRH1 that binds MUC16

<400> SEQUENCE: 179

Thr Leu Gly Met Gly Val Gly
1               5

<210> SEQ ID NO 180
<211> LENGTH: 16
<212> TYPE: PRT
<213> ORGANISM: Artificial Sequence
<220> FEATURE:
<223> OTHER INFORMATION: CDRH2 that binds MUC16

<400> SEQUENCE: 180

His Ile Trp Trp Asp Asp Asp Lys Tyr Tyr Asn Pro Ala Leu Lys Ser
1               5                   10                  15

<210> SEQ ID NO 181
<211> LENGTH: 12
<212> TYPE: PRT
<213> ORGANISM: Artificial Sequence
<220> FEATURE:
<223> OTHER INFORMATION: CDRH3 that binds MUC16

<400> SEQUENCE: 181

Ile Gly Thr Ala Gln Ala Thr Asp Ala Leu Asp Tyr
1               5                   10

<210> SEQ ID NO 182
<211> LENGTH: 15
<212> TYPE: PRT
<213> ORGANISM: Artificial Sequence
<220> FEATURE:
<223> OTHER INFORMATION: CDRL1 that binds FOLR

<400> SEQUENCE: 182

Lys Ala Ser Gln Ser Val Ser Phe Ala Gly Thr Ser Leu Met His
1               5                   10                  15

<210> SEQ ID NO 183
```

-continued

```
<210> SEQ ID NO 183
<211> LENGTH: 7
<212> TYPE: PRT
<213> ORGANISM: Artificial Sequence
<220> FEATURE:
<223> OTHER INFORMATION: CDRL2 that binds FOLR

<400> SEQUENCE: 183

Arg Ala Ser Asn Leu Glu Ala
1               5

<210> SEQ ID NO 184
<211> LENGTH: 9
<212> TYPE: PRT
<213> ORGANISM: Artificial Sequence
<220> FEATURE:
<223> OTHER INFORMATION: CDRL3 that binds FOLR

<400> SEQUENCE: 184

Gln Gln Ser Arg Glu Tyr Pro Tyr Thr
1               5

<210> SEQ ID NO 185
<211> LENGTH: 5
<212> TYPE: PRT
<213> ORGANISM: Artificial Sequence
<220> FEATURE:
<223> OTHER INFORMATION: CDRH1 that binds FOLR

<400> SEQUENCE: 185

Gly Tyr Phe Met Asn
1               5

<210> SEQ ID NO 186
<211> LENGTH: 17
<212> TYPE: PRT
<213> ORGANISM: Artificial Sequence
<220> FEATURE:
<223> OTHER INFORMATION: CDRH2 that binds FOLR

<400> SEQUENCE: 186

Arg Ile His Pro Tyr Asp Gly Asp Thr Phe Tyr Asn Gln Lys Phe Gln
1               5                   10                  15
Gly

<210> SEQ ID NO 187
<211> LENGTH: 9
<212> TYPE: PRT
<213> ORGANISM: Artificial Sequence
<220> FEATURE:
<223> OTHER INFORMATION: CDRH3 that binds FOLR

<400> SEQUENCE: 187

Tyr Asp Gly Ser Arg Ala Met Asp Tyr
1               5

<210> SEQ ID NO 188
<211> LENGTH: 119
<212> TYPE: PRT
<213> ORGANISM: Artificial Sequence
<220> FEATURE:
<223> OTHER INFORMATION: Variable heavy chain of Amatuximab

<400> SEQUENCE: 188

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
```

```
                20                  25                  30
Thr Met Asn Trp Val Lys Gln Ser His Gly Lys Ser Leu Glu Trp Ile
            35                  40                  45
Gly Leu Ile Thr Pro Tyr Asn Gly Ala Ser Ser Tyr Asn Gln Lys Phe
        50                  55                  60
Arg Gly Lys Ala Thr Leu Thr Val Asp Lys Ser Ser Ser Thr Ala Tyr
65                  70                  75                  80
Met Asp Leu Leu Ser Leu Thr Ser Glu Asp Ser Ala Val Tyr Phe Cys
                85                  90                  95
Ala Arg Gly Gly Tyr Asp Gly Arg Gly Phe Asp Tyr Trp Gly Ser Gly
            100                 105                 110
Thr Pro Val Thr Val Ser Ser
            115

<210> SEQ ID NO 189
<211> LENGTH: 106
<212> TYPE: PRT
<213> ORGANISM: Artificial Sequence
<220> FEATURE:
<223> OTHER INFORMATION: Variable light chain of Amatuximab

<400> SEQUENCE: 189

Asp Ile Glu Leu Thr Gln Ser Pro Ala Ile Met Ser Ala Ser Pro Gly
1               5                   10                  15
Glu Lys Val Thr Met Thr Cys Ser Ala Ser Ser Ser Val Ser Tyr Met
                20                  25                  30
His Trp Tyr Gln Gln Lys Ser Gly Thr Ser Pro Lys Arg Trp Ile Tyr
            35                  40                  45
Asp Thr Ser Lys Leu Ala Ser Gly Val Pro Gly Arg Phe Ser Gly Ser
        50                  55                  60
Gly Ser Gly Asn Ser Tyr Ser Leu Thr Ile Ser Ser Val Glu Ala Glu
65                  70                  75                  80
Asp Asp Ala Thr Tyr Tyr Cys Gln Gln Trp Ser Lys His Pro Leu Thr
                85                  90                  95
Phe Gly Ser Gly Thr Lys Val Glu Ile Lys
            100                 105

<210> SEQ ID NO 190
<211> LENGTH: 10
<212> TYPE: PRT
<213> ORGANISM: Artificial Sequence
<220> FEATURE:
<223> OTHER INFORMATION: CDRH1 of Amatuximab

<400> SEQUENCE: 190

Gly Tyr Ser Phe Thr Gly Tyr Thr Met Asn
1               5                   10

<210> SEQ ID NO 191
<211> LENGTH: 13
<212> TYPE: PRT
<213> ORGANISM: Artificial Sequence
<220> FEATURE:
<223> OTHER INFORMATION: CDRH2 of Amatuximab

<400> SEQUENCE: 191

Leu Ile Thr Pro Tyr Asn Gly Ala Ser Ser Tyr Asn Gln
1               5                   10

<210> SEQ ID NO 192
```

```
<211> LENGTH: 10
<212> TYPE: PRT
<213> ORGANISM: Artificial Sequence
<220> FEATURE:
<223> OTHER INFORMATION: CDRH3 of Amatuximab

<400> SEQUENCE: 192

Gly Gly Tyr Asp Gly Arg Gly Phe Asp Tyr
1               5                   10

<210> SEQ ID NO 193
<211> LENGTH: 9
<212> TYPE: PRT
<213> ORGANISM: Artificial Sequence
<220> FEATURE:
<223> OTHER INFORMATION: CDRL1 of Amatuximab

<400> SEQUENCE: 193

Ser Ala Ser Ser Ser Val Ser Tyr Met
1               5

<210> SEQ ID NO 194
<211> LENGTH: 9
<212> TYPE: PRT
<213> ORGANISM: Artificial Sequence
<220> FEATURE:
<223> OTHER INFORMATION: CDRL3 of Amatuximab

<400> SEQUENCE: 194

Gln Gln Trp Ser Lys His Pro Leu Thr
1               5

<210> SEQ ID NO 195
<211> LENGTH: 8
<212> TYPE: PRT
<213> ORGANISM: Artificial Sequence
<220> FEATURE:
<223> OTHER INFORMATION: Flag tag

<400> SEQUENCE: 195

Asp Tyr Lys Asp Asp Asp Asp Lys
1               5

<210> SEQ ID NO 196
<211> LENGTH: 8
<212> TYPE: PRT
<213> ORGANISM: Artificial Sequence
<220> FEATURE:
<223> OTHER INFORMATION: Xpress tag

<400> SEQUENCE: 196

Asp Leu Tyr Asp Asp Asp Asp Lys
1               5

<210> SEQ ID NO 197
<211> LENGTH: 26
<212> TYPE: PRT
<213> ORGANISM: Artificial Sequence
<220> FEATURE:
<223> OTHER INFORMATION: Calmodulin tag

<400> SEQUENCE: 197

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

<210> SEQ ID NO 198
<211> LENGTH: 9
<212> TYPE: PRT
<213> ORGANISM: Artificial Sequence
<220> FEATURE:
<223> OTHER INFORMATION: HA tag

<400> SEQUENCE: 198

Tyr Pro Tyr Asp Val Pro Asp Tyr Ala
1               5

<210> SEQ ID NO 199
<211> LENGTH: 10
<212> TYPE: PRT
<213> ORGANISM: Artificial Sequence
<220> FEATURE:
<223> OTHER INFORMATION: Myc tag

<400> SEQUENCE: 199

Glu Gln Lys Leu Ile Ser Glu Glu Asp Leu
1               5                   10

<210> SEQ ID NO 200
<211> LENGTH: 13
<212> TYPE: PRT
<213> ORGANISM: Artificial Sequence
<220> FEATURE:
<223> OTHER INFORMATION: Softag 1

<400> SEQUENCE: 200

Ser Leu Ala Glu Leu Leu Asn Ala Gly Leu Gly Gly Ser
1               5                   10

<210> SEQ ID NO 201
<211> LENGTH: 8
<212> TYPE: PRT
<213> ORGANISM: Artificial Sequence
<220> FEATURE:
<223> OTHER INFORMATION: Softag 3

<400> SEQUENCE: 201

Thr Gln Asp Pro Ser Arg Val Gly
1               5

<210> SEQ ID NO 202
<211> LENGTH: 8
<212> TYPE: PRT
<213> ORGANISM: Artificial Sequence
<220> FEATURE:
<223> OTHER INFORMATION: STREP tag

<400> SEQUENCE: 202

Trp Arg His Pro Gln Phe Gly Gly
1               5

<210> SEQ ID NO 203
<211> LENGTH: 8
<212> TYPE: PRT
<213> ORGANISM: Artificial Sequence
<220> FEATURE:
<223> OTHER INFORMATION: STREP tag II

<400> SEQUENCE: 203

Trp Ser His Pro Gln Phe Glu Lys
1               5

```
<210> SEQ ID NO 204
<211> LENGTH: 14
<212> TYPE: PRT
<213> ORGANISM: Artificial Sequence
<220> FEATURE:
<223> OTHER INFORMATION: V5 tag

<400> SEQUENCE: 204

Gly Lys Pro Ile Pro Asn Pro Leu Leu Gly Leu Asp Ser Thr
1               5                   10

<210> SEQ ID NO 205
<211> LENGTH: 112
<212> TYPE: PRT
<213> ORGANISM: Homo sapiens

<400> SEQUENCE: 205

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 206
<211> LENGTH: 114
<212> TYPE: PRT
<213> ORGANISM: Homo sapiens

<400> SEQUENCE: 206

Glu Leu Arg Val Lys Phe Ser Arg Ser Ala Asp Ala Pro Ala Tyr Gln
1               5                   10                  15

Gln Gly Gln Asn Gln Leu Tyr Asn Glu Leu Asn Leu Gly Arg Arg Glu
                20                  25                  30

Glu Tyr Asp Val Leu Asp Lys Arg Arg Gly Arg Asp Pro Glu Met Gly
            35                  40                  45

Gly Lys Pro Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg

<210> SEQ ID NO 207
<211> LENGTH: 43
<212> TYPE: PRT
<213> ORGANISM: Artificial Sequence
<220> FEATURE:
<223> OTHER INFORMATION: 4-1BB cytoplasmic domain
```

<400> SEQUENCE: 207

Val Lys Arg Gly Arg Lys Lys Leu Leu Tyr Ile Phe Lys Gln Pro Phe
1               5                   10                  15

Met Arg Pro Val Gln Thr Thr Gln Glu Glu Asp Gly Cys Ser Cys Arg
            20                  25                  30

Phe Pro Glu Glu Glu Glu Gly Gly Cys Glu Leu
            35                  40

<210> SEQ ID NO 208
<211> LENGTH: 41
<212> TYPE: PRT
<213> ORGANISM: Artificial Sequence
<220> FEATURE:
<223> OTHER INFORMATION: 4-1BB cytoplasmic domain

<400> SEQUENCE: 208

Val Lys Arg Gly Arg Lys Lys Leu Leu Tyr Ile Phe Lys Gln Pro Phe
1               5                   10                  15

Met Arg Pro Val Gln Thr Thr Gln Glu Glu Asp Gly Cys Ser Cys Arg
            20                  25                  30

Phe Pro Glu Glu Glu Glu Gly Gly Cys
            35                  40

<210> SEQ ID NO 209
<211> LENGTH: 27
<212> TYPE: PRT
<213> ORGANISM: Artificial Sequence
<220> FEATURE:
<223> OTHER INFORMATION: CD28 Transmembrane domain

<400> SEQUENCE: 209

Met Phe Trp Val Leu Val Val Val Gly Gly Val Leu Ala Cys Tyr Ser
1               5                   10                  15

Leu Leu Val Thr Val Ala Phe Ile Ile Phe Trp
            20                  25

<210> SEQ ID NO 210
<211> LENGTH: 26
<212> TYPE: PRT
<213> ORGANISM: Artificial Sequence
<220> FEATURE:
<223> OTHER INFORMATION: CD28 Transmembrane domain

<400> SEQUENCE: 210

Phe Trp Val Leu Val Val Val Gly Gly Val Leu Ala Cys Tyr Ser Leu
1               5                   10                  15

Leu Val Thr Val Ala Phe Ile Ile Phe Trp
            20                  25

<210> SEQ ID NO 211
<211> LENGTH: 26
<212> TYPE: PRT
<213> ORGANISM: Artificial Sequence
<220> FEATURE:
<223> OTHER INFORMATION: P2A

<400> SEQUENCE: 211

Gly Ser Gly Ala Thr Asn Phe Ser Leu Leu Lys Gln Ala Gly Asp Val
1               5                   10                  15

Glu Glu Asn Pro Gly Pro Gly Ala Ser Gly
            20                  25

```
<210> SEQ ID NO 212
<211> LENGTH: 21
<212> TYPE: PRT
<213> ORGANISM: Artificial Sequence
<220> FEATURE:
<223> OTHER INFORMATION: T2A

<400> SEQUENCE: 212

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 213
<211> LENGTH: 24
<212> TYPE: PRT
<213> ORGANISM: Artificial Sequence
<220> FEATURE:
<223> OTHER INFORMATION: E2A

<400> SEQUENCE: 213

Gly Ser Gly Gln Cys Thr Asn Tyr Ala Leu Leu Lys Leu Ala Gly Asp
1               5                   10                  15

Val Glu Ser Asn Pro Gly Pro Pro
            20

<210> SEQ ID NO 214
<211> LENGTH: 25
<212> TYPE: PRT
<213> ORGANISM: Artificial Sequence
<220> FEATURE:
<223> OTHER INFORMATION: F2A

<400> SEQUENCE: 214

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 215
<211> LENGTH: 11
<212> TYPE: PRT
<213> ORGANISM: Artificial Sequence
<220> FEATURE:
<223> OTHER INFORMATION: IgG4 linker

<400> SEQUENCE: 215

Glu Ser Lys Tyr Gly Pro Pro Cys Pro Pro Cys
1               5                   10
```